US010258676B2

(12) United States Patent
Zeng

(10) Patent No.: US 10,258,676 B2
(45) Date of Patent: Apr. 16, 2019

(54) POLYPEPTIDE VACCINE

(75) Inventor: Qi Zeng, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 393 days.

(21) Appl. No.: 14/342,644

(22) PCT Filed: Aug. 29, 2012

(86) PCT No.: PCT/SG2012/000305
§ 371 (c)(1),
(2), (4) Date: Apr. 17, 2014

(87) PCT Pub. No.: WO2013/036201
PCT Pub. Date: Mar. 14, 2013

(65) Prior Publication Data
US 2015/0306196 A1    Oct. 29, 2015

Related U.S. Application Data

(60) Provisional application No. 61/531,290, filed on Sep. 6, 2011.

(30) Foreign Application Priority Data

Feb. 17, 2012  (SG) ................................ 201201158-1
Jun. 21, 2012  (SG) ................................ 201204644-7

(51) Int. Cl.
| | | |
|---|---|---|
| *A61K 39/00* | (2006.01) | |
| *A61K 39/12* | (2006.01) | |
| *C07K 16/08* | (2006.01) | |
| *C07K 16/18* | (2006.01) | |
| *C07K 16/28* | (2006.01) | |
| *C07K 16/30* | (2006.01) | |
| *C07K 16/40* | (2006.01) | |
| *A61K 38/16* | (2006.01) | |
| *A61K 38/17* | (2006.01) | |
| *A61K 38/46* | (2006.01) | |

(52) U.S. Cl.
CPC ........ *A61K 39/0011* (2013.01); *A61K 38/162* (2013.01); *A61K 38/177* (2013.01); *A61K 38/465* (2013.01); *A61K 39/12* (2013.01); *C07K 16/084* (2013.01); *C07K 16/18* (2013.01); *C07K 16/28* (2013.01); *C07K 16/30* (2013.01); *C07K 16/40* (2013.01); *A61K 2039/505* (2013.01); *A61K 2039/55566* (2013.01); *A61K 2039/575* (2013.01); *A61K 2039/585* (2013.01); *C07K 2317/77* (2013.01); *C12N 2710/22034* (2013.01); *C12N 2730/10134* (2013.01)

(58) Field of Classification Search
None
See application file for complete search history.

(56) References Cited

U.S. PATENT DOCUMENTS

| | | |
|---|---|---|
| 6,333,169 B1 | 12/2001 | Hudziak et al. |
| 2003/0027766 A1 | 2/2003 | Ioannides et al. |
| 2003/0099641 A1 | 5/2003 | Smith et al. |

FOREIGN PATENT DOCUMENTS

| | | |
|---|---|---|
| CN | 102357246 A | 2/2012 |
| EP | 1418235 A2 | 5/2004 |
| EP | 1712620 A1 | 10/2006 |
| WO | WO-2001/062969 A2 | 8/2001 |
| WO | WO-2007/110098 A1 | 10/2007 |
| WO | WO-2008/008311 A1 | 1/2008 |
| WO | WO-2009/022988 A2 | 2/2009 |
| WO | WO-2010/016806 A1 | 2/2010 |
| WO | WO-2011/065923 A1 | 6/2011 |
| WO | WO-2012/049229 A1 | 4/2012 |
| WO | WO-2012/122941 A1 | 9/2012 |
| WO | WO-2012/122942 A1 | 9/2012 |
| WO | WO-2012/122943 A1 | 9/2012 |

OTHER PUBLICATIONS

Disis, J. Clinical Oncology, 22: 1916-1925, 2004.*
Disis, M.L., et al, Immunology, 93: 192-199, 1998.*
Maslak, P.G., et al., Blood, 116(2): 171-179, 2010.*
Kanodia, S., et al., Expert Rev. Vaccines, 7(10): 1533-1545, 2008.*
Abou-Alfa et al., Targeting Mutated K-ras in Pancreatic Adenocarcinoma Using an Adjuvant Vaccine, American Journal of Clinical Oncology, 34(3): 321-325 (2011).
Ciesielski et al., Cellular Antitumour Immune Response to a Branched Lysine Multiple Antigenic Peptide Containing Epitopes of a Common Tumor-Specific Antigen in a Rat Glioma Model, Cancer Immunology, Immunotherapy, 54(2): 107-119 (2004).
Disis et al., Humoral Epitope-Spreading Following Immunization with a HER-2/neu Peptide Based Vaccine in Cancer Patients. Journal of Clinical Immunology, 24(5): 571-578 (2004).
Ferrone, Hidden Immunotherapy Targets Challenge Dogma, Perspective, 3(99): 1-3 (2011).
Fred Hutchinson Cancer Research Center, Vaccine Therapy in Treating Patients with Stage IV Breast Cancer, ClinicalTrials.gov (Sep. 2, 2011).
Gjertsen et al., Vaccination with Mutant Ras Peptides and Induction of T-cell Responsiveness in Pancreatic Carcinoma Patients Carrying the Corresponding RAS Mutation, The Lancet, 346: 1399-1400 (1995).
Guo et al., Targeting Intracellular Oncoproteins with Antibody Therapy or Vaccination, Sci. Transl. Med., 3(99): 1-11 (2011).
Kaiser, Antibodies Target Cancer's Insides, Science Now, 2 pages (Sep. 7, 2011).
Saha et al, A Phosphatase Associated with Metastasis of Colorectal Cancer, Science, 294(9) 1343-1346 (2011).

(Continued)

*Primary Examiner* — Mark Halvorson
(74) *Attorney, Agent, or Firm* — Choate, Hall & Stewart LLP

(57) ABSTRACT

We provide a polypeptide vaccine for treatment and prevention of cancer, particularly prevention of metastasis of cancer. Also provided are methods of treating or preventing cancer, and pharmaceutical compositions comprising the polypeptide vaccine.

23 Claims, 54 Drawing Sheets

Specification includes a Sequence Listing.

(56) References Cited

OTHER PUBLICATIONS

Somasundaram et al., Human Leukocyte Antigen-A2-Restricted CTL Responses to Mutated BRAF Peptides in Melanoma Patients, Cancer Research, 66(6): 3287-3293 (2006).
Su et al., Production and Characterization of an Estrogen Receptor Beta Subtype-Specific Mouse Monoclonal Antibody, Hybridoma, 481-487 (2000).
Tan et al., Induction of CTLs by DCs Pulsed with K-ras Mutant Peptide on the Surface of Nanoparticles in the Treatment of Pancreatic Cancer, Oncology Reports 26: 215-221 (2011).
Tang et al., A PTP4A3 Peptide PIMAP39 Modulates TNF-alpha Levels and Endotoxic Shock, Journal of Innate Immunity, 2(1): 43-45 (2009).
Traish et al., Development and Characterization of Monoclonal Antibodies to a Specific Domain of Human Estrogen Receptor, Steroids, 55: 196-208 (1990).
Wang et al., PCBP1 Suppresses the Translation of Metastasis-Associated PRL-3 Phosphatase, Cancer Cell, 18: 52-62 (2010).
International Search Report of PCT/SG2012/000305, 5 pages (dated Nov. 21, 2012).
Written Opinion of PCT/SG2012/000305, 10 pages (dated Nov. 21, 2012).

\* cited by examiner

FIGURE 1
A
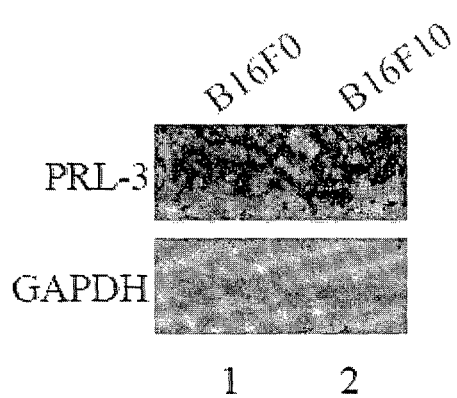
B
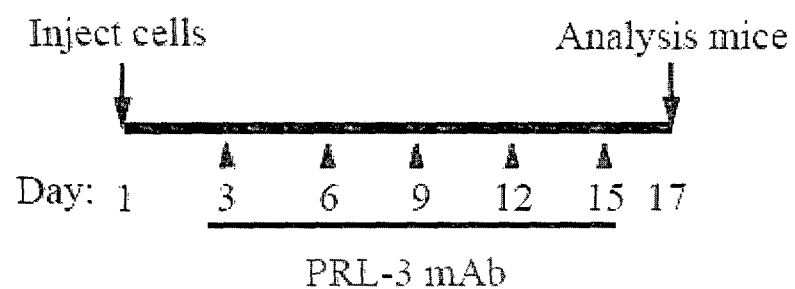

FIGURE 3
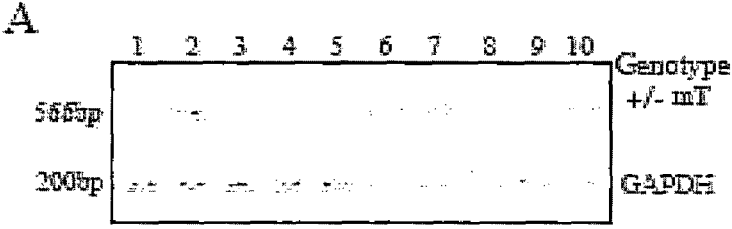
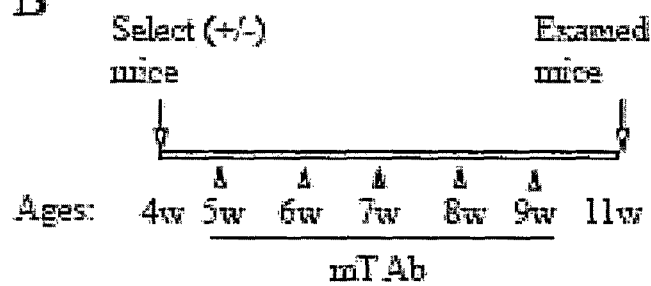
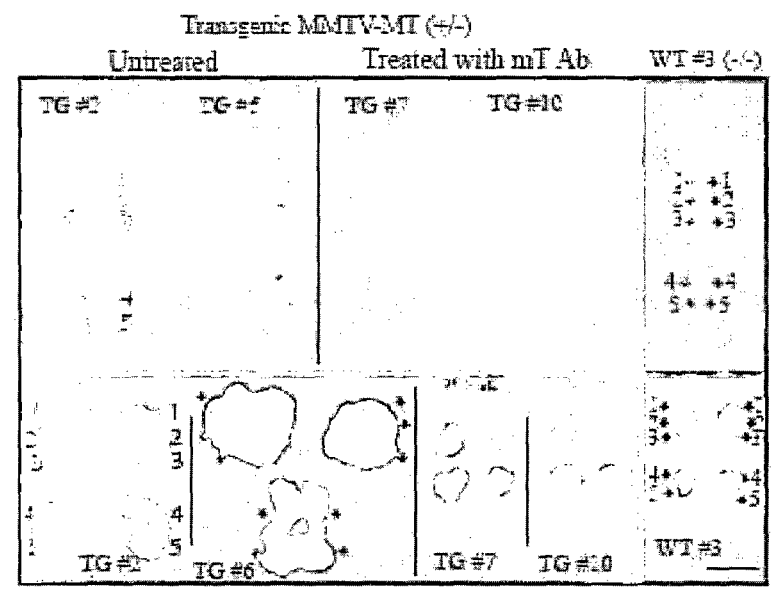

FIGURE 3 (CONTINUED)
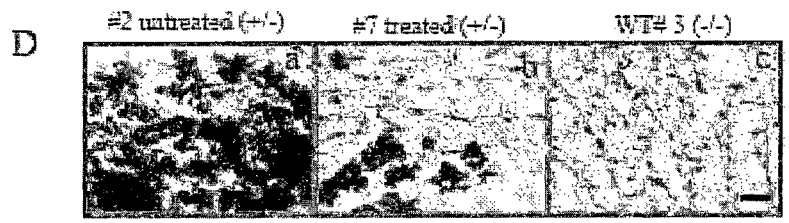
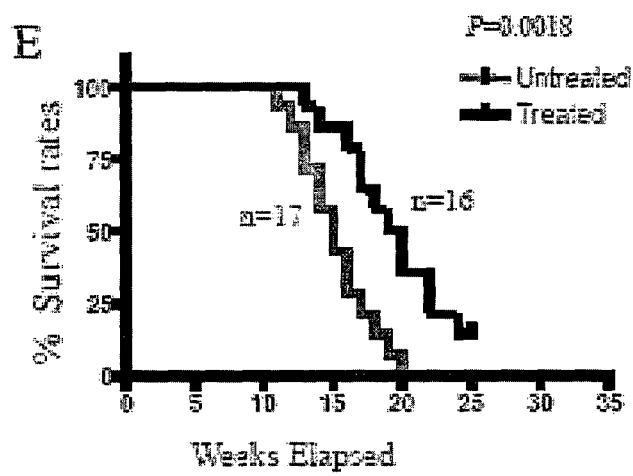
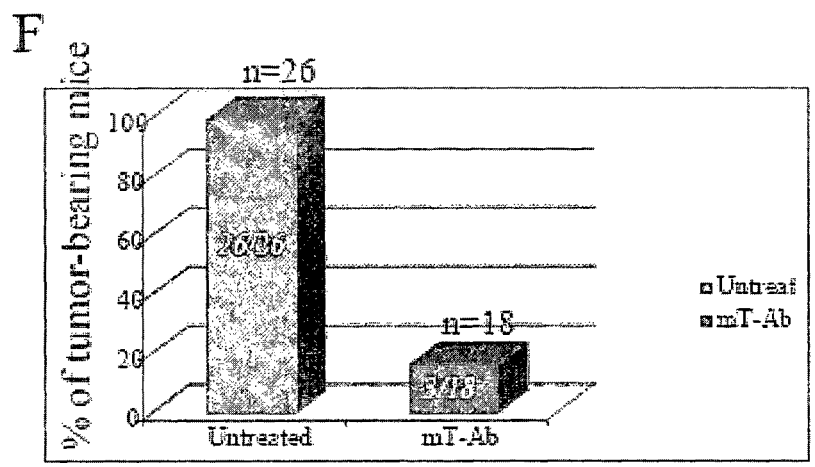

FIGURE 4
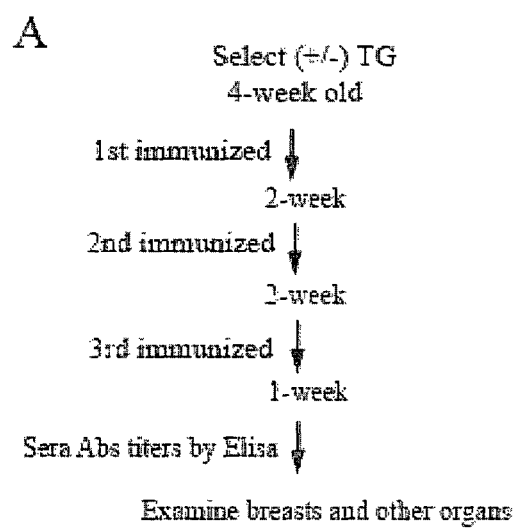
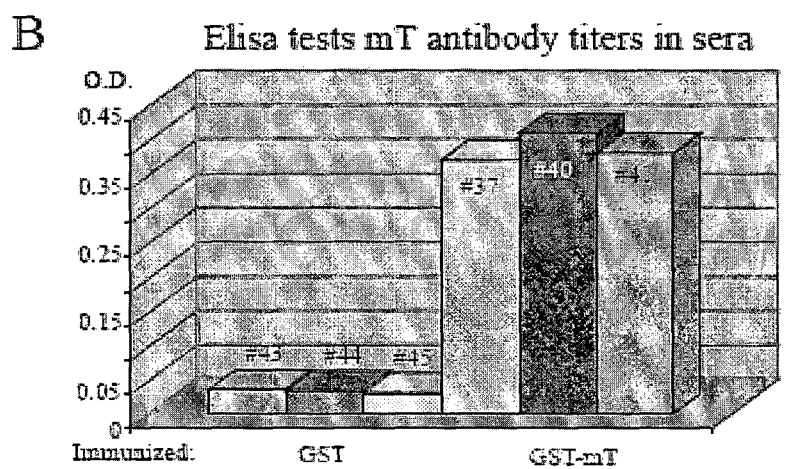

FIGURE 4 (CONTINUED)
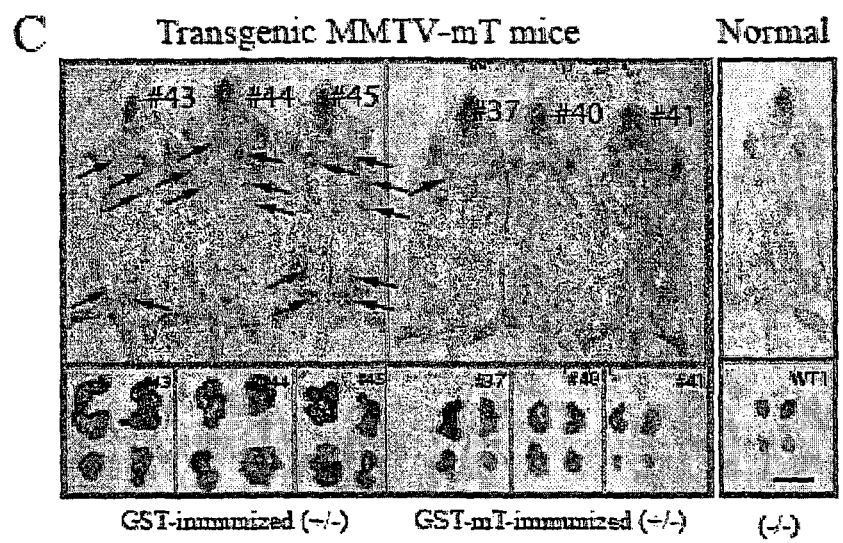
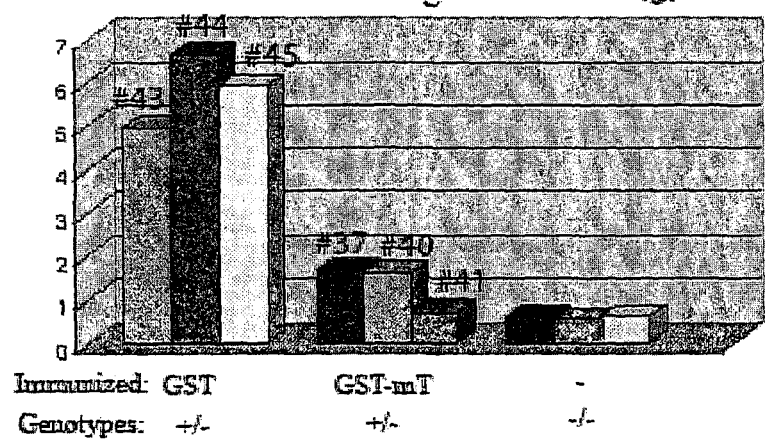

FIGURE 4 (CONTINUED)
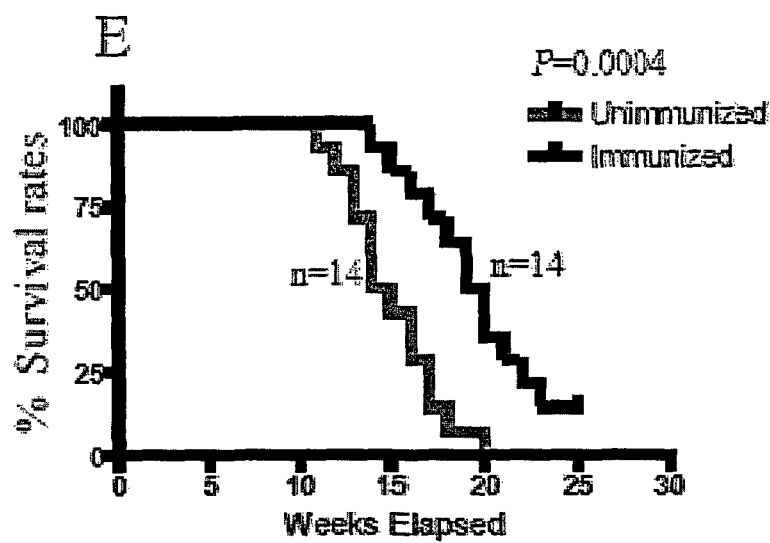
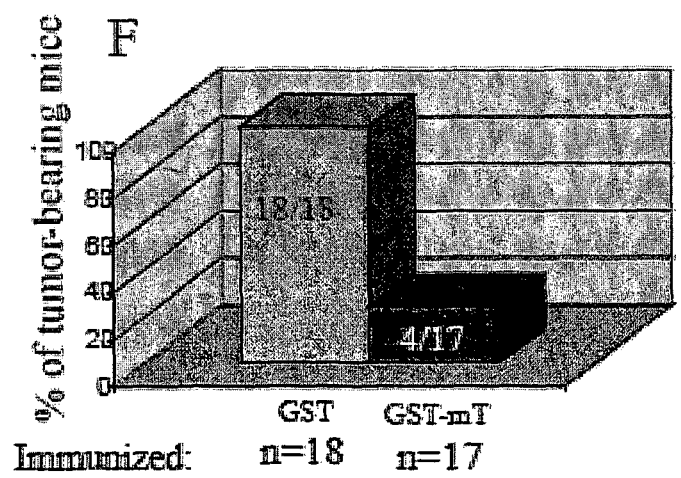

FIGURE 5 (CONTINUED)
F
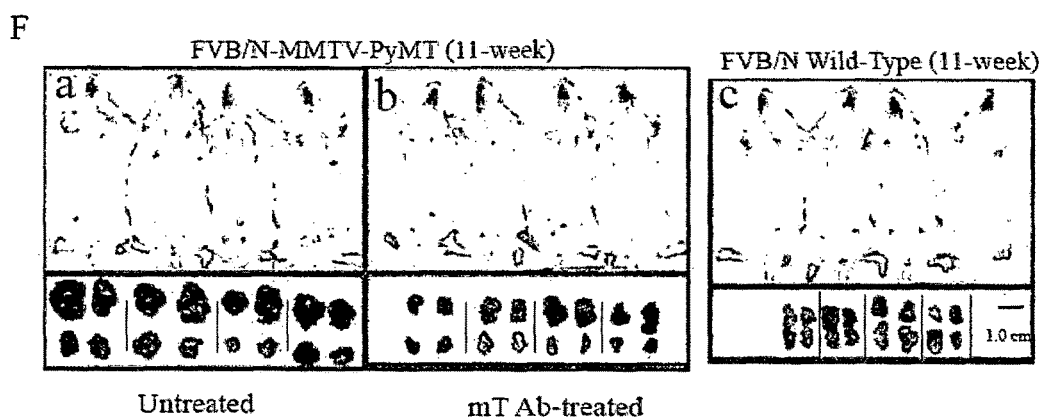
G
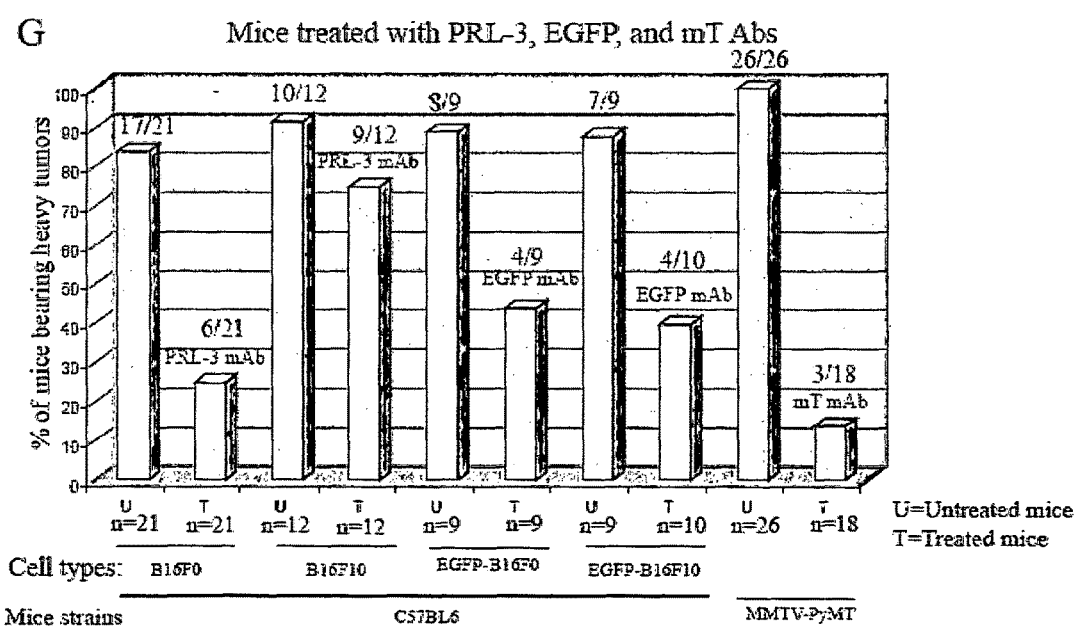

FIGURE 6
A
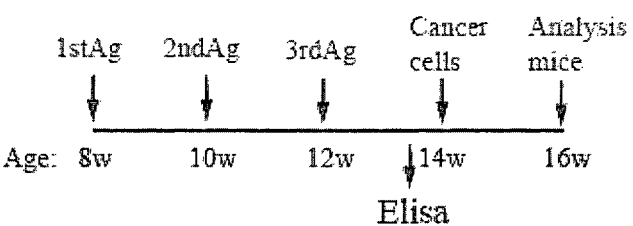
B
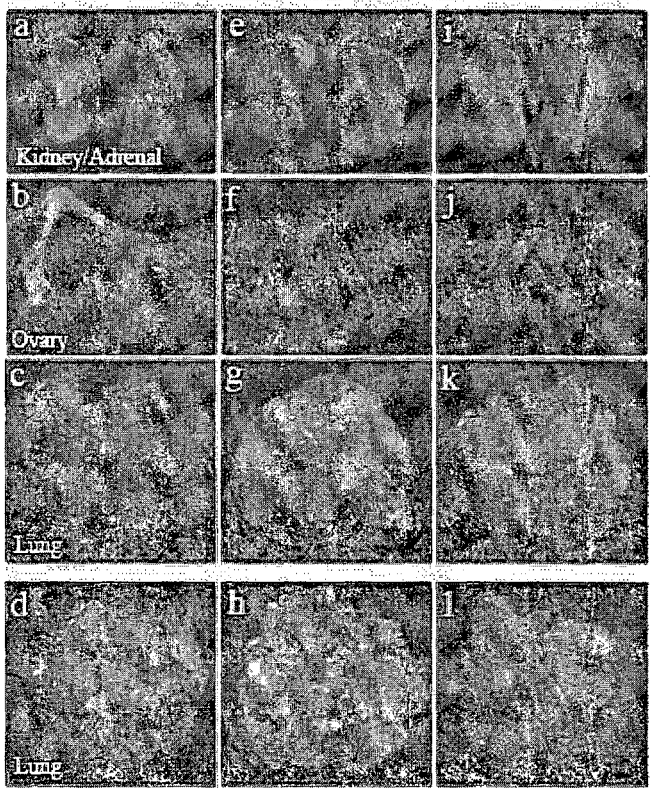

FIGURE 6 (CONTINUED)
C                 12.5-week
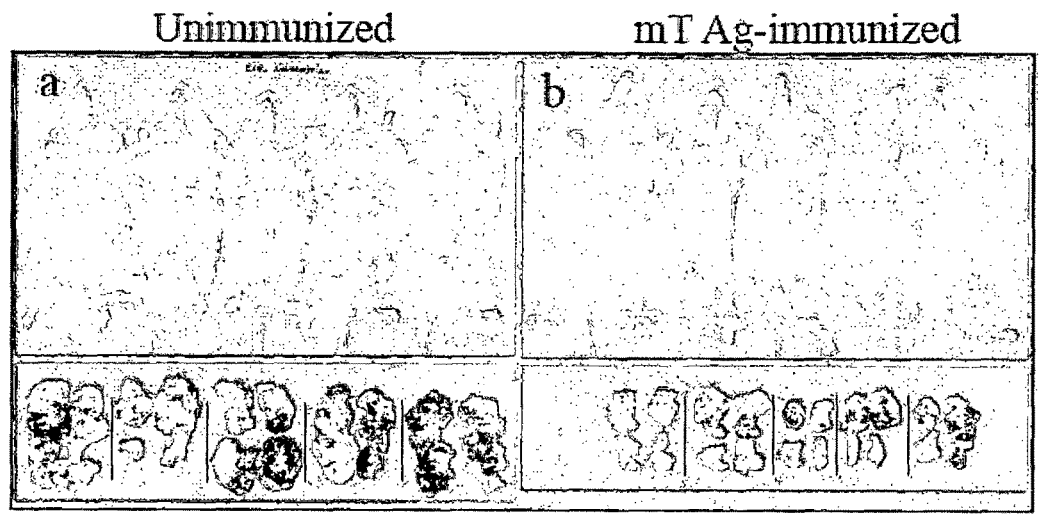
D
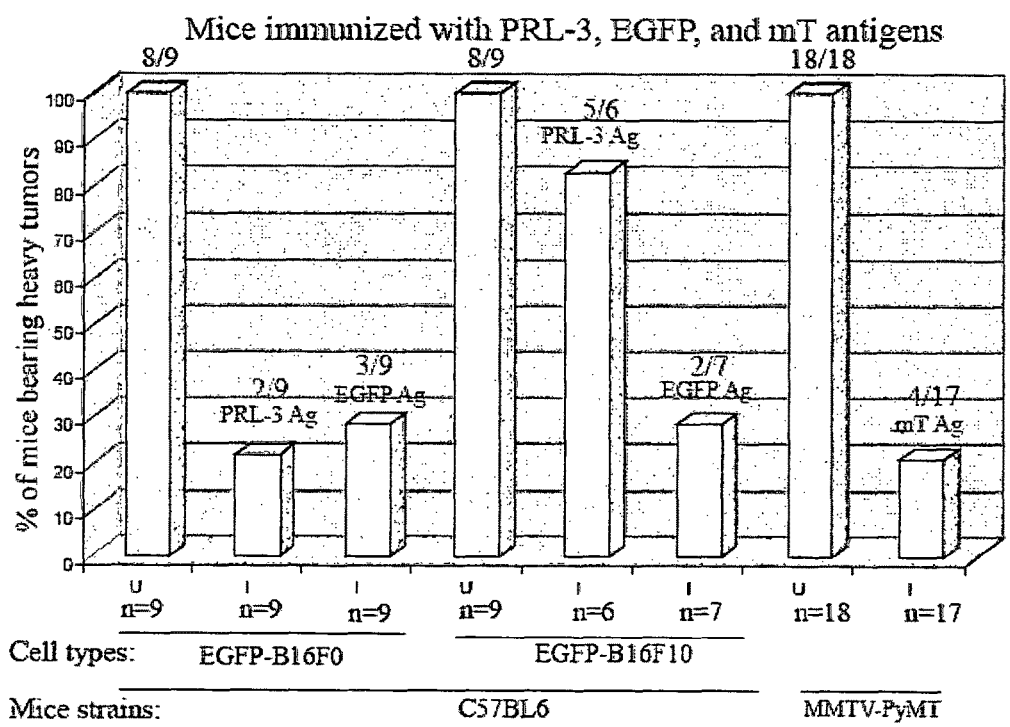
U=Unimmunized mice
I=Immunized mice

FIGURE 7
A Outline of PRL-3 chimeric antibody construction
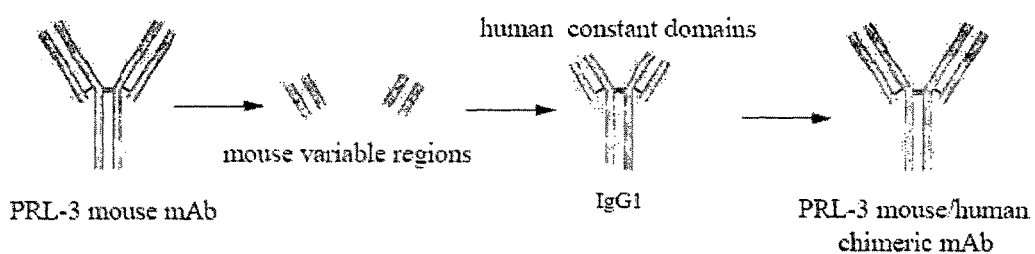
B
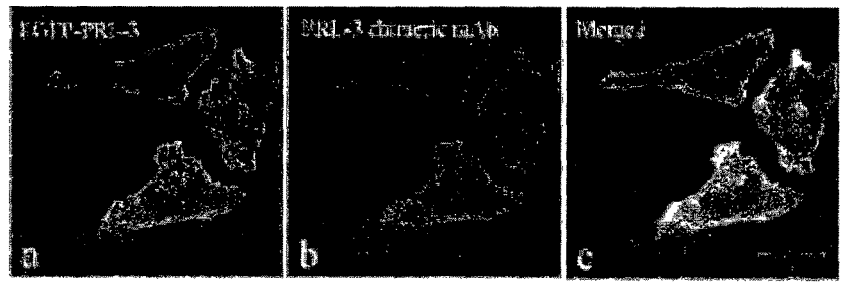
C
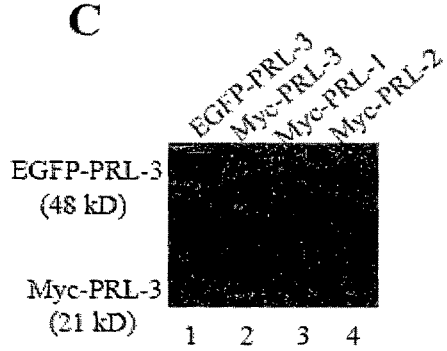

E

FIGURE 9
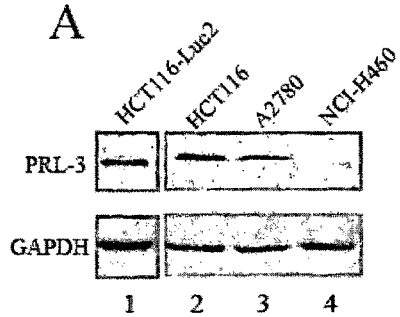
A
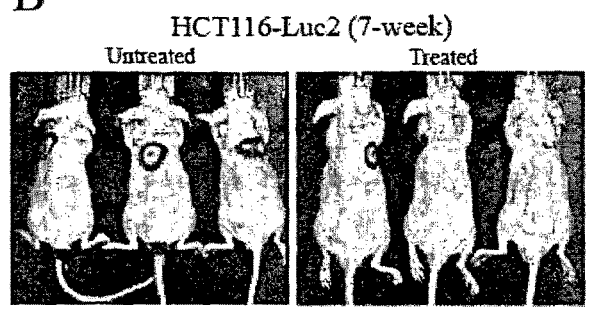
B
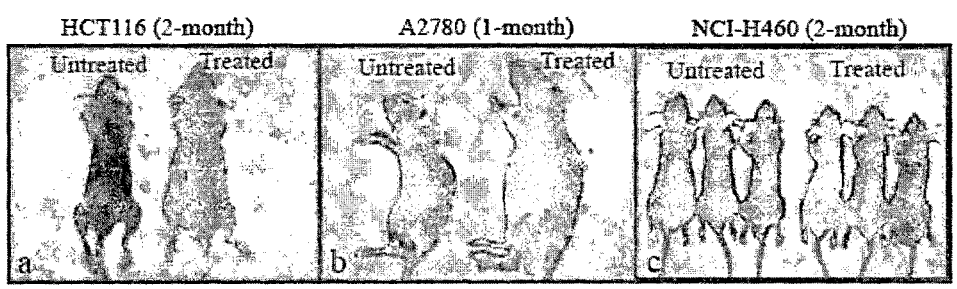
C
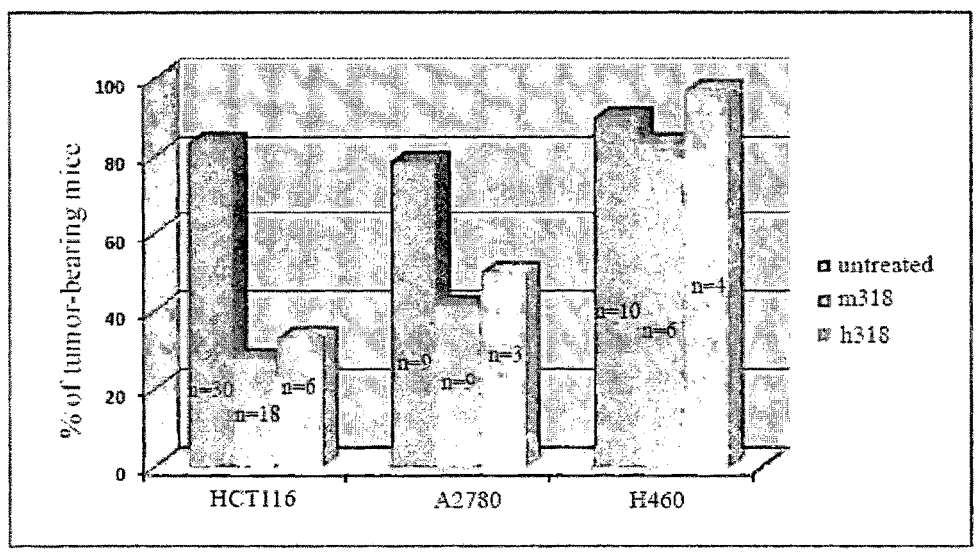
D

FIGURE 10
A
a
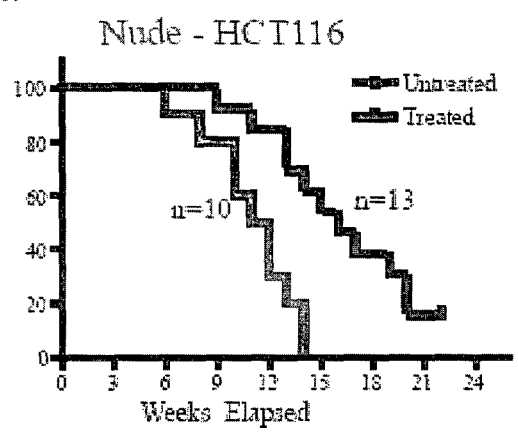
b
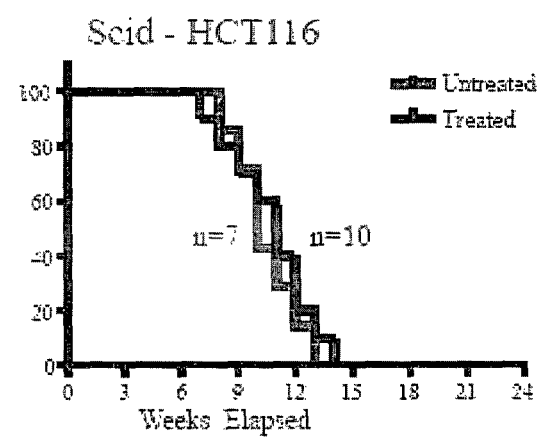

FIGURE 10A (CONTINUED)
c
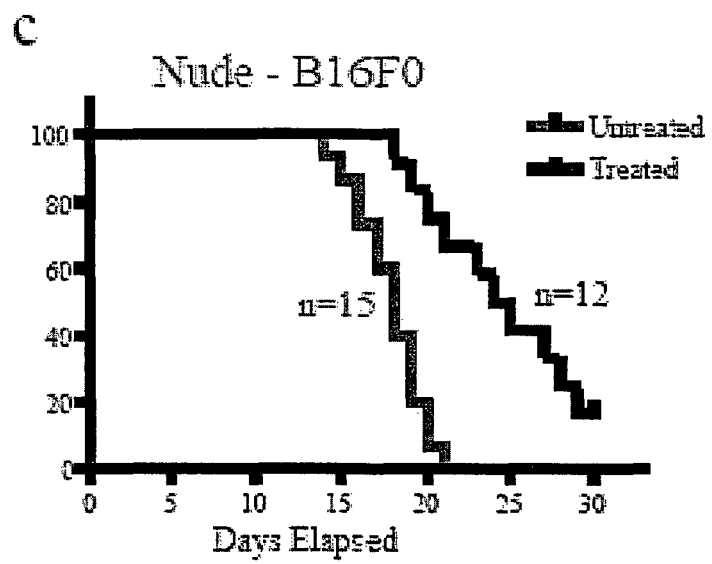
d
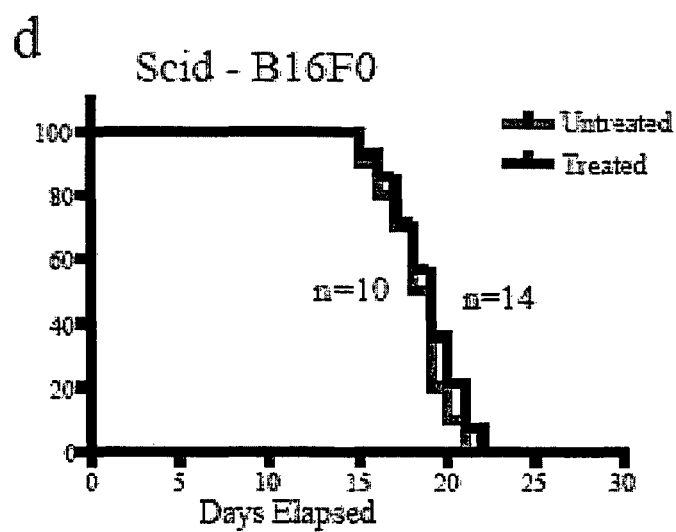

FIGURE 11A
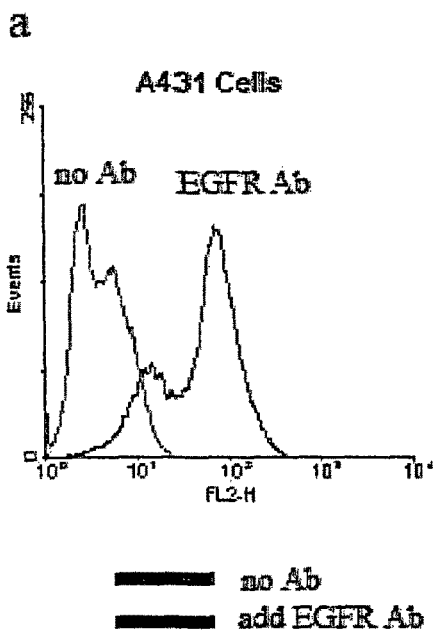
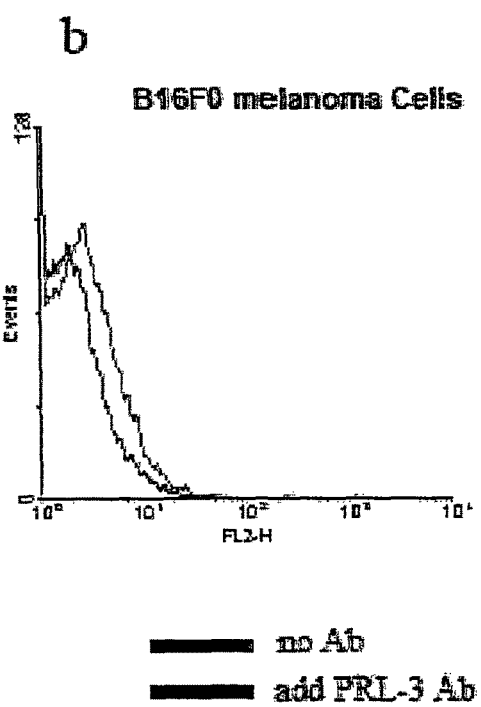

FIGURE 12
A  Squamous cell carcinoma
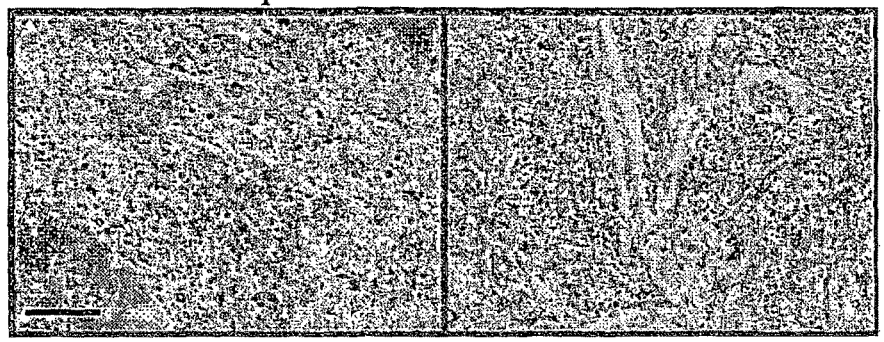
B  Adeno-carcinoma
C  Summary of PRL-3 expression in human lung cancers
| Subtypes of lung cancers | Squamous cell carcinoma | Adeno-carcinoma | Small cell carcinoma | Large cell carcinoma | Carcinoid | Normal lung |
|---|---|---|---|---|---|---|
| Total samples | 74 | 68 | 12 | 5 | 4 | 8 |
| PRL-3 positive samples | 23 | 18 | 1 | 1 | 1 | 0 |
| % of PRL-3 positive samples | 31.1% | 26.4% | 8.3% | 1/5 | 1/4 | 0/8 |

D  PRL-3 overexpressed in 35 % of AML

FIGURE 14
A
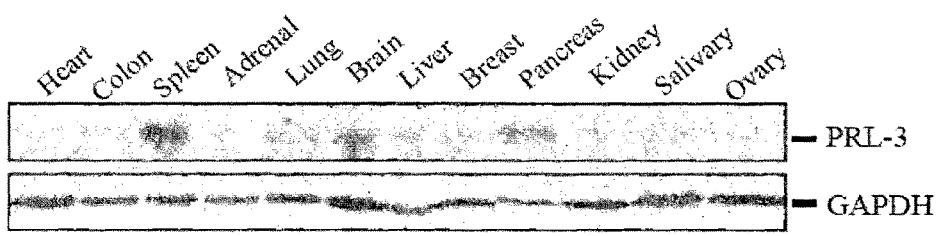
B
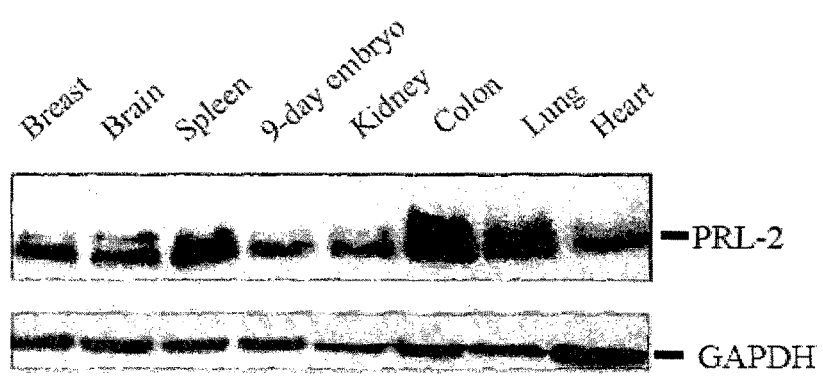
C
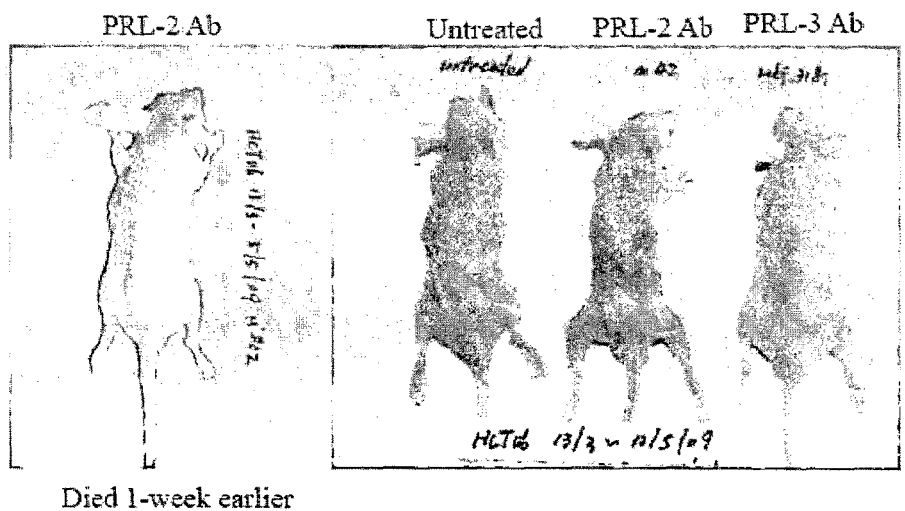
Died 1-week earlier

FIGURE 16

Her2 Target:
1. Her2 extracellular DNA sequences and peptide sequences:
ATCACAGGTCCCCTATACATCTCAGCATGGCCGGACAGCCTGCCTGACCTCAG
CGTCTTCCAGAACCTGCAAGTAATCCGGGGACGAATTCTGCACAATGGCGCCTA
CTCGCTGACCCTGCAAGGGCTGGGCATCAGCTGGCTGGGGCTGCGCTCACTG
AGGGAACTGGGCAGTGGACTGGCCCTCATC (SEQ ID NO: 1)

ITGPLYISAWPDSLPDLSVFQNLQVIRGRILHNGAYSLTLQGLGISWLGLRSLRELGS
GLALI (SEQ ID NO: 2)

2. Her 2 intracellular mid region DNA and peptide
ACCCACCAGAGTGATGTGTGGAGTTATGGTGTGACTGTGTGGGAGCTGATGAC
TTTTGGGGCCAAACCTTACGATGGGATCCCAGCCCGGGAGATCCCTGACCTGC
TGGAAAAGGGGGAGCGGCTGCCCCAGCCCCCCATCTGCACCATTGATGTCTAC
ATGATCATGGTCAAATGTTGGATG (SEQ ID NO: 3)

THQSDVWSYGVTVWELMTFGAKPYDGIPAREIPDLLEKGERLPQPPICTIDVYMIMV
KCWM (SEQ ID NO: 4)

3. Her2 intracellular C-Terminal

GAGAACCCCGAGTACTTGACACCCCAGGGAGGAGCTGCCCCTCAGCCCCACC
CTCCTCCTGCCTTCAGCCCAGCCTTCGACAACCTCTATTACTGGGACCGGGACC
CACCAGAGCGGGGGGCTCCACCCAGCACCTTCAAAGGGACACCTACGGCAGA
GAACCCAGAGTACCTGGGTCTGGACGTGCCAGTGTAA (SEQ ID NO: 5)

ENPEYLTPQGGAAPQPHPPPAFSPAFDNLYYWDRDPPERGAPPSTFKGTPTAENP
EYLGLDVPV (SEQ ID NO: 6)

4. Her2a intracellular peptide: VHHRHRSSSTRSGGGDLT (SEQ ID NO: 7)

mT Target:
5. MMTV-PymT mT peptide sequence:
Cys-MDRVLSRADKERLLELLKLPRQLWGD (SEQ ID NO: 8)

FIGURE 17 (CONTINUED)
C
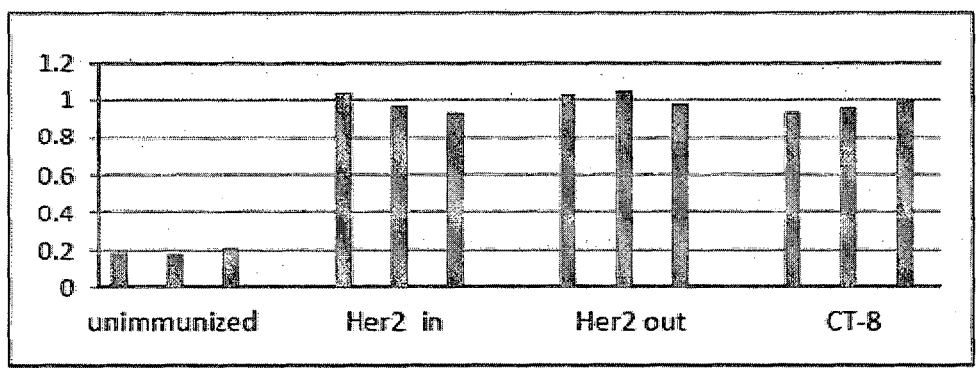
Elisa of Her2 Antibodies in the Sera of C57BL6 Mice
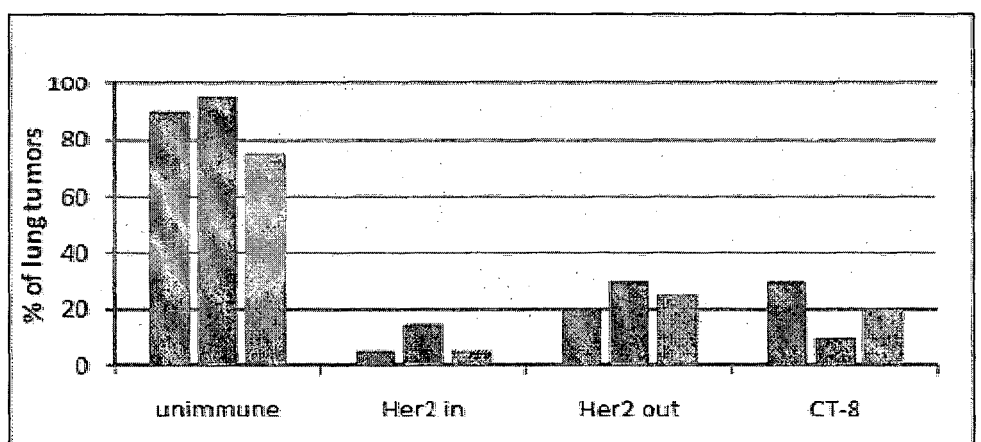
Lung tumors in unimmunized and immunized C57BL6 mice

FIGURE 18
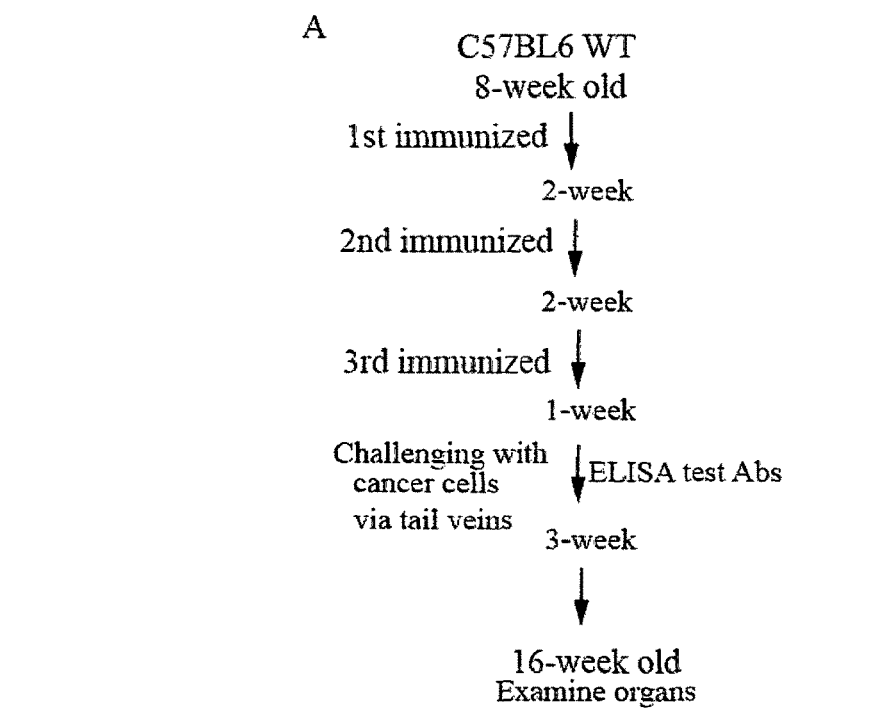
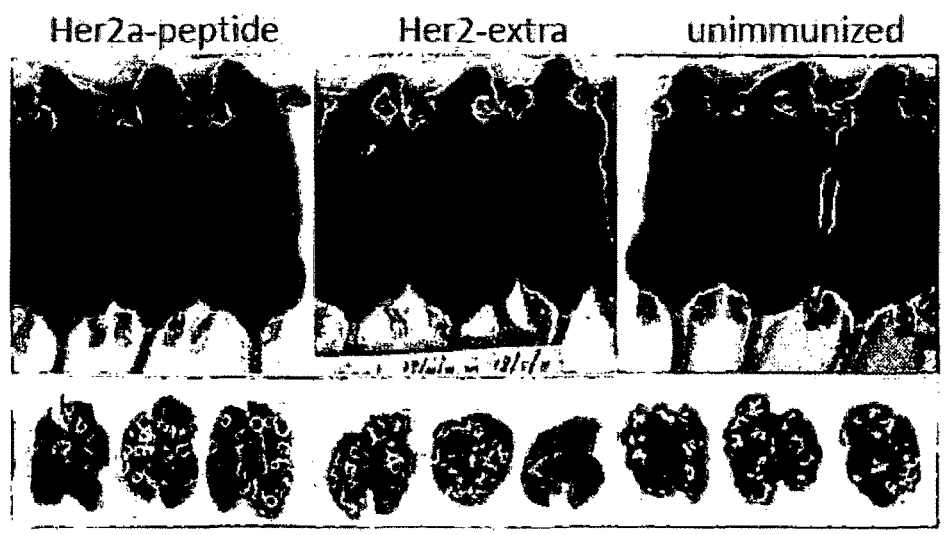

FIGURE 18 (CONTINUED)
C
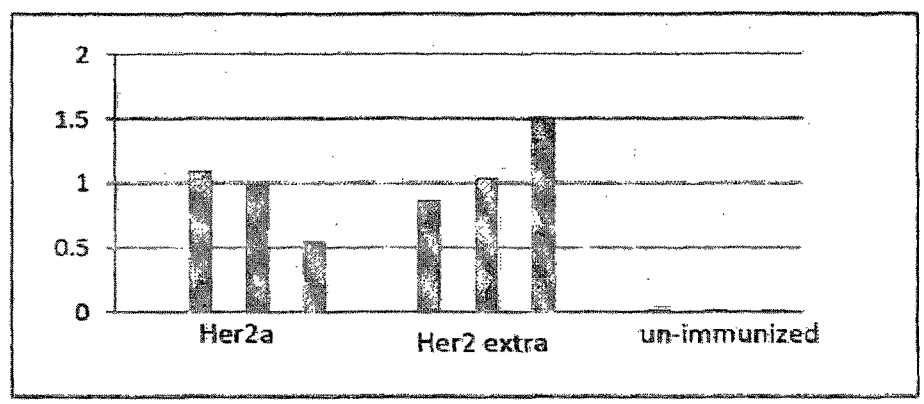
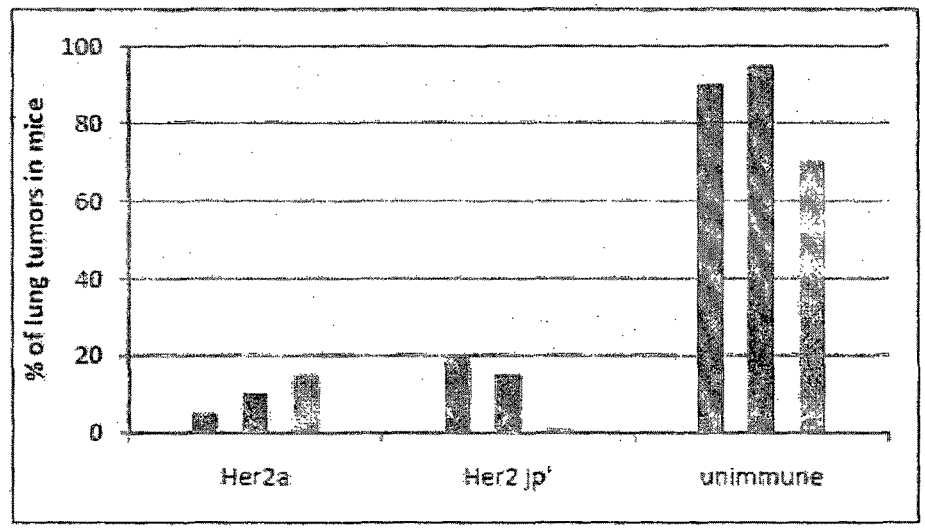

C

FIGURE 20
Targeting Estrogen Receptor with antibody and vaccination in PymT-transgenic mice model Human ESR1 full protein sequence:

MTMTLHTKASGMALLHQIQGNELEPLNRPQLKIPLERPLGEVYLDSSKPAVYNYPEGAAYEFNAAAAANAQVY
GQTGLPYGPGSEAAAFGSNGLGGFPPLNSVSPSPLMLLHPPPQLSPFLQPHGQQVPYYLENEPSGYTVREAGPP
AFYRPNSDNRRQGGRERLASTNDKGSMAMESAKETRYCAVCNDYASGYHYGVWSCEGCKAFFKRSIQGHNDY
MCPATNQCTIDKNRRKSCQACRLRKCYEVGMMKGGIRKDRRGGRMLKHKRQRDDGEGRGEVGSAGDMRAA
NLWPSPLMIKRSKKNSLALSLTADQMVSALLDAEPPILYSEYDPTRPFSEASMMGLLTNLADRELVHMINWAKRV
PGFVDLTLHDQVHLLECAWLEILMIGLVWRSMEHPGKLLFAPNLLLDRNQGKCVEGMVEIFDMLLATSSRFRMM
NLQGEEFVCLKSIILLNSGVYTFLSSTLKSLEEKDHIHRVLDKITDTLIHLMAKAGLTLQQQHQRLAQLLLILSHIRHMS
NKGMEHLYSMKCKNVVPLYDLLLEMLDAHRLHAPTSRGGASVEETDQSHLATAGSTSSHSLQKYYITGEAEGFPAT
V

ER-red area:

Peptide: CGYTVREAGPPAFYRPNSDNRRQGGRE

Fragment:NRPQLKIPLERPLGEVYLDSSKPAVYNYPEGAAYEFNAAAAANAQVYGQTGLPYGPGSEAAAFGSNGL
GGFPPLNSVSPSPLMLLHPPPQLSPFLQPHGQQVPYYLENEPSGYTVREAGPPAFYRPNSDNRRQGGRERLASTN
DKGSMAMESAKETR
cDNA:aaccgtccgcagctcaagatcccctggagcggccctgggcgaggtgtacctggacagcagcaagcccgccgtgtacaactacccg
gaggcgccgcctacgagttcaacgccgcggccgccgccaacgcgcaggtctacggtcagaccggcctccctacggccccgggtctgaggctgc
ggcgttcggctccaacggctggggggtttccccactcaacagcgtgtcctccgagcccgctgatgctactgcacccgccgccgcagctgtcgc
ctttcctgcagcccacggccagcaggtgccctactacctggagaacgagcccagcggctacacggtgcgcgaggccggccgccggcattcta
caggccaaattcagataatcgacgccagggtggcagagaaagattggccagtaccaatgacaaggggaagtatggctatggaatctgccaagg
agactcgc ER-purple area:

Peptide: LKHKRQRDDGEGRGEVGSAGDMRAANLC

Fragment:GGIRKDRRGGRMLKHKRQRDDGEGRGEVGSAGDMRAANLWPSPLMIKRSKKNSLALSLTADQMVS
AL cDNA:
ggtgggatacgaaaagaccgaagaggaggggagaatgttgaaacacaagtgccagagagatgatggggagggcagggggtgaagtgggggtct
gctggagacatgagagctgccaaccttttggccaagccgctcatgatcaaacgctctaagaagaacagcctggccttgtccctgacggccgacc
agatggtcagtgccttg

Targeting HBV-X protein with antibody and vaccination as liver cancer model in nude mice HBV-X protein: maarlccqld ptrdvldrp vgaesrgrpv sgplgdlpsp saspvptidr ahlslrglpvcafssagpca
lftsarrme ttvnthmilp kvlhkrtlgl parnstidlea yfkdclfkdweelgeeirlk vfvlggchk lvcspapcnf ftsa HBV-X-peptide
FKDWEELGEEIRLKVFVLGGC (conserve sequence among the genotypes).

FIGURE 21
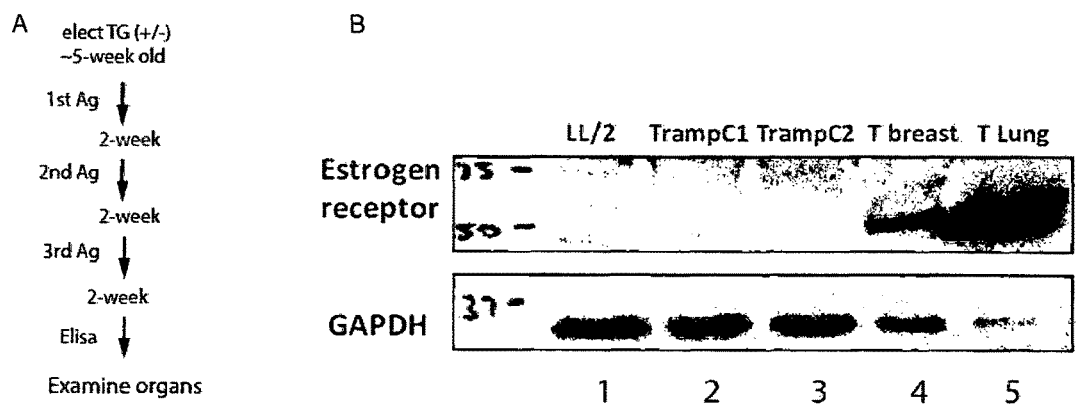
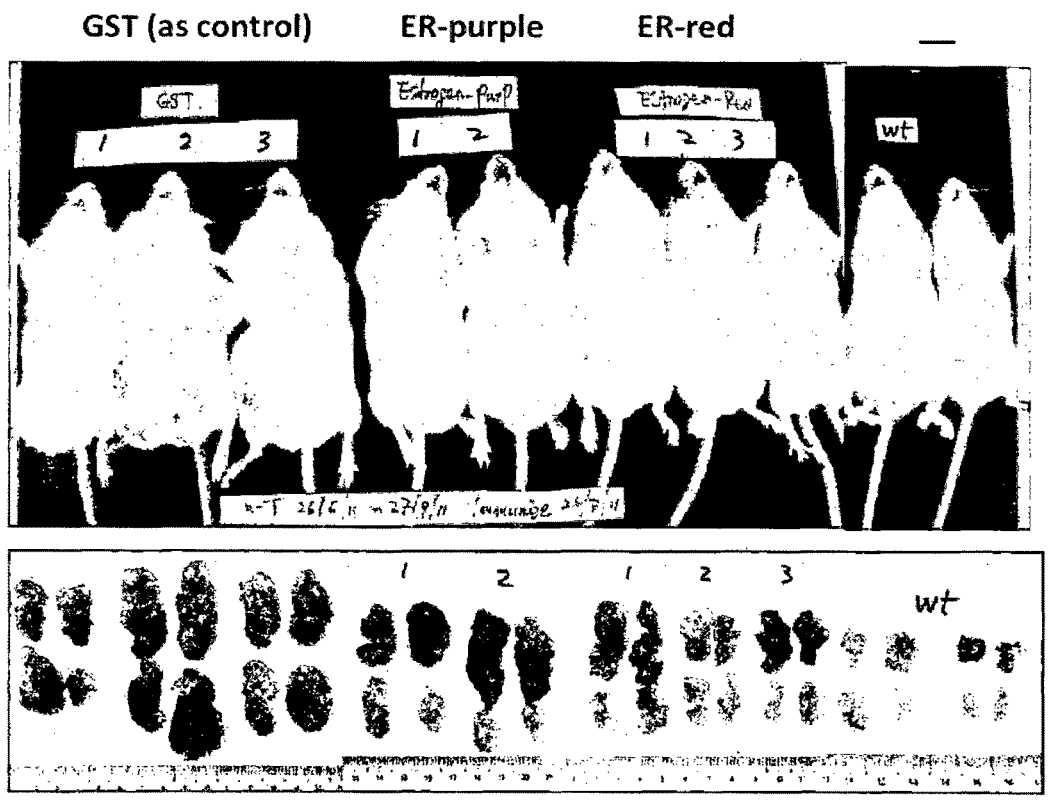

D

FIGURE 22 (CONTINUED)
C
Average weight (g) of breasts per mouse (13-week)
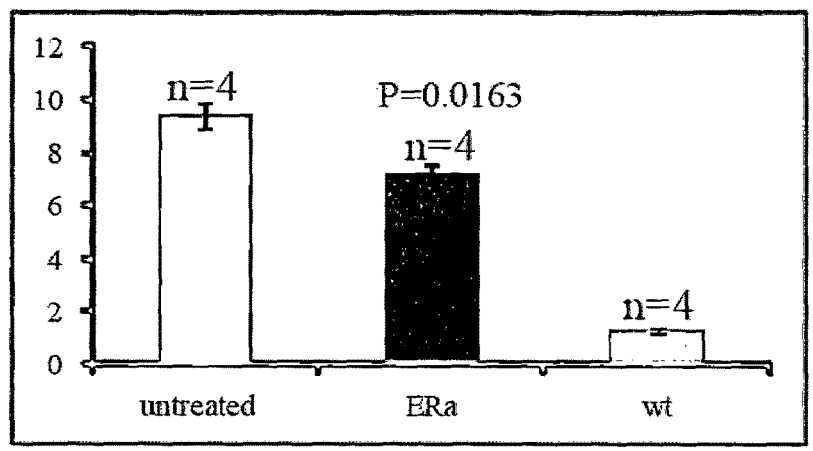
D     Transgenic MMTV-PymT (+/-) at 13-week
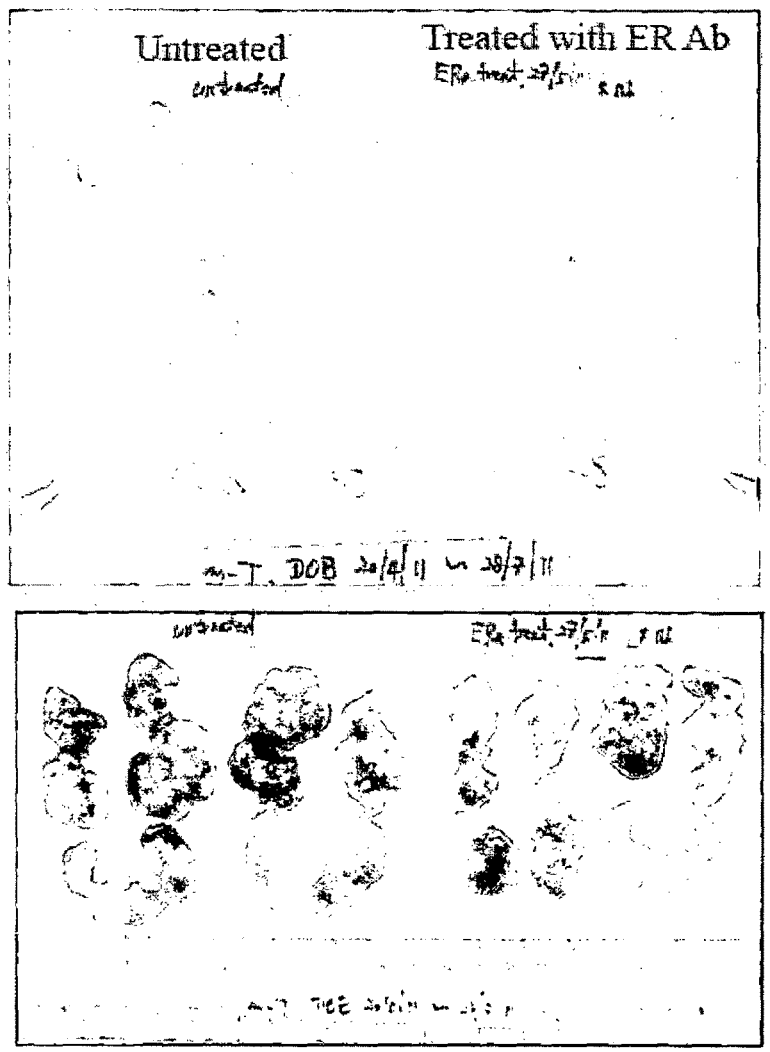

FIGURE 24
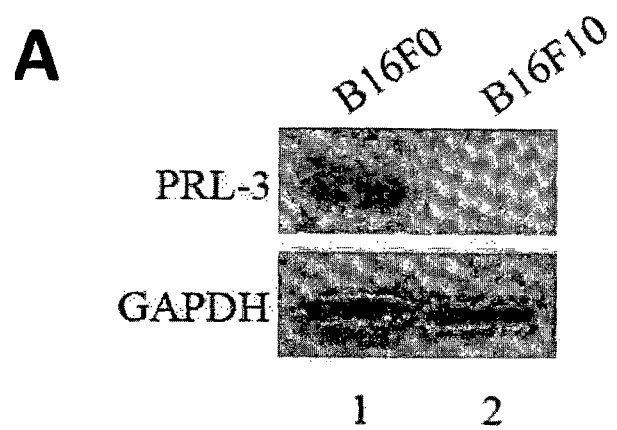
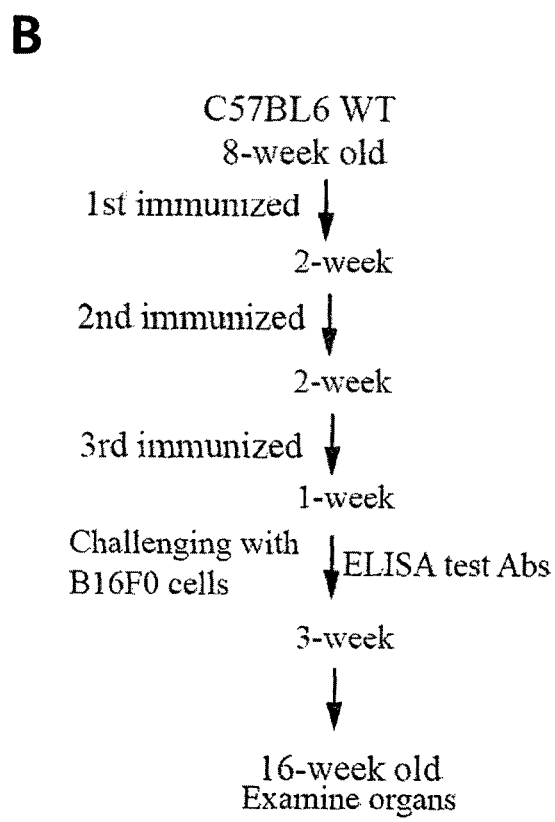

FIGURE 25 (CONTINUED)
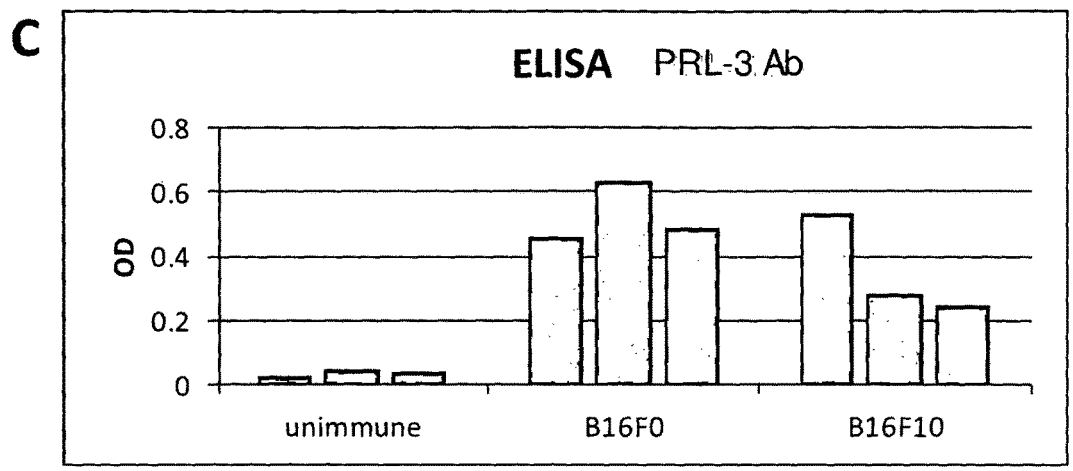
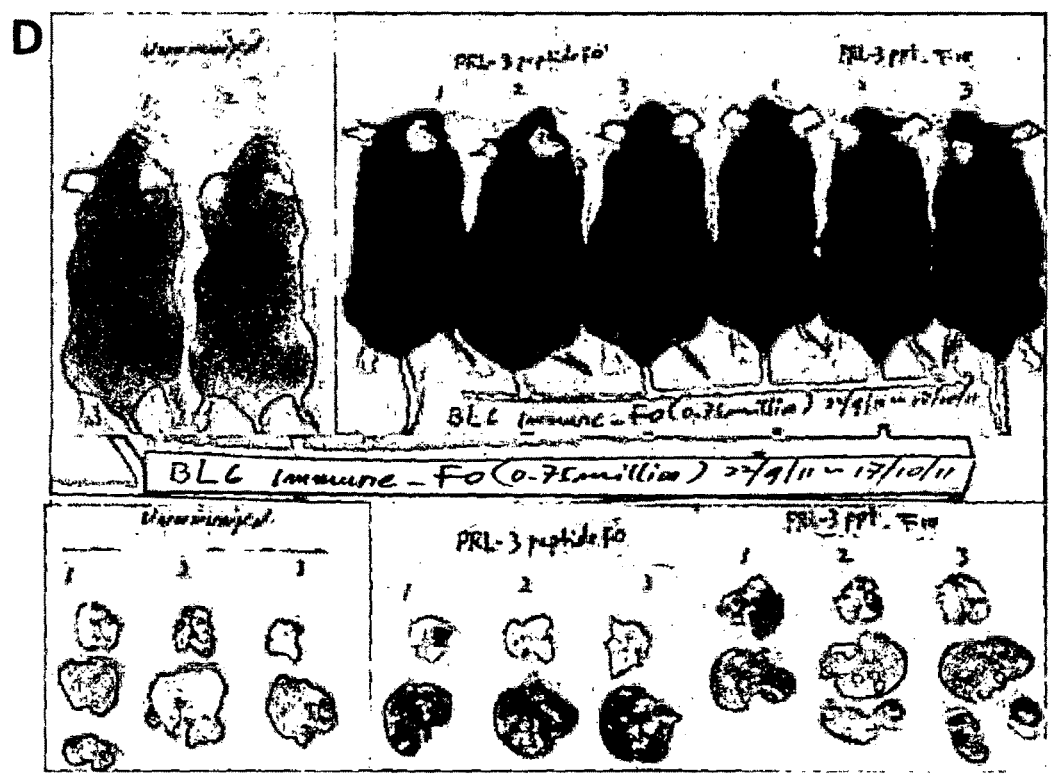

FIGURE 26
A
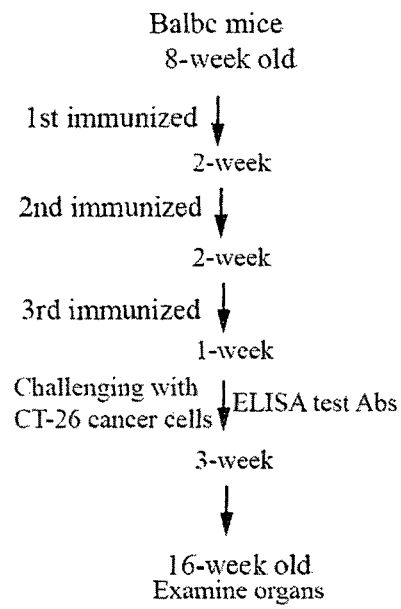
B
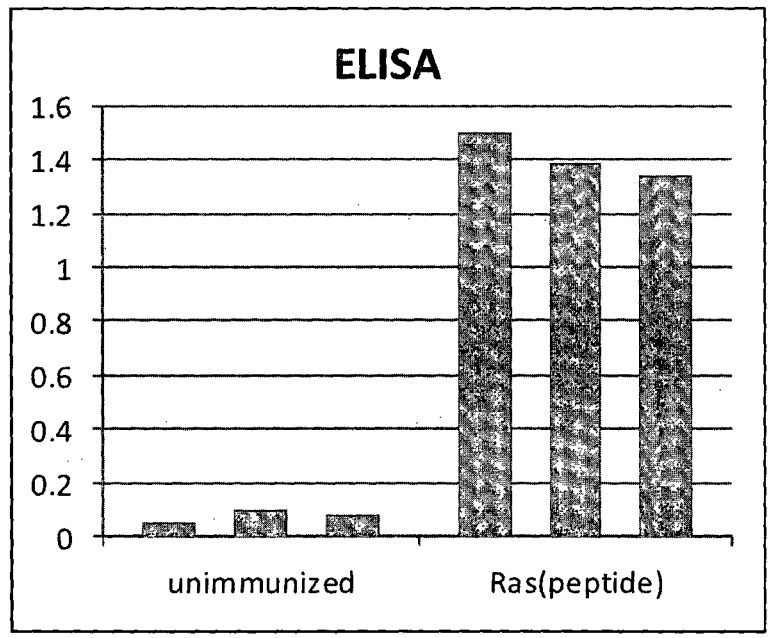

1. MTYKVVVGADGVGKSATNH (K-Ras-G12D) (SEQ ID NO: 20)
2. MTYKVVVGAVGVGKSATNH (K-Ras-G12V) (SEQ ID NO: 21)
3. MTYKVVVGARGVGKSATNH (K-Ras-G12R) (SEQ ID NO: 22)
4. MTYKVVVGAGRVGKSATNH (K-Ras-G13R) (SEQ ID NO: 23)
5. QHVKITDFGRAKLLGAEEKE (EGFR-L858R) (SEQ ID NO: 24)
6. KIGDFGLATEKSRWSGSHQ (B-Raf-V600E) (SEQ ID NO: 25)
7. LTSTVQLIMQLMPFGC (EGFR-T790M) (SEQ ID NO: 26)
8. KVKIPVAIK------TSPKANKEI (EGFR-E746-A750 del) (SEQ ID NO: 27)
9. KAISTRDPLSKITEQEKDF (PI3KCA-E542K) (SEQ ID NO: 28)
10. TRDPLSEITKQEKDFLWSH (PI3KCA-E545K) (SEQ ID NO: 29)
11. EYFMKQMNDARHGGWTTKMD (PI3KCA-H1047R) (SEQ ID NO: 30)
12. DSGIHSGATATAPSLSGKGN (beta-catenin-T41A) (SEQ ID NO: 31)
13. HSGATTTAPFLSGKGNPEE (beta-catenin-S45F) (SEQ ID NO: 32)
14. HSGATTTAPPLSGKGNPEE (beta-catenin-S45P) (SEQ ID NO: 33)
15. SDQDLLRCCVLTSGIFETK (GNAS-R201C) (SEQ ID NO: 34)
16. RSQGRIPVKWTAIESLFDH (Ret-M918T) (SEQ ID NO: 35)
17. QKNEFISEFCGEIISQDEAD (EZH2-Y646F) (SEQ ID NO: 36)
18. QKNEFISENCGEIISQDEAD (EZH2-Y646N) (SEQ ID NO: 37)
19. QKNEFISESCGEIISQDEAD (EZH2-Y646S) (SEQ ID NO: 38)
20. QKNEFISEHCGEIISQDEAD (EZH2-Y646H) (SEQ ID NO: 39)
21. FRMVDVGGLRSERRKWIH (GNA11/GNAQ-Q209L) (SEQ ID NO: 40)
22. FRMVDVGGPRSERRKWIH (GNAQ-Q209P) (SEQ ID NO: 41)

FIGURE 27 (CONTINUED)

| | |
|---|---|
| ALK (F1174L)<br>ALK (R1275Q) | K-Ras (G12D) (LS-174T, COLO-678, GP5d, LS-513, SNU-C2B)<br>K-Ras (G12V) (SW620, RCM-1, SK-CO-1)<br>K-Ras (G12C) (SW1463, SW837)<br>K-Ras (G13D) (HCT-116, HCT-15, T84)<br><br>The majority of pancreatic and colon cancer |
| BRAF (V600E) (SK-MEL-1, 3, 5, 24 and 28, A375, A2058, HT-144, MDA-MB-435)<br><br>The majority of skin cancer | EGFR (L858R)  (NCI-H1975)<br>EGFR (E746_A750del) (PC-14, NCI-H1650)<br>EGFR (T790M) (NCI-H1975)<br><br>The majority of lung cancer |
| PIK3CA (H1047R) (T47D, BT-20)<br>PIK3CA (E545K) (MCF7, MDA-MB-361)<br>PIK3CA (E542K) (CAL-51)<br><br>20% breast cancer has PI3K mutations, corresponding to basal/triple negative? Not. | HNF1A/TCF1 (W206C)<br>HNF1A/TCF1 (W206L) |
| CTNNB1/beta-catenin (S45F) (LS-174T)<br>CTNNB1/beta-catenin (S45P) (NCI-H295)<br>CTNNB1/beta-catenin (T41A) (LXF-289, A427)<br><br>20% mutations in liver cancer | GNA11 (Q209L)<br>GNAQ (Q209L)<br>GNAQ (Q209P)<br><br>Eye, uveal melanoma (together, GNA11 and GNAQ are mutated in over 50%) |
| IDH1 (R132C) (HT-1080)<br>IDH1 (R132G)<br>IDH1 (R132H) (mostly in glioma)<br>IDH1 (R132L)<br>IDH1 (R132S)<br>Bone, Chondrosarcoma<br>Glioma | IDH2 (R140Q)<br>IDH2 (R172K)<br><br>haematopoietic neoplasm |
| EZH2 (Y646F)<br>EZH2 (Y646N)<br>EZH2 (Y646H)<br>EZH2 (Y646S) | PPP2R1A (R183W)<br>PPP2R1A (R183Q)<br><br>haematopoietic and lymphoid tissue |
| PTEN (R130G)<br>PTEN (R130Q)<br>PTEN (R130*)<br>Endometrium carcinoma | STK11 (LKB1)<br><br>mutations suggest a tumor suppressor in lung cancer<br>Notch1 (releasing cytoplasmic domain)<br><br>Lymphoid neoplasm |
| N-Ras (Q61R) (HT-1197, KMOE-2, SK-MEL-2)<br>RET (M918T)<br><br>Mostly in thyroid cancer | GNAS (R201C)<br><br>Mostly in pituitary cancer |
| AKT1 (E17K) | MET (N375S) |
| FGFR3 (K650E)<br>FGFR3 (K650M)<br>FGFR3 (R248C)<br>FGFR3 (S249C)<br>FGFR3 (Y373C)<br>FGFR3 (S371C)<br>FGFR3 (G370C) | Mostly in skin cancer |

FIGURE 28

| Gene | Mutation | Gene | Mutation | Gene | Mutation | Gene | Mutation |
|---|---|---|---|---|---|---|---|
| ABL1 | D276G | BRAF | I592V | CTNNB1 | I35T | EGFR | G873E |
| ABL1 | E255K | BRAF | K439Q | CTNNB1 | K19D | EGFR | H773L |
| ABL1 | E255V | BRAF | K439T | CTNNB1 | K49E | EGFR | H773R |
| ABL1 | E352G | BRAF | K475M | CTNNB1 | K49R | EGFR | H835L |
| ABL1 | E355G | BRAF | K601E | CTNNB1 | L31L | EGFR | H850N |
| ABL1 | E373G | BRAF | K601N | CTNNB1 | L46L | EGFR | I715S |
| ABL1 | E459K | BRAF | L584L | CTNNB1 | L46V | EGFR | I853T |
| ABL1 | F311L | BRAF | L597L | CTNNB1 | M3I | EGFR | K846R |
| ABL1 | F317L | BRAF | L597Q | CTNNB1 | N287S | EGFR | L685P |
| ABL1 | F359A | BRAF | L597R | CTNNB1 | P44L | EGFR | L707L |
| ABL1 | F359V | BRAF | L597S | CTNNB1 | P44S | EGFR | L718L |
| ABL1 | F382L | BRAF | L597V | CTNNB1 | P52L | EGFR | L730F |
| ABL1 | F486S | BRAF | L618S | CTNNB1 | Q61R | EGFR | L792P |
| ABL1 | G250E | BRAF | N581S | CTNNB1 | S23R | EGFR | L798F |
| ABL1 | G321E | BRAF | Q456Q | CTNNB1 | S29A | EGFR | L833V |
| ABL1 | H396P | BRAF | R444R | CTNNB1 | S29F | EGFR | L838V |
| ABL1 | H396R | BRAF | R444W | CTNNB1 | S29P | EGFR | L858M |
| ABL1 | L248V | BRAF | R462I | CTNNB1 | S33A | EGFR | L858R |
| ABL1 | L387M | BRAF | S605F | CTNNB1 | S33C | EGFR | L961Q |
| ABL1 | M237I | BRAF | S605N | CTNNB1 | S33F | EGFR | N826S |
| ABL1 | M244V | BRAF | S614P | CTNNB1 | S33L | EGFR | P694L |
| ABL1 | M343T | BRAF | S616P | CTNNB1 | S33N | EGFR | P694S |
| ABL1 | M351T | BRAF | T440P | CTNNB1 | S33P | EGFR | P733L |
| ABL1 | Q252E | BRAF | T599I | CTNNB1 | S33S | EGFR | P753S |
| ABL1 | Q252H | BRAF | V459L | CTNNB1 | S33Y | EGFR | P772P |
| ABL1 | Q252R | BRAF | V600D | CTNNB1 | S37A | EGFR | R776C |
| ABL1 | R47G | BRAF | V600E | CTNNB1 | S37C | EGFR | S720F |
| ABL1 | S417Y | BRAF | V600G | CTNNB1 | S37F | EGFR | S752Y |
| ABL1 | T315I | BRAF | V600K | CTNNB1 | S37P | EGFR | S768I |
| ABL1 | T315N | BRAF | V600L | CTNNB1 | S37T | EGFR | S784F |
| ABL1 | T389A | BRAF | V600M | CTNNB1 | S37Y | EGFR | T725M |
| ABL1 | V304G | BRAF | V600R | CTNNB1 | S45A | EGFR | T751I |
| ABL1 | V371A | BRAF | W604G | CTNNB1 | S45C | EGFR | T790M |
| ABL1 | V379I | CEBPA | A152A | CTNNB1 | S45F | EGFR | I847I |
| ABL1 | Y253F | CEBPA | H191H | CTNNB1 | S45P | EGFR | V742A |
| ABL1 | Y253H | CEBPA | H94L | CTNNB1 | S45S | EGFR | V769L |
| ABL1 | Y353H | CTNNB1 | A13T | CTNNB1 | S45T | EGFR | V769M |
| ABL2 | E63Q | CTNNB1 | A163S | CTNNB1 | S45Y | EGFR | V774M |
| ABL2 | R483I | CTNNB1 | A163T | CTNNB1 | S47G | EGFR | V815V |
| ALK | L560F | CTNNB1 | A20A | CTNNB1 | S47N | EGFR | V851A |
| ALK | Y262Y | CTNNB1 | A20V | CTNNB1 | S47R | EGFR | V851I |
| APC | S2621C | CTNNB1 | A21T | CTNNB1 | S47T | EGFR | Y727C |
| ATM | E848Q | CTNNB1 | A39A | CTNNB1 | S60F | EGFR | Y764Y |
| ATM | L1794L | CTNNB1 | A39S | CTNNB1 | T214T | ERBB2 | E914K |
| ATM | M1916I | CTNNB1 | A39T | CTNNB1 | T40A | ERBB2 | G776S |
| ATM | P2842R | CTNNB1 | A43P | CTNNB1 | T40I | ERBB2 | L755P |
| ATM | Q2441P | CTNNB1 | A43T | CTNNB1 | T40T | ERBB2 | N857S |
| ATM | T2666A | CTNNB1 | A43V | CTNNB1 | T41A | FGFR1 | P252T |
| ATM | T93ST | CTNNB1 | D11N | CTNNB1 | T41I | FGFR1 | S125L |
| BRAF | D587A | CTNNB1 | D17H | CTNNB1 | T41N | FGFR2 | D283N |
| BRAF | D587E | CTNNB1 | D32A | CTNNB1 | T41P | FGFR2 | R203C |
| BRAF | D594E | CTNNB1 | D32G | CTNNB1 | T41S | FGFR2 | R496T |
| BRAF | D594G | CTNNB1 | D32H | CTNNB1 | T41T | FGFR2 | S267P |
| BRAF | D594K | CTNNB1 | D32N | CTNNB1 | T42A | FGFR2 | W290C |
| BRAF | D594V | CTNNB1 | D32V | CTNNB1 | T42I | FGFR3 | A369A |
| BRAF | E586E | CTNNB1 | D32Y | CTNNB1 | T42R | FGFR3 | A391E |
| BRAF | E586K | CTNNB1 | D56N | CTNNB1 | T75A | FGFR3 | E322K |
| BRAF | F468C | CTNNB1 | D58N | CTNNB1 | V22A | FGFR3 | F384L |
| BRAF | F583F | CTNNB1 | D6G | CTNNB1 | V57M | FGFR3 | G370C |
| BRAF | F595L | CTNNB1 | E53K | CTNNB1 | W25L | FGFR3 | G382D |
| BRAF | F595S | CTNNB1 | E54K | CTNNB1 | W6L | FGFR3 | I414I |
| BRAF | G464E | CTNNB1 | E55G | CTNNB1 | Y30C | FGFR3 | K650E |
| BRAF | G464R | CTNNB1 | E55K | EGFR | A750P | FGFR3 | K650M |
| BRAF | G464V | CTNNB1 | E65E | EGFR | A839T | FGFR3 | K650Q |
| BRAF | G466A | CTNNB1 | E67K | EGFR | A859T | FGFR3 | K650T |
| BRAF | G466E | CTNNB1 | G245A | EGFR | A864T | FGFR3 | R248C |
| BRAF | G466R | CTNNB1 | G34E | EGFR | D761N | FGFR3 | S249C |
| BRAF | G466V | CTNNB1 | G34R | EGFR | E709A | FGFR3 | Y241C |
| BRAF | G469A | CTNNB1 | G34V | EGFR | E709G | FGFR3 | Y373C |
| BRAF | G469E | CTNNB1 | G38A | EGFR | E709H | FLT3 | A680V |
| BRAF | G469R | CTNNB1 | G38D | EGFR | E709K | FLT3 | D835E |
| BRAF | G469S | CTNNB1 | G48D | EGFR | E709V | FLT3 | D835H |
| BRAF | G469V | CTNNB1 | G48V | EGFR | E746K | FLT3 | D835N |
| BRAF | G596R | CTNNB1 | G50D | EGFR | E746V | FLT3 | D835V |
| BRAF | G606E | CTNNB1 | H24Y | EGFR | E866K | FLT3 | D835Y |
| BRAF | G615R | CTNNB1 | H36P | EGFR | G719A | FLT3 | G4G |
| BRAF | H608R | CTNNB1 | H36Y | EGFR | G719C | HRAS | A11A |
| BRAF | I463S | CTNNB1 | I138L | EGFR | G719S | HRAS | A18T |
| BRAF | I582M | CTNNB1 | I35I | EGFR | G735S | HRAS | A59T |
| BRAF | I592M | CTNNB1 | I35N | EGFR | G779F | HRAS | G12A |
| | | CTNNB1 | I35S | EGFR | G810S | HRAS | G12C |

FIGURE 28 (CONTINUED)

| Gene | Mutation | Gene | Mutation | Gene | Mutation | Gene | Mutation |
|---|---|---|---|---|---|---|---|
| HRAS | G12D | KIT | Y553V | MSH6 | P1092P | PIK3CA | E542G |
| HRAS | G12R | KIT | Y568C | MSH6 | R249R | PIK3CA | E542K |
| HRAS | G12S | KIT | Y568D | MSH6 | S315F | PIK3CA | E542V |
| HRAS | G12V | KIT | Y568Y | MSH6 | V474A | PIK3CA | E545D |
| HRAS | G13C | KRAS | A11P | MSH6 | V480L | PIK3CA | E545G |
| HRAS | G13D | KRAS | A11V | MSH6 | V509A | PIK3CA | E545K |
| HRAS | G13G | KRAS | A18D | MSH6 | Y397C | PIK3CA | F909L |
| HRAS | G13R | KRAS | A18T | NOTCH1 | A1702P | PIK3CA | G1049R |
| HRAS | G13S | KRAS | A59E | NOTCH1 | A2280V | PIK3CA | G1049S |
| HRAS | G13V | KRAS | A59T | NOTCH1 | A2554D | PIK3CA | G106V |
| HRAS | K117E | KRAS | D92Y | NOTCH1 | D1610V | PIK3CA | G118D |
| HRAS | Q61E | KRAS | E62D | NOTCH1 | F1541L | PIK3CA | G122D |
| HRAS | Q61H | KRAS | G12A | NOTCH1 | F1593S | PIK3CA | H1047L |
| HRAS | Q61K | KRAS | G12C | NOTCH1 | H2508Y | PIK3CA | H1047R |
| HRAS | Q61L | KRAS | G12D | NOTCH1 | I1681N | PIK3CA | H1047Y |
| HRAS | Q61P | KRAS | G12E | NOTCH1 | L1575P | PIK3CA | H1065Y |
| HRAS | Q61Q | KRAS | G12F | NOTCH1 | L1586P | PIK3CA | H510H |
| HRAS | Q61R | KRAS | G12G | NOTCH1 | L1594P | PIK3CA | H701P |
| HRAS | S17G | KRAS | G12L | NOTCH1 | L1601P | PIK3CA | K111N |
| JAK2 | V617F | KRAS | G12N | NOTCH1 | L1679P | PIK3CA | K733R |
| KIT | A829P | KRAS | G12R | NOTCH1 | P2413T | PIK3CA | M1043I |
| KIT | D52N | KRAS | G12S | NOTCH1 | R1595P | PIK3CA | M1043T |
| KIT | D572Y | KRAS | G12V | NOTCH1 | R1609S | PIK3CA | M1043V |
| KIT | D816F | KRAS | G13A | NOTCH1 | R1628H | PIK3CA | N1044K |
| KIT | D816H | KRAS | G13C | NOTCH1 | T2467M | PIK3CA | N345K |
| KIT | D816N | KRAS | G13D | NOTCH1 | V1677D | PIK3CA | N345S |
| KIT | D816V | KRAS | G13G | NRAS | A11T | PIK3CA | P1011S |
| KIT | D816Y | KRAS | G13I | NRAS | A18T | PIK3CA | P104R |
| KIT | D820G | KRAS | G13N | NRAS | A59T | PIK3CA | P124T |
| KIT | D820V | KRAS | G13R | NRAS | G12A | PIK3CA | P539R |
| KIT | E554D | KRAS | G13S | NRAS | G12C | PIK3CA | Q546E |
| KIT | E554G | KRAS | G13V | NRAS | G12D | PIK3CA | Q546K |
| KIT | E561E | KRAS | G15D | NRAS | G12G | PIK3CA | Q546P |
| KIT | E561K | KRAS | G15S | NRAS | G12P | PIK3CA | Q546R |
| KIT | E839K | KRAS | G60A | NRAS | G12R | PIK3CA | Q60K |
| KIT | F584S | KRAS | H27L | NRAS | G12S | PIK3CA | Q661K |
| KIT | G51G | KRAS | K5N | NRAS | G12V | PIK3CA | R108P |
| KIT | G565R | KRAS | L19F | NRAS | G12Y | PIK3CA | R38C |
| KIT | I798I | KRAS | Q22K | NRAS | G13A | PIK3CA | R38H |
| KIT | I805I | KRAS | Q22Q | NRAS | G13C | PIK3CA | R537R |
| KIT | K550I | KRAS | Q22R | NRAS | G13D | PIK3CA | R88Q |
| KIT | K550N | KRAS | Q61E | NRAS | G13G | PIK3CA | S1008P |
| KIT | K550R | KRAS | Q61H | NRAS | G13R | PIK3CA | S405F |
| KIT | K558K | KRAS | Q61K | NRAS | G13S | PIK3CA | T1025A |
| KIT | K558N | KRAS | Q61L | NRAS | G13V | PIK3CA | T1025N |
| KIT | K642E | KRAS | Q61P | NRAS | G13Y | PIK3CA | T1025S |
| KIT | K818R | KRAS | Q61R | NRAS | Q61E | PIK3CA | Y1021C |
| KIT | L576P | KRAS | S17G | NRAS | Q61H | PIK3CA | Y1021N |
| KIT | L799L | KRAS | V8V | NRAS | Q61K | PTEN | A121E |
| KIT | L862L | KRAS | V9V | NRAS | Q61L | PTEN | A121P |
| KIT | M541L | MAP2K4 | Q142L | NRAS | Q61P | PTEN | A126P |
| KIT | M552K | MET | A1209G | NRAS | Q61Q | PTEN | A126T |
| KIT | M552L | MET | D1246H | NRAS | Q61R | PTEN | A126V |
| KIT | N564K | MET | E168D | NRAS | S65C | PTEN | A137V |
| KIT | N566D | MET | G1137V | NRAS | Y64N | PTEN | A148T |
| KIT | N566H | MET | H1112L | NTRK1 | L213L | PTEN | A151T |
| KIT | N822H | MET | H1112R | NTRK3 | H677Y | PTEN | A309A |
| KIT | N822K | MET | H1112Y | NTRK3 | R678Q | PTEN | A34A |
| KIT | N822N | MET | H1124D | NTRK3 | R721F | PTEN | A39T |
| KIT | P551S | MET | K1262R | PDGFRA | D1071N | PTEN | A3S |
| KIT | P551T | MET | L1130L | PDGFRA | D842I | PTEN | A79T |
| KIT | P577S | MET | L1213V | PDGFRA | D842V | PTEN | C105F |
| KIT | P585P | MET | L229F | PDGFRA | D842Y | PTEN | C105G |
| KIT | S890N | MET | M1149T | PDGFRA | D846Y | PTEN | C105S |
| KIT | T574I | MET | M1268I | PDGFRA | F808L | PTEN | C105Y |
| KIT | V497V | MET | M1268T | PDGFRA | N870S | PTEN | C124S |
| KIT | V530I | MET | N1118Y | PDGFRA | I674I | PTEN | C124Y |
| KIT | V559A | MET | N375S | PDGFRA | V561D | PTEN | C136F |
| KIT | V559D | MET | R988C | PDGFRA | I852I | PTEN | C136R |
| KIT | V559G | MET | S283S | PIK3CA | A1046A | PTEN | C211Y |
| KIT | V559I | MET | T1010I | PIK3CA | A1045V | PTEN | C304G |
| KIT | V560D | MET | T1191I | PIK3CA | A1066V | PTEN | C304S |
| KIT | V560E | MET | V1290L | PIK3CA | C378R | PTEN | C71Y |
| KIT | V560G | MET | Y1248C | PIK3CA | C420R | PTEN | D107A |
| KIT | V560V | MET | Y1248H | PIK3CA | C901F | PTEN | D107Y |
| KIT | V569A | MET | Y1253D | PIK3CA | D350S | PTEN | D153D |
| KIT | V825A | MSH6 | D390D | PIK3CA | E1034G | PTEN | D153N |
| KIT | W557G | MSH6 | D390N | PIK3CA | E110K | PTEN | D153Y |
| KIT | W557R | MSH6 | D575Y | PIK3CA | E418K | PTEN | D162H |
| KIT | W557S | MSH6 | E198A | PIK3CA | E453K | PTEN | D19N |
| KIT | Y553N | MSH6 | G1416 | PIK3CA | E453Q | PTEN | D24E |

FIGURE 28 (CONTINUED)

| Gene | Mutation | Gene | Mutation | Gene | Mutation | Gene | Mutation |
|------|----------|------|----------|------|----------|------|----------|
| PTEN | D24G | PTEN | I67K | PTEN | R84G | PTPN11 | P491S |
| PTEN | D24N | PTEN | I67R | PTEN | S10N | PTPN11 | Q510K |
| PTEN | D24Y | PTEN | K125E | PTEN | S113R | PTPN11 | R138Q |
| PTEN | D252D | PTEN | K128N | PTEN | S170G | PTPN11 | R289G |
| PTEN | D252G | PTEN | K13E | PTEN | S170I | PTPN11 | S502L |
| PTEN | D252Y | PTEN | K13Q | PTEN | S170N | PTPN11 | S502P |
| PTEN | D326G | PTEN | K144I | PTEN | S179I | PTPN11 | T507K |
| PTEN | D331G | PTEN | K254E | PTEN | S227F | PTPN11 | T73I |
| PTEN | D375N | PTEN | K342N | PTEN | S338T | PTPN11 | V45L |
| PTEN | D52G | PTEN | K344R | PTEN | S59P | PTPN11 | Y63C |
| PTEN | D52N | PTEN | K62I | PTEN | T131I | RB1 | A14A |
| PTEN | D58Y | PTEN | K62R | PTEN | T131N | RB1 | C706F |
| PTEN | D92A | PTEN | K66E | PTEN | T160T | RB1 | D715N |
| PTEN | D92G | PTEN | K66N | PTEN | T167A | RB1 | F839F |
| PTEN | D92N | PTEN | K66Q | PTEN | T167P | RB1 | H673P |
| PTEN | D92V | PTEN | K6R | PTEN | T26P | RB1 | I126S |
| PTEN | E150D | PTEN | K80E | PTEN | T348I | RB1 | I133S |
| PTEN | E150G | PTEN | K80N | PTEN | T382S | RB1 | K122K |
| PTEN | E150Q | PTEN | L108R | PTEN | T401I | RB1 | L159S |
| PTEN | E242K | PTEN | L112P | PTEN | T78A | RB1 | L669P |
| PTEN | E284K | PTEN | L112V | PTEN | T78T | RB1 | M205V |
| PTEN | E288K | PTEN | L139F | PTEN | V119D | RB1 | M704V |
| PTEN | E291K | PTEN | L146V | PTEN | V133I | RB1 | N325H |
| PTEN | E307E | PTEN | L152V | PTEN | V146L | RB1 | Q444H |
| PTEN | E314K | PTEN | L162F | PTEN | V216M | RB1 | R621S |
| PTEN | E73V | PTEN | L23F | PTEN | V217A | RB1 | R661W |
| PTEN | E91A | PTEN | L345Q | PTEN | V217I | RB1 | R798W |
| PTEN | E91Q | PTEN | L42P | PTEN | V222A | RB1 | S187T |
| PTEN | F154F | PTEN | L42R | PTEN | V255A | RB1 | S474N |
| PTEN | F154L | PTEN | L57S | PTEN | V365I | RB1 | S612P |
| PTEN | F241S | PTEN | L57W | PTEN | V369G | RB1 | S794I |
| PTEN | F257L | PTEN | L70P | PTEN | V45V | RB1 | V754G |
| PTEN | F341V | PTEN | M134L | PTEN | V53G | RET | A664D |
| PTEN | F37S | PTEN | M205I | PTEN | V54L | RET | A876V |
| PTEN | F56V | PTEN | M35R | PTEN | W111R | RET | A883F |
| PTEN | F81C | PTEN | M35V | PTEN | W274G | RET | A883P |
| PTEN | F90L | PTEN | N194I | PTEN | Y135C | RET | A919V |
| PTEN | F90S | PTEN | N31N | PTEN | Y155C | RET | C609Y |
| PTEN | G127E | PTEN | N323K | PTEN | Y155H | RET | C618Y |
| PTEN | G127V | PTEN | N48D | PTEN | Y155N | RET | C630R |
| PTEN | G129R | PTEN | N48I | PTEN | Y16C | RET | C634A |
| PTEN | G129V | PTEN | N62T | PTEN | Y174N | RET | C634R |
| PTEN | G132D | PTEN | N94I | PTEN | Y188S | RET | C634T |
| PTEN | G132S | PTEN | N94Y | PTEN | Y225C | RET | C634W |
| PTEN | G132V | PTEN | P169H | PTEN | Y27C | RET | C634Y |
| PTEN | G156R | PTEN | P204S | PTEN | Y27N | RET | D631G |
| PTEN | G165E | PTEN | P204T | PTEN | Y27S | RET | D925H |
| PTEN | G165R | PTEN | P244S | PTEN | T336F | RET | E884K |
| PTEN | G20E | PTEN | P246L | PTEN | Y65C | RET | E901K |
| PTEN | G230R | PTEN | P339L | PTEN | Y65D | RET | G748C |
| PTEN | G251C | PTEN | P38S | PTEN | Y65N | RET | M918T |
| PTEN | G251V | PTEN | P95L | PTEN | Y68H | RET | P766S |
| PTEN | G36E | PTEN | P95S | PTEN | Y76Y | RET | R348R |
| PTEN | G36R | PTEN | P96L | PTEN | Y88C | RET | R908K |
| PTEN | G36V | PTEN | P96Q | PTEN | Y88S | RET | V778V |
| PTEN | G44D | PTEN | P96S | PTPN11 | A16A | ROS1 | Q865H |
| PTEN | G44G | PTEN | Q149R | PTPN11 | A72D | SMARCB1 | A203T |
| PTEN | H123Y | PTEN | Q171E | PTPN11 | A72T | SMARCB1 | N152D |
| PTEN | H141Y | PTEN | Q171H | PTPN11 | A72V | SMARCB1 | P173S |
| PTEN | H272R | PTEN | Q171P | PTPN11 | D61N | SMARCB1 | P48S |
| PTEN | H272Y | PTEN | Q17P | PTPN11 | D61V | SMARCB1 | R127G |
| PTEN | H397Y | PTEN | R130G | PTPN11 | D61Y | SMARCB1 | R341L |
| PTEN | H61L | PTEN | R130L | PTPN11 | E139D | SMARCB1 | R374Q |
| PTEN | H61P | PTEN | R130P | PTPN11 | E69K | SMARCB1 | R377H |
| PTEN | H61R | PTEN | R130Q | PTPN11 | E69V | SMARCB1 | S284L |
| PTEN | H93D | PTEN | R130R | PTPN11 | E76A | SMARCB1 | S299S |
| PTEN | H93Q | PTEN | R142Q | PTPN11 | E76G | SMARCB1 | S49X |
| PTEN | H93R | PTEN | R142W | PTPN11 | E76K | SMARCB1 | T372T |
| PTEN | H93Y | PTEN | R14G | PTPN11 | E76Q | SMO | A324T |
| PTEN | I101I | PTEN | R159S | PTPN11 | E76V | SMO | A401A |
| PTEN | I101M | PTEN | R15I | PTPN11 | F71K | SMO | A652V |
| PTEN | I101N | PTEN | R15K | PTPN11 | F71L | SMO | A68V |
| PTEN | I101T | PTEN | R15S | PTPN11 | G503A | SMO | L514F |
| PTEN | I122S | PTEN | R173C | PTPN11 | G503E | SMO | F755F |
| PTEN | I135K | PTEN | R173H | PTPN11 | G503V | SMO | R199W |
| PTEN | I135M | PTEN | R173R | PTPN11 | G60A | SMO | R464W |
| PTEN | I135V | PTEN | R233R | PTPN11 | G60R | SMO | R562Q |
| PTEN | I168F | PTEN | R234W | PTPN11 | G60V | SMO | S533N |
| PTEN | I253N | PTEN | R302C | PTPN11 | N58S | SMO | T349I |
| PTEN | I33S | PTEN | R335G | PTPN11 | N58Y | SMO | T640A |
| PTEN | I5L | PTEN | R55G | PTPN11 | P491L | SMO | V404M |

FIGURE 28 (CONTINUED)

| | | | |
|---|---|---|---|
| SMO | W535L | | |
| SUFU | F197F | | |
| SUFU | P187L | | |
| TEC | R563K | | |
| IIF1 | T403N | | |
| TP53 | A159V | | |
| TP53 | A161D | | |
| TP53 | C124R | | |
| TP53 | C135F | | |
| TP53 | C135R | | |
| TP53 | C176F | | |
| TP53 | C176Y | | |
| TP53 | C238Y | | |
| TP53 | C242F | | |
| TP53 | C242R | | |
| TP53 | C242S | | |
| TP53 | C242W | | |
| TP53 | C275F | | |
| TP53 | C275G | | |
| TP53 | C275Y | | |
| TP53 | D281G | | |
| TP53 | D281Y | | |
| TP53 | E11Q | | |
| TP53 | E155K | | |
| TP53 | E285K | | |
| TP53 | E286K | | |
| TP53 | F113C | | |
| TP53 | F113S | | |
| TP53 | G244A | | |
| TP53 | G244C | | |
| TP53 | G244D | | |
| TP53 | G244S | | |
| TP53 | G245C | | |
| TP53 | G245S | | |
| TP53 | G245V | | |
| TP53 | G262V | | |
| TP53 | G266E | | |
| TP53 | G266V | | |
| TP53 | G334V | TP53 | R175H |
| TP53 | G389W | TP53 | R175L |
| TP53 | H179Q | TP53 | R213Q |
| TP53 | H179R | TP53 | R248L |
| TP53 | H193L | TP53 | R248Q |
| TP53 | H193R | TP53 | R248W |
| TP53 | I162N | TP53 | R249G |
| TP53 | I195T | TP53 | R249S |
| TP53 | I232N | TP53 | R267L |
| TP53 | I251N | TP53 | R267P |
| TP53 | I251T | TP53 | R267W |
| TP53 | I254D | TP53 | R273C |
| TP53 | I255S | TP53 | R273H |
| TP53 | I255T | TP53 | R273L |
| TP53 | K132E | TP53 | R280G |
| TP53 | K132Q | TP53 | R280K |
| TP53 | K132R | TP53 | R280T |
| TP53 | K320N | TP53 | R282W |
| TP53 | L130V | TP53 | R283C |
| TP53 | L145R | TP53 | R283H |
| TP53 | L194F | TP53 | R283P |
| TP53 | L264R | TP53 | R337C |
| TP53 | L265P | TP53 | R337L |
| TP53 | M133K | TP53 | R379C |
| TP53 | M237I | TP53 | S241C |
| TP53 | M246I | TP53 | S241F |
| TP53 | N239D | TP53 | S241Y |
| TP53 | N263I | TP53 | V143A |
| TP53 | P151S | TP53 | V157F |
| TP53 | P152L | TP53 | V216L |
| TP53 | P177T | TP53 | V216M |
| TP53 | P250L | TP53 | V272M |
| TP53 | P278A | TP53 | V274F |
| TP53 | P278L | TP53 | Y126C |
| TP53 | P278R | TP53 | Y163C |
| TP53 | P278S | TP53 | Y220C |
| TP53 | P309S | TP53 | Y220D |
| TP53 | Q16L | TP53 | Y236C |
| TP53 | R110L | TRIM33 | E811K |
| TP53 | R110P | | |
| TP53 | R156P | | |
| TP53 | R158S | | |
| TP53 | R158L | | |

SEQUENCE LISTING

```
<160> NUMBER OF SEQ ID NOS: 126

<210> SEQ ID NO 1
<211> LENGTH: 189
<212> TYPE: DNA
<213> ORGANISM: Homo sapiens

<400> SEQUENCE: 1
atcacaggtc ccctatacat ctcagcatgg ccggacagcc tgcctgacct cagcgtcttc      60
cagaacctgc aagtaatccg gggacgaatt ctgcacaatg gcgcctactc gctgaccctg     120
caagggctgg gcatcagctg gctggggctg cgctcactga gggaactggg cagtggactg     180
gccctcatc                                                             189

<210> SEQ ID NO 2
<211> LENGTH: 63
<212> TYPE: PRT
<213> ORGANISM: Homo sapiens
```

<400> SEQUENCE: 2

Ile Thr Gly Pro Leu Tyr Ile Ser Ala Trp Pro Asp Ser Leu Pro Asp
1               5                   10                  15

Leu Ser Val Phe Gln Asn Leu Gln Val Ile Arg Gly Arg Ile Leu His
            20                  25                  30

Asn Gly Ala Tyr Ser Leu Thr Leu Gln Gly Leu Gly Ile Ser Trp Leu
        35                  40                  45

Gly Leu Arg Ser Leu Arg Glu Leu Gly Ser Gly Leu Ala Leu Ile
    50                  55                  60

<210> SEQ ID NO 3
<211> LENGTH: 183
<212> TYPE: DNA
<213> ORGANISM: Homo sapiens

<400> SEQUENCE: 3
acccaccaga gtgatgtgtg gagttatggt gtgactgtgt gggagctgat gacttttggg      60
gccaaacctt acgatgggat cccagcccgg gagatccctg acctgctgga aaaggggag     120 cggctgcccc agcccccat ctgcaccatt gatgtctaca tgatcatggt caaatgttgg     180
atg                                                                  183

<210> SEQ ID NO 4
<211> LENGTH: 61
<212> TYPE: PRT
<213> ORGANISM: Homo sapiens

<400> SEQUENCE: 4

Thr His Gln Ser Asp Val Trp Ser Tyr Gly Val Thr Val Trp Glu Leu
1               5                   10                  15

Met Thr Phe Gly Ala Lys Pro Tyr Asp Gly Ile Pro Ala Arg Glu Ile
            20                  25                  30

Pro Asp Leu Leu Glu Lys Gly Glu Arg Leu Pro Gln Pro Pro Ile Cys
        35                  40                  45

Thr Ile Asp Val Tyr Met Ile Met Val Lys Cys Trp Met
    50                  55                  60

<210> SEQ ID NO 5
<211> LENGTH: 195
<212> TYPE: DNA
<213> ORGANISM: Homo sapiens

<400> SEQUENCE: 5
gagaaccccg agtacttgac accccaggga ggagctgccc ctcagcccca ccctcctcct      60
gccttcagcc cagccttcga caacctctat tactgggacc gggacccacc agagcggggg    120
gctccaccca gcaccttcaa agggacacct acggcagaga acccagagta cctgggtctg    180
gacgtgccag tgtaa                                                     195

<210> SEQ ID NO 6
<211> LENGTH: 64
<212> TYPE: PRT
<213> ORGANISM: Homo sapiens

<400> SEQUENCE: 6

Glu Asn Pro Glu Tyr Leu Thr Pro Gln Gly Gly Ala Ala Pro Gln Pro
1               5                   10                  15

His Pro Pro Pro Ala Phe Ser Pro Ala Phe Asp Asn Leu Tyr Tyr Trp

```
                    20                  25                  30

Asp Arg Asp Pro Pro Glu Arg Gly Ala Pro Pro Ser Thr Phe Lys Gly
            35                  40                  45

Thr Pro Thr Ala Glu Asn Pro Glu Tyr Leu Gly Leu Asp Val Pro Val
        50                  55                  60

<210> SEQ ID NO 7
<211> LENGTH: 18
<212> TYPE: PRT
<213> ORGANISM: Homo sapiens

<400> SEQUENCE: 7

Val His His Arg His Arg Ser Ser Ser Thr Arg Ser Gly Gly Gly Asp
1               5                   10                  15

Leu Thr

<210> SEQ ID NO 8
<211> LENGTH: 27
<212> TYPE: PRT
<213> ORGANISM: Artificial
<220> FEATURE:
<223> OTHER INFORMATION: Synthetic sequence: MMTV-PymT mT peptide
      sequence of PCT/SG2012/000305

<400> SEQUENCE: 8

Cys Met Asp Arg Val Leu Ser Arg Ala Asp Lys Glu Arg Leu Leu Glu
1               5                   10                  15

Leu Leu Lys Leu Pro Arg Gln Leu Trp Gly Asp
            20                  25

<210> SEQ ID NO 9
<211> LENGTH: 595
<212> TYPE: PRT
<213> ORGANISM: Homo sapiens

<400> SEQUENCE: 9

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175
```

```
Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
                450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
                515                 520                 525

Lys Cys Lys Asn Val Val Pro Leu Tyr Asp Leu Leu Leu Glu Met Leu
                530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
```

<210> SEQ ID NO 10
<211> LENGTH: 27
<212> TYPE: PRT
<213> ORGANISM: Artificial
<220> FEATURE:
<223> OTHER INFORMATION: Synthetic sequence

<400> SEQUENCE: 10

Cys Gly Tyr Thr Val Arg Glu Ala Gly Pro Pro Ala Phe Tyr Arg Pro
1               5                   10                  15

Asn Ser Asp Asn Arg Arg Gln Gly Gly Arg Glu
            20                  25

<210> SEQ ID NO 11
<211> LENGTH: 157
<212> TYPE: PRT
<213> ORGANISM: Homo sapiens

<400> SEQUENCE: 11

Asn Arg Pro Gln Leu Lys Ile Pro Leu Glu Arg Pro Leu Gly Glu Val
1               5                   10                  15

Tyr Leu Asp Ser Ser Lys Pro Ala Val Tyr Asn Tyr Pro Glu Gly Ala
            20                  25                  30

Ala Tyr Glu Phe Asn Ala Ala Ala Ala Asn Ala Gln Val Tyr Gly
        35                  40                  45

Gln Thr Gly Leu Pro Tyr Gly Pro Gly Ser Glu Ala Ala Phe Gly
    50                  55                  60

Ser Asn Gly Leu Gly Gly Phe Pro Pro Leu Asn Ser Val Ser Pro Ser
65                  70                  75                  80

Pro Leu Met Leu Leu His Pro Pro Pro Gln Leu Ser Pro Phe Leu Gln
                85                  90                  95

Pro His Gly Gln Gln Val Pro Tyr Tyr Leu Glu Asn Glu Pro Ser Gly
            100                 105                 110

Tyr Thr Val Arg Glu Ala Gly Pro Pro Ala Phe Tyr Arg Pro Asn Ser
        115                 120                 125

Asp Asn Arg Arg Gln Gly Gly Arg Glu Arg Leu Ala Ser Thr Asn Asp
    130                 135                 140

Lys Gly Ser Met Ala Met Glu Ser Ala Lys Glu Thr Arg
145                 150                 155

<210> SEQ ID NO 12
<211> LENGTH: 471
<212> TYPE: DNA
<213> ORGANISM: Homo sapiens

<400> SEQUENCE: 12
aaccgtccgc agctcaagat cccccctggag cggcccctgg gcgaggtgta cctggacagc    60
agcaagcccg ccgtgtacaa ctaccccgag ggcgccgcct acgagttcaa cgccgcggcc   120
gccgccaacg cgcaggtcta cggtcagacc ggcctcccct acggcccggg tctgaggct    180 gcggcgttcg gctccaacgg cctggggggt ttccccccac tcaacagcgt gtctccgagc   240
ccgctgatgc tactgcaccc gccgccgcag ctgtcgcctt cctgcagcc ccacggccag    300 caggtgccct actacctgga gaacgagccc agcggctaca cggtgcgcga ggccggcccg   360
ccggcattct acaggccaaa ttcagataat cgacgccagg gtggcagaga aagattggcc   420
agtaccaatg acaagggaag tatggctatg gaatctgcca aggagactcg c            471

<210> SEQ ID NO 13
<211> LENGTH: 28
<212> TYPE: PRT
<213> ORGANISM: Artificial
<220> FEATURE:
<223> OTHER INFORMATION: Synthetic sequence

<400> SEQUENCE: 13

Leu Lys His Lys Arg Gln Arg Asp Asp Gly Glu Gly Arg Gly Glu Val
1               5                   10                  15

Gly Ser Ala Gly Asp Met Arg Ala Ala Asn Leu Cys
            20                  25

<210> SEQ ID NO 14
<211> LENGTH: 67
<212> TYPE: PRT
<213> ORGANISM: Homo sapiens

<400> SEQUENCE: 14

Gly Gly Ile Arg Lys Asp Arg Arg Gly Gly Arg Met Leu Lys His Lys
1               5                   10                  15

Arg Gln Arg Asp Asp Gly Glu Gly Arg Gly Glu Val Gly Ser Ala Gly
            20                  25                  30

Asp Met Arg Ala Ala Asn Leu Trp Pro Ser Pro Leu Met Ile Lys Arg
        35                  40                  45

Ser Lys Lys Asn Ser Leu Ala Leu Ser Leu Thr Ala Asp Gln Met Val
    50                  55                  60

Ser Ala Leu
65

<210> SEQ ID NO 15
<211> LENGTH: 201
<212> TYPE: DNA
<213> ORGANISM: Homo sapiens

<400> SEQUENCE: 15
ggtgggatac gaaaagaccg aagaggaggg agaatgttga acacaagcg ccagagagat      60 gatgggagg gcaggggtga agtggggtct gctggagaca tgagagctgc caacctttgg    120
ccaagcccgc tcatgatcaa acgctctaag aagaacagcc tggccttgtc cctgacggcc    180
gaccagatgg tcagtgccctt g                                              201

<210> SEQ ID NO 16
<211> LENGTH: 154
<212> TYPE: PRT
<213> ORGANISM: Hepatitis B virus

<400> SEQUENCE: 16

Met Ala Ala Arg Leu Cys Cys Gln Leu Asp Pro Thr Arg Asp Val Leu
1               5                   10                  15

Cys Leu Arg Pro Val Gly Ala Glu Ser Arg Gly Arg Pro Val Ser Gly
            20                  25                  30

Pro Leu Gly Asp Leu Pro Ser Pro Ser Ala Ser Pro Val Pro Thr Ile
        35                  40                  45

Asp Arg Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

-continued

```
Thr Thr Val Asn Thr His Met Ile Leu Pro Lys Val Leu His Lys Arg
            85                  90                  95

Thr Leu Gly Leu Pro Ala Met Ser Thr Ile Asp Leu Glu Ala Tyr Phe
        100                 105                 110

Lys Asp Cys Leu Phe Lys Asp Trp Glu Glu Leu Gly Glu Glu Ile Arg
    115                 120                 125

Leu Lys Val Phe Val Leu Gly Gly Cys Arg His Lys Leu Val Cys Ser
130                 135                 140

Pro Ala Pro Cys Asn Phe Phe Thr Ser Ala
145                 150

<210> SEQ ID NO 17
<211> LENGTH: 21
<212> TYPE: PRT
<213> ORGANISM: Hepatitis B virus

<400> SEQUENCE: 17

Phe Lys Asp Trp Glu Glu Leu Gly Glu Glu Ile Arg Leu Lys Val Phe
1               5                   10                  15

Val Leu Gly Gly Cys
            20

<210> SEQ ID NO 18
<211> LENGTH: 29
<212> TYPE: PRT
<213> ORGANISM: Artificial sequence
<220> FEATURE:
<223> OTHER INFORMATION: Synthetic sequence: PRL-3 peptide

<400> SEQUENCE: 18

Glu Val Thr Tyr Asp Lys Thr Pro Leu Glu Lys Asp Gly Ile Thr Val
1               5                   10                  15

Gly Gly Ser Gly Asp Pro His Thr His Lys Thr Arg Cys
            20                  25

<210> SEQ ID NO 19
<211> LENGTH: 21
<212> TYPE: PRT
<213> ORGANISM: Artificial sequence
<220> FEATURE:
<223> OTHER INFORMATION: Synthetic sequence: Ras mutated peptide

<400> SEQUENCE: 19

Cys Met Thr Glu Tyr Lys Leu Val Val Val Gly Ala Asp Gly Val Gly
1               5                   10                  15

Lys Ser Ala Leu Thr
            20

<210> SEQ ID NO 20
<211> LENGTH: 19
<212> TYPE: PRT
<213> ORGANISM: Artificial sequence
<220> FEATURE:
<223> OTHER INFORMATION: Synthetic sequence: K-Ras-G12D

<400> SEQUENCE: 20

Met Thr Tyr Lys Val Val Val Gly Ala Asp Gly Val Gly Lys Ser Ala
1               5                   10                  15

Thr Asn His

<210> SEQ ID NO 21
<211> LENGTH: 19
```

```
<212> TYPE: PRT
<213> ORGANISM: Artificial sequence
<220> FEATURE:
<223> OTHER INFORMATION: Synthetic sequence: K-Ras-G12V

<400> SEQUENCE: 21

Met Thr Tyr Lys Val Val Val Gly Ala Val Gly Val Gly Lys Ser Ala
1               5                   10                  15

Thr Asn His

<210> SEQ ID NO 22
<211> LENGTH: 19
<212> TYPE: PRT
<213> ORGANISM: Artificial sequence
<220> FEATURE:
<223> OTHER INFORMATION: Synthetic sequence: K-Ras-G12R

<400> SEQUENCE: 22

Met Thr Tyr Lys Val Val Val Gly Ala Arg Gly Val Gly Lys Ser Ala
1               5                   10                  15

Thr Asn His

<210> SEQ ID NO 23
<211> LENGTH: 19
<212> TYPE: PRT
<213> ORGANISM: Artificial sequence
<220> FEATURE:
<223> OTHER INFORMATION: Synthetic sequence: K-Ras-G13R

<400> SEQUENCE: 23

Met Thr Tyr Lys Val Val Val Gly Ala Gly Arg Val Gly Lys Ser Ala
1               5                   10                  15

Thr Asn His

<210> SEQ ID NO 24
<211> LENGTH: 20
<212> TYPE: PRT
<213> ORGANISM: Artificial sequence
<220> FEATURE:
<223> OTHER INFORMATION: Synthetic sequence: EGFR-L858R

<400> SEQUENCE: 24

Gln His Val Lys Ile Thr Asp Phe Gly Arg Ala Lys Leu Leu Gly Ala
1               5                   10                  15

Glu Glu Lys Glu
            20

<210> SEQ ID NO 25
<211> LENGTH: 19
<212> TYPE: PRT
<213> ORGANISM: Artificial sequence
<220> FEATURE:
<223> OTHER INFORMATION: Synthetic sequence: B-Raf-V600E

<400> SEQUENCE: 25

Lys Ile Gly Asp Phe Gly Leu Ala Thr Glu Lys Ser Arg Trp Ser Gly
1               5                   10                  15

Ser His Gln

<210> SEQ ID NO 26
<211> LENGTH: 16
<212> TYPE: PRT
<213> ORGANISM: Artificial sequence
<220> FEATURE:
```

<223> OTHER INFORMATION: Synthetic sequence: EGFR-T790M

<400> SEQUENCE: 26

Leu Thr Ser Thr Val Gln Leu Ile Met Gln Leu Met Pro Phe Gly Cys
1               5                   10                  15

<210> SEQ ID NO 27
<211> LENGTH: 18
<212> TYPE: PRT
<213> ORGANISM: Artificial sequence
<220> FEATURE:
<223> OTHER INFORMATION: Synthetic sequence: EGFR-E746-A750 del

<400> SEQUENCE: 27

Lys Val Lys Ile Pro Val Ala Ile Lys Thr Ser Pro Lys Ala Asn Lys
1               5                   10                  15

Glu Ile

<210> SEQ ID NO 28
<211> LENGTH: 19
<212> TYPE: PRT
<213> ORGANISM: Artificial sequence
<220> FEATURE:
<223> OTHER INFORMATION: Synthetic sequence: PI3KCA-E542K

<400> SEQUENCE: 28

Lys Ala Ile Ser Thr Arg Asp Pro Leu Ser Lys Ile Thr Glu Gln Glu
1               5                   10                  15

Lys Asp Phe

<210> SEQ ID NO 29
<211> LENGTH: 19
<212> TYPE: PRT
<213> ORGANISM: Artificial sequence
<220> FEATURE:
<223> OTHER INFORMATION: Synthetic sequence: PI3KCA-E545K

<400> SEQUENCE: 29

Thr Arg Asp Pro Leu Ser Glu Ile Thr Lys Gln Glu Lys Asp Phe Leu
1               5                   10                  15

Trp Ser His

<210> SEQ ID NO 30
<211> LENGTH: 20
<212> TYPE: PRT
<213> ORGANISM: Artificial sequence
<220> FEATURE:
<223> OTHER INFORMATION: Synthetic sequence: PI3KCA-H1047R

<400> SEQUENCE: 30

Glu Tyr Phe Met Lys Gln Met Asn Asp Ala Arg His Gly Gly Trp Thr
1               5                   10                  15

Thr Lys Met Asp
            20

<210> SEQ ID NO 31
<211> LENGTH: 20
<212> TYPE: PRT
<213> ORGANISM: Artificial sequence
<220> FEATURE:
<223> OTHER INFORMATION: Synthetic sequence: beta-catenin-T41A

<400> SEQUENCE: 31

Asp Ser Gly Ile His Ser Gly Ala Thr Ala Thr Ala Pro Ser Leu Ser

```
1               5                   10                  15
Gly Lys Gly Asn
            20

<210> SEQ ID NO 32
<211> LENGTH: 19
<212> TYPE: PRT
<213> ORGANISM: Artificial sequence
<220> FEATURE:
<223> OTHER INFORMATION: Synthetic sequence: beta-catenin-S45F

<400> SEQUENCE: 32

His Ser Gly Ala Thr Thr Thr Ala Pro Phe Leu Ser Gly Lys Gly Asn
1               5                   10                  15

Pro Glu Glu

<210> SEQ ID NO 33
<211> LENGTH: 19
<212> TYPE: PRT
<213> ORGANISM: Artificial sequence
<220> FEATURE:
<223> OTHER INFORMATION: Synthetic sequence: beta-catenin-S45P

<400> SEQUENCE: 33

His Ser Gly Ala Thr Thr Thr Ala Pro Pro Leu Ser Gly Lys Gly Asn
1               5                   10                  15

Pro Glu Glu

<210> SEQ ID NO 34
<211> LENGTH: 19
<212> TYPE: PRT
<213> ORGANISM: Artificial sequence
<220> FEATURE:
<223> OTHER INFORMATION: Synthetic sequence: GNAS-R201C

<400> SEQUENCE: 34

Ser Asp Gln Asp Leu Leu Arg Cys Cys Val Leu Thr Ser Gly Ile Phe
1               5                   10                  15

Glu Thr Lys

<210> SEQ ID NO 35
<211> LENGTH: 19
<212> TYPE: PRT
<213> ORGANISM: Artificial sequence
<220> FEATURE:
<223> OTHER INFORMATION: Synthetic sequence: Ret-M918T

<400> SEQUENCE: 35

Arg Ser Gln Gly Arg Ile Pro Val Lys Trp Thr Ala Ile Glu Ser Leu
1               5                   10                  15

Phe Asp His

<210> SEQ ID NO 36
<211> LENGTH: 20
<212> TYPE: PRT
<213> ORGANISM: Artificial sequence
<220> FEATURE:
<223> OTHER INFORMATION: Synthetic sequence: EZH2-Y646F

<400> SEQUENCE: 36

Gln Lys Asn Glu Phe Ile Ser Glu Phe Cys Gly Glu Ile Ile Ser Gln
1               5                   10                  15

Asp Glu Ala Asp
```

20

<210> SEQ ID NO 37
<211> LENGTH: 20
<212> TYPE: PRT
<213> ORGANISM: Artificial sequence
<220> FEATURE:
<223> OTHER INFORMATION: Synthetic sequence: EZH2-Y646N

<400> SEQUENCE: 37

Gln Lys Asn Glu Phe Ile Ser Glu Asn Cys Gly Glu Ile Ile Ser Gln
1               5                   10                  15

Asp Glu Ala Asp
            20

<210> SEQ ID NO 38
<211> LENGTH: 20
<212> TYPE: PRT
<213> ORGANISM: Artificial sequence
<220> FEATURE:
<223> OTHER INFORMATION: Synthetic sequence: EZH2-Y646S

<400> SEQUENCE: 38

Gln Lys Asn Glu Phe Ile Ser Glu Ser Cys Gly Glu Ile Ile Ser Gln
1               5                   10                  15

Asp Glu Ala Asp
            20

<210> SEQ ID NO 39
<211> LENGTH: 20
<212> TYPE: PRT
<213> ORGANISM: Artificial sequence
<220> FEATURE:
<223> OTHER INFORMATION: Synthetic sequence: EZH2-Y646H

<400> SEQUENCE: 39

Gln Lys Asn Glu Phe Ile Ser Glu His Cys Gly Glu Ile Ile Ser Gln
1               5                   10                  15

Asp Glu Ala Asp
            20

<210> SEQ ID NO 40
<211> LENGTH: 18
<212> TYPE: PRT
<213> ORGANISM: Artificial sequence
<220> FEATURE:
<223> OTHER INFORMATION: Synthetic sequence: GNA11/GNAQ-Q209L

<400> SEQUENCE: 40

Phe Arg Met Val Asp Val Gly Gly Leu Arg Ser Glu Arg Arg Lys Trp
1               5                   10                  15

Ile His

<210> SEQ ID NO 41
<211> LENGTH: 18
<212> TYPE: PRT
<213> ORGANISM: Artificial sequence
<220> FEATURE:
<223> OTHER INFORMATION: Synthetic sequence: GNAQ-Q209P

<400> SEQUENCE: 41

Phe Arg Met Val Asp Val Gly Gly Pro Arg Ser Glu Arg Arg Lys Trp
1               5                   10                  15

Ile His

<210> SEQ ID NO 42
<211> LENGTH: 595
<212> TYPE: PRT
<213> ORGANISM: Homo sapiens

<400> SEQUENCE: 42

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
```

```
                    370                 375                 380
Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 43
<211> LENGTH: 154
<212> TYPE: PRT
<213> ORGANISM: Hepatitis B virus

<400> SEQUENCE: 43

Met Ala Ala Arg Leu Tyr Cys Gln Leu Asp Pro Ala Arg Asp Val Leu
1               5                   10                  15

Cys Leu Arg Pro Val Gly Ala Glu Ser Cys Gly Arg Pro Leu Ser Gly
                20                  25                  30

Pro Leu Gly Asp Leu Pro Ser Ser Ser Ser Ala Val Pro Ser Val
            35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Leu Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Lys Asp Trp Glu Glu Leu Gly Glu Glu Met Arg
        115                 120                 125

Leu Lys Val Phe Val Leu Gly Gly Cys Arg His Lys Leu Val Cys Ser
    130                 135                 140
```

```
Pro Thr Pro Cys Asn Phe Phe Thr Ser Ala
145                 150
```

<210> SEQ ID NO 44
<211> LENGTH: 3215
<212> TYPE: DNA
<213> ORGANISM: Hepatitis B virus

<400> SEQUENCE: 44

```
ctccacaaca ttccaccaag ctcttctaga ccccagagtg aggggcctat actttcctgc      60
tggtggctcc agttccggaa cagtaaaccc tgttccgact actgcctcac ccatatcgtc     120
aatcttctcg aggactgggg accctgcacc gaacatggag aacacaacat caggattcct     180
aggacccctg ctcgtgttac aggcggggtt tttcttgttg acaagaatcc tcacaatacc     240
acagagtcta gactcgtggt ggacttctct caattttcta gggggagcac ccacgtgtcc     300
tggccaaaat tcgcagtccc caacctccaa tcactcacca acctcttgtc ctccaatttg     360
tcctggctat cgctggatgt gtctgcggcg ttttatcata ttcctcttca tcctgctgct     420
atgcctcatc ttcttgttgg ttcttctgga ctaccaaggt atgttgcccg tttgtcctct     480
acttccagga acatcaacta ccagcacggg accatgcaag acctgcacga ttcctgctca     540
aggaacctct atgtttccct cttgttgctg tacaaaacct tcggacggaa actgcacttg     600
tattcccatc ccatcatcct gggctttcgc aagattccta tgggagtggg cctcagtccg     660
tttctcctgg ctcagtttac tagtgccatt tgttcagtgg ttcgtagggc tttcccccac     720
tgtttggctt tcagttatat ggatgatgtg gtattggggg ccaagtctgt acaacatctt     780
gagtcccttt ttgcctctat taccaatttt cttttgtctt gggtataca tttgaaccct     840
aataaaacca aacgttgggg ctactcccct aacttcatgg gatatgtaat tggatgttgg     900
ggtactttac cacaagaaca tattgtacta aaaatcaagc aatgttttcg aaaactgcct     960
gtaaatagac ctattgattg aaagtatgt cagagaattg taggtctttt gggctttgct    1020
gcccctttta cacaatgtgg ctatcctgcc ttaatgcctt tatatgcatg catacaatct    1080
aagcaggctt tcactttctc gccaacttac aaggcctttc tgtgtaaaca atatctgaac    1140
ctttaccccg ttgcccggca acggtcaggt ctctgccaag tgtttgctga cgcaaccccc    1200
actggatggg gcttggctat tggccatcgc cgcatgcgtg gaacctttgt ggctcctctg    1260
ccgatccata ctgcggaact cctagcagct tgttttgctc gcagccggtc tggagcgaaa    1320
cttatcggaa ccgacaactc tgtcgtcctc tctcggaaat acaccgcctt ccatggctg    1380
ctaggggtgtg ctgccaactg gatcctgcgc gggacgtcct ttgtctacgt cccgtcggcg    1440
ctgaatcccg cggacgaccc gtctcggggc cgtttgggac tctaccgtcc cctccttcag    1500
ctgccgtacc gaccgaccac ggggcgcacc tctctttacg cggtctcccc gtctgtgcct    1560
tctcatctgc cggaccgtgt gcacttcgct tcacctctgc acgtcgcatg gagaccaccg    1620
tgaacgccca tcaggccttg cccaaggtct tacataagag gactcttgga ctctcagcaa    1680
tgtcaacgac cgaccttgag gcatacttca aagactgttt gtttaaggac tgggaggagt    1740
tgggggagga gattaggtta atgatctttg tactaggagg ctgtaggcat aaattggtct    1800
gttcaccagc accatgcaac ttttttcacct ctgcctaatc atctcatgtt catgtcctac    1860
tgttcaagcc tccaagctgt gccttgggtg gctttgggc atggacattg acccgtataa    1920
agaatttgga gcttctgtgg agttactctc tttttttgcct tctgacttct ttccttctat    1980
tcgagatctc ctcgacaccg cttcagctct gtatcgggag gccttagagt ctccggaaca    2040
```

```
ttgttcacct caccatacag cactcaggca agctattctg tgttggggtg agttgatgaa    2100
tctggccacc tgggtgggaa gtaatttgga agacccagca tccagggaat tagtagtcag    2160
ctatgtcaat gttaatatgg gcctaaaaat cagacaacta ctgtggtttc acatttcctg    2220
tcttactttt ggaagagaaa ctgttcttga gtatttggtg tcttttggag tgtggattcg    2280
cactcctcyt gcttatagac caccaaatgc ccctatctta tcaacacttc cggaaactac    2340
tgttgttaga cgacgaggca ggtccccctag aagaagaact ccctcgcctc gcagacgaag    2400
gtctcaatcg ccgcgtcgca gaagatctca atctcgggaa tctcaatgtt agtataccct    2460
ggactcataa ggtgggaaac tttactgggc tttattcttc tactgtacct gtctttaatc    2520
ctgagtggca aactccctcc tttcctcaaa ttcatttaca ggaggacatt attaatagat    2580
gtcaacaata cgtgggccct cttacagtta atgaaaaaag gagattaaaa ttaattatgc    2640
ctgctaggtt ctatcctaac cttaccaaat atttgcccct tgataaaggc attaaaccct    2700
attatcctga acatgcagtt aatcattact tcaaaactag gcattattta catactctgt    2760
ggaaggctgg cattctatat aagagagaaa ctacacgcag cgcctcattt tgtgggtcac    2820
catattcttg gaacaagag ctacagcatg ggaggttggt cttccaaacc tcgacaaggc    2880
atggggacaa atctttctgt tcccaatcct ctgggattct ttcccgatca ccagttggac    2940
cctgcgttcg gagccaactc aaacaatcca gattgggact tcaaccccaa caaggatcac    3000
tggccagagg caaatcaggt aggagcggga gcattcgggc cagggttcac cccaccacac    3060
ggcggtcttt tggggtggag ccctcaggct cagggcatat tgacaacagt gccagtagca    3120
cctcctcctg cctccaccaa tcggcagtca ggaagacagc ctactcccat ctctccacct    3180
ctaagagaca gtcatcctca ggccatgcag tggaa                              3215
```

<210> SEQ ID NO 45
<211> LENGTH: 1006
<212> TYPE: DNA
<213> ORGANISM: Homo sapiens

<400> SEQUENCE: 45

```
aagagttggg ttttcttttt taattatcca aacagtgggc agcttcctcc cccacaccca     60
agtatttgca caatatttgt gcggggtatg ggggtgggtt tttaaatctc gtttctcttg    120
gacaagcaca gggatctcgt tctcctcatt tttgggggt gtgtgggac ttctcaggtc      180
gtgtccccag ccttctctgc agtccttct gccctgccgg gcccgtcggg aggcgccatg    240
gctcggatga accgcccggc cccggtggag gtgagctaca acacatgcg cttcctcatc    300
acccacaacc ccaccaacgc cacgctcagc accttcattg aggacctgaa gaagtacggg    360
gctaccactg tggtgcgtgt gtgtgaagtg acctatgaca aaacgccgct ggagaaggat    420
ggcatcaccg ttgtggactg ccgtttgac gatgggcgc cccgcctgg caaggtagtg      480
gaagactggc tgagcctggt gaaggccaag ttctgtgagg ccccggcag ctgcgtggct    540
gtgcactgcg tggcgggcct ggggcgggct ccagtccttg tggcgctggc gcttattgag    600
agcgggatga agtacgagga cgccatccag ttcatccgcc agaagcgccg cggacgcatc    660
aacagcaagc agctcaccta cctggagaaa taccggccca acagaggct gcggttcaaa    720
gacccacaca cgcacaagac ccggtgctgc gttatgtagc tcaggacctt ggctgggcct    780
ggtcgtcatg taggtcagga ccttggctgg acctggaggc cctgccagcc ctgctctgcc    840
cagcccagca gggctccagg ccttggctgg ccccacatcg ccttttcctc cccgacacct    900
ccgtgcactt gtgtccgagg agcgaggagc ccctcggcgc cttgggtggc ttctgggccc    960
```

```
tttctcctgt ctccgtactc cctctggcgg cgctggcgtg gctctg              1006

<210> SEQ ID NO 46
<211> LENGTH: 447
<212> TYPE: DNA
<213> ORGANISM: Homo sapiens

<400> SEQUENCE: 46
atggcccgga tgaaccgccc ggccccggtg gaggtgagct acaaacacat gcgcttcctc   60
atcacccaca accccaccaa cgccacgctc agcaccttca ttgaggacct gaagaagtac  120
ggggctacca ctgtggtgcg tgtgtgtgaa gtgacctatg acaaaacgcc gctggagaag  180
gatggcatca ccgttgtgga ctggccgttt gacgatgggg cgccccgcc cggcaaggta   240 gtggaagact ggctgagcct ggtgaaggcc aagttctgtg aggcccccgg cagctgcgtg  300
gctgtgcact gcgtggcggg cctgggccgg aagcgccgcg agccatcaa cagcaagcag   360 ctcacctacc tggagaaaata ccggcccaaa cagaggctgc ggttcaaaga cccacacacg  420
cacaagaccc ggtgctgcgt tatgtag                                      447

<210> SEQ ID NO 47
<211> LENGTH: 2963
<212> TYPE: DNA
<213> ORGANISM: Homo sapiens

<400> SEQUENCE: 47
cacaagcaca tgtgtgccca cacagaccca ggcatacgca ggcacacaca ggcaggtgtg   60
tgaacacagg cacatacaga caagcgggta tttgcacaca tggacacaca tggatgcact  120
caggcatgta cacacgtgtg cactcataca tgacatgcac tctcacacat gcgggtgcac  180
accttccccg ggttctctct ccaccccacg tctcaccgag caagggcttg tctctccctt   240
gtggcttttg ctgtgtggct ccccgcacct gaggctgcgc tggtcaggac aggttgggcc  300
atgctgcgga acagccagg cctgaacccc aacgactcag aacagcacgg gcgtttcttg    360
cccctgttgc gtgtctgttg gtgggggccc tacccggagg cgtggctgag ggctgcgcct  420
tccccagtgt gccggctgct gggtgaggaa acgagcacgg tggagccaca cggggcacct  480
gcagctttgc tgggcagaga ctcctcgcgc tactgctgct cccacttcct tggccagggc  540
cagcctgtgg ccacgcctga ggtcatggca ggtggggatg gatgagcctc cagaggcgct  600
gggtgggcag cccccgcccc tcaacgcctg tcacctcagg gcctctcagg tgtggctgca  660
gcatcctctc caggaagtct tcctgttcac cccagccagg tacatgtggt caaggaccag   720
gtggcggggc agggtgagca catagcccag gtccctgctg taaggaccag gtggcgggag  780
cagggtgagt gtacagccca ggtttctgct gtaaggaccc ggtggcgggg acagggtaag  840
cgcacagccc acgtccccgc tgtaaggacc aggtggcagg gacagggtga gcacacagtc  900
caggtccccg ctgtaaggac caggtggcgg ggacagggtg agcgcacagt ccaggtcccc  960
gctgtaagga ccaggtggcg gggacagggt gagcgcacag tccgggtccc cgctgtaagg 1020
acccggtggc ggggacaggg tgagcgcaca gcccgggtcc ccgctgtaag gacccggtgg 1080
cggggacagg gtgagcgcac agcccacgtc cccgctgtaa ggaccaggtg gcgggacag  1140 ggtgagcgca cagtccgggt ccccgctgta aggaccaggt ggcggggaca gggtgagcgc 1200
acagtccggg tccccgctgt aaggaccagg tggcgggac agggtgagcg cacagtccgg  1260
gtccccgctg taaggacccg gtggcgggga cagggtgagc gcacagtccg ggtccccgct 1320
```

| | |
|---|---:|
| gtaaggaccc ggtggcgggg acagggtgag cgcacagtcc gggtccccgc tgtaaggacc | 1380 |
| cggtggcggg gacagggtga gcgtacagcc caggtttccg ctgtaaggac caggtggcgg | 1440 |
| ggacagggtg agcacacagt ccgggtcccc gctgtaagga ccaggtggcg gggacagggt | 1500 |
| gagcacacag tccgggtccc cgctgtaagg accaggtggc ggggacaggg tgagcgtaca | 1560 |
| gcccaggttt ccgctgtaag gaccaggtgg cggggacagg gtgagcacac agtccaggtc | 1620 |
| cccgctgtaa ggaccaggtg gcggggacag ggtgagcgca tagcccaggt ccccgctgta | 1680 |
| aggaccaggt ggtggggatg gtggggacag ggtgagcaca cagtccgggt ccccgctgta | 1740 |
| aggacccggt ggcggggaca gggtgagcac acagtccagg tccccgctgt aaggacccgg | 1800 |
| tggcggggac agggtaagcg cacagcccac gtccccgctg taaggaccag gtggcgggga | 1860 |
| cagggtgagc gcatagccca ggtccccgct gtaaggacca ggtggtgggg atggtgggga | 1920 |
| caggttgagc atgcagccca ggtccctgct gtaagggaag gtcgcgcagc tgggctggaa | 1980 |
| ttctgggctc agcccctccc ttactcacag gcccccttc ctggatggtg gaggtgccca | 2040 |
| ggcaccaccc ttgttgtctg ctcatggcct tgggtgggt cctaccgagc tggggaagcc | 2100 |
| tgggggccgt agggagccca gagtcagcct ggaggaggtg gcgctttggt gagtttggaa | 2160 |
| ggcaagcagg ggtgagctgc aggggccag gaaagggtga ctgtgactct gggagcagcc | 2220 |
| gtgccaaggc cctgggactg aggggcttg gccagcctca aggccttact ccagcccact | 2280 |
| gcactctcag attccagctc cctggggcag gtgagatggc cgagccaggt ccttggatga | 2340 |
| tctctgttcc tgttcccctc ttcccaggaa gcgccgcgga gccatcaaca gcaagcagct | 2400 |
| cacctacctg gagaaatacc ggcccaaaca gaggctgcgg ttcaaagacc cacacacgca | 2460 |
| caagacccgg tgctgcgtta tgtagctcag gaccttggct gggcctggtc gtcatgtagg | 2520 |
| tcaggaccctt ggctggacct ggaggccctg cccagccctg ctctgcccag cccagcaggg | 2580 |
| gctccaggcc ttggctggcc ccacatcgcc ttttcctccc cgacacctcc gtgcacttgt | 2640 |
| gtccgaggag cgaggagccc ctcgggccct ggtggcctc tgggccctt ctcctgtctc | 2700 |
| cgccactccc tctggcggcg ctggccgtgg ctctgtctct ctgaggtggg tcgggcgccc | 2760 |
| tctgcccgcc ccctcccaca ccagccaggc tggtctcctc tagcctgttt gttgtggggt | 2820 |
| gggggtatat tttgtaacca ctgggccccc agccctctt ttgcgacccc ttgtcctgac | 2880 |
| ctgttctcgg cacctaaaat tattagaccc cggggcagtc aggtgctccg gacacccgaa | 2940 |
| ggcaataaaa caggagccgt ggc | 2963 |

<210> SEQ ID NO 48
<211> LENGTH: 1321
<212> TYPE: DNA
<213> ORGANISM: Homo sapiens

<400> SEQUENCE: 48

| | |
|---|---:|
| tgactatcca gctctgagag acgggagttt ggagttgccc gctttacttt ggttgggttg | 60 |
| ggggggggcgg cgggctgttt tgttcctttt ctttttttaag agttgggttt tcttttttaa | 120 |
| ttatccaaac agtgggcagc ttcctccccc acacccaagt atttgcacaa tatttgtgcg | 180 |
| gggtatgggg gtgggttttt aaatctcgtt tctcttggac aagcacaggg atctcgttct | 240 |
| cctcattttt tgggggtgtg tggggacttc tcaggtcgtg tccccagcct tctctgcagt | 300 |
| cccttctgcc ctgccgggcc cgtcgggagg cgccatggct cggatgaacc gcccggcccc | 360 |
| ggtggaggtg agctacaaac acatgcgctt cctcatcacc cacaacccca ccaacgccac | 420 |
| gctcagcacc ttcattgagg acctgaagaa gtacgggct accactgtgg tgcgtgtgtg | 480 |

-continued

```
tgaagtgacc tatgacaaaa cgccgctgga aaggatggc atcaccgttg tggactggcc      540
gtttgacgat ggggcgcccc cgcccggcaa ggtagtggaa gactggctga gcctggtgaa      600
ggccaagttc tgtgaggccc ccggcagctg cgtggctgtg cactgcgtgg cgggcctggg      660
ccggaagcgc cgcggagcca tcaacagcaa gcagctcacc tacctggaga ataccggcc       720 caaacagagg ctgcggttca aagacccaca cacgcacaag acccggtgct gcgttatgta     780
gctcaggacc ttggctgggc ctggtcgtca tgtaggtcag gaccttggct ggacctggag     840
gccctgccca gcctgctct gcccagccca gcagggctc caggccttgg ctggccccac       900
atcgcctttt cctccccgac acctccgtgc acttgtgtcc gaggagcgag gagcccctcg     960
ggccctgggt ggcctctggg ccctttctcc tgtctccgcc actccctctg cggcgctgg    1020 ccgtggctct gtctctctga ggtgggtcgg gcgccctctg cccgcccct cccacaccag    1080 ccaggctggt ctcctctagc ctgtttgttg tggggtgggg gtatattttg taaccactgg   1140 gccccagcc cctcttttgc gaccccttgt cctgacctgt tctcggcacc ttaaattatt   1200
agaccccggg gcagtcaggt gctccggaca cccgaaggca ataaaacagg agccgtgaaa  1260
aaaaaaaaaa aaaaaaaaaa aaaaaaaaaa aaaaaaaaaa aaaaaaaaaa aaaaaaaaaa 1320
a                                                                   1321
```

<210> SEQ ID NO 49
<211> LENGTH: 495
<212> TYPE: DNA
<213> ORGANISM: Homo sapiens

<400> SEQUENCE: 49

```
atggtggagg tgcccaggca ccaccctgt tgtctgctca tggccttggg gtgggtccta      60
ccgagctggg gaagcctggg ggccgtaggg agcccagagt cagcctggag gaggtggcgc    120
tttggtgagt ttggaaggca agcaggggtg agctgcaggg ggccaggaaa gggtgactgt    180
gactctggga gcagccgtgc caaggccctg ggactggagg ggcttggcca gcctcaaggc   240
cttactccag cccactgcac tctcagattc cagctccctg gggcaggtga gatggccgag  300
ccaggtcctt ggatgatctc tgttcctgtt ccctcttcc caggaagcgc cgcggagcca    360
tcaacagcaa gcagctcacc tacctggaga ataccggcc caaacagagg ctgcggttca   420
aagacccaca cacgcacaag acccggtgct gcgttatgta gctcaggacc ttggctgggc  480
ctggtcgtca tgtag                                                     495
```

<210> SEQ ID NO 50
<211> LENGTH: 1329
<212> TYPE: DNA
<213> ORGANISM: Homo sapiens

<400> SEQUENCE: 50

```
tgactatcca gctctgagag acggagtttg gagttgccc gctttacttt ggttgggttg      60 ggggggggcgg cgggctgttt tgttccttt cttttttaag agttgggttt tctttttaa     120 ttatccaaac agtgggcagc ttcctccccc acacccaagt atttgcacaa tatttgtgcg    180
gggtatgggg gtgggttttt aaatctcgtt tctcttggac aagcacaggg atctcgttct    240
cctcattttt tgggggtgtg tggggacttc tcaggtcgtg tccccagcct tctctgcagt    300
cccttctgcc ctgccgggcc cgtcgggagg cgccatggct cggatgaacc gcccggcccc   360
ggtggaggtg agctacaaac acatgcgctt cctcatcacc cacaacccca ccaacgccac    420
```

```
gctcagcacc ttcattgagg acctgaagaa gtacggggct accactgtgg tgcgtgtgtg      480
tgaagtgacc tatgacaaaa cgccgctgga aaggatggc atcaccgttg tggactggcc       540
gtttgacgat ggggcgcccc cgcccggcaa ggtagtggaa gactggctga gcctggtgaa      600
ggccaagttc tgtgaggccc ccggcagctg cgtggctgtg cactgcgtgg cgggcctggg      660
ccggaagcgc gcggagcca tcaacagcaa gcagctcacc tacctggaga ataccggcc        720
caaacagagg ctgcggttca aagacccaca cacgcacaag acccggtgct gcgttatgta     780
gctcaggacc ttggctgggc ctggtcgtca tgtaggtcag gaccttggct ggacctggag      840
gccctgccca gccctgctct gcccagccca gcagggggctc caggccttgg ctggccccac   900
atcgccttt cctccccgac acctccgtgc acttgtgtcc gaggagcgag gagcccctcg       960
ggccctgggt ggcctctggg ccctttctcc tgtctccgcc actccctctg gcggcgctgg     1020
ccgtggctct gtctctctga ggtgggtcgg gcgccctctg cccgccccct cccacaccag    1080
ccaggctggt ctcctctagc ctgtttgttg tggggtgggg gtatattttg taaccactgg    1140
gcccccagcc cctcttttgc gaccccttgt cctgacctgt tctcggcacc ttaaattatt   1200
agacccccggg gcagtcaggt gctccggaca cccgaaggca ataaaacagg agccgtgaaa  1260
aaaaaaaaaa aaaaaaaaaa aaaaaaaaaa aaaaaaaaaa aaaaaaaaaa aaaaaaaaaa   1320
accctcggg                                                            1329

<210> SEQ ID NO 51
<211> LENGTH: 1396
<212> TYPE: DNA
<213> ORGANISM: Homo sapiens

<400> SEQUENCE: 51
tgactatcca gctctgagag acgggagttt ggagttgccc gctttacttt ggttgggttg      60
ggggggggcgg cgggctgttt tgttcctttt ctttttttaag agttgggttt tctttttttaa  120
ttatccaaac agtgggcagc ttcctccccc acacccaagt attttgcacaa tatttgtgcg   180
gggtatgggg gtgggtttttt aaatctcgtt tctcttggac aagcacaggg atctcgttct   240
cctcattttt tggggtgtg tggggacttc tcaggtcgtg tccccagcct tctctgcagt     300
cccttctgcc ctgccgggcc cgtcgggagg cgccatggct cggatgaacc gcccggcccc   360
ggtggaggtg agctacaaac acatgcgctt cctcatcacc cacaaccccca ccaacgccac   420
gctcagcacc ttcattgagg acctgaagaa gtacggggct accactgtgg tgcgtgtgtg    480
tgaagtgacc tatgacaaaa cgccgctgga aaggatggc atcaccgttg tggactggcc    540
gtttgacgat ggggcgcccc cgcccggcaa ggtagtggaa gactggctga gcctggtgaa   600
ggccaagttc tgtgaggccc ccggcagctg cgtggctgtg cactgcgtgg cgggcctggg   660
ccgggctcca gtccttgtgg cgctggcgct tattgagagc gggatgaagt acgaggacgc   720
catccagttc atccgccaga agcgccgcgg agccatcaac agcaagcagc tcacctacct   780
ggagaaatac cggcccaaac agaggctgcg gttcaaagac ccacacacgc acaagacccg   840
gtgctgcgtt atgtagctca ggaccttggc tgggcctggt cgtcatgtag gtcaggacct  900
tggctggacc tggaggccct gcccagccct gctctgccca gccagcagg ggctccaggc   960
cttggctggc cccacatcgc cttttcctcc ccgacacctc cgtgcacttg tgtccgagga  1020
gcgaggagcc cctcgggccc tgggtggcct ctgggccctt tctcctgtct ccgccactcc  1080
ctctggcggc gctggccgtg gctctgtctc tctgaggtgg gtcgggcgcc ctctgcccgc  1140
cccctcccac accagccagg ctggtctcct ctagcctgtt tgttgtgggg tgggggtata  1200
```

```
tttttgtaacc actgggcccc cagcccctct tttgcgaccc cttgtcctga cctgttctcg   1260
gcaccttaaa ttattagacc ccggggcagt caggtgctcc ggacacccga aggcaataaa   1320
acaggagccg tgaaaaaaaa aaaaaaaaaa aaaaaaaaaa aaaaaaaaaa aaaaaaaaaa   1380
aaaaaaaaaa aaaaaa                                                   1396

<210> SEQ ID NO 52
<211> LENGTH: 849
<212> TYPE: DNA
<213> ORGANISM: Homo sapiens

<400> SEQUENCE: 52
gtgcgcgagg gcgcgcgcgt cccgagccct ccacccgtcg tgccggcgcc gcccggaccg     60
ccagatgctg tgtgctgtgg acccacctgg ggttcatgga gtgggccacg gggcccagcc    120
ctaagcactg ctgcgcccag ggtcgccgcg cctcctgctg aggggtcccc gtgccactgg    180
ctctcaccat tgccctcgcc tgccgatggc ctctgctgcc cagcctgggg ccagctctac    240
cgcctgagcc ccctgcccca ctccaggact caccgtaccc cgatggggta acgtgacaca    300
ggccccacac gtcagaggcc gctgtcccca cggccactgc ccgtgacccc tggcccaagg    360
cagctggagt tggttcagtt caagttcatt cttcctctgg cccttggggg cttggggccc    420
acctctgagt gaaggggggct gtctgcccat ccaccaatgt ggagagggcg ccccggtgt    480 ggggtccagc tctggacact gcttggcggc cgggttcact ttgagttttt aagttttctt    540
tgctgagctt ttttggttgt ctttttatt ttttgcctct ttatgactat ccagctctga    600
gagacgggag tttggagttg cccgctttac tttggttggg ttggggggg cggcgggctg     660 ttttgttcct tttctttttt aagagttggg ttttcttttt taattatcca aacagtgggc    720
agcttcctcc cccacaccca agtatttgca caatatttgt gcggggtatg ggggtgggtt    780
tttaaatctc gtttctcttg gacaagcaca gggatctcgt tctcctcatt ttttgggggt    840
gtgtgggga                                                            849

<210> SEQ ID NO 53
<211> LENGTH: 168
<212> TYPE: DNA
<213> ORGANISM: Homo sapiens

<400> SEQUENCE: 53
tgtgaggccc ccggcagctg cgtggctgtg cactgcgtgg cgggcctggg ccgggctcca     60
gtccttgtgg cgctggccct tattgagagc gggatgaagt acgaggacgc catccagttc    120
atccgccaga agcgccgcgg agccatcaac agcaagcagc tcacctac                 168

<210> SEQ ID NO 54
<211> LENGTH: 963
<212> TYPE: DNA
<213> ORGANISM: Homo sapiens

<400> SEQUENCE: 54 ctttttttaat tatccaaaca gtgggcagct tcctcccccca cacccaagta tttgcacaat     60
atttgtgcgg ggtatggggg tgggttttta aatctcgttt ctcttggaca agcacaggga    120
tctcgttctc ctcatttttt gggggtgtgt ggggacttct caggtcgtgt cccccagcctt    180 ctctgcagtc ccttctgccc tgccgggccc gtcgggaggc gccatggctc ggatgaaccg    240
cccggccccg gtggaggtga gctacaaaca catgcgcttc ctcatcaccc acaaccccac    300
```

| | | |
|---|---|---|
| caacgccacg ctcagcacct tcattgagga cctgaagaag tacgaggacg ccatccagtt | 360 | |
| catccgccag aagcgccgcg gagccatcaa cagcaagcag ctcacctacc tggagaaata | 420 | |
| ccggcccaaa cagaggctgc ggttcaaaga cccacacacg cacaagaccc ggtgctgcgt | 480 | |
| tatgtagctc aggaccttgg ctgggcctgg tcgtcatgta ggtcaggacc ttggctggac | 540 | |
| ctggaggccc tgcccagccc tgctctgccc agcccagcag gggctccagg ccttggctgg | 600 | |
| ccccacatcg ccttttcctc ccgacacct ccgtgcactt gtgtccgagg agcgaggagc | 660 | |
| ccctcgggcc ctgggtggcc tctgggccct ttcttctgtc ccgccactc cctctggcgg | 720 | |
| cgctggccgt ggctctgtct ctctgaggtg ggtcgggcgc cctctgcccg cccctccca | 780 | |
| caccagccag gctggtctcc tctagcctgt ttgttgtggg gtgggggtat attttgtaac | 840 | |
| cactgggccc ccagcccctc ttttgcgacc ccttgtcctg acctgttctc ggcaccttaa | 900 | |
| attattagac cccggggcag tcaggtgctc cggacaccg aaggcaataa aacaggagcc | 960 | |
| gtg | 963 | |

<210> SEQ ID NO 55
<211> LENGTH: 2291
<212> TYPE: DNA
<213> ORGANISM: Mus musculus

<400> SEQUENCE: 55

| | | |
|---|---|---|
| gacgcgcgcc ggtctgagtg tttgctcccg gcggggccg cgccccgcgg cagcccctgt | 60 | |
| gtgaacccgg ccggtggttg ccacgtgcag ggccggagcc gcagggaggc caggagtggg | 120 | |
| gactcagcca gctgtttttt cggtgtggcg accagacctg atgggtgaaa agggtgactc | 180 | |
| tgctcccatt tctaggggtg cggaagattc cctcaacatc tgcccggttt tcatcttccc | 240 | |
| taagagatcc ctatctagga tttggttcgc ctcaatttcc ttctctgcat agcttggggg | 300 | |
| cataggaccc catatccttt cttgcctccc gcatgaatgt cagtgggtca cctttgaagg | 360 | |
| ctgggcatta agtcttgggt cccttagaga cccgagtcct ggcttaggca ctctgggtca | 420 | |
| ggccagatgg gacagcacct cactgtccat ggggtcctgc cgtagcctgt ccacatgcag | 480 | |
| ccggcttaag caggcgactc ctggtaggga gctgcaggca tggctggact ggatgccatg | 540 | |
| cttagccccc aaggcaggca gagtgaccat ccctctgacc ctatcagtga ggggcagagt | 600 | |
| ggattccagg ccggttgtca cagtgtgctg tgtccattgg attgtgcctt ctgaagacca | 660 | |
| gggtgggatt gatggagaag ccccaggagg gcagctctga ctactgccgt tcccaacacc | 720 | |
| gtgggtgctg ccgctgagga gacctgtaca cctctggccc tcaccattgt ccttgcctcc | 780 | |
| caatggcctc tgctgccagg ccggaggcca gcactgctgc ctgagcccgc tgcccctctt | 840 | |
| caggacttgc cgttccctga tggggtaacg tgacagaccg gatcagaggc tgcctgccca | 900 | |
| ccacggccca gggccgctag agtttggttg agttcaagtt cattttccct ttggtcctga | 960 | |
| cttctggggc caactctga ccaaagggga cactcctccg tccacccatg cagagagggt | 1020 | |
| gtctccagcg acgccccat agaggacact gctctgcgc cggagtcacc aacccgaagt | 1080 | |
| tctctctgct cagttttttt tggttgttgt tatttttatt ttgactcctt gtaacttctc | 1140 | |
| cactctgagg acaggactt tggcgctgcc cgtcttgctg cggggtgggg ggagaagtgt | 1200 | |
| gcttgtttct tttcttttt agaattggtt ttttggaat tatccgccac gaggcagctt | 1260 | |
| cctctccctc tcccaggtat ttgcacaata tttgtgcggg gcgtaggggc gaggttttaa | 1320 | |
| gaagtctttt ctttgtggac aagcacgggg atctcactgg acttggtgtg gggggctggg | 1380 | |
| ggacccccg tgcagccctt gctggctagt cccctctggg tccccggagg aggcatggcc | 1440 | |

```
cgcatgaacc ggcctgcgcc tgtggaggtg agctaccggc acatgcgctt cctcatcacc      1500
cacaacccca gcaatgccac cctcagcacg ttcatcgagg acctgaagaa gtacggggct      1560
accactgtgg tgcgcgtgtg tgaagtgacc tatgacaaga ccccctgga aaggacggc       1620 atcactgttg tggactggcc cttttgatgat ggagcgcccc ctcctggcaa agtggtagag     1680
gactggctga gcctgctgaa ggccaagttc tacaatgacc cgggaagctg cgtagctgtg     1740
cactgtgtgg cgggcctggg aagggcccca gtgctcgtgg ctctcgccct catcgagagc     1800
gggatgaagt acgaggacgc catccagttc atccgacaga gcgccgtgg ggccatcaac      1860 agcaagcagc tcacctacct ggagaagtac cggcctaagc agagactgag gttcaaagac     1920
ccacacacgc acaagaccag atgctgcgtc atgtagctca ggccctggcc ctgtacctca     1980
ttacatctgt gtctaaggag tccaacggct atgtgcgtcc ctgctctgtc ccatctgta      2040 cccacggctg tctttctgaa gctgtccctg gaccctctgc cagtcctgtc caacccctgt     2100
ccctcacccc ccactgccca ggccttcccc ctggcctgtg tattgcaggt gggagttttt     2160
aaaccactgg gcccaatgcc tcagcggcgt ggccctcacc ctaacctttt ccagcacct     2220 ttgttaccag gtgctctgga ctctcaaggc aataaatcag gagctgtgaa acaaaaaaaa     2280
aaaaaaaaaa a                                                         2291

<210> SEQ ID NO 56
<211> LENGTH: 296
<212> TYPE: DNA
<213> ORGANISM: Mus musculus
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 56
cggcctaagc agagactgag gttcaaagac ccacacacgc acaagaccag atgctgcgtc      60
atgtagctca ggccctggcc ctgtacctca ttanatctgt gtctaaggag tccaacggct     120
atgtgcgtcc ctgctctgtc ccatctgta cccacggctg tctttctgaa gctgtccctg     180
gaccctctgc cagtcctgtc caaccctgt ccctcacccc ccactgccca ggccttcccc     240
ctggcctgtg tattgcaggt gggaggtttt aaaccactgg gcccaatgnc tcagcg         296

<210> SEQ ID NO 57
<211> LENGTH: 522
<212> TYPE: DNA
<213> ORGANISM: Mus musculus

<400> SEQUENCE: 57
atggcccgca tgaaccggcc tgcgcctgtg gaggtgagct accggcacat gcgcttcctc      60
atcacccaca accccagcaa tgccaccctc agcacgttca tcgaggacct gaagaagtac     120
ggggctacca ctgtggtgcg cgtgcgtgaa gtgacctatg acaagacccc cctggagaag     180
gacggcatca ctgttgtgga ctggcccttt gatgatggag cgcccctcc tggcaaagtg      240 gtagaggact ggctgagcct gctgaaggcc aagttctaca atgacccggg aagctgcgta     300
gctgtgcact gtgtggcggg cctgggaagg gccccagtgc tcgtggctct cgccctcatc     360
gagagcggga tgaagtacga ggacgccatc cagttcatcc gacagaagcg ccgtggggcc     420
```

| | |
|---|---:|
| atcaacagca agcagctcac ctacctggag aagtaccggc ctaagcagag actgaggttc | 480 |
| aaagacccac acacgcacaa gaccagatgc tgcgtcatgt ag | 522 |

<210> SEQ ID NO 58
<211> LENGTH: 6461
<212> TYPE: DNA
<213> ORGANISM: Mus musculus

<400> SEQUENCE: 58

| | |
|---|---:|
| gagtctggga gtggtggctc ttaaggtgaa gtgtgggcta gtgcggctga gcacacagta | 60 |
| gctgttcagt gtgcgcatat gaagctggag agctggaagg gttcctcctg gcttgtggcc | 120 |
| cctctgcaga aggaggtctc ctacccagca ggatgcagag gggatggcag gcgggtccgc | 180 |
| ggtggtcctc tcccttcctc cttcctcttc ctctgctggc cgcgcctttg tttgcgtgct | 240 |
| atctttaggc agcaggtgcg ggagccgctg tgagtcgggt cgcccgccgg tcaccgcccc | 300 |
| cccacgtgac gccgggcgct ataaatagct gggcggcggg cggcgggcat ccgcccggag | 360 |
| ccggcgccgc tgcggagggc gcgcacgggt cccggcccgg ccggccggcg catggaggcg | 420 |
| gccgcacgcc tgcgggcgcg ggtgagccgg gctgcgggcg gcgggaccc ggcctcgagg | 480 |
| acgctcccga accctaaccc tactgggatg ggccctgcac gggatggcgg ctccctggcg | 540 |
| ggctgggtgg gaagtcccgc tgaggtcggg gagctgtgtg ccctccccac gccccactac | 600 |
| gggtccttgg ggtccccagc ccatccacgg agcagtcttg cctgtcttga cagcacagag | 660 |
| tcctgaactg tgacccctga ctcctaagtg tcacacaggg tcccatttag gtcccttctg | 720 |
| aagctagatg cactcccacc ccaccacttg agggtgtggc ttctgactac ctctgtgtct | 780 |
| ttttttcccc cctggggttc aagtgttccc gattactaga ctcgatgttg agaaaacctg | 840 |
| ggtgtctgga cggccggagc tggccagggt ccagagaagg tccttccacg cccctctgtc | 900 |
| ccatgtcctc ctctggcaaa cagggacaaa atgggtctt gaaaaacatg ccggtctggg | 960 |
| agcagctgag ggcttaagat actgctagag gaggctgggc ggggatagag aagggcccag | 1020 |
| gtcatagtag ggtccttaag caccaggggt ggggagggtg tggtggcttg actgagtgcc | 1080 |
| tgttgaggca aggtgagctc agcttctgtt cacacctaga gctgctggga taggggtgta | 1140 |
| ggtagccggt gggcccacaa gccttggctc aggcctgcta gaatgcagta gaggtagacc | 1200 |
| cccccacccc cccaccttgt tctctggtct tcttaacccc atagaagtga tgtgtccacc | 1260 |
| tgggcatggt ggcagatgcc ttaagtccta gcactcagga ggcccagcca ggtggatctc | 1320 |
| tgtgagtctg aggtcagcct ggtctacaaa gtgcggtcca ggaggtaaga cagggacaga | 1380 |
| gaaacactgt ctccaaaggg ggtgagcgga gtgatgtgtc ggcagagggg ctcctttttg | 1440 |
| ggagggcagc caccatgtgg ttgagcctgg gtagactcag gcatgctgtg ggcatgcccc | 1500 |
| tttttgccca cacttagggg tgtggcccag actgcagtga actgtgcatg tattataaga | 1560 |
| tgcagttcag cctggtgtca cctatacatc tggacccctg gctccatccc ctcaggcctg | 1620 |
| gggggagcat gataggcggt tcaggcttcc ttttctcaga tgttgcttct gttgcccctg | 1680 |
| gaatcttaca acccagcccc aaccctgca agtagccagt aggtgcagtt agctctacag | 1740 |
| gagcctgcca gtgttctctg actccctggg gccttctctt cttttctcct gcacacacaa | 1800 |
| gggcattgca gtgtgcacac atgggatgct catctcagta ggcccgggtg tttgtgtcat | 1860 |
| aacatgagag aaggctctcc ttgcttatag cgggctagtc gtggctccgc atgcacaggg | 1920 |
| cgttgagaac ctggcctgcc caagcaggca caggactcct ttctgccctc ctccaagggg | 1980 |
| cccctctatc ttagccctt cagaatggtg gcagggacta gctgtgagcc atggcactga | 2040 |

```
cttggagtgg agtgctgagc tgttctcagg tgtaggaggt agcgagggag gattctgtgc   2100
tatctagtac agtcgagcct tggacggtgg ggcctgtgcc cgaagcttgg ggccagagac   2160
cagggtctta tgctggcctg aggctccaag ggcctggttt gcttggtggg cagctggaga   2220
agggagagct ggggacgaga cagagaggta agaggtacgg gcagaactct tccagatgcg   2280
atccagaagg ggccttccag aaagatgaat gctgggtggg ggatgggctg agtccagggg   2340
ctcaggctct actaactact ggatcatagc ccaagggact gtggtgccct cttttcaac    2400 cttcatcgtg ttgatgggaa acgggtccag agaggccagt gacatgccca aggtctccca   2460
ggccgtccag ggggtggcag ggtgttagct agctgttctt tggggtcctt gcagaggaga   2520
aggtggaggc cgatgtcctc cagtagtgcc cttccctgg gtcctgtcaa cggtgtgact    2580
cccttcctgg ccacctgtgc tgtcacctcc ttggcatgag cctggcagct ggcccttgg    2640 cctgtggtct cttgcaaagc agaacgtctt gtttacctct agtgcctggc aagtccccgt   2700
aagttgtggc tgtgggtaga gatttcagaa agcctgaggg gcagcaattg aggccactca   2760
gccccttgtc cctctggcag tacccactgt ccctgagacc tgcccttgca gaacgatctg   2820
agcttaatat tgtgctgtgg ctagcagtcc caagagaggg accactgccc ttatgggctg   2880
tgagatgggg gacctggctt ctgctgctgt aggtgtactc tgcttgtggg gttcatatgc   2940
tcctggggtg agccctgata ccctcttcac cctatctcgg tggctatgta tggctctctt   3000
gtcaccacag gggcctgggg tagcccaggc aggagttgtc tgtctgtttc tgggtttcac   3060
gtggagaatc tgaggacctc ccatttcttt ctcccctccc atagattgtg ccttctgaag   3120
accagggtgg gattgatgga gaagcccag gagggcagct ctgactactg ccgttcccaa    3180
caccgtgggt gctgccgctg aggagacctg tacacctctg gccctcacca ttgtccttgc   3240
ctcccaatgg cctctgctgc caggccggag gccagcactg ctgcctgagc ccgctgcccc   3300
tcttcaggac ttgccgttcc ctgatggggt aacgtgacag accggatcag aggctgcctg   3360
cccaccacgg cccagggccg ctagagtttg gttgagttca agttcatttt ccctttggtc   3420
ctgacttctg ggcccaact ctgaccaaag gggacactcc tccgtccacc catgcagaga    3480
gggtgtctcc agcgacggcc ccatagagga cactgctctg cggccggagt caccaacccg   3540
aagttctctc tgctcagttt ttttggttg ttgttatttt tattttgact ccttgtaact    3600
tctccactct gagggacagg actttggcgc tgcccgtctt gctgcggggt ggggggagaa   3660
gtgtgcttgt ttctttctt ttttagaatt ggttttttg gaattatccg ccacgaggca    3720
gcttcctctc cctctcccag gtatttgcac aatatttgtg cggggcgtag gggcgaggtt   3780
ttaagaagtc ttttctttgt ggacaagcac ggggatctca ctggacttgg tgtgggggc    3840 tgggggaccc cccgtgcagc ccttgctggc tagtcccctc tgggtccccg gaggaggcat   3900
ggcccgcatg aaccggcctg cgcctgtgga ggtgagctac cggcacatgc gcttcctcat   3960
cacccacaac cccagcaatg ccaccctcag cacgttcatc gaggtgagtg ggccttcagg   4020
gccgggtggg tgtcctgcac agctcagggt gcgatgggtg ctcacgatcc gatggctttc   4080
ctggagggct gtcagcatcc gtgcttcggg gaatggacat tgtctagtct gtggctgtcc   4140
agaccctggg cgaccttagc ctctgcagag acagagcaaa taagaggcc gaggagggag    4200 gggctgacag ggaaacggct cagagacagg cagattggaa gaaggactgg gagagctacc   4260
ctgtggctag gccagcccac aagctcaggt gttaggaagc cttagggaac agagagtgac   4320
cattgcagtc tgtggaggtg acgtgtggag agtccacaag tgtctgtggt ctgtggccac   4380
```

```
cctcacttca cccctagatg tgaccaggta ttttttttctg agcctgggtg ggggaatata    4440
gctgggtggg gtgggggagt gctgtcagca tggcctcact ggggaccctg ggcagggctc    4500
cttactgcag atctggagct gcttgcagag tctgcatctg gatgctgggc cattggtgga    4560
atggactttt gtggctttat gttcttagtc cttttctctg tggcacgagc taagccccat    4620
gggctcgtgg gcatcaaaaa gggacgaccg catagaggaa gacaatggac acccgaagac    4680
tgccgactct cagttgagaa gctttgtgac agtagaggct gatgaagggc taggaaaaca    4740
aaacaagaca aaaccaaaa caaccaaaa caaaccacca cgagtgacca ggacaggggc      4800
tcgctcggtg tgtgaccaga atgagggttt cgcaaccata gtcaaggctc actgtatcac    4860
cagggtcagg gaccacatgg caaacatgat ctgatcaggg ttcagggtgt gagcagagtt    4920
gggcctgaag cctgagctgg cttttctcctt gatggactct gcagcacccc atggtctctg    4980
aggtggaccc cctccctcgt tttctgcttt ttgtttttt ttgcactctc aaaatagttg      5040
ggtcttggcc ttgctgtgtc tgttgttcct atcacatggc cagccagacc gtcatccctc    5100
accactccca aaatatccac tgggggcagg taggtggggg ccggccctgc ttgtggctgt    5160
gggtataaat actccacatt ggctgtgagc tgagtgaact tttctctgga ggaatggggc    5220
ttcccccgtg gtatttgagt ggtgccaccc agatggcgct ggggttccaa ctcctggggt    5280
ctacttgctg gacactcggg aaggactctg tgggacccac ccatgaagct caggaagggg   5340
tctatctgag gcctaggcca ccctgccggg gacctagagc tttatctgga gaaccaggct    5400
ttgcagtcaa gacccttgt cctaggtgct gcaagggtga gagggacagg aggggcttga     5460
atcacagcag ctgagctgtg tgtggcacag gtgggacagg gacaagtgac cccgaagcat    5520
caccaggcta ccttgttagt cgctaagcat ccaagccccc ctgttgattt atgaaatctg    5580
cttgtctcaa gggaagcagc ttgagggac actgctctgt ttaggagttc tagagggtag    5640
gcctgtgggg actcagcatg ggtagaggcc tgggctggag gccgttctgg gttctgaact    5700
gtcccccccc catctctctc tttctgtccc aggacctgaa gaagtacggg gctaccactg    5760
tggtgcgcgt gtgtgaagtg acctatgaca agaccccccct ggagaaggac ggcatcactg   5820
ttgtggactg gccctttgat gatggagcgc cccctcctgg caaagtggta gaggactggc    5880
tgagcctgct gaaggccaag ttctacaatg acccgggaag ctgcgtagct gtgcactgtg    5940
tggcgggcct gggaagggcc ccagtgctcg tggctctcgc cctcatcgag agcgggatga    6000
agtacgagga cgccatccag ttcatccgac agaagcgccg tgggccatc aacagcaagc     6060
agctcaccta cctggagaag taccggccta agcagagact gaggttcaaa gacccacaca    6120
cgcacaagac cagatgctgc gtcatgtagc tcaggccctg gccctgtacc tcattacatc    6180
ggtgtctaag gagtccaacg gctatgtgcg tccctgctct gtccccatcc gtacccacgg    6240
ctgtctttct gaagctgtcc ctggaccctc tgccagtcct gtccaacccc gtccctcac     6300
cccccactgc ccaggccttc ccctggcct gtgtattgca ggtgggagtt tttaaaccac     6360
tgggcccaat gcctcagcgg cgtggccctc accctaacct ttttccagca cctttgttac    6420
caggtgctct ggactctcaa ggcaataaat caggagctgt g                        6461
```

<210> SEQ ID NO 59
<211> LENGTH: 1722
<212> TYPE: DNA
<213> ORGANISM: Mus musculus

<400> SEQUENCE: 59

```
gttccgcccg gagccggcgc cgctgcggag ggcgcgcacg ggtcccggcc cggccggccg      60
```

| | |
|---|---|
| gcgcatggag gcggccgcac gcctgcgggc gcggattgtg ccttctgaag accagggtgg | 120 |
| gattgatgga gaagccccag gagggcagct ctgactactg ccgttcccaa caccgtgggt | 180 |
| gctgccgctg aggagacctg tacacctctg ccctcacca ttgtccttgc ctcccaatgg | 240 |
| cctctgctgc caggccggag ccagcactg ctgcctgagc ccgctgcccc tcttcaggac | 300 |
| ttgccgttcc ctgatggggt aacgtgacag accggatcag aggctgcctg cccaccacgg | 360 |
| cccagggccg ctagagtttg gttgagttca agttcatttt ccctttggtc ctgacttctg | 420 |
| gggcccaact ctgaccaaag gggacactcc tccgtccacc catgcagaga gggtgtctcc | 480 |
| agcgacggcc ccatagagga cactgctctg cggccggagt caccaacccg aagttctctc | 540 |
| tgctcagttt ttttggttg ttgttatttt tattttgact ccttgtaact tctccactct | 600 |
| gagggacagg actttggcgc tgcccgtctt gctgcgggt gggggagaa gtgtgcttgt | 660 |
| ttcttttctt ttttagaatt gggttttttg gaattatccg ccacgaggca gcttcctctc | 720 |
| cctctcccag gtatttgcac aatatttgtg cggggcgtag gggcgaggtt ttaagaagtc | 780 |
| ttttctttgt ggacaagcac ggggatctca ctggacttgg tgtgggggc tgggggaccc | 840 |
| cccgtgcagc ccttgctggc tagtcccctc tgggtccccg gaggaggcat ggcccgcatg | 900 |
| aaccggcctg cgcctgtgga ggtgagctac cggcacatgc gcttcctcat cacccacaac | 960 |
| cccagcaatg ccaccctcag cacgttcatc gaggacctga agaagtacgg gctaccact | 1020 |
| gtggtgcgcg tgtgtgaagt gacctatgac aagaccccc tggagaagga cggcatcact | 1080 |
| gttgtggact ggccctttga tgatggagcg ccccctcctg gcaaagtggt agaggactgg | 1140 |
| ctgagcctgc tgaaggccaa gttctacaat gacccgggaa gctgcgtagc tgtgcactgt | 1200 |
| gtggcgggcc tgggaagggc cccagtgctc gtggctctcg ccctcatcga gagcgggatg | 1260 |
| aagtacgagg acgccatcca gttcatccga cagaagcgcc gtggggccat caacagcaag | 1320 |
| cagctcacct acctggagaa gtaccggcct aagcagagac tgaggttcaa agacccacac | 1380 |
| acgcacaaga ccagatgctg cgtcatgtag ctcaggccct ggccctgtac ctcattacat | 1440 |
| ctgtgtctaa ggagtccaac ggctatgtgc gtccctgctc tgtccccatc tgtacccacg | 1500 |
| gctgtctttc tgaagctgtc cctggaccct ctgccagtcc tgtccaaccc ctgtccctca | 1560 |
| cccccccactg cccaggcctt cccctggcc tgtgtattgc aggtgggagt ttttaaacca | 1620 |
| ctgggcccaa tgcctcagcg gcgtggccct caccctaacc tttttccagc accttttgtta | 1680 |
| ccaggtgctc tggactctca aggcaataaa tcaggagctg tg | 1722 |

<210> SEQ ID NO 60
<211> LENGTH: 1720
<212> TYPE: DNA
<213> ORGANISM: Mus musculus

<400> SEQUENCE: 60

| | |
|---|---|
| tccgcccgga gccggcgccg ctgcggaggg cgcgcacggg tcccggcccg gccggccggc | 60 |
| gcatggaggc ggccgcacgc ctgcgggcgc ggattgtgcc ttctgaagac cagggtggga | 120 |
| ttgatggaga agccccagga gggcagctct gactactgcc gttcccaaca ccgtgggtgc | 180 |
| tgccgctgag gagacctgta cacctctggc cctcaccatt gtccttgcct cccaatggcc | 240 |
| tctgctgcca ggccggaggc cagcactgct gcctgagccc gctgcccctc ttcaggactt | 300 |
| gccgttccct gatggggtaa cgtgacagac cggatcagag gctgcctgcc accacggcc | 360 |
| cagggccgct agagtttggt tgagttcaag ttcatttcc ctttggtcct gacttctggg | 420 |

```
gcccaactct gaccaaaggg gacactcctc cgtccaccca tgcagagagg gtgtctccag    480
cgacggcccc atagaggaca ctgctctgcg gccggagtca ccaacccgaa gttctctctg    540
ctcagttttt tttggttgtt gttatttta ttttgactcc ttgtaacttc tccactctga     600
gggacaggac tttggcgctg cccgtcttgc tgcggggtgg ggggagaagt gtgcttgttt    660
cttttctttt ttagaattgg ttttttggga attatccgcc acgaggcagc ttcctctccc    720
tctcccaggt atttgcacaa tatttgtgcg gggcgtaggg gcgaggtttt aagaagtctt    780
ttctttgtgg acaagcacgg ggatctcact ggacttggtg tgggggctg ggggaccccc     840
cgtgcagccc ttgctggcta gtcccctctg ggtccccgga ggaggcatgg cccgcatgaa    900
ccggcctgcg cctgtggagg tgagctaccg gcacatgcgc ttcctcatca cccacaaccc    960
cagcaatgcc accctcagca cgttcatcga ggacctgaag aagtacgggg ctaccactgt   1020
ggtgcgcgtg tgtgaagtga cctatgacaa gaccccctg gagaaggacg gcatcactgt    1080
tgtggactgg ccctttgatg atggagcgcc cctcctggc aaagtggtag aggactggct    1140
gagcctgctg aaggccaagt tctacaatga cccgggaagc tgcgtagctg tgcactgtgt   1200
ggcgggcctg ggaagggccc cagtgctcgt ggctctcgcc ctcatcgaga gcgggatgaa   1260
gtacgaggac gccatccagt tcatccgaca gaagcgccgt ggggccatca acagcaagca   1320
gctcacctac ctggagaagt accggcctaa gcagagactg aggttcaaag acccacacac   1380
gcacaagacc agatgctgcg tcatgtagct caggccctgg ccctgtacct cattacatct   1440
gtgtctaagg agtccaacgg ctatgtgcgt ccctgctctg tccccatctg tacccacggc   1500
tgtctttctg aagctgtccc tggaccctct gccagtcctg tccaacccct gtccctcacc   1560
ccccactgcc caggccttcc ccctggcctg tgtattgcag gtgggagttt ttaaaccact   1620
gggcccaatg cctcagcggc gtggccctca ccctaacctt tttccagcac ctttgttacc   1680
aggtgctctg gactctcaag gcaataaatc aggagctgtg                         1720

<210> SEQ ID NO 61
<211> LENGTH: 817
<212> TYPE: DNA
<213> ORGANISM: Mus musculus

<400> SEQUENCE: 61
tagaattggt ttttttggaa ttatccgcca cgaggcagct tcctctccct ctcccaggta     60
tttgcacaat atttgtgcgg ggcgtagggg cgaggtttta agaagtcttt tctttgtgga    120
caagcacggg gatctcactg gacttggtgt gggggctgg gggaccccc gtgcagccct      180
tgctggctag tcccctctgg gtccccggag gaggcatggc ccgcatgaac cggcctgcgc    240
ctgtggaggt gagctaccgg cacatgcgct tcctcatcac ccacaacccc agcaatgcca    300
ccctcagcac gttcatcgag gacctgaaga agtacggggc taccactgtg gtgcgcgtgt    360
gtgaagtgac ctatgacaag accccctgg agaaggacgg catcactgtt gtggactggc     420
cctttgatga tggagcgccc ctcctggca aagtggtaga ggactggctg agcctgctga     480
aggccaagtt ctacaatgac ccgggaagct gcgtacttgt gcactgtgtg gcgggcctgg    540
gaagggcccc agtgctcgtg gctctcgccc tcatcgagag cgggatgaag tacgaggacg    600
ccatccagtt catccgacag aagcgccgtg gggccatcaa cagcaagcag ctcacctacc    660
tggagaagta ccggcctaag cagagactga ggttcaaaga cccacacacg cacaagacca    720
gatgctgcgt catgtagctc aggccctggc cgtgtacctc attacatctg tgtctaagga    780
gtccacggct atgtgcgtcc tgctctgtcc catctgt                             817
```

<210> SEQ ID NO 62
<211> LENGTH: 3222
<212> TYPE: DNA
<213> ORGANISM: Mus musculus

<400> SEQUENCE: 62

| | | | | | |
|---|---|---|---|---|---|
| ggtcccggcc | cggccggcct | ggcgcatgga | ggcggccgca | cgcctgcggg | cgcggattgt | 60 |
| gccttctgaa | gaccagggtg | ggattgatgg | agaagcccca | ggagggcagc | tctgactact | 120 |
| gccgttccca | acaccgtggg | tgctgccgct | gaggagacct | gtacacctct | ggccctcacc | 180 |
| attgtccttg | cctcccaatg | gcctctgctg | ccaggccgga | ggcagcactg | ctgcctgagc | 240 |
| ccgctgcccc | tcttcaggac | ttgccgttcc | ctgatggggt | aacgtgacag | accggatcag | 300 |
| aggctgcctg | cccaccacgg | cccagggccg | ctagagtttg | gttgagttca | agttcatttt | 360 |
| cccttttggtc | ctgacttctg | gggcccaact | ctgaccaaag | gggacactcc | tccgtccacc | 420 |
| catgcagaga | gggtgtctcc | agcgacggcc | ccatagagga | cactgctctg | cggccggagt | 480 |
| caccaacccg | aagttctctc | tgctcagttt | ttttggttg | ttgttatttt | tattttgact | 540 |
| ccttgtaact | tctccactct | gagggacagg | actttggcgc | tgcccgtctt | gctgcggggt | 600 |
| ggggggagaa | gtgtgcttgt | ttcttttctt | ttttagaatt | ggtttttttg | gaattatccg | 660 |
| ccacgaggca | gcttcctctc | cctctcccag | gtatttgcac | aatatttgtg | cggggcgtag | 720 |
| gggcgaggtt | ttaagaagtc | ttttctttgt | ggacaagcac | ggggatctca | ctggacttgg | 780 |
| tgtgggggc | tggggaccc | cccgtgcagc | ccttgctggc | tagtcccctc | tgggtccccg | 840 |
| gaggaggcat | ggcccgcatg | aaccggcctg | cgcctgtgga | ggtgagctac | cggcacatgc | 900 |
| gcttcctcat | cacccacaac | cccagcaatg | ccaccctcag | cacgttcatc | gaggacctga | 960 |
| agaagtacgg | ggctaccact | gtggtgcgcg | tgtgtgaagt | gacctatgac | aagacccccc | 1020 |
| tggagaagga | cggcatcact | gttgtggact | ggccctttga | tgatggagcg | cccccctcctg | 1080 |
| gcaaagtggt | agaggactgg | ctgagcctgc | tgaaggccaa | gttctacaat | gacccgggaa | 1140 |
| gctgcgtagc | tgtgcactgt | gtggcgggcc | tgggaagggc | cccagtgctc | gtggctctcg | 1200 |
| ccctcatcga | gagcgggatg | aagtacgagg | acgccatcca | gttcatccga | cagaagcgcc | 1260 |
| gtggggccat | caacagcaag | cagctcacct | acctggagaa | gtaccggcct | aagcagagac | 1320 |
| tgaggttcaa | agacccacac | acgcacaaga | ccagatgctg | cgtcatgtag | ctcaggccct | 1380 |
| ggccctgtac | ctcattacat | ctgtgtctaa | ggagtccaac | ggctatgtgc | gtccctgctc | 1440 |
| tgtccccatc | tgtacccacg | gctgtctttc | tgaagctgtc | cctggaccct | ctgccagtcc | 1500 |
| tgtccaaccc | ctgtccctca | cccccactg | cccaggcctt | cccctggcc | tgtgtattgc | 1560 |
| aggtgggagt | ttttaaaacca | ctgggcccaa | tgcctcagcg | gcgtggccct | cacctaacc | 1620 |
| ttttccagc | acctttgtta | ccaggtgctc | tggactctca | aggcaataaa | tcaggagctg | 1680 |
| tggatgtgtg | tgaagagtgt | tatagagcag | gggaatagg | tgtggatccc | gggaggccat | 1740 |
| ggtctccatc | tcttctgtcc | tattgctgct | gctgctactg | ctgctgcagt | ggcgtgcctc | 1800 |
| catggcgccc | tctggtggcc | atcccttgct | ctgcctccct | gacttgttct | acaagttctt | 1860 |
| gacgcaaaaa | tcagcacagc | ttggactggt | gacggtttgt | aacattagga | ggtgagactg | 1920 |
| atcacctctg | caggacagag | taggggggtca | cttggaactt | tcagtggcct | cccaccccga | 1980 |
| ccttcatgca | accagaggtg | tgggttgcag | gtagatctga | gtgtagatgg | cctttggtga | 2040 |
| catgggtctg | cctaggacct | catcctgctt | ataagttctg | agcagtgggc | tgactcttcc | 2100 |

| cttagctgag gaaagggtat catgagggac agggctggct atatgtgtgt cttagccagg | 2160 |
| gtttttatggc tgtgaacaga caccgggacc aaggcaactc ttacaaggac aacatttagt | 2220 |
| tggggctgcc ttacaggttc agaggttcag tctgtcatca aggtgggagc atggcagcat | 2280 |
| ccatgcaggc atgggcagc tgtagctgag agctctacac cttcatctga aggctactag | 2340 |
| tggaagactg atttccaggg agctagaatg agggccttaa agcccatgcc cacagtgaca | 2400 |
| cacctactcc aacaaggtca gacctccaaa cggtgccact ccccaggcca gtcgtattta | 2460 |
| aacagtgaca atgtgtcagt gtggatgtgc tggctgtctt atagcactga catacttagg | 2520 |
| acgtgatcct caggcctttg cagacccagt cccctctgtg cccagaacag agatccaggg | 2580 |
| cgcctctcac tggtacctgc tgcctgcttg catcattccc tcttcaagtt ccacctagct | 2640 |
| ctggactagg tcccagaaac catccgggcc cacgtagact cccagcagtc cctgttcttg | 2700 |
| cctgtcctag tagggagtga caaggtgtag ccaaactcag taatggtgac cttgtgtggg | 2760 |
| ctggaaactc actaccccgg tgccatattt ccacaaagtc actggttttt gttttgttt | 2820 |
| tagtctgcca agcttttttt tttttaaaa gatttattta ttttatgtat atgaatatac | 2880 |
| tgtagctgta cagatggttg tgagccttca tgtggttgtc gggaattgaa tttaggacct | 2940 |
| ctgcttgctc tggtcaactc cgctcactcc ggttcgccaa tctctctcag tccttgctag | 3000 |
| cttcggccca agatttatt tattatacat aagtacactg ttgctgtctt cagacatacc | 3060 |
| agaagaggac gccagatctc attaccggtg gttgtgagcc accatgtggt tgctgagatt | 3120 |
| tgaactcagg actttcggaa gagccatctg accagcccca agctttttta tttttatttt | 3180 |
| ttaaatcttt aaatttaaaa aaaattatta tttgtttgct gt | 3222 |

<210> SEQ ID NO 63
<211> LENGTH: 3222
<212> TYPE: DNA
<213> ORGANISM: Mus musculus

<400> SEQUENCE: 63

| ggtcccggcc cggccggcct ggcgcatgga ggcggccgca cgcctgcggg cgcggattgt | 60 |
| gccttctgaa gaccagggtg ggattgatgg agaagcccca ggagggcagc tctgactact | 120 |
| gccgttccca acaccgtggg tgctgccgct gaggagacct gtacacctct ggccctcacc | 180 |
| attgtccttg cctcccaatg gcctctgctg ccaggccgga ggcagcactg ctgcctgagc | 240 |
| ccgctgcccc tcttcaggac ttgccgttcc ctgatggggt aacgtgacag accggatcag | 300 |
| aggctgcctg cccaccacgg cccagggccg ctagagtttg gttgagttca agttcatttt | 360 |
| cccttttggtc ctgacttctg gggcccaact ctgaccaaag gggacactcc tccgtccacc | 420 |
| catgcagaga gggtgtctcc agcgacggcc ccatagagga cactgctctg cggccggagt | 480 |
| caccaacccg aagttctctc tgctcagttt ttttttggttg ttgttatttt tattttgact | 540 |
| ccttgtaact tctccactct gagggacagg actttggcgc tgcccgtctt gctgcggggt | 600 |
| gggggagaa gtgtgcttgt ttcttttctt ttttagaatt ggttttttttg gaattatccg | 660 |
| ccacgaggca gcttcctctc cctctcccag gtatttgcac aatatttgtg cggggcgtag | 720 |
| gggcgaggtt ttaagaagtc ttttctttgt ggacaagcac ggggatctca ctggacttgg | 780 |
| tgtgggggc tggggaccc ccgtgcagc ccttgctggc tagtcccctc tgggtccccg | 840 |
| gaggaggcat ggcccgcatg aaccggcctg cgcctgtgga ggtgagctac cggcacatgc | 900 |
| gcttcctcat caccccacaac cccagcaatg ccaccctcag cacgttcatc gaggacctga | 960 |
| agaagtacgg ggctaccact gtggtgcgcg tgtgtgaagt gacctatgac aagaccccc | 1020 |

-continued

```
tggagaagga cggcatcact gttgtggact ggccctttga tgatggagcg ccccctcctg    1080
gcaaagtggt agaggactgg ctgagcctgc tgaaggccaa gttctacaat gacccgggaa    1140
gctgcgtagc tgtgcactgt gtggcgggcc tgggaagggc cccagtgctc gtggctctcg    1200
ccctcatcga gagcgggatg aagtacgagg acgccatcca gttcatccga cagaagcgcc    1260
gtggggccat caacagcaag cagctcacct acctggagaa gtaccggcct aagcagagac    1320
tgaggttcaa agaccacac acgcacaaga ccagatgctg cgtcatgtag ctcaggccct    1380
ggccctgtac ctcattacat ctgtgtctaa ggagtccaac ggctatgtgc gtccctgctc    1440
tgtccccatc tgtacccacg ctgtctttc tgaagctgtc cctggaccct ctgccagtcc    1500
tgtccaaccc ctgtccctca cccccactg cccaggcctt ccccctggcc tgtgtattgc    1560
aggtgggagt ttttaaacca ctgggcccaa tgcctcagcg gcgtggccct caccctaacc    1620 ttttccagc acctttgtta ccaggtgctc tggactctca aggcaataaa tcaggagctg    1680
tggatgtgtg tgaagagtgt tatagagcag gggaataggg tgtggatccc gggaggccat    1740
ggtctccatc tcttctgtcc tattgctgct gctgctactg ctgctgcagt ggcgtgcctc    1800
catggcgccc tctggtggcc atcccttgct ctgcctccct gacttgttct acaagttctt    1860
gacgcaaaaa tcagcacagc ttggactggt gacggtttgt aacattagga ggtgagactg    1920
atcacctctg caggacagag tagggggtca cttggaactt tcagtggcct ccaccccga    1980 ccttcatgca accagaggtg tgggttgcag gtagatctga gtgtagatgg cctttggtga    2040
catgggtctg cctaggacct catcctgctt ataagttctg agcagtgggc tgactcttcc    2100
cttagctgag gaaagggtat catgagggac agggctggct atatgtgtgt cttagccagg    2160
gttttatggc tgtgaacaga caccgggacc aaggcaactc ttacaaggac aacatttagt    2220
tggggctgcc ttacaggttc agaggttcag tctgtcatca aggtgggagc atggcagcat    2280
ccatgcaggc atgggcagc tgtagctgag agctctacac cttcatctga aggtactag    2340 tggaagactg atttccaggg agctagaatg agggccttaa agcccatgcc cacagtgaca    2400
cacctactcc aacaaggtca gacctccaaa cggtgccact ccccaggcca gtcgtattta    2460
aacagtgaca atgtgtcagt gtggatgtgc tggctgtctt atagcactga catacttagg    2520
acgtgatcct caggcctttg cagacccagt cccctctgtg cccagaacag agatccaggg    2580
cgcctctcac tggtacctgc tgcctgcttg catcattccc tcttcaagtt ccacctagct    2640
ctggactagg tcccagaaac catccgggcc cacgtagact cccagcagtc cctgttcttg    2700
cctgtcctag tagggagtga caaggtgtag ccaaactcag taatggtgac cttgtgtggg    2760
ctggaaactc actaccccgg tgccatattt ccacaaagtc actggttttt gtttttgttt    2820
tagtctgcca agcttttttt tttttaaaa gatttattta tttatgtat atgaatatac    2880 tgtagctgta cagatggttg tgagccttca tgtggttgtc gggaattgaa tttaggacct    2940
ctgcttgctc tggtcaactc cgctcactcc ggttcgccaa tctctctcag tccttgctag    3000
cttcggccca agatttatt tattatacat aagtacactg ttgctgtctt cagacatacc    3060
agaagaggac gccagatctc attaccggtg gttgtgagcc accatgtggt tgctgagatt    3120
tgaactcagg actttcggaa gagccatctg accagcccca agcttttta tttttatttt    3180 ttaaatcttt aaatttaaaa aaaattatta tttgtttgct gt                      3222
```

<210> SEQ ID NO 64
<211> LENGTH: 1678
<212> TYPE: DNA

<213> ORGANISM: Mus musculus
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 64

```
ggcgcgtgcc gagccctccg cgtcgtgccg gcgccggcgc ccggaccgcc agattgtgcc      60
ttctgaagac cagggtggga ttgatggaga agccccaaga gggcagctct gactactgcc     120
gttcccaaca ccgtgggtgc tgccgctgag gagacctgta cacctctggc cctcaccatt     180
gtccttgcct cccaatggcc tctgctgcca ggccggagcn gncactgctg cctgagcccg     240
ctgcccctct tcaggacttg ccgttccctg atggggtaac gtgacagacc ggatcagagg     300
ctgcctgccc accacggccc agggccgcta gagtttggtt gagttcaagt tcattttccc     360
tttggtcctg acttctgggg cccaactctg accaaagggg acactcctcc gtccacccat     420
gcagagaggg tgtctccagc gacggcccca tagaggacac tgctctgcgg ccggagtcac     480
caacccgaag ttctctctgc tcagtttttt ttttggttgt tgttattttt attttgactc     540
cttgtaactt ctccactctg agggacagga cttttggcgct gcccgtcttg ctgcggggtg    600
gggggagaag tgtgcttgtt tcttttcttt tttagaattg gttttttttgg aattatccgc    660
cacgaggcag cttcctctcc ctctcccagg tatttgcaca atatttgtgc ggggcgtagg     720
ggcgaggttt taagaagtct tttctttgtg gacaagcacg gggatctcac tggacttggt     780
gtgtggggct gggggacccc cgtgcagcct tgctggctag tccctctggg tccccggagg     840
aggcatggcc cgcatgaacc ggcctgcgcc tgtggaggtg agctaccggc acatgcgctt     900
cctcatcacc cacaacccca gcaatgccac cctcagcacg ttcatcgagg acctgaagaa     960
gtacgggggct accactgtgg tgcgcgtgtg tgaagtgacc tatgacaaga ccccctgga   1020
gaaggacggc atcactgttg tggactggcc ctttgatgat ggagcgcccc ctcctggcaa    1080
agtggtagag gactggctga gcctgctgaa ggccaagttc tacaatgacc cgggaagctg    1140
cgtagctgtg cactgtgtgg cgggcctggg aagggcccca gtgctcgtgc tctcgccctc    1200
atcgagagcg ggatgaagta cgaggacgcc atccagttca tccgacagaa gcgccgtggg    1260
gccatcaaca gcaagcagct cacctacctg gagaagtacc ggcctaagca gagactgagg    1320
ttcaaagacc cacacacgca caagaccaga tgctgcgtca tgtagctcag gccctggccc    1380
tgtacctcat tacatctgtg tctaaggagt ccaacggcta tgtgcgtccc tgctctgtcc    1440
ccatctgtac ccacggctgt ctttctgaag ctgtccctgg accctctgcc agtcctgtcc    1500
aaccctgtc cctcaccccc cactgcccag gccttccccc tggcctgtgt attgcaggtg    1560
ggagttttta aaccactggg cccaatgcct cagcggcgtg gccctcaccc taacctttt    1620
ccagcacctt tgttaccagg tgctctggac tctcaaggca ataaatcagg agctgtgg     1678
```

<210> SEQ ID NO 65
<211> LENGTH: 806
<212> TYPE: DNA
<213> ORGANISM: Mus musculus

<400> SEQUENCE: 65

```
tggaggtgag ctaccggcac atgcgcttcc tcatcaccca caaccccagc aatgccaccc      60
tcagcacgtt catcgaggac ctgaagaagt acgggggctac cactgtggtg cgcgtgtgtg    120
```

```
aagtgaccta tgacaagacc ccctggaga aggacggcat cactgttgtg gactggccct      180
ttgatgatgg agcgccccct cctggcaaag tggtagagga ctggctgagc ctgctgaagg      240
ccaagttcta caatgacccg ggaagctgcg tagctgtgca ctgtgtggcg ggcctgggaa      300 gggcccagt gctcgtggct ctcgccctca tcgagagcgg gatgaagtac gaggacgcca      360
tccagttcat ccgacagaag cgccgtgggg ccatcaacag caagcagctc acctacctgg      420
agaagtaccg gcctaagcag agactgaggt tcaaagaccc acacgcac aagaccagat      480 gctgcgtcat gtagctcagg ccctggccct gtacctcatt acatctgtgt ctaaggagtc      540
caacggctat gtgcgtccct gctctgtccc catctgtacc cacggctgtc tttctgaagc      600
tgtccctgga ccctctgcca gtcctgttca accctgtcc ctcaccccc actgccagg      660 ccttcccct ggcctgtgta ttgcaggtgg gagttttta accactgggc caatgcctc      720 agcggcgtgg ccctcacct aacctttttc cagcaccttt gttaccaggt gctctggact      780
ctcaaggcaa taaatcagga gctgcg                                          806
```

<210> SEQ ID NO 66
<211> LENGTH: 899
<212> TYPE: DNA
<213> ORGANISM: Mus musculus

<400> SEQUENCE: 66

```
gtgcagccct tgctggctag tccctctgg gtccccggag gaggcatggc ccgcatgaac       60
cggcctgcgc ctgtggaggt gagctaccgg cacatgcgct tcctcatcac ccacaacccc      120
agcaatgcca ccctcagcac gttcatcgag gacctgaaga agtacggggc taccactgtg      180
gtgcgcgtgt gtgaagtgac ctatgacaag acccccctgg agaaggacgg catcactgtt      240
gtggactggc cctttgatga tggagcgccc cctcctggca aagtggtaga ggactggctg      300
agcctgctga aggccaagtt ctacaatgac ccgggaagct gcgtagctgt gcactgtgtg      360
gcgggcctgg gaagggcccc agtgctcgtg gctctcgccc tcatcgagag cgggatgaag      420
tacgaggacg ccatccagtt catccgacag aagcgccgtg gggccatcaa cagcaagcag      480
ctcacctacc tggagaagta ccggcctaag cagagactga ggttcaaaga cccacacacg      540
cacaagacca gatgctgcgt catgtagctc aggccctggc cctgtacctc attacatctg      600
tgtctaagga gtccaacggc tatgtgcgtc cctgctctgt cccatctgt acccacggct      660 gtctttctga agctgtccct ggaccctctg ccagtcctgt ccaaccctg tccctcaccc      720 cccactgccc aggccttccc cctggcctgt gtattgcagg tgggagtttt taaaccactg      780
ggcccaatgc ctcagcggcg tggccctcac cctaaccttt ttccagcacc tttgttacca      840
ggtgctctgg actctcaagg caataaatca ggagctgtga aaaaaaaaa aaaaaaaa      899
```

<210> SEQ ID NO 67
<211> LENGTH: 150
<212> TYPE: PRT
<213> ORGANISM: Homo sapiens

<400> SEQUENCE: 67

Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
        35                  40                  45

```
His Ser Asp Ser Cys Pro Gly Leu Thr Leu His Arg Leu Arg Ile Pro
 50                  55                  60

Asp Phe Cys Pro Pro Ala Pro Asp Gln Ile Asp Arg Phe Val Gln Ile
 65                  70                  75                  80

Val Asp Glu Ala Asn Ala Arg Gly Glu Ala Val Gly Val His Cys Ala
                 85                  90                  95

Leu Gly Phe Gly Arg Thr Gly Thr Met Leu Ala Cys Tyr Leu Val Lys
                100                 105                 110

Glu Arg Gly Leu Ala Ala Gly Asp Ala Ile Ala Glu Ile Arg Arg Leu
            115                 120                 125

Arg Pro Gly Ser Ile Glu Thr Tyr Glu Gln Glu Lys Ala Val Phe Gln
        130                 135                 140

Phe Tyr Gln Arg Thr Lys
145                 150

<210> SEQ ID NO 68
<211> LENGTH: 150
<212> TYPE: PRT
<213> ORGANISM: Mus musculus

<400> SEQUENCE: 68

Met Gly Val Gln Pro Pro Asn Phe Ser Trp Val Leu Pro Gly Arg Leu
1                5                  10                  15

Ala Gly Leu Ala Leu Pro Arg Leu Pro Ala His Tyr Gln Phe Leu Leu
                20                  25                  30

Asp Gln Gly Val Arg His Leu Val Ser Leu Thr Glu Arg Gly Pro Pro
            35                  40                  45

His Ser Asp Ser Cys Pro Gly Leu Thr Leu His Arg Met Arg Ile Pro
 50                  55                  60

Asp Phe Cys Pro Pro Ser Pro Glu Gln Ile Asp Gln Phe Val Lys Ile
 65                  70                  75                  80

Val Asp Glu Ala Asn Ala Arg Gly Glu Ala Val Gly Val His Cys Ala
                 85                  90                  95

Leu Gly Phe Gly Arg Thr Gly Thr Met Leu Ala Cys Tyr Leu Val Lys
                100                 105                 110

Glu Arg Ala Leu Ala Ala Gly Asp Ala Ile Ala Glu Ile Arg Arg Leu
            115                 120                 125

Arg Pro Gly Ser Ile Glu Thr Tyr Glu Gln Glu Lys Ala Val Phe Gln
        130                 135                 140

Phe Tyr Gln Arg Thr Lys
145                 150

<210> SEQ ID NO 69
<211> LENGTH: 150
<212> TYPE: PRT
<213> ORGANISM: Rattus norvegicus

<400> SEQUENCE: 69

Met Gly Val Gln Pro Pro Asn Phe Ser Trp Val Leu Pro Gly Arg Leu
1                5                  10                  15

Ala Gly Leu Ala Leu Pro Arg Leu Pro Ala His Tyr Gln Phe Leu Leu
                20                  25                  30

Asp Leu Gly Val Arg His Leu Val Ser Leu Thr Glu Arg Gly Pro Pro
            35                  40                  45

His Ser Asp Ser Cys Pro Gly Leu Thr Leu His Arg Leu Arg Ile Pro
 50                  55                  60
```

```
Asp Phe Cys Pro Pro Ala Pro Glu Gln Ile Asp Gln Phe Val Lys Ile
 65                  70                  75                  80

Val Asp Glu Ala Asn Ala Arg Gly Glu Ala Val Gly Val His Cys Ala
                 85                  90                  95

Leu Gly Phe Gly Arg Thr Gly Thr Met Leu Ala Cys Tyr Leu Val Lys
            100                 105                 110

Glu Gln Gly Leu Ala Ala Gly Glu Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150

<210> SEQ ID NO 70
<211> LENGTH: 150
<212> TYPE: PRT
<213> ORGANISM: Pan troglodytes

<400> SEQUENCE: 70

Met Gly Val Gln Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
                 20                  25                  30

Asp Leu Gly Val Arg His Leu Val Ser Leu Thr Glu Arg Gly Pro Pro
            35                  40                  45

His Ser Asp Ser Cys Pro Gly Leu Thr Leu His Arg Leu Arg Ile Pro
        50                  55                  60

Asp Phe Cys Pro Pro Ala Pro Asp Gln Ile Asp Arg Phe Val Gln Ile
 65                  70                  75                  80

Val Asp Glu Ala Asn Ala Arg Gly Glu Ala Val Gly Val His Cys Ala
                 85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150

<210> SEQ ID NO 71
<211> LENGTH: 63
<212> TYPE: PRT
<213> ORGANISM: Canis familiaris

<400> SEQUENCE: 71

Met Ala Ala Val Gly Val His Cys Ala Leu Gly Phe Gly Arg Thr Gly
1               5                   10                  15

Thr Met Leu Ala Cys Tyr Leu Val Lys Glu Arg Gly Leu Ala Ala Gly
                 20                  25                  30

Asp Ala Ile Ala Glu Ile Arg Arg Leu Arg Pro Gly Ser Ile Glu Thr
            35                  40                  45

Tyr Glu Gln Glu Lys Ala Val Phe Gln Phe Tyr Gln Arg Thr Lys
        50                  55                  60

<210> SEQ ID NO 72
```

```
<211> LENGTH: 150
<212> TYPE: PRT
<213> ORGANISM: Bos taurus

<400> SEQUENCE: 72

Met Gly Val Gln Pro Pro Asn Phe Ser Trp Val Leu Pro Arg Arg Leu
1               5                   10                  15

Ala Gly Leu Ala Leu Pro Arg Leu Pro Ala His Tyr Gln Phe Leu Leu
                20                  25                  30

Asp Gln Gly Val Arg His Leu Val Ser Leu Thr Glu Arg Gly Pro Pro
35                  40                  45

His Ser Asp Ser Cys Pro Gly Leu Thr Leu His Arg Leu Arg Ile Pro
50                  55                  60

Asp Phe Cys Pro Pro Gly Pro Glu Gln Ile Asp Arg Phe Val Lys Ile
65                  70                  75                  80

Val Asp Glu Ala Asn Ala Arg Gly Glu Ala Val Ala Val His Cys Ala
                85                  90                  95

Leu Gly Phe Gly Arg Thr Gly Thr Met Leu Ala Cys Tyr Leu Val Lys
                100                 105                 110

Glu Arg Gly Leu Ala Ala Gly Asp Ala Ile Ala Glu Ile Arg Arg Leu
            115                 120                 125

Arg Pro Gly Ser Ile Glu Thr Tyr Glu Gln Gly Lys Ala Val Phe Gln
        130                 135                 140

Phe Tyr Gln Arg Thr Lys
145                 150

<210> SEQ ID NO 73
<211> LENGTH: 132
<212> TYPE: PRT
<213> ORGANISM: Xenopus tropicalis

<400> SEQUENCE: 73

Met Ala Met Pro Arg Leu Pro Ala His Tyr Glu Tyr Leu Cys Glu Asn
1               5                   10                  15

Gly Ile Arg His Leu Ile Thr Leu Thr Glu His Lys Pro Pro Tyr His
                20                  25                  30

Asp Thr Cys Pro Gly Ile Thr Leu His Arg Ile Arg Ile Leu Asp Phe
            35                  40                  45

Cys Ala Pro Ser Leu Glu Gln Ile Lys Asn Phe Leu Lys Ile Val Asp
        50                  55                  60

Asp Ala Lys Ala Lys Gly Glu Ala Val Gly Val His Cys Leu His Gly
65                  70                  75                  80

Phe Gly Arg Thr Gly Thr Met Leu Ala Cys Tyr Leu Val Lys Val Trp
                85                  90                  95

Lys Ile Thr Gly Val Asp Ala Ile Asn Glu Ile Arg Ser Leu Arg Arg
                100                 105                 110

Gly Ser Ile Glu Thr Thr Glu Gln Glu Lys Ala Ile Ile Gln Phe His
            115                 120                 125

His His Ile Lys
        130

<210> SEQ ID NO 74
<211> LENGTH: 201
<212> TYPE: PRT
<213> ORGANISM: Homo sapiens

<400> SEQUENCE: 74
```

Met Ala Ala Thr Ala Leu Leu Glu Ala Gly Leu Ala Arg Val Leu Phe
1               5                   10                  15

Tyr Pro Thr Leu Leu Tyr Thr Leu Phe Arg Gly Lys Val Pro Gly Arg
            20                  25                  30

Ala His Arg Asp Trp Tyr His Arg Ile Asp Pro Thr Val Leu Leu Gly
        35                  40                  45

Ala Leu Pro Leu Arg Ser Leu Thr Arg Gln Leu Val Gln Asp Glu Asn
50                  55                  60

Val Arg Gly Val Ile Thr Met Asn Glu Glu Tyr Glu Thr Arg Phe Leu
65                  70                  75                  80

Cys Asn Ser Ser Gln Glu Trp Lys Arg Leu Gly Val Glu Gln Leu Arg
                85                  90                  95

Leu Ser Thr Val Asp Met Thr Gly Ile Pro Thr Leu Asp Asn Leu Gln
            100                 105                 110

Lys Gly Val Gln Phe Ala Leu Lys Tyr Gln Ser Leu Gly Gln Cys Val
        115                 120                 125

Tyr Val His Cys Lys Ala Gly Arg Ser Arg Ser Ala Thr Met Val Ala
    130                 135                 140

Ala Tyr Leu Ile Gln Val His Lys Trp Ser Pro Glu Glu Ala Val Arg
145                 150                 155                 160

Ala Ile Ala Lys Ile Arg Ser Tyr Ile His Ile Arg Pro Gly Gln Leu
                165                 170                 175

Asp Val Leu Lys Glu Phe His Lys Gln Ile Thr Ala Arg Ala Thr Lys
            180                 185                 190

Asp Gly Thr Phe Val Ile Ser Lys Thr
        195                 200

<210> SEQ ID NO 75
<211> LENGTH: 161
<212> TYPE: PRT
<213> ORGANISM: Danio rerio

<400> SEQUENCE: 75

Met Ser Ser Gln Gln Asn Pro Ala Glu Pro Asn Phe Ser Trp Val
1               5                   10                  15

Glu Pro Cys Lys Leu Ala Gly Leu Ala Arg Pro Thr Met Val His His
            20                  25                  30

Tyr Arg Tyr Leu Leu Asp His Gly Ile Lys His Leu Val Ser Leu Leu
        35                  40                  45

Glu Ile Lys Pro Pro Asn Tyr Glu Lys Cys Pro Glu Leu Ser Leu His
50                  55                  60

Gln Ile Ser Ile Val Asp Phe Thr Pro Pro Ser Arg Ser Gln Ile Leu
65                  70                  75                  80

Gln Phe Leu Ser Ile Val Glu Lys Ala Asn Ala Lys Gly Glu Gly Val
                85                  90                  95

Ala Val His Cys Ala His Gly His Gly Arg Thr Gly Thr Met Leu Ala
            100                 105                 110

Cys Tyr Leu Val Lys Ser Arg His Leu Ser Gly Glu Glu Ala Ile Lys
        115                 120                 125

Glu Ile Arg Arg Leu Arg Glu Gly Ser Val Glu Thr Lys Glu Gln Glu
    130                 135                 140

Gln Ala Val Ile Asp Phe His Asn Tyr Ile His Ser Gly Cys Gln Lys
145                 150                 155                 160

His

<210> SEQ ID NO 76
<211> LENGTH: 150
<212> TYPE: PRT
<213> ORGANISM: Macaca mulatta

<400> SEQUENCE: 76

```
Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
        35                  40                  45

His Ser Asp Ser Cys Pro Gly Leu Thr Leu His Arg Leu Arg Ile Pro
    50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150
```

<210> SEQ ID NO 77
<211> LENGTH: 718
<212> TYPE: DNA
<213> ORGANISM: Homo sapiens

<400> SEQUENCE: 77

```
gtggcccggg aggcgccgag ccagcgatgg gcgtgcagc ccccaactt ctcctgggtg      60 cttccgggcc ggctggcggg actggcgctg ccgcggctcc ccgcccacta ccagttcctg     120
ttggacctgg gcgtgcggca cctggtgtcc ctgacggagc gcgggccccc tcacagcgac     180
agctgccccg gcctcaccct gcaccgcctg cgcatccccg acttctgccc gccgccccc      240 gaccagatcg accgcttcgt gcagatcgtg gacgaggcca acgcacgggg agaggctgtg     300
ggagtgcact gtgctctggg ctttggccgc actggcacca tgctggcctg ttacctggtg     360
aaggagcggg gcttggctgc aggagatgcc attgctgaaa tccgacgact acgacccggc     420
tccatcgaga cctatgagca ggagaaagca gtcttccagt tctaccagcg aacgaaataa     480
ggggccttag taccctcta ccaggccctc actcccttc cccatgttgt cgatggggcc      540
agagatgaag ggaagtggac taaagtatta aaccctctag ctcccattgg ctgaagacac     600
tgaagtagcc caccctgca ggcaggtcct gattgaaggg gaggcttgta ctgctttgtt      660
gaataaatga gttttacgaa ccaggaaaaa aaaaaaaaa aaaaaaaaa aaaaaaa         718
```

<210> SEQ ID NO 78
<211> LENGTH: 1417
<212> TYPE: DNA
<213> ORGANISM: Mus musculus

<400> SEQUENCE: 78

```
gcggggacgg aatccagccc cagaggggg gtgacccaat ctcccggcag agtaggaaag      60
```

```
gccagcctcg ccctgagtaa actcccccca cgatgggcgt gcaaccccccc aacttctcct      120 gggtgcttcc gggacggctg gccggactgg cgttgccccg gctgcccgcg cactaccagt      180
tcctgctgga ccagggtgtg cggcacctgg tgtccctgac ggagcgcgga ccccctcaca      240
gtgacagctg tcccggcctc acgctgcacc gaatgcgcat ccctgacttt tgcccgccgt      300
ccccggaaca gatcgaccaa tttgtgaaga tcgtggacga ggccaatgcc cggggagagg      360
ctgttggagt gcactgtgcc ctaggctttg gccgcactgg caccatgcta gcctgctact      420
tggtgaagga gcgggctttg gccgcaggag atgccattgc tgagatccgg cgcctgcgac      480
caggatccat tgagacgtat gaacaggaga aggccgtctt ccagttctac cagcgaacaa      540
aatgaggact tcaacagccc gcctttcccc ctccccaact cctgcggcca gggaggaagg      600
ggagtgaact aaagtactgc atccttcagg tccctctgac tcctattgga caaaagtagt      660
ccttccccaa agccataacg tggccggcag gatggccgag accccacaaa aatgaggtaa      720
taactgataa gaactcatca ccgctgcata gcatgtacac agcactccca atacatctgg      780
gtggttgaaa agacaaaaaa aaaaaaaaca aaaaaaaaaa aaaaaaaacc acttctgttc      840
tttggatgag gtgtctagag ttcagaaagg cctccggtca cagttctggg aaacagaagg      900
ataggccagg actccagcac acacctttgt catcctgagg atgatgggat tctaagtgct      960
gttccctgac atgtgataga ggagaactgg tcagtgaagg agacccatgt ccctggccac     1020
atggcctcca agcagcctca ggccgctgca ctcctacacc agcagtgccc ccttgacatc     1080 acccctttatg tagggtcatc cgtcctacct gagccaccttt tgttctctca gggtacagaa     1140
gacctgcata tcgtgctaca gatgaggtct ctctctgtct tatctgtttc tctcttggtc     1200 tcccctccc actctccctc ttaatctccc tctctccctc cccttcctc ccccaccag     1260 ggctggccac ctcttaccag cctcaggtga ctcagctcat ctgtcacctc caaccctat     1320 gtcgtccca gcctcagacc aacgaatgct gaaactgtgt cttggtggtt ttagagtgga     1380
tattaagtga tcaaataaat aactctggga ctatgaa                              1417
```

<210> SEQ ID NO 79
<211> LENGTH: 654
<212> TYPE: DNA
<213> ORGANISM: Rattus norvegicus

<400> SEQUENCE: 79

```
gcaggggcgg aacccagccc cagcgggtga cccgatcgca gggcgtagga aaggccagcc       60
tcgctccggg tacctccccc ccacgatggg cgtgcagccc cccaacttct cctgggtgct      120
cccgggacgg ctggccgggc tggcgttacc gcggctaccc gcgcactacc agttcctgct      180
ggacctgggc gtgcgacact tggtgtccct gacggagcgc gggccccctc acagtgacag      240
ctgtcccggc ctcacgctgc accgactgcg catccccgac ttttgcccgc cggccccga      300 acagatcgac caatttgtga agatcgtgga cgaggccaat gccgggggag aggctgttgg      360
agtgcactgt gctctaggct ttggccgcac tggaaccatg ctggcctgct acctggtgaa      420
ggagcagggt ttggccgcag gagaagccat tgctgagatt cggcgcctgc gaccaggatc      480
catcgagacg tatgaacaag agaaggccgt cttccagttc taccagcgaa caaaatgagg      540
ggttcggtag cccccttccc cctcccccgac tcctgctgct tatagcaagt gtggcgggct      600
ggaagggaaa aggactaaaa aagtactacc tccttcagcg ccctctggct ccta            654
```

<210> SEQ ID NO 80

```
<211> LENGTH: 707
<212> TYPE: DNA
<213> ORGANISM: Pan troglodytes

<400> SEQUENCE: 80 cggcgcccg  cagaccacgt  ggcccgggag  gcgccgaggc  cagcgatggg  cgtgcagccc      60
cccaacttct  cctgggtgct  tccgggccgg  ctggcggggc  tggcgctgcc  gcggctcccc    120
gcccactacc  agttcctgtt  ggacctgggc  gtgcggcacc  tggtgtccct  gacggagcgc    180
gggccccctc  acagcgacag  ctgccccggc  ctcaccctgc  accgctgcg   catcccgac     240
ttctgcccgc  cggccccga   ccagatcgac  cgcttcgtgc  agatcgtgga  cgaggccaac    300
gcacggggag  aggctgtggg  agtgcactgt  gctctgggct  ttggccgcac  tggcaccatg    360
ctggcctgtt  acctggtgaa  ggagcgggc   ttggctgcag  gagatgccat  tgctgaaatc    420
cgacgactac  gacccggctc  catcgagacc  tatgagcagg  agaaagcagt  cttccagttc    480
taccagcgaa  cgaaataagg  ggccttagta  cccttctacc  aggccctcac  tccccttccc    540
catgttgtcg  atggggccag  agatgaaggg  aagtggactt  aagtattaaa  ccgtctagct    600
cccattggct  gaagacactg  aagtagccca  cccctgcagg  caggtcctga  ttgaagggga    660
ggcttgtact  gctttgttga  ataaatgagt  tttacgaacc  agggcac                   707

<210> SEQ ID NO 81
<211> LENGTH: 581
<212> TYPE: DNA
<213> ORGANISM: Homo sapiens

<400> SEQUENCE: 81
atgaggacct  gttcagaagc  aattcaacaa  ctacgaacag  aagctcacaa  ggagatacat    60
tcccagcaag  tgaaggagca  caggactgct  gttctggatt  tcattgaaga  ttacttaaaa    120
aaagtgtgta  aactttactc  agaacaaaga  gccatccgag  ttaaaagagt  ggtggataag    180
aaaagaatat  ctaagctgga  accagaacca  aatgcaaaga  caagagaatc  acatcttct     240
gagaaagttt  cacagtgtcc  ttcaaaagac  tgaagaaaac  cctgccactg  aagaacatcc    300
agaaaagatt  ttgactgaaa  gacaacctga  attgggaaca  tggggagatg  gcaaaggtga    360
agatgagtta  tccccagaag  aaatacaaat  gcagatcaaa  gggagagtgg  ttgagatttc    420
cagacttcaa  gagatattca  cggaaaaggt  tttgcaacag  gaagctgaga  ttgatggcgt    480
tcaccagtta  gttgtggggg  caactgaaaa  tatcaaggaa  ggcaacgaag  acataagaga    540
ggccattaaa  aacaacgctg  gcttccgcgt  atggatcctc  t                        581

<210> SEQ ID NO 82
<211> LENGTH: 192
<212> TYPE: DNA
<213> ORGANISM: Canis familiaris

<400> SEQUENCE: 82
atggcggcgg  tgggagtgca  ctgtgccctg  ggctttggcc  gcacgggcac  catgctggcc    60
tgctacctgg  tgaaggagcg  gggcctggct  gccggggacg  ccatcgccga  gatccgacgc    120
cttcgacctg  gctccatcga  gacctacgag  caggagaaag  ccgtcttcca  gttctaccag    180
cggaccaagt  aa                                                            192

<210> SEQ ID NO 83
<211> LENGTH: 824
<212> TYPE: DNA
<213> ORGANISM: Bos taurus
```

<400> SEQUENCE: 83

```
gggtcccagg aggcgccact gcctgccatg ggcgtgcagc cccccaactt ctcgtgggtg    60
ctgccccgcc ggctggcggg gctggcgctg ccccggctcc ccgcccacta ccagttcctg   120
ctggaccaag gtgtacggca tctggtgtca ctgacggagc gcgggccccc gcacagcgac   180
agctgccccg gcctcaccct gcaccgactg cgcatcccag acttctgccc gccgggccca   240
gagcagatcg accgcttcgt gaagatcgtc gacgaggcca acgccagggg agaggcggtg   300
gcggtgcact gtgccctggg cttttggccgc actggcacca tgctggcctg ttacctggtg   360
aaggagcggg gcctggctgc cggagacgcc atcgctgaga tccggcgcct tcgacccggc   420
tccatcgaga cctatgagca agagaaggcg gtcttccagt tctaccagcg aacgaaataa   480
ggggcctccg tacccttctg cagggccccc gcggccctga tctttgcgtt agatgggggcc   540
agagacgcag aagtgggcta agagtgctaa gctctccagt acccagctgg ctcaagagac   600
tgaaggagcc cttccctgca ggcaggacct ggtaggagga atggctggag ctgcactgat   660
gtgggggggtc cctctgctgc tgccttgaat aaataactta acagctaaaa aaaaaaaaaa   720
aaaaaaaaaa aaaaaaaaaa aaaaaaaaaa aaaaaaaaaa aaaaaaaaaa aaaaaaaaaa   780
aaaaaaaaaa aaaaaaaaaa aaaaaaaaaa aaaaaaaaaa aaaa                    824
```

<210> SEQ ID NO 84
<211> LENGTH: 1499
<212> TYPE: DNA
<213> ORGANISM: Xenopus tropicalis

<400> SEQUENCE: 84

```
ctcataattt ctcctgggtg gagcccgggc tattggccgg catggcgatg ccaagacttc    60
ctgcccacta cgagtacctc tgtgagaatg gcatccgaca cctgataacc ctgacagagc   120
acaagccgcc ctatcacgac acttgtcctg gtatcacttt acatcgcatt cgcatcctgg   180
atttctgtgc ccccagccta gaacagatca agaacttcct caagatcgtg gatgatgcaa   240
aagctaaggg agaggcagtc ggggtgcact gcttacatgg ttttgggagg acaggtacca   300
tgttggcttg ctacttggtg aaggtctgga agatcaccgg cgtcgatgcc atcaatgaga   360
tccggagtct acgtcggggc tccatagaga caactgagca ggaaaaagcc atcatacagt   420
tccaccacca catcaagtga ccttcatggt gtgtccagtg gcccattggc ttggagaacc   480
catgtctccc atctttcttc ttcatcctag aggtcaagga ggaactctag acttctactg   540
tgtgtgtgtt tgtattaaat gtatctcaag tacatctaga atgttggcca gtttctcctg   600
cagttgccca aaatgggtga cctgcatggc gtgtccagtt acccattggc ttgaagaacc   660
catgtctccc gtctttcgtc ttcatcccag aggtcaagga ggaactctag acttctactg   720
tgtgtgtgtt tgtattaaat gtatctcaag tacatctaga atgttggcca gtttctcctg   780
cagttgccca aaatgagtga cctgcatggt gtgtccagtt gcccattggc ttgaagaacc   840
cttgtctctc attttcttc ttcatcctag aggtcaagga ggagccctag acttctactg   900
tgtgtgttg tatttaatgt atctcaagta tatctagaac gttggtggat gttggccagt   960
ttctcctgca gttgcccaca acaggggaat agggcattac aatggcggat agctgaggga  1020
cctgattgtg tttccagttt ggggacgga atgggaagcg ctcaaaggaa atggagggaa  1080
tgagatttat gtgaacgtt aaatgctcaa agccgattgg gtttctagat gaggagcaac  1140
atgttcaact gttaatgctg atactgtagc tctggaacac tagattgttc ttcagccaat  1200
```

| | |
|---|---|
| gttctgtacc agctgctaga ccttactctc accccatagg ggttggatat ggctgattat | 1260 |
| gttatggggg gagggaaaga ccagaacctg gagtagtttg ttgacccaaa cccacatgtc | 1320 |
| ccttgggttt caagacaacc tgcttgttgc atgatgggag ctgtagtcca tcagccacat | 1380 |
| agacggatca tgggttccag agccggccaa tcacttgttg tcttcataac ctcaaatcac | 1440 |
| agatgttggt ccaatttcac tggaaaataa accatattta taaaaaaaaa aaaaaaaa | 1499 |

<210> SEQ ID NO 85
<211> LENGTH: 859
<212> TYPE: DNA
<213> ORGANISM: Homo sapiens

<400> SEQUENCE: 85

| | |
|---|---|
| gaccgcgagc gcgggggccg acgggtcgcc gctgcgccgg gccgggatgg cggccaccgc | 60 |
| gctgctggag gccggcctgg cgcgggtgct cttctacccg acgctgctct acaccctgtt | 120 |
| ccgcgggaag gtgccgggtc gggcgcaccg ggactggtac caccgcatcg accccaccgt | 180 |
| gctgctgggc gcgctgccgt tgcggagctt gacgcgccag ctggtacagg acgagaacgt | 240 |
| gcgcggggtg atcaccatga acgaggagta cgagacgagg ttcctgtgca actcttcaca | 300 |
| ggagtggaag agactaggag tcgagcagct gcggctcagc acagtagaca tgactgggat | 360 |
| ccccaccttg gacaacctcc agaagggagt ccaatttgct ctcaagtacc agtcgctggg | 420 |
| ccagtgtgtt tacgtgcatt gtaaggctgg gcgctccagg agtgccacta tggtggcagc | 480 |
| atacctgatt caggtgcaca aatggagtcc agaggaggct gtaagagcca tcgccaagat | 540 |
| ccggtcatac atccacatca ggcctggcca gctggatgtt cttaaagagt tccacaagca | 600 |
| gattactgca cgggcaacaa aggatgggac ttttgtcatt tcaaagacat gatgtatggg | 660 |
| gattagaaag aactcaagac actcctgctt gatacagaac aaaaagagct taacaggacc | 720 |
| aacagggctt aagcccagac ttgacgtaac agaaatgtgc caataggtaa taggtaattt | 780 |
| ttctttctct gacttgtttt gttttcttga ataacactg ttgtgtggct agaaaggaaa | 840 |
| aaaaaaaaaa aaaaaaaaa | 859 |

<210> SEQ ID NO 86
<211> LENGTH: 1121
<212> TYPE: DNA
<213> ORGANISM: Danio rerio

<400> SEQUENCE: 86

| | |
|---|---|
| aacagcacac gccctcggtc tgattcattc tccaggtggc tttataaagc tgctgtggag | 60 |
| aagcacactt catcatcata gctgcagttc ttcatcatct gataacaata ataatataat | 120 |
| catgtcatct caacaaaacc ccgccgagcc gccgaacttc tcttgggtcg agccatgcaa | 180 |
| actcgccggt ctggcccgtc ctacaatggt ccaccactac aggtacctgc tggaccacgg | 240 |
| catcaaacac ctggtctcct tgttagagat aaaaccaccg aattatgaga agtgtccaga | 300 |
| gctgagcctg catcagatca gtatagtgga cttcactccg ccgagtcgca gtcaaatcct | 360 |
| gcagttcctg agcatcgtgg agaaggctaa tgctaaagga gaggggggtgg cggttcactg | 420 |
| tgcgcatggt cacggcagga cgggcaccat gttggcctgt tacctggtca aaagcagaca | 480 |
| cctgagcggt gaagaggcca tcaaagaaat ccgccgactc cgagaaggct ccgtcgagac | 540 |
| caaagagcag gaacaggcgg tgatagactt ccacaactac atccacagcg gctgtcagaa | 600 |
| gcattaaagc agtagtgaat caaaatctac tcactattta ctcaccatca agcagttaac | 660 |
| aatgagtttc tttcttctgt tgaacacgga tgaagatatt ttgaagaaag ctgaacacct | 720 |

| | | |
|---|---|---|
| gtaaccattg actcccttg tggaaaaac aaatactatt gaagtcagtg gttagagctt | 780 | |
| tcttcaaagt atcttcaaca gaaataaaga aactcattaa ggattgtaat aaggctgagt | 840 | |
| aaatgacaga attttcaatt ttgggtgaac tgtccctta agccactgct tgcgttttac | 900 | |
| accattagga taaagatgag ctgctttgtg taatctggcc tattgtttat tgtaataatg | 960 | |
| ataagggtgt gttggttat actgaaaaat gaaagctgtt cagcggctcc tgctgcttta | 1020 | |
| taatatgaat caggatgcta aacgggtgaa tgatagtcat gtctgtattc agatctattg | 1080 | |
| atttattcta actgcattca aaataaagct cccgcaacaa a | 1121 | |

<210> SEQ ID NO 87
<211> LENGTH: 1440
<212> TYPE: DNA
<213> ORGANISM: Mus musculus

<400> SEQUENCE: 87

| | | |
|---|---|---|
| tggcccgcta aggcaagtgc tgagcgggga cggaatccag ccccagaggg ggggtgaccc | 60 | |
| aatctcccgg cagagtagga aaggccagcc tcgccctgag taaactcccc ccacacacac | 120 | |
| gatgggcgtg caacccccca acttctcctg ggtgcttccg ggacggctgg ccgggctggc | 180 | |
| gttgccccgg ctgcccgcgc actaccagtt cctgctggac cagggtgtgc ggcacctggt | 240 | |
| gtccctgacg gagcgcgggc cccctcacag tgacagctgt cccggcctca cgctgcaccg | 300 | |
| aatgcgcatc cctgactttt gcccgccgtc cccggaacag atcgaccaat ttgtgaagat | 360 | |
| cgtggacgag gccaatgccc ggggagaggc tgttggagtg cactgcgccc taggttttgg | 420 | |
| ccgcactggc accatgctag cctgctactt ggtgaaggag cgggctttgg ccgcaggaga | 480 | |
| tgccattgct gagatccggc gcctgcgacc aggatccatt gagacgtatg aacaggagaa | 540 | |
| ggccgtcttc cagttctacc agcgaacaaa atgaggactt caacagcccg cctttccccc | 600 | |
| tccccaactc ctgcggccag ggaggaaggg gagtgaacta agtgactgca tccttcaggt | 660 | |
| ccctctgact cctattggac aaaagtagtc cttccccaaa gccataacgt ggccggcagg | 720 | |
| atggccgaga ccccacaaaa atgaggtaat aactgataag aactcatcac cgctgcatag | 780 | |
| catgtacaca gcactcccaa tacatctggg tggttgaaaa gacaaaaaaa aaaaaaaaaa | 840 | |
| aaaaaaaaaa accacttctg ttcttggat gaggtgtcta gagttcaaaa aggcctccat | 900 | |
| tcacagttct aggaaacaga aggataggcc aggactccag cacacacctt tgtcatcctg | 960 | |
| aggatgatgg gattctaggt gctgttccct gacatgtgat agaggagaac tggtcagtga | 1020 | |
| aggagaccca tgtccctagc cacatggcct ccaagcagcc tcaggccgct gcactcctac | 1080 | |
| accggcagtg ccccttgac atcacccctt atgtagggtc atccgtccta cctgagccac | 1140 | |
| ctttgttctc tcagggtaca gaagacctgc atatcgtgct acagatgagg tctctctctg | 1200 | |
| tcttatctgt ttctctcttg gtctcccct cccattctcc ctcttgatct ccctctctcc | 1260 | |
| ctcccccttc ctccccccac cagggctggc cacctcttac cagcctcagg tgactcagct | 1320 | |
| catctgtcac ctccaacccc tatgtcgtcc ccagcctcag accaacgaat gctgaaactg | 1380 | |
| tgtcttggtg gttttagagt agatattaag tgatcaaata aataactctg ggactatgaa | 1440 | |

<210> SEQ ID NO 88
<211> LENGTH: 696
<212> TYPE: DNA
<213> ORGANISM: Macaca mulatta

<400> SEQUENCE: 88

```
gtggcccggg aggcgccgag gccaggtagg cgcgatgggc gtgcagcccc ccaacttctc    60
ctgggtgctc ccaggccggc tggcggggct ggcgctgccg cggctccccg cccactacca   120
gttcctgttg gacctgggcg tgcggcacct ggtgtccctg acagagcgcg ggccccctca   180
cagcgacagc tgccccggcc tcaccctgca ccgtctgcgc atccccgact tctgcccgcc   240
ggcccctgac cagatcgacc gcttcgtgca gatcgtggac gaggccaacg cacggggaga   300
ggctgtggga gtgcactgtg ccctgggctt tggccgcact ggcaccatgc tggcctgtta   360
cctggtaaag gagcggggct ggctgcagg agatgccatt gctgaaatcc gacgactacg   420
acccggctcc atcgagactt atgagcagga gaaagcagtc ttccagttct accagcgaac   480
gaaataaggg gcctcagtac ccttctaccg gcccctcact ccctgcccc atgttgtcga   540 tggggtcaga gatgaaggga gtggactaa agtattaaac cctctagctc ccagtggctc   600
aagacactga agtagcccac ccctgcaggc aggtcttgat tgaaggggag gcttgtactt   660
ttttgttgaa taaatgagtt gtacaaacca gggcac                             696
```

<210> SEQ ID NO 89
<211> LENGTH: 776
<212> TYPE: DNA
<213> ORGANISM: Macaca mulatta

<400> SEQUENCE: 89

```
gccgaggcca ggtaggcggt gggttaccca gctcggagcc ggcgaggaga cgggtgggcg    60
gagcggggct ggccagcctc gccccccatg acccgctgtt ctgtgccctc tcccagcgat   120
gggcgtgcag ccccccaact tctcctgggt gctcccaggc cggctggcgg ggctggcgct   180
gccgcggctc cccgcccact accagttcct gttggacctg ggcgtgcggc acctggtgtc   240
cctgacagag cgcgggcccc ctcacagcga cagctgcccc ggcctcaccc tgcaccgtct   300
gcgcatcccc gacttctgcc cgccggcccc tgaccagatc gaccgcttcg tgcagatcgt   360
ggacgaggcc aacgcacggg gagaggctgt gggagtgcac tgtgccctgg gctttggccg   420
cactggcacc atgctggcct gttacctggt aaaggagcgg ggcttggctg caggagatgc   480
cattgctgaa atccgacgac tacgacccgg ctccatcgag acttatgagc aggagaaagc   540
agtcttccag ttctaccagc gaacgaaata aggggcctca gtaccttct accggcccct   600 cactcccctg ccccatgttg tcgatggggt cagagatgaa gggaagtgga ctaaagtatt   660
aaaccctcta gctcccagtg ctcaagaca ctgaagtagc ccacccctgc aggcaggtct   720
tgattgaagg ggaggcttgt acttttttgt tgaataaatg agttgtacaa accagg       776
```

<210> SEQ ID NO 90
<211> LENGTH: 1255
<212> TYPE: PRT
<213> ORGANISM: Homo sapiens

<400> SEQUENCE: 90

```
Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
```

-continued

```
                65                  70                  75                  80
Gln Gly Tyr Val Leu Ile Ala His Asn Gln Val Arg Gln Val Pro Leu
                    85                  90                  95
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
                115                 120                 125
Val Thr Gly Ala Ser Pro Gly Gly Leu Arg Glu Leu Gln Leu Arg Ser
                130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
                210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
                290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
                370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
Gly Ile Ser Trp Leu Gly Leu Arg Ser Leu Arg Glu Leu Gly Ser Gly
                450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
```

```
Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910
```

```
Trp Glu Leu Met Thr Phe Gly Ala Lys Pro Tyr Asp Gly Ile Pro Ala
    915                 920                 925

Arg Glu Ile Pro Asp Leu Leu Glu Lys Gly Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 91
<211> LENGTH: 1225
<212> TYPE: PRT
<213> ORGANISM: Homo sapiens

<400> SEQUENCE: 91

Met Lys Leu Arg Leu Pro Ala Ser Pro Glu Thr His Leu Asp Met Leu
1               5                   10                  15
```

Arg His Leu Tyr Gln Gly Cys Gln Val Val Gln Gly Asn Leu Glu Leu
             20                  25                  30

Thr Tyr Leu Pro Thr Asn Ala Ser Leu Ser Phe Leu Gln Asp Ile Gln
         35                  40                  45

Glu Val Gln Gly Tyr Val Leu Ile Ala His Asn Gln Val Arg Gln Val
     50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                 85                  90                  95

Thr Pro Val Thr Gly Ala Ser Pro Gly Gly Leu Arg Glu Leu Gln Leu
             100                 105                 110

Arg Ser Leu Thr Glu Ile Leu Lys Gly Gly Val Leu Ile Gln Arg Asn
         115                 120                 125

Pro Gln Leu Cys Tyr Gln Asp Thr Ile Leu Trp Lys Asp Ile Phe His
     130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                 165                 170                 175

Glu Ser Ser Glu Asp Cys Gln Ser Leu Thr Arg Thr Val Cys Ala Gly
             180                 185                 190

Gly Cys Ala Arg Cys Lys Gly Pro Leu Pro Thr Asp Cys Cys His Glu
         195                 200                 205

Gln Cys Ala Ala Gly Cys Thr Gly Pro Lys His Ser Asp Cys Leu Ala
     210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                 245                 250                 255

Gly Arg Tyr Thr Phe Gly Ala Ser Cys Val Thr Ala Cys Pro Tyr Asn
             260                 265                 270

Tyr Leu Ser Thr Asp Val Gly Ser Cys Thr Leu Val Cys Pro Leu His
         275                 280                 285

Asn Gln Glu Val Thr Ala Glu Asp Gly Thr Gln Arg Cys Glu Lys Cys
     290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                 325                 330                 335

Cys Lys Lys Ile Phe Gly Ser Leu Ala Phe Leu Pro Glu Ser Phe Asp
             340                 345                 350

Gly Asp Pro Ala Ser Asn Thr Ala Pro Leu Gln Pro Glu Gln Leu Gln
         355                 360                 365

Val Phe Glu Thr Leu Glu Glu Ile Thr Gly Tyr Leu Tyr Ile Ser Ala
     370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                 405                 410                 415

Gly Leu Gly Ile Ser Trp Leu Gly Leu Arg Ser Leu Arg Glu Leu Gly
             420                 425                 430

```
Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
                500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
        530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
```

```
                      850                 855                 860
Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
        995                1000                1005

Ala Gly Gly Met Val His His Arg His Arg Ser Ser Ser Thr Arg
   1010                1015                1020

Ser Gly Gly Gly Asp Leu Thr Leu Gly Leu Glu Pro Ser Glu Glu
   1025                1030                1035

Glu Ala Pro Arg Ser Pro Leu Ala Pro Ser Glu Gly Ala Gly Ser
   1040                1045                1050

Asp Val Phe Asp Gly Asp Leu Gly Met Gly Ala Ala Lys Gly Leu
   1055                1060                1065

Gln Ser Leu Pro Thr His Asp Pro Ser Pro Leu Gln Arg Tyr Ser
   1070                1075                1080

Glu Asp Pro Thr Val Pro Leu Pro Ser Glu Thr Asp Gly Tyr Val
   1085                1090                1095

Ala Pro Leu Thr Cys Ser Pro Gln Pro Glu Tyr Val Asn Gln Pro
   1100                1105                1110

Asp Val Arg Pro Gln Pro Pro Ser Pro Arg Glu Gly Pro Leu Pro
   1115                1120                1125

Ala Ala Arg Pro Ala Gly Ala Thr Leu Glu Arg Pro Lys Thr Leu
   1130                1135                1140

Ser Pro Gly Lys Asn Gly Val Val Lys Asp Val Phe Ala Phe Gly
   1145                1150                1155

Gly Ala Val Glu Asn Pro Glu Tyr Leu Thr Pro Gln Gly Gly Ala
   1160                1165                1170

Ala Pro Gln Pro His Pro Pro Ala Phe Ser Pro Ala Phe Asp
   1175                1180                1185

Asn Leu Tyr Tyr Trp Asp Gln Asp Pro Pro Glu Arg Gly Ala Pro
   1190                1195                1200

Pro Ser Thr Phe Lys Gly Thr Pro Thr Ala Glu Asn Pro Glu Tyr
   1205                1210                1215

Leu Gly Leu Asp Val Pro Val
   1220                1225

<210> SEQ ID NO 92
<211> LENGTH: 1256
<212> TYPE: PRT
<213> ORGANISM: Mus musculus
```

<400> SEQUENCE: 92

```
Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
        115                 120                 125

Ala Ala Pro Gly Arg Thr Pro Glu Gly Leu Arg Glu Leu Gln Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
    290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
    370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
```

```
            405                 410                 415
Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
            435                 440                 445

Leu Gly Ile His Ser Leu Gly Leu Arg Ser Leu Arg Glu Leu Gly Ser
            450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
            485                 490                 495

Ser Gly Asn Arg Pro Glu Ala Cys Gly Leu Glu Gly Leu Val Cys
            500                 505                 510

Asn Ser Leu Cys Ala Arg Gly His Cys Trp Gly Pro Gly Pro Thr Gln
            515                 520                 525

Cys Val Asn Cys Ser Gln Phe Leu Arg Gly Gln Glu Cys Val Glu Glu
            530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
            565                 570                 575

Cys Tyr Gly Ser Glu Ala Asp Gln Cys Glu Ala Cys His Tyr Lys
            580                 585                 590

Asp Ser Ser Ser Cys Val Ala Arg Cys Pro Ser Gly Val Lys Pro Asp
            595                 600                 605

Leu Ser Tyr Met Pro Ile Trp Lys Tyr Pro Asp Glu Glu Gly Ile Cys
            610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe Ile Ile
            645                 650                 655

Ala Thr Val Val Gly Val Leu Leu Phe Leu Ile Ile Val Val Val Ile
            660                 665                 670

Gly Ile Leu Ile Lys Arg Arg Arg Gln Lys Ile Arg Lys Tyr Thr Met
            675                 680                 685

Arg Arg Leu Leu Gln Glu Thr Glu Leu Val Glu Pro Leu Thr Pro Ser
            690                 695                 700

Gly Ala Val Pro Asn Gln Ala Gln Met Arg Ile Leu Lys Glu Thr Glu
705                 710                 715                 720

Leu Arg Lys Leu Lys Val Leu Gly Ser Gly Ala Phe Gly Thr Val Tyr
            725                 730                 735

Lys Gly Ile Trp Ile Pro Asp Gly Glu Asn Val Lys Ile Pro Val Ala
            740                 745                 750

Ile Lys Val Leu Arg Glu Asn Thr Ser Pro Lys Ala Asn Lys Glu Ile
            755                 760                 765

Leu Asp Glu Ala Tyr Val Met Ala Gly Val Gly Ser Pro Tyr Val Ser
            770                 775                 780

Arg Leu Leu Gly Ile Cys Leu Thr Ser Thr Val Gln Leu Val Thr Gln
785                 790                 795                 800

Leu Met Pro Tyr Gly Cys Leu Leu Asp His Val Arg Glu His Arg Gly
            805                 810                 815

Arg Leu Gly Ser Gln Asp Leu Leu Asn Trp Cys Val Gln Ile Ala Lys
            820                 825                 830
```

```
Gly Met Ser Tyr Leu Glu Glu Val Arg Leu Val His Arg Asp Leu Ala
        835                 840                 845

Ala Arg Asn Val Leu Val Lys Ser Pro Asn His Val Lys Ile Thr Asp
850                 855                 860

Phe Gly Leu Ala Arg Leu Leu Asp Ile Asp Glu Thr Glu Tyr His Ala
865                 870                 875                 880

Asp Gly Gly Lys Val Pro Ile Lys Trp Met Ala Leu Glu Ser Ile Leu
                885                 890                 895

Arg Arg Arg Phe Thr His Gln Ser Asp Val Trp Ser Tyr Gly Val Thr
                900                 905                 910

Val Trp Glu Leu Met Thr Phe Gly Ala Lys Pro Tyr Asp Gly Ile Pro
        915                 920                 925

Ala Arg Glu Ile Pro Asp Leu Leu Glu Lys Gly Glu Arg Leu Pro Gln
930                 935                 940

Pro Pro Ile Cys Thr Ile Asp Val Tyr Met Ile Met Val Lys Cys Trp
945                 950                 955                 960

Met Ile Asp Ser Glu Cys Arg Pro Arg Phe Arg Glu Leu Val Ser Glu
                965                 970                 975

Phe Ser Arg Met Ala Arg Asp Pro Gln Arg Phe Val Val Ile Gln Asn
                980                 985                 990

Glu Asp Leu Gly Pro Ser Ser Pro Met Asp Ser Thr Phe Tyr Arg Ser
        995                 1000                1005

Leu Leu Glu Asp Asp Asp Met Gly Glu Leu Val Asp Ala Glu Glu
    1010                1015                1020

Tyr Leu Val Pro Gln Gln Gly Phe Phe Ser Pro Asp Pro Ala Leu
    1025                1030                1035

Gly Thr Gly Ser Thr Ala His Arg Arg His Arg Ser Ser Ser Ala
    1040                1045                1050

Arg Ser Gly Gly Gly Glu Leu Thr Leu Gly Leu Glu Pro Ser Glu
    1055                1060                1065

Glu Glu Pro Pro Arg Ser Pro Leu Ala Pro Ser Glu Gly Ala Gly
    1070                1075                1080

Ser Asp Val Phe Asp Gly Asp Leu Ala Val Gly Val Thr Lys Gly
    1085                1090                1095

Leu Gln Ser Leu Ser Pro His Asp Leu Ser Pro Leu Gln Arg Tyr
    1100                1105                1110

Ser Glu Asp Pro Thr Leu Pro Leu Pro Pro Glu Thr Asp Gly Tyr
    1115                1120                1125

Val Ala Pro Leu Ala Cys Ser Pro Gln Pro Glu Tyr Val Asn Gln
    1130                1135                1140

Pro Glu Val Arg Pro Gln Ser Pro Leu Thr Pro Glu Gly Pro Pro
    1145                1150                1155

Pro Pro Ile Arg Pro Ala Gly Ala Thr Leu Glu Arg Pro Lys Thr
    1160                1165                1170

Leu Ser Pro Gly Lys Asn Gly Val Val Lys Asp Val Phe Ala Phe
    1175                1180                1185

Gly Gly Ala Val Glu Asn Pro Glu Tyr Leu Ala Pro Arg Ala Gly
    1190                1195                1200

Thr Ala Ser Gln Pro His Pro Ser Pro Ala Phe Ser Pro Ala Phe
    1205                1210                1215

Asp Asn Leu Tyr Tyr Trp Asp Gln Asn Ser Ser Glu Gln Gly Pro
    1220                1225                1230
```

-continued

```
Pro Pro Ser Thr Phe Glu Gly Thr Pro Thr Ala Glu Asn Pro Glu
    1235                1240                1245

Tyr Leu Gly Leu Asp Val Pro Val
    1250            1255

<210> SEQ ID NO 93
<211> LENGTH: 1255
<212> TYPE: PRT
<213> ORGANISM: Homo sapiens

<400> SEQUENCE: 93

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65              70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350
```

```
Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765
```

```
Asp Glu Ala Tyr Val Met Ala Gly Val Gly Ser Pro Tyr Val Ser Arg
    770             775             780

Leu Leu Gly Ile Cys Leu Thr Ser Thr Val Gln Leu Val Thr Gln Leu
785             790             795                 800

Met Pro Tyr Gly Cys Leu Leu Asp His Val Arg Glu Asn Arg Gly Arg
                805             810             815

Leu Gly Ser Gln Asp Leu Leu Asn Trp Cys Met Gln Ile Ala Lys Gly
            820             825             830

Met Ser Tyr Leu Glu Asp Val Arg Leu Val His Arg Asp Leu Ala Ala
        835             840             845

Arg Asn Val Leu Val Lys Ser Pro Asn His Val Lys Ile Thr Asp Phe
850             855             860

Gly Leu Ala Arg Leu Leu Asp Ile Asp Glu Thr Glu Tyr His Ala Asp
865             870             875             880

Gly Gly Lys Val Pro Ile Lys Trp Met Ala Leu Glu Ser Ile Leu Arg
                885             890             895

Arg Arg Phe Thr His Gln Ser Asp Val Trp Ser Tyr Gly Val Thr Val
            900             905             910

Trp Glu Leu Met Thr Phe Gly Ala Lys Pro Tyr Asp Gly Ile Pro Ala
        915             920             925

Arg Glu Ile Pro Asp Leu Leu Glu Lys Gly Glu Arg Leu Pro Gln Pro
930             935             940

Pro Ile Cys Thr Ile Asp Val Tyr Met Ile Met Val Lys Cys Trp Met
945             950             955             960

Ile Asp Ser Glu Cys Arg Pro Arg Phe Arg Glu Leu Val Ser Glu Phe
                965             970             975

Ser Arg Met Ala Arg Asp Pro Gln Arg Phe Val Val Ile Gln Asn Glu
            980             985             990

Asp Leu Gly Pro Ala Ser Pro Leu Asp Ser Thr Phe Tyr Arg Ser Leu
        995             1000            1005

Leu Glu Asp Asp Asp Met Gly Asp Leu Val Asp Ala Glu Glu Tyr
    1010            1015            1020

Leu Val Pro Gln Gln Gly Phe Phe Cys Pro Asp Pro Ala Pro Gly
    1025            1030            1035

Ala Gly Gly Met Val His His Arg His Arg Ser Ser Ser Thr Arg
    1040            1045            1050

Ser Gly Gly Gly Asp Leu Thr Leu Gly Leu Glu Pro Ser Glu Glu
    1055            1060            1065

Glu Ala Pro Arg Ser Pro Leu Ala Pro Ser Glu Gly Ala Gly Ser
    1070            1075            1080

Asp Val Phe Asp Gly Asp Leu Gly Met Gly Ala Ala Lys Gly Leu
    1085            1090            1095

Gln Ser Leu Pro Thr His Asp Pro Ser Pro Leu Gln Arg Tyr Ser
    1100            1105            1110

Glu Asp Pro Thr Val Pro Leu Pro Ser Glu Thr Asp Gly Tyr Val
    1115            1120            1125

Ala Pro Leu Thr Cys Ser Pro Gln Pro Glu Tyr Val Asn Gln Pro
    1130            1135            1140

Asp Val Arg Pro Gln Pro Pro Ser Pro Arg Glu Gly Pro Leu Pro
    1145            1150            1155

Ala Ala Arg Pro Ala Gly Ala Thr Leu Glu Arg Pro Lys Thr Leu
    1160            1165            1170

Ser Pro Gly Lys Asn Gly Val Val Lys Asp Val Phe Ala Phe Gly
```

```
                    1175                1180                1185

Gly Ala Val Glu Asn Pro Glu Tyr Leu Thr Pro Gln Gly Gly Ala
            1190                1195                1200

Ala Pro Gln Pro His Pro Pro Ala Phe Ser Pro Ala Phe Asp
        1205                1210                1215

Asn Leu Tyr Tyr Trp Asp Gln Asp Pro Pro Glu Arg Gly Ala Pro
        1220                1225                1230

Pro Ser Thr Phe Lys Gly Pro Thr Ala Glu Asn Pro Glu Tyr
    1235                1240                1245

Leu Gly Leu Asp Val Pro Val
    1250                1255

<210> SEQ ID NO 94
<211> LENGTH: 1210
<212> TYPE: PRT
<213> ORGANISM: Homo sapiens

<400> SEQUENCE: 94

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285
```

```
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
    515                 520                 525
Val Ser Arg Gly Arg Glu Cys Val Asp Lys Cys Lys Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
    595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
```

-continued

```
            705                 710                 715                 720
        Gly Ala Phe Gly Thr Val Tyr Lys Gly Leu Trp Ile Pro Glu Gly Glu
                        725                 730                 735
        Lys Val Lys Ile Pro Val Ala Ile Lys Glu Leu Arg Glu Ala Thr Ser
                        740                 745                 750
        Pro Lys Ala Asn Lys Glu Ile Leu Asp Glu Ala Tyr Val Met Ala Ser
                        755                 760                 765
        Val Asp Asn Pro His Val Cys Arg Leu Leu Gly Ile Cys Leu Thr Ser
                        770                 775                 780
        Thr Val Gln Leu Ile Thr Gln Leu Met Pro Phe Gly Cys Leu Leu Asp
        785                 790                 795                 800
        Tyr Val Arg Glu His Lys Asp Asn Ile Gly Ser Gln Tyr Leu Leu Asn
                        805                 810                 815
        Trp Cys Val Gln Ile Ala Lys Gly Met Asn Tyr Leu Glu Asp Arg Arg
                        820                 825                 830
        Leu Val His Arg Asp Leu Ala Ala Arg Asn Val Leu Val Lys Thr Pro
                        835                 840                 845
        Gln His Val Lys Ile Thr Asp Phe Gly Leu Ala Lys Leu Leu Gly Ala
                        850                 855                 860
        Glu Glu Lys Glu Tyr His Ala Glu Gly Gly Lys Val Pro Ile Lys Trp
        865                 870                 875                 880
        Met Ala Leu Glu Ser Ile Leu His Arg Ile Tyr Thr His Gln Ser Asp
                        885                 890                 895
        Val Trp Ser Tyr Gly Val Thr Val Trp Glu Leu Met Thr Phe Gly Ser
                        900                 905                 910
        Lys Pro Tyr Asp Gly Ile Pro Ala Ser Glu Ile Ser Ser Ile Leu Glu
                        915                 920                 925
        Lys Gly Glu Arg Leu Pro Gln Pro Pro Ile Cys Thr Ile Asp Val Tyr
                        930                 935                 940
        Met Ile Met Val Lys Cys Trp Met Ile Asp Ala Asp Ser Arg Pro Lys
        945                 950                 955                 960
        Phe Arg Glu Leu Ile Ile Glu Phe Ser Lys Met Ala Arg Asp Pro Gln
                        965                 970                 975
        Arg Tyr Leu Val Ile Gln Gly Asp Glu Arg Met His Leu Pro Ser Pro
                        980                 985                 990
        Thr Asp Ser Asn Phe Tyr Arg Ala  Leu Met Asp Glu Glu  Asp Met Asp
                        995                1000                1005
        Asp Val Val Asp Ala Asp Glu  Tyr Leu Ile Pro Gln  Gln Gly Phe
                       1010                1015                1020
        Phe Ser  Ser Pro Ser Thr  Ser Arg Thr Pro Leu Leu  Ser Ser Leu
             1025                1030                1035
        Ser Ala  Thr Ser Asn Asn Ser  Thr Val Ala Cys Ile  Asp Arg Asn
             1040                1045                1050
        Gly Leu  Gln Ser Cys Pro Ile  Lys Glu Asp Ser Phe  Leu Gln Arg
             1055                1060                1065
        Tyr Ser  Ser Asp Pro Thr Gly  Ala Leu Thr Glu Asp  Ser Ile Asp
             1070                1075                1080
        Asp Thr  Phe Leu Pro Val Pro  Glu Tyr Ile Asn Gln  Ser Val Pro
             1085                1090                1095
        Lys Arg  Pro Ala Gly Ser Val  Gln Asn Pro Val Tyr  His Asn Gln
             1100                1105                1110
        Pro Leu  Asn Pro Ala Pro Ser  Arg Asp Pro His Tyr  Gln Asp Pro
             1115                1120                1125
```

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 95
<211> LENGTH: 1167
<212> TYPE: PRT
<213> ORGANISM: Homo sapiens

<400> SEQUENCE: 95

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Gly Gln Lys
130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
        195                 200                 205

Phe Arg Asp Glu Ala Thr Cys Lys Asp Thr Cys Pro Pro Leu Met Leu
210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys

```
            275                 280                 285
Arg Lys Val Cys Asn Gly Ile Gly Ile Gly Glu Phe Lys Asp Ser Leu
290                 295                 300
Ser Ile Asn Ala Thr Asn Ile Lys His Phe Lys Asn Cys Thr Ser Ile
305                 310                 315                 320
Ser Gly Asp Leu His Ile Leu Pro Val Ala Phe Arg Gly Asp Ser Phe
                325                 330                 335
Thr His Thr Pro Pro Leu Asp Pro Gln Glu Leu Asp Ile Leu Lys Thr
                340                 345                 350
Val Lys Glu Ile Thr Gly Phe Leu Leu Ile Gln Ala Trp Pro Glu Asn
                355                 360                 365
Arg Thr Asp Leu His Ala Phe Glu Asn Leu Glu Ile Ile Arg Gly Arg
370                 375                 380
Thr Lys Gln His Gly Gln Phe Ser Leu Ala Val Val Ser Leu Asn Ile
385                 390                 395                 400
Thr Ser Leu Gly Leu Arg Ser Leu Lys Glu Ile Ser Asp Gly Asp Val
                405                 410                 415
Ile Ile Ser Gly Asn Lys Asn Leu Cys Tyr Ala Asn Thr Ile Asn Trp
                420                 425                 430
Lys Lys Leu Phe Gly Thr Ser Gly Gln Lys Thr Lys Ile Ile Ser Asn
                435                 440                 445
Arg Gly Glu Asn Ser Cys Lys Ala Thr Gly Gln Val Cys His Ala Leu
450                 455                 460
Cys Ser Pro Glu Gly Cys Trp Gly Pro Glu Pro Arg Asp Cys Val Ser
465                 470                 475                 480
Cys Arg Asn Val Ser Arg Gly Arg Glu Cys Val Asp Lys Cys Asn Leu
                485                 490                 495
Leu Glu Gly Glu Pro Arg Glu Phe Val Glu Asn Ser Glu Cys Ile Gln
                500                 505                 510
Cys His Pro Glu Cys Leu Pro Gln Ala Met Asn Ile Thr Cys Thr Gly
                515                 520                 525
Arg Gly Pro Asp Asn Cys Ile Gln Cys Ala His Tyr Ile Asp Gly Pro
530                 535                 540
His Cys Val Lys Thr Cys Pro Ala Gly Val Met Gly Glu Asn Asn Thr
545                 550                 555                 560
Leu Val Trp Lys Tyr Ala Asp Ala Gly His Val Cys His Leu Cys His
                565                 570                 575
Pro Asn Cys Thr Tyr Gly Cys Thr Gly Pro Gly Leu Glu Gly Cys Pro
                580                 585                 590
Thr Asn Gly Pro Lys Ile Pro Ser Ile Ala Thr Gly Met Val Gly Ala
                595                 600                 605
Leu Leu Leu Leu Leu Val Val Ala Leu Gly Ile Gly Leu Phe Met Arg
                610                 615                 620
Arg Arg His Ile Val Arg Lys Arg Thr Leu Arg Arg Leu Leu Gln Glu
625                 630                 635                 640
Arg Glu Leu Val Glu Pro Leu Thr Pro Ser Gly Glu Ala Pro Asn Gln
                645                 650                 655
Ala Leu Leu Arg Ile Leu Lys Glu Thr Glu Phe Lys Lys Ile Lys Val
                660                 665                 670
Leu Gly Ser Gly Ala Phe Gly Thr Val Tyr Lys Gly Leu Trp Ile Pro
                675                 680                 685
Glu Gly Glu Lys Val Lys Ile Pro Val Ala Ile Lys Glu Leu Arg Glu
                690                 695                 700
```

```
Ala Thr Ser Pro Lys Ala Asn Lys Glu Ile Leu Asp Glu Ala Tyr Val
705                 710                 715                 720

Met Ala Ser Val Asp Asn Pro His Val Cys Arg Leu Leu Gly Ile Cys
            725                 730                 735

Leu Thr Ser Thr Val Gln Leu Ile Thr Gln Leu Met Pro Phe Gly Cys
            740                 745                 750

Leu Leu Asp Tyr Val Arg Glu His Lys Asp Asn Ile Gly Ser Gln Tyr
            755                 760                 765

Leu Leu Asn Trp Cys Val Gln Ile Ala Lys Gly Met Asn Tyr Leu Glu
770                 775                 780

Asp Arg Arg Leu Val His Arg Asp Leu Ala Ala Arg Asn Val Leu Val
785                 790                 795                 800

Lys Thr Pro Gln His Val Lys Ile Thr Asp Phe Gly Leu Ala Lys Leu
                805                 810                 815

Leu Gly Ala Glu Glu Lys Glu Tyr His Ala Glu Gly Gly Lys Val Pro
            820                 825                 830

Ile Lys Trp Met Ala Leu Glu Ser Ile Leu His Arg Ile Tyr Thr His
            835                 840                 845

Gln Ser Asp Val Trp Ser Tyr Gly Val Thr Val Trp Glu Leu Met Thr
850                 855                 860

Phe Gly Ser Lys Pro Tyr Asp Gly Ile Pro Ala Ser Glu Ile Ser Ser
865                 870                 875                 880

Ile Leu Glu Lys Gly Glu Arg Leu Pro Gln Pro Ile Cys Thr Ile
            885                 890                 895

Asp Val Tyr Met Ile Met Val Lys Cys Trp Met Ile Asp Ala Asp Ser
            900                 905                 910

Arg Pro Lys Phe Arg Glu Leu Ile Ile Glu Phe Ser Lys Met Ala Arg
            915                 920                 925

Asp Pro Gln Arg Tyr Leu Val Ile Gln Gly Asp Glu Arg Met His Leu
            930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
            980                 985                 990

Leu Ser Ala Thr Ser Asn Asn Ser Thr Val Ala Cys Ile Asp Arg Asn
            995                 1000                1005

Gly Leu Gln Ser Cys Pro Ile Lys Glu Asp Ser Phe Leu Gln Arg
            1010                1015                1020

Tyr Ser Ser Asp Pro Thr Gly Ala Leu Thr Glu Asp Ser Ile Asp
            1025                1030                1035

Asp Thr Phe Leu Pro Val Pro Glu Tyr Ile Asn Gln Ser Val Pro
            1040                1045                1050

Lys Arg Pro Ala Gly Ser Val Gln Asn Pro Val Tyr His Asn Gln
            1055                1060                1065

Pro Leu Asn Pro Ala Pro Ser Arg Asp Pro His Tyr Gln Asp Pro
            1070                1075                1080

His Ser Thr Ala Val Gly Asn Pro Glu Tyr Leu Asn Thr Val Gln
            1085                1090                1095

Pro Thr Cys Val Asn Ser Thr Phe Asp Ser Pro Ala His Trp Ala
            1100                1105                1110
```

```
Gln Lys Gly Ser His Gln Ile  Ser Leu Asp Asn Pro  Asp Tyr Gln
    1115             1120              1125

Gln Asp Phe Phe Pro Lys Glu  Ala Lys Pro Asn Gly  Ile Phe Lys
    1130             1135              1140

Gly Ser Thr Ala Glu Asn Ala  Glu Tyr Leu Arg Val  Ala Pro Gln
    1145             1150              1155

Ser Ser Glu Phe Ile Gly Ala  Val Pro
    1160             1165

<210> SEQ ID NO 96
<211> LENGTH: 595
<212> TYPE: PRT
<213> ORGANISM: Homo sapiens

<400> SEQUENCE: 96

Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Arg Pro Ser
             20                  25                  30

Arg Lys Asn Gln Gly Asp Phe Ser Leu Ser Val Arg Val Gly Asp Gln
         35                  40                  45

Val Thr His Ile Arg Ile Gln Asn Ser Gly Asp Phe Tyr Asp Leu Tyr
     50                  55                  60

Gly Gly Glu Lys Phe Ala Thr Leu Thr Glu Leu Val Glu Tyr Tyr Thr
 65                  70                  75                  80

Gln Gln Gln Gly Val Leu Gln Asp Arg Asp Gly Thr Ile Ile His Leu
                 85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320
```

Tyr Ile Ala Ser Gln Gly Cys Leu Glu Ala Thr Val Asn Asp Phe Trp
            325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
            355                 360                 365

Gly Met Gln Arg Ala Tyr Gly Pro Tyr Ser Val Thr Asn Cys Gly Glu
            370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
            405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
            450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
            580                 585                 590

Lys Arg Lys
        595

<210> SEQ ID NO 97
<211> LENGTH: 597
<212> TYPE: PRT
<213> ORGANISM: Homo sapiens

<400> SEQUENCE: 97

Met Leu Ser Arg Gly Trp Phe His Arg Asp Leu Ser Gly Leu Asp Ala
1               5                   10                  15

Glu Thr Leu Leu Lys Gly Arg Gly Val His Gly Ser Phe Leu Ala Arg
            20                  25                  30

Pro Ser Arg Lys Asn Gln Gly Asp Phe Ser Leu Ser Val Arg Val Gly
            35                  40                  45

Asp Gln Val Thr His Ile Arg Ile Gln Asn Ser Gly Asp Phe Tyr Asp
            50                  55                  60

Leu Tyr Gly Gly Glu Lys Phe Ala Thr Leu Thr Glu Leu Val Glu Tyr
65                  70                  75                  80

Tyr Thr Gln Gln Gln Gly Val Leu Gln Asp Arg Asp Gly Thr Ile Ile

-continued

His Leu Lys Tyr Pro Leu Asn Cys Ser Asp Pro Thr Ser Glu Arg Trp
             85              90              95
                100             105             110

Tyr His Gly His Met Ser Gly Gly Gln Ala Glu Thr Leu Leu Gln Ala
                115             120             125

Lys Gly Glu Pro Trp Thr Phe Leu Val Arg Glu Ser Leu Ser Gln Pro
130             135             140

Gly Asp Phe Val Leu Ser Val Leu Ser Asp Gln Pro Lys Ala Gly Pro
145             150             155             160

Gly Ser Pro Leu Arg Val Thr His Ile Lys Val Met Cys Glu Gly Gly
                165             170             175

Arg Tyr Thr Val Gly Gly Leu Glu Thr Phe Asp Ser Leu Thr Asp Leu
                180             185             190

Val Glu His Phe Lys Lys Thr Gly Ile Glu Ala Ser Gly Ala Phe
                195             200             205

Val Tyr Leu Arg Gln Pro Tyr Tyr Ala Thr Arg Val Asn Ala Ala Asp
            210             215             220

Ile Glu Asn Arg Val Leu Glu Leu Asn Lys Lys Gln Glu Ser Glu Asp
225             230             235             240

Thr Ala Lys Ala Gly Phe Trp Glu Glu Phe Glu Ser Leu Gln Lys Gln
                245             250             255

Glu Val Lys Asn Leu His Gln Arg Leu Glu Gly Gln Arg Pro Glu Asn
                260             265             270

Lys Gly Lys Asn Arg Tyr Lys Asn Ile Leu Pro Phe Asp His Ser Arg
                275             280             285

Val Ile Leu Gln Gly Arg Asp Ser Asn Ile Pro Gly Ser Asp Tyr Ile
            290             295             300

Asn Ala Asn Tyr Ile Lys Asn Gln Leu Leu Gly Pro Asp Glu Asn Ala
305             310             315             320

Lys Thr Tyr Ile Ala Ser Gln Gly Cys Leu Glu Ala Thr Val Asn Asp
                325             330             335

Phe Trp Gln Met Ala Trp Gln Glu Asn Ser Arg Val Ile Val Met Thr
                340             345             350

Thr Arg Glu Val Glu Lys Gly Arg Asn Lys Cys Val Pro Tyr Trp Pro
            355             360             365

Glu Val Gly Met Gln Arg Ala Tyr Gly Pro Tyr Ser Val Thr Asn Cys
            370             375             380

Gly Glu His Asp Thr Thr Glu Tyr Lys Leu Arg Thr Leu Gln Val Ser
385             390             395             400

Pro Leu Asp Asn Gly Asp Leu Ile Arg Glu Ile Trp His Tyr Gln Tyr
                405             410             415

Leu Ser Trp Pro Asp His Gly Val Pro Ser Glu Pro Gly Gly Val Leu
                420             425             430

Ser Phe Leu Asp Gln Ile Asn Gln Arg Gln Glu Ser Leu Pro His Ala
            435             440             445

Gly Pro Ile Ile Val His Cys Ser Ala Gly Ile Gly Arg Thr Gly Thr
            450             455             460

Ile Ile Val Ile Asp Met Leu Met Glu Asn Ile Ser Thr Lys Gly Leu
465             470             475             480

Asp Cys Asp Ile Asp Ile Gln Lys Thr Ile Gln Met Val Arg Ala Gln
                485             490             495

Arg Ser Gly Met Val Gln Thr Glu Ala Gln Tyr Lys Phe Ile Tyr Val
                500             505             510

```
Ala Ile Ala Gln Phe Ile Glu Thr Thr Lys Lys Leu Glu Val Leu
        515                 520                 525

Gln Ser Gln Lys Gly Gln Glu Ser Glu Tyr Gly Asn Ile Thr Tyr Pro
    530                 535                 540

Pro Ala Met Lys Asn Ala His Ala Lys Ala Ser Arg Thr Ser Ser Lys
545                 550                 555                 560

His Lys Glu Asp Val Tyr Glu Asn Leu His Thr Lys Asn Lys Arg Glu
                565                 570                 575

Glu Lys Val Lys Lys Gln Arg Ser Ala Asp Lys Glu Lys Ser Lys Gly
            580                 585                 590

Ser Leu Lys Arg Lys
        595

<210> SEQ ID NO 98
<211> LENGTH: 624
<212> TYPE: PRT
<213> ORGANISM: Homo sapiens

<400> SEQUENCE: 98

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
```

|       |       |       | 275   |       |       |       | 280   |       |       |       | 285   |
|-------|-------|-------|-------|-------|-------|-------|-------|-------|-------|-------|-------|

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
                340                 345                 350

Glu Val Glu Lys Gly Arg Asn Lys Cys Val Pro Tyr Trp Pro Glu Val
            355                 360                 365

Gly Met Gln Arg Ala Tyr Gly Pro Tyr Ser Val Thr Asn Cys Gly Glu
            370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
                420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
            450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys Ser Leu
545                 550                 555                 560

Glu Ser Ser Ala Gly Thr Val Ala Ala Ser Pro Val Arg Arg Gly Gly
                565                 570                 575

Gln Arg Gly Leu Pro Val Pro Gly Pro Pro Val Leu Ser Pro Asp Leu
            580                 585                 590

His Gln Leu Pro Val Leu Ala Pro Leu His Pro Ala Ala Asp Thr Arg
        595                 600                 605

Arg Met Cys Met Arg Thr Cys Thr Leu Arg Thr Arg Gly Arg Arg Lys
    610                 615                 620

<210> SEQ ID NO 99
<211> LENGTH: 1591
<212> TYPE: PRT
<213> ORGANISM: Homo sapiens

<400> SEQUENCE: 99

Met Gly Asn Ala Glu Ser Gln His Val Glu His Glu Phe Tyr Gly Glu
1               5                   10                  15

Lys His Ala Ser Leu Gly Arg Lys His Thr Ser Arg Ser Leu Arg Leu
            20                  25                  30

-continued

```
Ser His Lys Thr Arg Arg Thr Arg His Ala Ser Ser Gly Lys Val Ile
     35                  40                  45

His Arg Asn Ser Glu Val Ser Thr Arg Ser Ser Ser Thr Pro Ser Ile
 50                  55                  60

Pro Gln Ser Leu Ala Glu Asn Gly Leu Glu Pro Phe Ser Gln Asp Gly
 65                  70                  75                  80

Thr Leu Glu Asp Phe Gly Ser Pro Ile Trp Val Asp Arg Val Asp Met
                 85                  90                  95

Gly Leu Arg Pro Val Ser Tyr Thr Asp Ser Ser Val Thr Pro Ser Val
            100                 105                 110

Asp Ser Ser Ile Val Leu Thr Ala Ala Ser Val Gln Ser Met Pro Asp
        115                 120                 125

Thr Glu Glu Ser Arg Leu Tyr Gly Asp Asp Ala Thr Tyr Leu Ala Glu
    130                 135                 140

Gly Gly Arg Arg Gln His Ser Tyr Thr Ser Asn Gly Pro Thr Phe Met
145                 150                 155                 160

Glu Thr Ala Ser Phe Lys Lys Lys Arg Ser Lys Ser Ala Asp Ile Trp
                165                 170                 175

Arg Glu Asp Ser Leu Glu Phe Ser Leu Ser Asp Leu Ser Gln Glu His
            180                 185                 190

Leu Thr Ser Asn Glu Glu Ile Leu Gly Ser Ala Glu Glu Lys Asp Cys
        195                 200                 205

Glu Glu Ala Arg Gly Met Glu Thr Arg Ala Ser Pro Arg Gln Leu Ser
    210                 215                 220

Thr Cys Gln Arg Ala Asn Ser Leu Gly Asp Leu Tyr Ala Gln Lys Asn
225                 230                 235                 240

Ser Gly Val Thr Ala Asn Gly Gly Pro Gly Ser Lys Phe Ala Gly Tyr
                245                 250                 255

Cys Arg Asn Leu Val Ser Asp Ile Pro Asn Leu Ala Asn His Lys Met
            260                 265                 270

Pro Pro Ala Ala Ala Glu Glu Thr Pro Pro Tyr Ser Asn Tyr Asn Thr
        275                 280                 285

Leu Pro Cys Arg Lys Ser His Cys Leu Ser Glu Gly Ala Thr Asn Pro
    290                 295                 300

Gln Ile Ser His Ser Asn Ser Met Gln Gly Arg Arg Ala Lys Thr Thr
305                 310                 315                 320

Gln Asp Val Asn Ala Gly Glu Gly Ser Glu Phe Ala Asp Ser Gly Ile
                325                 330                 335

Glu Gly Ala Thr Thr Asp Thr Asp Leu Leu Ser Arg Arg Ser Asn Ala
            340                 345                 350

Thr Asn Ser Ser Tyr Ser Pro Thr Thr Gly Arg Ala Phe Val Gly Ser
        355                 360                 365

Asp Ser Gly Ser Ser Ser Thr Gly Asp Ala Ala Arg Gln Gly Val Tyr
    370                 375                 380

Glu Asn Phe Arg Arg Glu Leu Glu Met Ser Thr Thr Asn Ser Glu Ser
385                 390                 395                 400

Leu Glu Glu Ala Gly Ser Ala His Ser Asp Glu Gln Ser Ser Gly Thr
                405                 410                 415

Leu Ser Ser Pro Gly Gln Ser Asp Ile Leu Leu Thr Ala Ala Gln Gly
            420                 425                 430

Thr Val Arg Lys Ala Gly Ala Leu Ala Val Lys Asn Phe Leu Val His
        435                 440                 445

Lys Lys Asn Lys Lys Val Glu Ser Ala Thr Arg Arg Lys Trp Lys His
```

```
                450             455             460
Tyr Trp Val Ser Leu Lys Gly Cys Thr Leu Phe Phe Tyr Glu Ser Asp
465                     470                     475             480

Gly Arg Ser Gly Ile Asp His Asn Ser Ile Pro Lys His Ala Val Trp
                485                     490                 495

Val Glu Asn Ser Ile Val Gln Ala Val Pro Glu His Pro Lys Lys Asp
            500                     505                 510

Phe Val Phe Cys Leu Ser Asn Ser Leu Gly Asp Ala Phe Leu Phe Gln
        515                     520                 525

Thr Thr Ser Gln Thr Glu Leu Glu Asn Trp Ile Thr Ala Ile His Ser
    530                     535                 540

Ala Cys Ala Thr Ala Val Ala Arg His His His Lys Glu Asp Thr Leu
545                     550                 555                 560

Arg Leu Leu Lys Ser Glu Ile Lys Lys Leu Glu Gln Lys Ile Asp Met
                565                     570                 575

Asp Glu Lys Met Lys Lys Met Gly Glu Met Gln Leu Ser Ser Val Thr
                580                     585                 590

Asp Ser Lys Lys Lys Thr Ile Leu Asp Gln Ile Phe Val Trp Glu
            595                     600                 605

Gln Asn Leu Glu Gln Phe Gln Met Asp Leu Phe Arg Phe Arg Cys Tyr
    610                     615                 620

Leu Ala Ser Leu Gln Gly Gly Glu Leu Pro Asn Pro Lys Arg Leu Leu
625                     630                 635                 640

Ala Phe Ala Ser Arg Pro Thr Lys Val Ala Met Gly Arg Leu Gly Ile
                645                     650                 655

Phe Ser Val Ser Ser Phe His Ala Leu Val Ala Ala Arg Thr Gly Glu
            660                     665                 670

Thr Gly Val Arg Arg Arg Thr Gln Ala Met Ser Arg Ser Ala Ser Lys
            675                     680                 685

Arg Arg Ser Arg Phe Ser Ser Leu Trp Gly Leu Asp Thr Thr Ser Lys
            690                     695                 700

Lys Lys Gln Gly Arg Pro Ser Ile Asn Gln Val Phe Gly Glu Gly Thr
705                     710                     715             720

Glu Ala Val Lys Lys Ser Leu Glu Gly Ile Phe Asp Asp Ile Val Pro
                725                     730                 735

Asp Gly Lys Arg Glu Lys Glu Val Val Leu Pro Asn Val His Gln His
            740                     745                 750

Asn Pro Asp Cys Asp Ile Trp Val His Glu Tyr Phe Thr Pro Ser Trp
            755                     760                 765

Phe Cys Leu Pro Asn Asn Gln Pro Ala Leu Thr Val Val Arg Pro Gly
        770                     775                 780

Asp Thr Ala Arg Asp Thr Leu Glu Leu Ile Cys Lys Thr His Gln Leu
785                     790                 795                 800

Asp His Ser Ala His Tyr Leu Arg Leu Lys Phe Leu Ile Glu Asn Lys
                805                     810                 815

Met Gln Leu Tyr Val Pro Gln Pro Glu Glu Asp Ile Tyr Glu Leu Leu
                820                     825                 830

Tyr Lys Glu Ile Glu Ile Cys Pro Lys Val Thr Gln Ser Ile His Ile
            835                     840                 845

Glu Lys Ser Asp Thr Ala Ala Asp Thr Tyr Gly Phe Ser Leu Ser Ser
    850                     855                 860

Val Glu Glu Asp Gly Ile Arg Arg Leu Tyr Val Asn Ser Val Lys Glu
865                     870                     875             880
```

```
Thr Gly Leu Ala Ser Lys Lys Gly Leu Lys Ala Gly Asp Glu Ile Leu
                885             890             895

Glu Ile Asn Asn Arg Ala Ala Asp Ala Leu Asn Ser Ser Met Leu Lys
                900             905             910

Asp Phe Leu Ser Gln Pro Ser Leu Gly Leu Leu Val Arg Thr Tyr Pro
            915             920             925

Glu Leu Glu Glu Gly Val Glu Leu Leu Glu Ser Pro Pro His Arg Val
        930             935             940

Asp Gly Pro Ala Asp Leu Gly Glu Ser Pro Leu Ala Phe Leu Thr Ser
945             950             955             960

Asn Pro Gly His Ser Leu Cys Ser Glu Gln Gly Ser Ser Ala Glu Thr
                965             970             975

Ala Pro Glu Glu Thr Glu Gly Pro Asp Leu Gly Ser Ser Asp Glu Thr
            980             985             990

Asp His Ser Ser Lys Ser Thr Glu Gln Val Ala Ala Phe Cys Arg Ser
            995             1000            1005

Leu His Glu Met Asn Pro Ser Asp Gln Ser Pro Ser Pro Gln Asp
        1010            1015            1020

Ser Thr Gly Pro Gln Leu Ala Thr Met Arg Gln Leu Ser Asp Ala
    1025            1030            1035

Asp Lys Leu Arg Lys Val Ile Cys Glu Leu Leu Glu Thr Glu Arg
    1040            1045            1050

Thr Tyr Val Lys Asp Leu Asn Cys Leu Met Glu Arg Tyr Leu Lys
    1055            1060            1065

Pro Leu Gln Lys Glu Thr Phe Leu Thr Gln Asp Glu Leu Asp Val
    1070            1075            1080

Leu Phe Gly Asn Leu Thr Glu Met Val Glu Phe Gln Val Glu Phe
    1085            1090            1095

Leu Lys Thr Leu Glu Asp Gly Val Arg Leu Val Pro Asp Leu Glu
    1100            1105            1110

Lys Leu Glu Lys Val Asp Gln Phe Lys Lys Val Leu Phe Ser Leu
    1115            1120            1125

Gly Gly Ser Phe Leu Tyr Tyr Ala Asp Arg Phe Lys Leu Tyr Ser
    1130            1135            1140

Ala Phe Cys Ala Ser His Thr Lys Val Pro Lys Val Leu Val Lys
    1145            1150            1155

Ala Lys Thr Asp Thr Ala Phe Lys Ala Phe Leu Asp Ala Gln Asn
    1160            1165            1170

Pro Lys Gln Gln His Ser Ser Thr Leu Glu Ser Tyr Leu Ile Lys
    1175            1180            1185

Pro Ile Gln Arg Ile Leu Lys Tyr Pro Leu Leu Leu Arg Glu Leu
    1190            1195            1200

Phe Ala Leu Thr Asp Ala Glu Ser Glu Glu His Tyr His Leu Asp
    1205            1210            1215

Val Ala Ile Lys Thr Met Asn Lys Val Ala Ser His Ile Asn Glu
    1220            1225            1230

Met Gln Lys Ile His Glu Glu Phe Gly Ala Val Phe Asp Gln Leu
    1235            1240            1245

Ile Ala Glu Gln Thr Gly Glu Lys Lys Glu Val Ala Asp Leu Ser
    1250            1255            1260

Met Gly Asp Leu Leu Leu His Thr Thr Val Ile Trp Leu Asn Pro
    1265            1270            1275
```

Pro Ala Ser Leu Gly Lys Trp Lys Lys Glu Pro Glu Leu Ala Ala
    1280                1285                1290

Phe Val Phe Lys Thr Ala Val Val Leu Val Tyr Lys Asp Gly Ser
    1295                1300                1305

Lys Gln Lys Lys Lys Leu Val Gly Ser His Arg Leu Ser Ile Tyr
    1310                1315                1320

Glu Asp Trp Asp Pro Phe Arg Phe Arg His Met Ile Pro Thr Glu
    1325                1330                1335

Ala Leu Gln Val Arg Ala Leu Ala Ser Ala Asp Ala Glu Ala Asn
    1340                1345                1350

Ala Val Cys Glu Ile Val His Val Lys Ser Glu Ser Glu Gly Arg
    1355                1360                1365

Pro Glu Arg Val Phe His Leu Cys Cys Ser Ser Pro Glu Ser Arg
    1370                1375                1380

Lys Asp Phe Leu Lys Ala Val His Ser Ile Leu Arg Asp Lys His
    1385                1390                1395

Arg Arg Gln Leu Leu Lys Thr Glu Ser Leu Pro Ser Ser Gln Gln
    1400                1405                1410

Tyr Val Pro Phe Gly Gly Lys Arg Leu Cys Ala Leu Lys Gly Ala
    1415                1420                1425

Arg Pro Ala Met Ser Arg Ala Val Ser Ala Pro Ser Lys Ser Leu
    1430                1435                1440

Gly Arg Arg Arg Arg Leu Ala Arg Asn Arg Phe Thr Ile Asp
    1445                1450                1455

Ser Asp Ala Val Ser Ala Ser Pro Glu Lys Glu Ser Gln Gln
    1460                1465                1470

Pro Pro Gly Gly Gly Asp Thr Asp Arg Trp Val Glu Glu Gln Phe
    1475                1480                1485

Asp Leu Ala Gln Tyr Glu Glu Gln Asp Ile Lys Glu Thr Asp
    1490                1495                1500

Ile Leu Ser Asp Asp Asp Glu Phe Cys Glu Ser Val Lys Gly Ala
    1505                1510                1515

Ser Val Asp Arg Asp Leu Gln Glu Arg Leu Gln Ala Thr Ser Ile
    1520                1525                1530

Ser Gln Arg Glu Arg Gly Arg Lys Thr Leu Asp Ser His Ala Ser
    1535                1540                1545

Arg Met Ala Gln Leu Lys Lys Gln Ala Ala Leu Ser Gly Ile Asn
    1550                1555                1560

Gly Gly Leu Glu Ser Ala Ser Glu Glu Val Ile Trp Val Arg Arg
    1565                1570                1575

Glu Asp Phe Ala Pro Ser Arg Lys Leu Asn Thr Glu Ile
    1580                1585                1590

<210> SEQ ID NO 100
<211> LENGTH: 1591
<212> TYPE: PRT
<213> ORGANISM: Homo sapiens

<400> SEQUENCE: 100

Met Gly Asn Ala Glu Ser Gln His Val Glu His Glu Phe Tyr Gly Glu
1               5                   10                  15

Lys His Ala Ser Leu Gly Arg Asn Asp Thr Ser Arg Ser Leu Arg Leu
                20                  25                  30

Ser His Lys Thr Arg Arg Thr Arg His Ala Ser Ser Gly Lys Val Ile
            35                  40                  45

-continued

```
His Arg Asn Ser Glu Val Ser Thr Arg Ser Ser Thr Pro Ser Ile
    50                  55                  60

Pro Gln Ser Leu Ala Glu Asn Gly Leu Glu Pro Phe Ser Gln Asp Gly
65                  70                  75                  80

Thr Leu Glu Asp Phe Gly Ser Pro Ile Trp Val Asp Arg Val Asp Met
                    85                  90                  95

Gly Leu Arg Pro Val Ser Tyr Thr Asp Ser Ser Val Thr Pro Ser Val
                100                 105                 110

Asp Ser Ser Ile Val Leu Thr Ala Ala Ser Val Gln Ser Met Pro Asp
            115                 120                 125

Thr Glu Glu Ser Arg Leu Tyr Gly Asp Asp Ala Thr Tyr Leu Ala Glu
        130                 135                 140

Gly Gly Arg Arg Gln His Ser Tyr Thr Ser Asn Gly Pro Thr Phe Met
145                 150                 155                 160

Glu Thr Ala Ser Phe Lys Lys Arg Ser Lys Ser Ala Asp Ile Trp
                    165                 170                 175

Arg Glu Asp Ser Leu Glu Phe Ser Leu Ser Asp Leu Ser Gln Glu His
                180                 185                 190

Leu Thr Ser Asn Glu Glu Ile Leu Gly Ser Ala Glu Glu Lys Asp Cys
            195                 200                 205

Glu Glu Ala Arg Gly Met Glu Thr Arg Ala Ser Pro Arg Gln Leu Ser
        210                 215                 220

Thr Cys Gln Arg Ala Asn Ser Leu Gly Asp Leu Tyr Ala Gln Lys Asn
225                 230                 235                 240

Ser Gly Val Thr Ala Asn Met Gly Pro Gly Ser Lys Phe Ala Gly Tyr
                    245                 250                 255

Cys Arg Asn Leu Val Ser Asp Ile Pro Asn Leu Ala Asn His Lys Met
                260                 265                 270

Pro Pro Ala Ala Ala Glu Glu Thr Pro Pro Tyr Ser Asn Tyr Asn Thr
            275                 280                 285

Leu Pro Cys Arg Lys Ser His Cys Leu Ser Glu Gly Ala Thr Asn Pro
        290                 295                 300

Gln Ile Ser His Ser Asn Ser Met Gln Gly Arg Arg Ala Lys Thr Thr
305                 310                 315                 320

Gln Asp Val Asn Ala Gly Glu Gly Ser Glu Phe Ala Asp Ser Gly Ile
                    325                 330                 335

Glu Gly Ala Thr Thr Asp Thr Asp Leu Leu Ser Arg Arg Ser Asn Ala
                340                 345                 350

Thr Asn Ser Ser Tyr Ser Pro Thr Thr Gly Arg Ala Phe Val Gly Ser
            355                 360                 365

Asp Ser Gly Ser Ser Thr Gly Asp Ala Ala Arg Gln Gly Val Tyr
        370                 375                 380

Glu Asn Phe Arg Arg Glu Leu Glu Met Ser Thr Thr Asn Ser Glu Ser
385                 390                 395                 400

Leu Glu Glu Ala Gly Ser Ala His Ser Asp Glu Gln Ser Ser Gly Thr
                    405                 410                 415

Leu Ser Ser Pro Gly Gln Ser Asp Ile Leu Leu Thr Ala Ala Gln Gly
                420                 425                 430

Thr Val Arg Lys Ala Gly Ala Leu Ala Val Lys Asn Phe Leu Val His
            435                 440                 445

Lys Lys Asn Lys Lys Val Glu Ser Ala Thr Arg Arg Lys Trp Lys His
450                 455                 460
```

Tyr Trp Val Ser Leu Lys Gly Cys Thr Leu Phe Tyr Glu Ser Asp
465                 470                 475                 480

Gly Arg Ser Gly Ile Asp His Asn Ser Ile Pro Lys His Ala Val Trp
            485                 490                 495

Val Glu Asn Ser Ile Val Gln Ala Val Pro Glu His Pro Lys Lys Asp
            500                 505                 510

Phe Val Phe Cys Leu Ser Asn Ser Leu Gly Asp Ala Phe Leu Phe Gln
            515                 520                 525

Thr Thr Ser Gln Thr Glu Leu Glu Asn Trp Ile Thr Ala Ile His Ser
    530                 535                 540

Ala Cys Ala Thr Ala Val Ala Arg His His Lys Glu Asp Thr Leu
545                 550                 555                 560

Arg Leu Leu Lys Ser Glu Ile Lys Lys Leu Glu Gln Lys Ile Asp Met
                565                 570                 575

Asp Glu Lys Met Lys Lys Met Gly Glu Met Gln Leu Ser Ser Val Thr
            580                 585                 590

Asp Ser Lys Lys Lys Thr Ile Leu Asp Gln Ile Phe Val Trp Glu
        595                 600                 605

Gln Asn Leu Glu Gln Phe Gln Met Asp Leu Phe Arg Phe Arg Cys Tyr
    610                 615                 620

Leu Ala Ser Leu Gln Gly Gly Glu Leu Pro Asn Pro Lys Arg Leu Leu
625                 630                 635                 640

Ala Phe Ala Ser Arg Pro Thr Lys Val Ala Met Gly Arg Leu Gly Ile
                645                 650                 655

Phe Ser Val Ser Ser Phe His Ala Leu Val Ala Ala Arg Thr Gly Glu
            660                 665                 670

Thr Gly Val Arg Arg Thr Gln Ala Met Ser Arg Ser Ala Ser Lys
        675                 680                 685

Arg Arg Ser Arg Phe Ser Ser Leu Trp Gly Leu Asp Thr Thr Ser Lys
    690                 695                 700

Lys Lys Gln Gly Arg Pro Ser Ile Asn Gln Val Phe Gly Glu Gly Thr
705                 710                 715                 720

Glu Ala Val Lys Lys Ser Leu Glu Gly Ile Phe Asp Asp Ile Val Pro
                725                 730                 735

Asp Gly Lys Arg Glu Lys Glu Val Val Leu Pro Asn Val His Gln His
            740                 745                 750

Asn Pro Asp Cys Asp Ile Trp Val His Glu Tyr Phe Thr Pro Ser Trp
        755                 760                 765

Phe Cys Leu Pro Asn Asn Gln Pro Ala Leu Thr Val Val Arg Pro Gly
    770                 775                 780

Asp Thr Ala Arg Asp Thr Leu Glu Leu Ile Cys Lys Thr His Gln Leu
785                 790                 795                 800

Asp His Ser Ala His Tyr Leu Arg Leu Lys Phe Leu Ile Glu Asn Lys
                805                 810                 815

Met Gln Leu Tyr Val Pro Gln Pro Glu Glu Asp Ile Tyr Glu Leu Leu
            820                 825                 830

Tyr Lys Glu Ile Glu Ile Cys Pro Lys Val Thr His Ser Ile His Ile
        835                 840                 845

Glu Lys Ser Asp Thr Ala Ala Asp Thr Tyr Gly Phe Ser Leu Ser Ser
    850                 855                 860

Val Glu Glu Asp Gly Ile Arg Arg Leu Tyr Val Asn Ser Val Lys Glu
865                 870                 875                 880

Thr Gly Leu Ala Ser Lys Lys Gly Leu Lys Ala Gly Asp Glu Ile Leu

-continued

```
                885                 890                 895
Glu Ile Asn Asn Arg Ala Ala Asp Ala Leu Asn Ser Ser Met Leu Lys
            900                 905                 910
Asp Phe Leu Ser Gln Pro Ser Leu Gly Leu Leu Val Arg Thr Tyr Pro
            915                 920                 925
Glu Leu Glu Glu Gly Val Glu Leu Leu Glu Ser Pro Pro His Arg Val
            930                 935                 940
Asp Gly Pro Ala Asp Leu Asp Glu Ser Pro Leu Ala Phe Leu Thr Ser
945                 950                 955                 960
Asn Pro Gly His Ser Leu Cys Ser Gln Gly Ser Ser Ala Glu Thr
                965                 970                 975
Ala Pro Glu Glu Thr Glu Gly Pro Asp Leu Glu Ser Ser Asp Glu Thr
            980                 985                 990
Asp His Ser Ser Lys Ser Thr Glu Gln Val Ala Ala Phe Cys Arg Ser
            995                 1000                1005
Leu His Glu Met Asn Pro Ser Asp Gln Asn Pro Ser Pro Gln Asp
        1010                1015                1020
Ser Thr Gly Pro Gln Leu Ala Thr Met Arg Gln Leu Ser Asp Ala
        1025                1030                1035
Asp Asn Val Arg Lys Val Ile Cys Glu Leu Leu Glu Thr Glu Arg
        1040                1045                1050
Thr Tyr Val Lys Asp Leu Asn Cys Leu Met Glu Arg Tyr Leu Lys
        1055                1060                1065
Pro Leu Gln Lys Glu Thr Phe Leu Thr Gln Asp Glu Leu Asp Val
        1070                1075                1080
Leu Phe Gly Asn Leu Thr Glu Met Val Glu Phe Gln Val Glu Phe
        1085                1090                1095
Leu Lys Thr Leu Glu Asp Gly Val Arg Leu Val Pro Asp Leu Glu
        1100                1105                1110
Lys Leu Glu Lys Val Asp Gln Phe Lys Lys Val Leu Phe Ser Leu
        1115                1120                1125
Gly Gly Ser Phe Leu Tyr Tyr Ala Asp Arg Phe Lys Leu Tyr Ser
        1130                1135                1140
Ala Phe Cys Ala Ile His Thr Lys Val Pro Lys Val Leu Val Lys
        1145                1150                1155
Ala Lys Thr Asp Thr Ala Phe Lys Ala Phe Leu Asp Ala Gln Asn
        1160                1165                1170
Pro Lys Gln Gln His Ser Ser Thr Leu Glu Ser Tyr Leu Ile Lys
        1175                1180                1185
Pro Ile Gln Arg Ile Leu Lys Tyr Pro Leu Leu Leu Arg Glu Leu
        1190                1195                1200
Phe Ala Leu Thr Asp Ala Glu Ser Glu Glu His Tyr His Leu Asp
        1205                1210                1215
Val Ala Ile Lys Thr Met Asn Lys Val Ala Ser His Ile Asn Glu
        1220                1225                1230
Met Gln Lys Ile His Glu Glu Phe Gly Ala Val Phe Asp Gln Leu
        1235                1240                1245
Ile Ala Glu Gln Thr Gly Glu Lys Lys Glu Val Ala Asp Leu Ser
        1250                1255                1260
Met Gly Asp Leu Leu Leu His Thr Thr Val Ile Trp Leu Asn Pro
        1265                1270                1275
Pro Ala Ser Leu Gly Lys Trp Lys Lys Glu Pro Glu Leu Ala Ala
        1280                1285                1290
```

```
Phe Val Phe Lys Thr Ala Val Val Leu Val Tyr Lys Asp Gly Ser
    1295                1300                1305

Lys Gln Lys Lys Lys Leu Val Gly Ser His Arg Leu Ser Ile Tyr
    1310                1315                1320

Glu Asp Trp Asp Pro Phe Arg Phe Arg His Met Ile Pro Thr Glu
    1325                1330                1335

Ala Leu Gln Val Arg Ala Leu Ala Ser Ala Asp Ala Glu Ala Asn
    1340                1345                1350

Ala Val Cys Glu Ile Val His Val Lys Ser Glu Ser Glu Gly Arg
    1355                1360                1365

Pro Glu Arg Val Phe His Leu Cys Cys Ser Ser Pro Glu Ser Arg
    1370                1375                1380

Lys Asp Phe Leu Lys Ala Val His Ser Ile Leu Arg Asp Lys His
    1385                1390                1395

Arg Arg Gln Leu Leu Lys Thr Glu Ser Leu Pro Ser Ser Gln Gln
    1400                1405                1410

Tyr Val Pro Phe Gly Gly Lys Arg Leu Cys Ala Leu Lys Gly Ala
    1415                1420                1425

Arg Pro Ala Met Ser Arg Ala Val Ser Ala Pro Ser Lys Ser Leu
    1430                1435                1440

Gly Arg Arg Arg Arg Arg Leu Ala Arg Asn Arg Phe Thr Ile Asp
    1445                1450                1455

Ser Asp Ala Val Ser Ala Ser Ser Pro Glu Lys Glu Ser Gln Gln
    1460                1465                1470

Pro Pro Gly Gly Gly Asp Thr Asp Arg Trp Val Glu Glu Gln Phe
    1475                1480                1485

Asp Leu Ala Gln Tyr Glu Glu Gln Asp Asp Ile Lys Glu Thr Asp
    1490                1495                1500

Ile Leu Ser Asp Asp Asp Glu Phe Cys Glu Ser Val Lys Gly Ala
    1505                1510                1515

Ser Val Asp Arg Asp Leu Gln Glu Arg Leu Gln Ala Thr Ser Ile
    1520                1525                1530

Ser Gln Arg Glu Arg Gly Arg Lys Thr Leu Asp Ser His Ala Ser
    1535                1540                1545

Arg Met Ala Gln Leu Lys Lys Gln Ala Ala Leu Ser Gly Ile Asn
    1550                1555                1560

Gly Gly Leu Glu Ser Ala Ser Glu Glu Val Ile Trp Val Arg Arg
    1565                1570                1575

Glu Asp Phe Ala Pro Ser Arg Lys Leu Asn Thr Glu Ile
    1580                1585                1590

<210> SEQ ID NO 101
<211> LENGTH: 188
<212> TYPE: PRT
<213> ORGANISM: Homo sapiens

<400> SEQUENCE: 101

Met Arg Gly Ser Gly Arg Leu Arg Thr Pro Glu Leu Val Cys Ser Arg
1               5                   10                  15

Pro Pro Pro Gly Pro Gly Arg Pro Trp Leu Pro Ser Cys Leu Glu
            20                  25                  30

Lys Gly Arg Ala Ser Gln Arg Leu Gly Gly Lys Lys Asn Gly Gly Arg
        35                  40                  45

Asp Arg Ala Glu Tyr Lys Ser Arg Phe Ser Gly Leu Tyr Leu Thr Arg
```

```
                 50                  55                  60
Cys Ser Asn Ser Ser Glu Arg Gln Arg Glu Arg Ala Gly Gly Arg Leu
 65                  70                  75                  80

Gly Trp Lys Ser Arg Ala Ser Arg Ala Ala Leu Arg Ala Ser Trp Glu
                 85                  90                  95

Gly Arg Ser Gly Ala Asn Arg Gly Leu Arg Leu Trp Pro Ser Pro Pro
                100                 105                 110

Ala Asp Pro Pro Ala Ser Arg Pro Gln Pro Leu Pro His Pro Arg Asn
            115                 120                 125

Phe Ala His Ser Ser Gly Arg Ala Leu Cys Thr Gly Thr Tyr Asn Thr
            130                 135                 140

Arg Ala Arg Thr Arg Leu Ser Arg Gly Glu Ala Ile Leu Pro Ile
145                 150                 155                 160

Trp Gly His Phe Pro Ala Ala Arg Thr Arg Phe Ser Glu Arg Leu
                165                 170                 175

Ser Leu Gln Leu Leu Arg Arg Trp Ile Phe Phe Gly
            180                 185
```

<210> SEQ ID NO 102
<211> LENGTH: 188
<212> TYPE: PRT
<213> ORGANISM: Homo sapiens

<400> SEQUENCE: 102

```
Met Arg Gly Ser Gly Arg Leu Arg Thr Pro Glu Leu Cys Cys Ser Arg
 1               5                  10                  15

Pro Pro Pro Pro Gly Pro Gly Arg Pro Trp Leu Pro Ser Cys Leu Glu
                 20                  25                  30

Lys Gly Arg Ala Ser Gln Arg Leu Gly Gly Lys Lys Asn Gly Gly Arg
                 35                  40                  45

Asp Arg Ala Glu Tyr Lys Ser Arg Phe Ser Gly Leu Tyr Leu Thr Arg
             50                  55                  60

Cys Ser Asn Ser Ser Glu Arg Gln Arg Glu Arg Ala Gly Gly Arg Leu
 65                  70                  75                  80

Gly Trp Lys Ser Arg Ala Ser Arg Ala Ala Leu Arg Ala Ser Trp Glu
                 85                  90                  95

Gly Arg Ser Gly Ala Asn Arg Gly Leu Arg Leu Trp Pro Ser Pro Pro
                100                 105                 110

Ala Asp Pro Pro Ala Ser Gly Pro Gln Pro Leu Pro His Pro Arg Asn
            115                 120                 125

Phe Ala His Ser Ser Gly Arg Ala Leu Cys Thr Gly Thr Tyr Asn Thr
            130                 135                 140

Arg Ala Arg Thr Arg Leu Ser Arg Gly Glu Ala Ile Leu Pro Ile
145                 150                 155                 160

Trp Gly His Phe Pro Ala Ala Arg Thr Arg Phe Ser Glu Arg Leu
                165                 170                 175

Ser Leu Gln Leu Leu Arg Arg Trp Ile Phe Phe Gly
            180                 185
```

<210> SEQ ID NO 103
<211> LENGTH: 439
<212> TYPE: PRT
<213> ORGANISM: Homo sapiens

<400> SEQUENCE: 103

Met Pro Leu Asn Val Ser Phe Thr Asn Arg Asn Tyr Asp Leu Asp Tyr

```
  1               5                  10                 15
Asp Ser Val Gln Pro Tyr Phe Tyr Cys Asp Glu Glu Asn Phe Tyr
            20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65              70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
                100                 105                 110

Gln Ser Phe Ile Cys Asp Pro Asp Asp Glu Thr Phe Ile Lys Asn Ile
                115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
                180                 185                 190

Val Val Phe Pro Tyr Pro Leu Asn Asp Ser Ser Ser Pro Lys Ser Cys
                195                 200                 205

Ala Ser Gln Asp Ser Ser Ala Phe Ser Pro Ser Ser Asp Ser Leu Leu
                210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
                275                 280                 285

Lys Pro Pro His Ser Pro Leu Val Leu Lys Arg Cys His Val Ser Thr
                290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
                370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
                420                 425                 430
```

Gln Leu Arg Asn Ser Cys Ala
        435

<210> SEQ ID NO 104
<211> LENGTH: 454
<212> TYPE: PRT
<213> ORGANISM: Homo sapiens

<400> SEQUENCE: 104

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn

```
            355                 360                 365
Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
            435                 440                 445

Leu Arg Asn Ser Cys Ala
    450

<210> SEQ ID NO 105
<211> LENGTH: 970
<212> TYPE: PRT
<213> ORGANISM: Saccharomyces cerevisiae

<400> SEQUENCE: 105

Met Asp Pro His Gln Ser Pro Ala Asp Asn Ala Ala Ser Pro Thr Lys
1               5                   10                  15

Ser Val Lys Ala Thr Thr Lys Asn Ser Ser Thr Asn Asn Asn Val Asn
                20                  25                  30

Ser Asn Asn Ser Asn Asn Asn Ser Asn His Asp Ile Leu Asn Phe Asn
            35                  40                  45

Asp Asn Tyr Thr Thr Ile Leu Gln His Leu Ala Asn Asp His Pro Asn
        50                  55                  60

Ile Leu Arg Glu Lys Gly Gly Ser Gln Gln Gln His Gln Gln Gln Gln
65                  70                  75                  80

Gln Gln Gln Gln Gln Gln Gln Gln Gln Gln Gln Gln Gln Gln Ser Leu
                85                  90                  95

Asp Thr Leu Leu His His Tyr Gln Ser Leu Leu Ser Lys Ser Asp Asn
                100                 105                 110

Ala Ile Ala Phe Asp Asp Asn Val Ser Asn Ser Ala Asp His Asn Gly
            115                 120                 125

Ser Asn Ser Asn Asn Asn Asn Asn Asn Asn Asp Ile Ser Ser Pro Gly
        130                 135                 140

Asn Leu Met Gly Ser Cys Asn Gln Cys Arg Leu Lys Lys Thr Lys Cys
145                 150                 155                 160

Asn Tyr Phe Pro Asp Leu Gly Asn Cys Leu Glu Cys Glu Thr Ser Arg
                165                 170                 175

Thr Lys Cys Thr Phe Ser Ile Ala Pro Asn Tyr Leu Lys Arg Thr Ser
            180                 185                 190

Ser Gly Ala Asn Asn Asn Met Pro Thr Ser Ser Asn Ser Lys Arg Met
        195                 200                 205

Lys Asn Phe Glu Asp Tyr Ser Asn Arg Leu Pro Ser Ser Met Leu Tyr
    210                 215                 220

Arg His Gln Gln Gln Gln Gln Gln Gln Gln Gln Gln Gln Arg Ile Gln
225                 230                 235                 240

Tyr Pro Arg Ser Ser Phe Phe Val Gly Pro Ala Ser Val Phe Asp Leu
                245                 250                 255

Asn Leu Thr Lys His Val Arg Leu Asp Asn Val Asp Gln Ile Gln Leu
            260                 265                 270
```

```
Ser Lys Thr Leu Ser Leu Arg Lys Val Ser Pro Thr Ala Gln Phe Ile
        275                 280                 285

Leu Gln Asp Asp Phe Asp Thr Thr Leu His Ser Lys Gln Glu Tyr Glu
    290                 295                 300

Val Asp Leu Val Glu Asn Leu Val His Pro His Gly His Leu Leu Val
305                 310                 315                 320

Glu Ile Phe Phe Lys Leu Ile His Pro Phe Leu Pro Ile Leu His Glu
                325                 330                 335

Arg Val Phe Leu Glu Lys Tyr Ser Ser Tyr Arg Glu Leu Thr Ala
                340                 345                 350

Pro Leu Leu Ala Ser Ile Tyr Ser Leu Ala Leu Gln Tyr Trp Asp Phe
        355                 360                 365

His Pro Ala Leu Leu Gly Phe Pro Lys Pro Asp Val Thr Ala Gln Leu
    370                 375                 380

Asn Asn Ile Ala Leu Glu Thr Phe Tyr Ala Arg Val Gly Arg Pro Lys
385                 390                 395                 400

Leu Ser Ile Ile Gln Thr Gly Leu Leu Ile Leu Gln Cys Arg Ser Glu
                405                 410                 415

Cys His Asn Asn Trp Val Leu Cys Ser Ser Val Val Ala Leu Ala Glu
                420                 425                 430

Glu Leu Gly Leu Gly Val Glu Cys Asn Asp Trp Lys Leu Pro Lys Trp
        435                 440                 445

Glu Lys Asp Leu Arg Lys Arg Leu Ala Trp Ala Val Trp Leu Met Asp
    450                 455                 460

Lys Trp Cys Ala Leu Asn Glu Gly Arg Gln Ser His Leu Ile Leu Gly
465                 470                 475                 480

Arg Asn Trp Met Ile Lys Leu Leu Asn Phe Asp Asp Phe Pro Leu Asn
                485                 490                 495

Ser Pro Thr Ile Leu Asn Ser Leu Gln Asn Asp Gln Ser Gly Ser Ser
            500                 505                 510

Pro Ser Ser Ser Asn Asp Val Lys Asn His Gln Ile Ala Phe Gly Asn
        515                 520                 525

Leu Pro Ile Phe Asn Ile Asn Pro Thr Leu Glu Asp Phe Lys Asn Gly
    530                 535                 540

Thr Leu Met Phe Gln Gln Met Val Ser Leu Ser Ile Ile Leu Gly Glu
545                 550                 555                 560

Ile Met Asp Thr Phe Tyr Thr Gln Gly Ser Met Thr Ile Asn Lys Ser
                565                 570                 575

Ile Glu Gln Val Leu Lys Leu Ala Lys Pro Leu Gln Leu Lys Leu Arg
                580                 585                 590

Glu Trp Tyr His Ser Leu Pro Lys Asn Leu Ser Met Ser Tyr Ala Thr
            595                 600                 605

Pro Gln Lys Leu Asn Ser Asn Ser Thr Leu Thr Leu Ala Tyr Phe Ala
        610                 615                 620

Thr Glu Ile Thr Leu His Arg Lys Ile Ile Cys Ala Leu Asn Pro Gln
625                 630                 635                 640

Thr Pro Lys Glu Leu Val Gln Val Cys Arg Thr Ala Ala Arg Thr Arg
                645                 650                 655

Leu Val Ala Ala Ile Glu Phe Ile Arg Asp Leu Lys Asn Glu His Ile
                660                 665                 670

Asn Ala Phe Trp Tyr Asn Cys Ser Thr Gly Asn Leu Met Leu Ile Gly
            675                 680                 685

Thr Phe Ala Ala Leu Leu Tyr Val Thr Ser Ala Thr Lys Glu Glu Ala
```

```
            690                 695                 700
Met Ile Phe Arg Asp Tyr Val Arg Asn Tyr Thr Trp Val Leu Lys Ile
705                 710                 715                 720

Gly Ser Lys Tyr Phe Asp Lys Leu Ser Asn Ala Leu Asn Asn Met His
                725                 730                 735

Leu Leu Phe Ala Gln Ile Pro Gly Leu Leu Thr Asp Glu Pro Val Val
            740                 745                 750

Val Ser Pro Asn Ser Asn Ile Asn Ser Val Asn Pro Gln Arg Ser Gly
            755                 760                 765

Val Gln Ser Gln Ile Pro Ile Gln Phe Asn Val Gly Ser Pro Ala Met
        770                 775                 780

Ala Glu Gln Gly Ser Pro Leu Asn Gln Trp Lys Asn Leu Pro Gln Glu
785                 790                 795                 800

Ile Leu Gln Gln Leu Asn Ser Phe Pro Asn Gly Thr Thr Ser Thr Thr
                805                 810                 815

Thr Pro Val Asn Pro Thr Ser Arg Gln Thr Gln Leu Glu Ser Gln Gly
            820                 825                 830

Ser Pro Ala Ile Asn Ser Ala Asn Asn Asn Ser Asn Asn Thr Pro Leu
            835                 840                 845

Pro Phe Ala Pro Asn Lys Ser Ser Lys Lys Thr Ser Gln Ser Ser Pro
        850                 855                 860

Asn Val Thr Pro Ser His Met Ser Arg His Pro Pro Ser Asn Thr Ser
865                 870                 875                 880

Ser Pro Arg Val Asn Ser Ser Thr Asn Val Asn Ser Asn Thr Gln Met
                885                 890                 895

Asn Ala Ser Pro Leu Thr Ser Ile Asn Glu Thr Arg Gln Glu Ser Gly
            900                 905                 910

Asp Ala Ala Asp Glu Lys Thr Ala Gly Arg Glu Arg Thr Ala Asn Glu
            915                 920                 925

Glu Ser Ser Thr Glu Leu Lys Asp Asp Asn Pro Asn Ser Asn Gln Glu
        930                 935                 940

Thr Ser Ala Thr Gly Asn Gln Thr Ile Lys Met Asn Asp Asp Lys Asn
945                 950                 955                 960

Val Thr Ile Asn Thr Arg Glu Thr Pro Leu
                965                 970

<210> SEQ ID NO 106
<211> LENGTH: 476
<212> TYPE: PRT
<213> ORGANISM: Xenopus laevis

<400> SEQUENCE: 106

Met Ala Ser His Ser Ala Phe Gln Ser Phe Pro Leu Tyr Pro Pro Cys
1               5                   10                  15

Phe Phe Arg Asp Thr Ser Thr Ser Arg Arg Phe Thr Pro Pro Ser Thr
                20                  25                  30

Thr Leu Ser Pro Gly Lys Met Ser Glu Pro Ile Pro Leu Asn Ile Ala
            35                  40                  45

Asp Ser Ser Ala Ala Leu Val Gly Lys Leu Arg Ser Thr Asp Arg Asn
        50                  55                  60

Met Val Glu Val Leu Ser Asp His Pro Gly Glu Leu Val Arg Thr Asp
65                  70                  75                  80

Ser Pro Asn Phe Leu Cys Ser Val Leu Pro Thr His Trp Arg Cys Asn
                85                  90                  95
```

```
Lys Thr Leu Pro Ile Ala Phe Lys Val Val Ala Leu Gly Glu Val Pro
                100                 105                 110

Asp Gly Thr Leu Val Thr Val Met Ala Gly Asn Asp Glu Asn Tyr Ser
            115                 120                 125

Ala Glu Leu Arg Asn Ala Thr Ala Ala Met Lys Ser Gln Val Ala Arg
        130                 135                 140

Phe Asn Asp Leu Arg Phe Val Gly Arg Ser Arg Gly Lys Ser Phe
145                 150                 155                 160

Thr Leu Thr Ile Thr Val Phe Thr Asn Pro Gln Val Ala Thr Tyr
                165                 170                 175

His Arg Ala Ile Lys Ile Thr Val Asp Gly Pro Arg Glu Pro Arg Arg
            180                 185                 190

His Arg Gln Lys Leu Asp Glu Gln Thr Lys Pro Gly Asn Leu Ser Phe
        195                 200                 205

Ser Glu Arg Leu Ser Glu Leu Glu His Phe Arg Arg Thr Ala Met Arg
    210                 215                 220

Val Ser Pro His His Pro Asn Pro Met Pro Asn Pro Arg Ala Thr Leu
225                 230                 235                 240

Asn His Ser Ala Ala Phe Asn Pro Gln Pro Gln Gly Gln Ile Gln Val
                245                 250                 255

Ala Asp Thr Arg Gln Val Gln Ala Ser Pro Pro Trp Ser Tyr Asp Gln
            260                 265                 270

Ser Tyr Gln Tyr Leu Gly Ser Ile Ala Thr Gln Ser Val His Pro Ala
        275                 280                 285

Thr Pro Ile Ser Pro Gly Arg Ala Ser Ser Met Thr Ser Leu Ser Ala
    290                 295                 300

Glu Leu Ser Ser Arg Leu Ser Gly Ala Ser Asp Leu Thr Ala Phe Ser
305                 310                 315                 320

Asp Pro Arg Val Gly Ile Asp Arg Gln Phe Ser Thr Leu Pro Ser Ile
                325                 330                 335

Ser Asp Pro Arg Met His Tyr Pro Gly Ala Phe Thr Tyr Thr Pro Thr
            340                 345                 350

Pro Val Thr Ser Gly Ile Gly Ile Gly Met Ser Ala Met Thr Ser Ala
        355                 360                 365

Thr Arg Tyr His Thr Tyr Leu Pro Pro Tyr Pro Gly Ser Ser Gln
    370                 375                 380

Ala Gln Ser Asn Pro Phe Gln Thr Ser Ser Pro Ser Tyr His Leu Tyr
385                 390                 395                 400

Tyr Gly Thr Ser Ala Gly Ser Tyr His Gln Phe Ser Met Met Ser Gly
                405                 410                 415

Gly Glu Arg Ser Pro Pro Arg Ile Leu Pro Pro Cys Thr Asn Ala Ser
            420                 425                 430

Thr Gly Ser Thr Leu Leu Asn Pro Asn Leu Pro Asn Gln Ser Asp Val
        435                 440                 445

Val Glu Ala Glu Gly Ser His Ser Asn Ser Pro Thr Asn Met Gly Ser
    450                 455                 460

Thr Pro Arg Leu Glu Glu Ala Val Trp Arg Pro Tyr
465                 470                 475
```

<210> SEQ ID NO 107
<211> LENGTH: 917
<212> TYPE: PRT
<213> ORGANISM: Homo sapiens

<400> SEQUENCE: 107

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
            35                  40                  45

Pro Pro Gly Ala Ser Leu Leu Leu Gln Gln Gln Gln Gln Gln Gln Gln
        50                  55                  60

Gln Gln Gln Gln Gln Gln Gln Gln Gln Gln Gln Gln Gln Glu Thr Ser
65                  70                  75                  80

Pro Arg Gln Gln Gln Gln Gln Gly Glu Asp Gly Ser Pro Gln Ala
                85                  90                  95

His Arg Arg Gly Pro Thr Gly Tyr Leu Val Leu Asp Glu Glu Gln Gln
                100                 105                 110

Pro Ser Gln Pro Gln Ser Ala Leu Glu Cys His Pro Glu Arg Gly Cys
            115                 120                 125

Val Pro Glu Pro Gly Ala Ala Val Ala Ala Ser Lys Gly Leu Pro Gln
            130                 135                 140

Gln Leu Pro Ala Pro Pro Asp Glu Asp Ser Ala Ala Pro Ser Thr
145                 150                 155                 160

Leu Ser Leu Leu Gly Pro Thr Phe Pro Gly Leu Ser Ser Cys Ser Ala
                165                 170                 175

Asp Leu Lys Asp Ile Leu Ser Glu Ala Ser Thr Met Gln Leu Leu Gln
            180                 185                 190

Gln Gln Gln Gln Glu Ala Val Ser Glu Gly Ser Ser Ser Gly Arg Ala
            195                 200                 205

Arg Glu Arg Ser Gly Ala Pro Thr Ser Ser Lys Asp Asn Tyr Leu Gly
        210                 215                 220

Gly Thr Ser Thr Ile Ser Asp Asn Ala Lys Glu Leu Cys Lys Ala Val
225                 230                 235                 240

Ser Val Ser Met Gly Leu Gly Val Glu Ala Leu Glu His Leu Ser Pro
                245                 250                 255

Gly Glu Gln Leu Arg Gly Asp Cys Met Tyr Ala Pro Leu Leu Gly Val
                260                 265                 270

Pro Pro Ala Val Arg Pro Thr Pro Cys Ala Pro Leu Ala Glu Cys Lys
            275                 280                 285

Gly Ser Leu Leu Asp Asp Ser Ala Gly Lys Ser Thr Glu Asp Thr Ala
        290                 295                 300

Glu Tyr Ser Pro Phe Lys Gly Gly Tyr Thr Lys Gly Leu Glu Gly Glu
305                 310                 315                 320

Ser Leu Gly Cys Ser Gly Ser Ala Ala Gly Ser Ser Gly Thr Leu
            325                 330                 335

Glu Leu Pro Ser Thr Leu Ser Leu Tyr Lys Ser Gly Ala Leu Asp Glu
            340                 345                 350

Ala Ala Ala Tyr Gln Ser Arg Asp Tyr Tyr Asn Phe Pro Leu Ala Leu
            355                 360                 365

Ala Gly Pro Pro Pro Pro Pro Pro Pro His Pro His Ala Arg Ile
        370                 375                 380

Lys Leu Glu Asn Pro Leu Asp Tyr Gly Ser Ala Trp Ala Ala Ala
385                 390                 395                 400

Ala Gln Cys Arg Tyr Gly Asp Leu Ala Ser Leu His Gly Ala Gly Ala
            405                 410                 415
```

```
Ala Gly Pro Gly Ser Gly Ser Pro Ser Ala Ala Ser Ser Ser Trp
                420             425             430

His Thr Leu Phe Thr Ala Glu Glu Gly Gln Leu Tyr Gly Pro Cys Gly
            435             440             445

Gly Gly Gly Gly Gly Gly Gly Gly Gly Gly Gly Gly Gly Gly
        450             455             460

Gly Gly Gly Gly Gly Glu Ala Gly Ala Val Ala Pro Tyr Gly Tyr
465             470             475             480

Thr Arg Pro Pro Gln Gly Leu Ala Gly Gln Glu Ser Asp Phe Thr Ala
                485             490             495

Pro Asp Val Trp Tyr Pro Gly Gly Met Val Ser Arg Val Pro Tyr Pro
            500             505             510

Ser Pro Thr Cys Val Lys Ser Glu Met Gly Pro Trp Met Asp Ser Tyr
            515             520             525

Ser Gly Pro Tyr Gly Asp Met Arg Leu Glu Thr Ala Arg Asp His Val
        530             535             540

Leu Pro Ile Asp Tyr Tyr Phe Pro Pro Gln Lys Thr Cys Leu Ile Cys
545             550             555             560

Gly Asp Glu Ala Ser Gly Cys His Tyr Gly Ala Leu Thr Cys Gly Ser
                565             570             575

Cys Lys Val Phe Phe Lys Arg Ala Ala Glu Gly Lys Gln Lys Tyr Leu
            580             585             590

Cys Ala Ser Arg Asn Asp Cys Thr Ile Asp Lys Phe Arg Arg Lys Asn
            595             600             605

Cys Pro Ser Cys Arg Leu Arg Lys Cys Tyr Glu Ala Gly Met Thr Leu
            610             615             620

Gly Ala Arg Lys Leu Lys Lys Leu Gly Asn Leu Lys Leu Gln Glu Glu
625             630             635             640

Gly Glu Ala Ser Ser Thr Thr Ser Pro Thr Glu Glu Thr Thr Gln Lys
                645             650             655

Leu Thr Val Ser His Ile Glu Gly Tyr Glu Cys Gln Pro Ile Phe Leu
            660             665             670

Asn Val Leu Glu Ala Ile Glu Pro Gly Val Val Cys Ala Gly His Asp
            675             680             685

Asn Asn Gln Pro Asp Ser Phe Ala Ala Leu Leu Ser Ser Leu Asn Glu
            690             695             700

Leu Gly Glu Arg Gln Leu Val His Val Val Lys Trp Ala Lys Ala Leu
705             710             715             720

Pro Gly Phe Arg Asn Leu His Val Asp Asp Gln Met Ala Val Ile Gln
                725             730             735

Tyr Ser Trp Met Gly Leu Met Val Phe Ala Met Gly Trp Arg Ser Phe
            740             745             750

Thr Asn Val Asn Ser Arg Met Leu Tyr Phe Ala Pro Asp Leu Val Phe
            755             760             765

Asn Glu Tyr Arg Met His Lys Ser Arg Met Tyr Ser Gln Cys Val Arg
            770             775             780

Met Arg His Leu Ser Gln Glu Phe Gly Trp Leu Gln Ile Thr Pro Gln
785             790             795             800

Glu Phe Leu Cys Met Lys Ala Leu Leu Leu Phe Ser Ile Ile Pro Val
                805             810             815

Asp Gly Leu Lys Asn Gln Lys Phe Phe Asp Glu Leu Arg Met Asn Tyr
            820             825             830

Ile Lys Glu Leu Asp Arg Ile Ile Ala Cys Lys Arg Lys Asn Pro Thr
```

835                 840                 845
Ser Cys Ser Arg Arg Phe Tyr Gln Leu Thr Lys Leu Leu Asp Ser Val
    850                 855                 860

Gln Pro Ile Ala Arg Glu Leu His Gln Phe Thr Phe Asp Leu Leu Ile
865                 870                 875                 880

Lys Ser His Met Val Ser Val Asp Phe Pro Glu Met Met Ala Glu Ile
                885                 890                 895

Ile Ser Val Gln Val Pro Lys Ile Leu Ser Gly Lys Val Lys Pro Ile
            900                 905                 910

Tyr Phe His Thr Gln
            915

<210> SEQ ID NO 108
<211> LENGTH: 1124
<212> TYPE: PRT
<213> ORGANISM: Homo sapiens

<400> SEQUENCE: 108

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Ala Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Ala Ile Arg Arg Thr Val Arg Arg Ala Leu Pro Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

```
Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Arg Leu
        355                 360                 365

Leu Glu Glu Val Ala Glu Gln Cys His Gly Pro Ile Thr Leu Asp Phe
370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Gly Leu His Val
450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525

His Gly Ser Phe Thr Lys Ile Tyr Arg Gly Cys Arg His Glu Val Val
530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
690                 695                 700

Glu Ala Asp Lys Trp Gly Phe Gly Ala Thr Val Trp Glu Val Phe Ser
```

```
                705                 710                 715                 720
            Gly Val Thr Met Pro Ile Ser Ala Leu Asp Pro Ala Lys Lys Leu Gln
                                725                 730                 735

Phe Tyr Glu Asp Arg Gln Gln Leu Pro Ala Pro Lys Trp Thr Glu Leu
                                740                 745                 750

Ala Leu Leu Ile Gln Gln Cys Met Ala Tyr Glu Pro Val Gln Arg Pro
                                755                 760                 765

Ser Phe Arg Ala Val Ile Arg Asp Leu Asn Ser Leu Ile Ser Ser Asp
                                770                 775                 780

Tyr Glu Leu Leu Ser Asp Pro Thr Pro Gly Ala Leu Ala Pro Arg Asp
            785                 790                 795                 800

Gly Leu Trp Asn Gly Ala Gln Leu Tyr Ala Cys Gln Asp Pro Thr Ile
                                805                 810                 815

Phe Glu Glu Arg His Leu Lys Tyr Ile Ser Gln Leu Gly Lys Gly Asn
                                820                 825                 830

Phe Gly Ser Val Glu Leu Cys Arg Tyr Asp Pro Leu Ala His Asn Thr
                                835                 840                 845

Gly Ala Leu Val Ala Val Lys Gln Leu Gln His Ser Gly Pro Asp Gln
                850                 855                 860

Gln Arg Asp Phe Gln Arg Glu Ile Gln Ile Leu Lys Ala Leu His Ser
            865                 870                 875                 880

Asp Phe Ile Val Lys Tyr Arg Gly Val Ser Tyr Gly Pro Gly Arg Pro
                                885                 890                 895

Glu Leu Arg Leu Val Met Glu Tyr Leu Pro Ser Gly Cys Leu Arg Asp
                                900                 905                 910

Phe Leu Gln Arg His Arg Ala Arg Leu Asp Ala Ser Arg Leu Leu Leu
                                915                 920                 925

Tyr Ser Ser Gln Ile Cys Lys Gly Met Glu Tyr Leu Gly Ser Arg Arg
                                930                 935                 940

Cys Val His Arg Asp Leu Ala Ala Arg Asn Ile Leu Val Glu Ser Glu
            945                 950                 955                 960

Ala His Val Lys Ile Ala Asp Phe Gly Leu Ala Lys Leu Leu Pro Leu
                                965                 970                 975

Asp Lys Asp Tyr Tyr Val Val Arg Glu Pro Gly Gln Ser Pro Ile Phe
                                980                 985                 990

Trp Tyr Ala Pro Glu Ser Leu Ser Asp Asn Ile Phe Ser Arg Gln Ser
                                995                1000                1005

Asp Val Trp Ser Phe Gly Val Val Leu Tyr Glu Leu Phe Thr Tyr
                1010                1015                1020

Cys Asp Lys Ser Cys Ser Pro Ser Ala Glu Phe Leu Arg Met Met
                1025                1030                1035

Gly Cys Glu Arg Asp Val Pro Ala Leu Cys Arg Leu Leu Glu Leu
                1040                1045                1050

Leu Glu Glu Gly Gln Arg Leu Pro Ala Pro Pro Ala Cys Pro Ala
                1055                1060                1065

Glu Val His Glu Leu Met Lys Leu Cys Trp Ala Pro Ser Pro Gln
                1070                1075                1080

Asp Arg Pro Ser Phe Ser Ala Leu Gly Pro Gln Leu Asp Met Leu
                1085                1090                1095

Trp Ser Gly Ser Arg Gly Cys Glu Thr His Ala Phe Thr Ala His
                1100                1105                1110

Pro Glu Gly Lys His His Ser Leu Ser Phe Ser
                1115                1120
```

<210> SEQ ID NO 109
<211> LENGTH: 993
<212> TYPE: PRT
<213> ORGANISM: Homo sapiens

<400> SEQUENCE: 109

```
Met Pro Ala Leu Ala Arg Asp Gly Gly Gln Leu Pro Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Arg Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
        130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
                180                 185                 190

Ile Val Glu Trp Val Leu Cys Asp Ser Gln Gly Glu Ser Cys Lys Glu
            195                 200                 205

Glu Ser Pro Ala Val Val Lys Lys Glu Glu Lys Val Leu His Glu Leu
        210                 215                 220

Phe Gly Met Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
                260                 265                 270

Lys Ala Val His Val Asn His Gly Phe Gly Leu Thr Trp Glu Leu Glu
            275                 280                 285

Asn Lys Ala Leu Glu Glu Gly Asn Tyr Phe Glu Met Ser Thr Tyr Ser
        290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
```

```
            370                 375                 380
Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
            435                 440                 445

Gln Ala Ser Cys Phe Ser Asp Gly Tyr Pro Leu Pro Ser Trp Thr Trp
        450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
                500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
            530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
            595                 600                 605

Asn Leu Glu Phe Gly Lys Val Leu Gly Ser Gly Ala Phe Gly Lys Val
            610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
                660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
                740                 745                 750

Ser Gly Leu His Gly Asn Ser Phe His Ser Glu Asp Glu Ile Glu Tyr
            755                 760                 765

Glu Asn Gln Lys Arg Leu Glu Glu Glu Glu Asp Leu Asn Val Leu Thr
            770                 775                 780

Phe Glu Asp Leu Leu Cys Phe Ala Tyr Gln Val Ala Lys Gly Met Glu
785                 790                 795                 800
```

```
Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 110
<211> LENGTH: 480
<212> TYPE: PRT
<213> ORGANISM: Homo sapiens

<400> SEQUENCE: 110

Met Ala Ser Asp Ser Ile Phe Glu Ser Phe Pro Ser Tyr Pro Gln Cys
1               5                   10                  15

Phe Met Arg Glu Cys Ile Leu Gly Met Asn Pro Ser Arg Asp Val His
                20                  25                  30

Asp Ala Ser Thr Ser Arg Arg Phe Thr Pro Pro Ser Thr Ala Leu Ser
            35                  40                  45

Pro Gly Lys Met Ser Glu Ala Leu Pro Leu Gly Ala Pro Asp Ala Gly
    50                  55                  60

Ala Ala Leu Ala Gly Lys Leu Arg Ser Gly Asp Arg Ser Met Val Glu
65                  70                  75                  80

Val Leu Ala Asp His Pro Gly Glu Leu Val Arg Thr Asp Ser Pro Asn
                85                  90                  95

Phe Leu Cys Ser Val Leu Pro Thr His Trp Arg Cys Asn Lys Thr Leu
            100                 105                 110

Pro Ile Ala Phe Lys Val Val Ala Leu Gly Asp Val Pro Asp Gly Thr
    115                 120                 125

Leu Val Thr Val Met Ala Gly Asn Asp Glu Asn Tyr Ser Ala Glu Leu
    130                 135                 140

Arg Asn Ala Thr Ala Ala Met Lys Asn Gln Val Ala Arg Phe Asn Asp
145                 150                 155                 160

Leu Arg Phe Val Gly Arg Ser Gly Arg Gly Lys Ser Phe Thr Leu Thr
                165                 170                 175
```

```
Ile Thr Val Phe Thr Asn Pro Pro Gln Val Ala Thr Tyr His Arg Ala
            180                 185                 190

Ile Lys Ile Thr Val Asp Gly Pro Arg Glu Pro Arg His Arg Gln
        195                 200                 205

Lys Leu Asp Asp Gln Thr Lys Pro Gly Ser Leu Ser Phe Ser Glu Arg
    210                 215                 220

Leu Ser Glu Leu Glu Gln Leu Arg Arg Thr Ala Met Arg Val Ser Pro
225                 230                 235                 240

His His Pro Ala Pro Thr Pro Asn Pro Arg Ala Ser Leu Asn His Ser
                245                 250                 255

Thr Ala Phe Asn Pro Gln Pro Gln Ser Gln Met Gln Asp Thr Arg Gln
                260                 265                 270

Ile Gln Pro Ser Pro Pro Trp Ser Tyr Asp Gln Ser Tyr Gln Tyr Leu
            275                 280                 285

Gly Ser Ile Ala Ser Pro Ser Val His Pro Ala Thr Pro Ile Ser Pro
    290                 295                 300

Gly Arg Ala Ser Gly Met Thr Thr Leu Ser Ala Glu Leu Ser Ser Arg
305                 310                 315                 320

Leu Ser Thr Ala Pro Asp Leu Thr Ala Phe Ser Asp Pro Arg Gln Phe
                325                 330                 335

Pro Ala Leu Pro Ser Ile Ser Asp Pro Arg Met His Tyr Pro Gly Ala
                340                 345                 350

Phe Thr Tyr Ser Pro Thr Pro Val Thr Ser Gly Ile Gly Ile Gly Met
            355                 360                 365

Ser Ala Met Gly Ser Ala Thr Arg Tyr His Thr Tyr Leu Pro Pro Pro
    370                 375                 380

Tyr Pro Gly Ser Ser Gln Ala Gln Gly Gly Pro Phe Gln Ala Ser Ser
385                 390                 395                 400

Pro Ser Tyr His Leu Tyr Tyr Gly Ala Ser Ala Gly Ser Tyr Gln Phe
                405                 410                 415

Ser Met Val Gly Gly Glu Arg Ser Pro Pro Arg Ile Leu Pro Pro Cys
            420                 425                 430

Thr Asn Ala Ser Thr Gly Ser Ala Leu Leu Asn Pro Ser Leu Pro Asn
            435                 440                 445

Gln Ser Asp Val Val Glu Ala Glu Gly Ser His Ser Asn Ser Pro Thr
    450                 455                 460

Asn Met Ala Pro Ser Ala Arg Leu Glu Glu Ala Val Trp Arg Pro Tyr
465                 470                 475                 480

<210> SEQ ID NO 111
<211> LENGTH: 422
<212> TYPE: PRT
<213> ORGANISM: Homo sapiens

<400> SEQUENCE: 111

Met Pro Arg Ser Phe Leu Val Lys Ser Lys Lys Ala His Ser Tyr His
1               5                   10                  15

Gln Pro Arg Ser Pro Gly Pro Asp Tyr Ser Leu Arg Leu Glu Asn Val
            20                  25                  30

Pro Ala Pro Ser Arg Ala Asp Ser Thr Ser Asn Ala Gly Gly Ala Lys
        35                  40                  45

Ala Glu Pro Arg Asp Arg Leu Ser Pro Glu Ser Gln Leu Thr Glu Ala
    50                  55                  60

Pro Asp Arg Ala Ser Ala Ser Pro Asp Ser Cys Glu Gly Ser Val Cys
```

```
                65                  70                  75                  80
        Glu Arg Ser Ser Glu Phe Glu Asp Phe Trp Arg Pro Ser Pro Ser
                         85                  90                  95

Ala Ser Pro Ala Ser Glu Lys Ser Met Cys Pro Ser Leu Asp Glu Ala
                        100                 105                 110

Gln Pro Phe Pro Leu Pro Phe Lys Pro Tyr Ser Trp Ser Gly Leu Ala
                        115                 120                 125

Gly Ser Asp Leu Arg His Leu Val Gln Ser Tyr Arg Pro Cys Gly Ala
                    130                 135                 140

Leu Glu Arg Gly Ala Gly Leu Gly Leu Phe Cys Glu Pro Ala Pro Glu
        145                 150                 155                 160

Pro Gly His Pro Ala Ala Leu Tyr Gly Pro Lys Arg Ala Ala Gly Gly
                            165                 170                 175

Ala Gly Ala Gly Ala Pro Gly Ser Cys Ser Ala Gly Ala Gly Ala Thr
                        180                 185                 190

Ala Gly Pro Gly Leu Gly Leu Tyr Gly Asp Phe Gly Ser Ala Ala Ala
                    195                 200                 205

Gly Leu Tyr Glu Arg Pro Thr Ala Ala Gly Leu Leu Tyr Pro Glu
                210                 215                 220

Arg Gly His Gly Leu His Ala Asp Lys Gly Ala Gly Val Lys Val Glu
        225                 230                 235                 240

Ser Glu Leu Leu Cys Thr Arg Leu Leu Leu Gly Gly Gly Ser Tyr Lys
                            245                 250                 255

Cys Ile Lys Cys Ser Lys Val Phe Ser Thr Pro His Gly Leu Glu Val
                        260                 265                 270

His Val Arg Arg Ser His Ser Gly Thr Arg Pro Phe Ala Cys Glu Met
                    275                 280                 285

Cys Gly Lys Thr Phe Gly His Ala Val Ser Leu Glu Gln His Lys Ala
                290                 295                 300

Val His Ser Gln Glu Arg Ser Phe Asp Cys Lys Ile Cys Gly Lys Ser
        305                 310                 315                 320

Phe Lys Arg Ser Ser Thr Leu Ser Thr His Leu Leu Ile His Ser Asp
                            325                 330                 335

Thr Arg Pro Tyr Pro Cys Gln Tyr Cys Gly Lys Arg Phe His Gln Lys
                        340                 345                 350

Ser Asp Met Lys Lys His Thr Phe Ile His Thr Gly Glu Lys Pro His
                    355                 360                 365

Lys Cys Gln Val Cys Gly Lys Ala Phe Ser Gln Ser Ser Asn Leu Ile
                370                 375                 380

Thr His Ser Arg Lys His Thr Gly Phe Lys Pro Phe Gly Cys Asp Leu
        385                 390                 395                 400

Cys Gly Lys Gly Phe Gln Arg Lys Val Asp Leu Arg Arg His Arg Glu
                            405                 410                 415

Thr Gln His Gly Leu Lys
                        420

<210> SEQ ID NO 112
<211> LENGTH: 467
<212> TYPE: PRT
<213> ORGANISM: Homo sapiens

<400> SEQUENCE: 112

Met Glu Tyr Met Ser Thr Gly Ser Asp Asn Lys Glu Glu Ile Asp Leu
1               5                   10                  15
```

```
Leu Ile Lys His Leu Asn Val Ser Asp Val Ile Asp Ile Met Glu Asn
             20                  25                  30

Leu Tyr Ala Ser Glu Glu Pro Ala Val Tyr Glu Pro Ser Leu Met Thr
         35                  40                  45

Met Cys Gln Asp Ser Asn Gln Asn Asp Glu Arg Ser Lys Ser Leu Leu
 50                  55                  60

Leu Ser Gly Gln Glu Val Pro Trp Leu Ser Ser Val Arg Tyr Gly Thr
 65                  70                  75                  80

Val Glu Asp Leu Leu Ala Phe Ala Asn His Ile Ser Asn Thr Ala Lys
                 85                  90                  95

His Phe Tyr Gly Gln Arg Pro Gln Glu Ser Gly Ile Leu Leu Asn Met
            100                 105                 110

Val Ile Thr Pro Gln Asn Gly Arg Tyr Gln Ile Asp Ser Asp Val Leu
            115                 120                 125

Leu Ile Pro Trp Lys Leu Thr Tyr Arg Asn Ile Gly Ser Asp Phe Ile
            130                 135                 140

Pro Arg Gly Ala Phe Gly Lys Val Tyr Leu Ala Gln Asp Ile Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
            180                 185                 190

Leu Tyr Gly Ala Val Leu Trp Gly Glu Thr Val His Leu Phe Met Glu
            195                 200                 205

Ala Gly Glu Gly Gly Ser Val Leu Glu Lys Leu Glu Ser Cys Gly Pro
210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
            260                 265                 270

Leu Ser Val Gln Met Thr Glu Asp Val Tyr Phe Pro Lys Asp Leu Arg
            275                 280                 285

Gly Thr Glu Ile Tyr Met Ser Pro Glu Val Ile Leu Cys Arg Gly His
            290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
            340                 345                 350

Ile Ala Asp Asp Cys Ser Pro Gly Met Arg Glu Leu Ile Glu Ala Ser
            355                 360                 365

Leu Glu Arg Asn Pro Asn His Arg Pro Arg Ala Ala Asp Leu Leu Lys
            370                 375                 380

His Glu Ala Leu Asn Pro Pro Arg Glu Asp Gln Pro Arg Cys Gln Ser
385                 390                 395                 400

Leu Asp Ser Ala Leu Leu Glu Arg Lys Arg Leu Leu Ser Arg Lys Glu
                405                 410                 415

Leu Glu Leu Pro Glu Asn Ile Ala Asp Ser Ser Cys Thr Gly Ser Thr
            420                 425                 430

Glu Glu Ser Glu Met Leu Lys Arg Gln Arg Ser Leu Tyr Ile Asp Leu
```

```
                      435                 440                 445
Gly Ala Leu Ala Gly Tyr Phe Asn Leu Val Arg Gly Ser Pro Thr Leu
    450                 455                 460

Glu Tyr Gly
465
```

<210> SEQ ID NO 113
<211> LENGTH: 59
<212> TYPE: PRT
<213> ORGANISM: Homo sapiens

<400> SEQUENCE: 113

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His
    50                  55
```

<210> SEQ ID NO 114
<211> LENGTH: 189
<212> TYPE: PRT
<213> ORGANISM: Homo sapiens

<400> SEQUENCE: 114

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 115
<211> LENGTH: 1210
<212> TYPE: PRT
<213> ORGANISM: Homo sapiens

<400> SEQUENCE: 115

-continued

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415
```

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro

```
                    835                 840                 845
Gln His Val Lys Ile Thr Asp Phe Gly Leu Ala Lys Leu Leu Gly Ala
    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                    885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
        930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe
    1010                1015                1020
Phe Ser Ser Pro Ser Thr Ser Arg Thr Pro Leu Leu Ser Ser Leu
    1025                1030                1035
Ser Ala Thr Ser Asn Asn Ser Thr Val Ala Cys Ile Asp Arg Asn
    1040                1045                1050
Gly Leu Gln Ser Cys Pro Ile Lys Glu Asp Ser Phe Leu Gln Arg
    1055                1060                1065
Tyr Ser Ser Asp Pro Thr Gly Ala Leu Thr Glu Asp Ser Ile Asp
    1070                1075                1080
Asp Thr Phe Leu Pro Val Pro Glu Tyr Ile Asn Gln Ser Val Pro
    1085                1090                1095
Lys Arg Pro Ala Gly Ser Val Gln Asn Pro Val Tyr His Asn Gln
    1100                1105                1110
Pro Leu Asn Pro Ala Pro Ser Arg Asp Pro His Tyr Gln Asp Pro
    1115                1120                1125
His Ser Thr Ala Val Gly Asn Pro Glu Tyr Leu Asn Thr Val Gln
    1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205                1210

<210> SEQ ID NO 116
<211> LENGTH: 766
<212> TYPE: PRT
<213> ORGANISM: Homo sapiens
```

<400> SEQUENCE: 116

```
Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly
            20                  25                  30

Ala Ala Ala Ser Ser Ala Ala Asp Pro Ala Ile Pro Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
```

```
                    405                 410                 415
Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 117
<211> LENGTH: 724
<212> TYPE: PRT
<213> ORGANISM: Homo sapiens

<400> SEQUENCE: 117

Met Ser Ala Glu Gly Tyr Gln Tyr Arg Ala Leu Tyr Asp Tyr Lys Lys
1               5                   10                  15
```

-continued

Glu Arg Glu Glu Asp Ile Asp Leu His Leu Gly Asp Ile Leu Thr Val
             20                  25                  30

Asn Lys Gly Ser Leu Val Ala Leu Gly Phe Ser Asp Gly Gln Glu Ala
             35                  40                  45

Arg Pro Glu Glu Ile Gly Trp Leu Asn Gly Tyr Asn Glu Thr Thr Gly
 50                      55                  60

Glu Arg Gly Asp Phe Pro Gly Thr Tyr Val Glu Tyr Ile Gly Arg Lys
 65                  70                  75                  80

Lys Ile Ser Pro Pro Thr Pro Lys Pro Arg Pro Pro Arg Pro Leu Pro
                 85                  90                  95

Val Ala Pro Gly Ser Ser Lys Thr Glu Ala Asp Val Glu Gln Gln Ala
                100                 105                 110

Leu Thr Leu Pro Asp Leu Ala Glu Gln Phe Ala Pro Asp Ile Ala
             115                 120                 125

Pro Pro Leu Leu Ile Lys Leu Val Glu Ala Ile Glu Lys Lys Gly Leu
             130                 135                 140

Glu Cys Ser Thr Leu Tyr Arg Thr Gln Ser Ser Asn Leu Ala Glu
145                 150                 155                 160

Leu Arg Gln Leu Leu Asp Cys Asp Thr Pro Ser Val Asp Leu Glu Met
                 165                 170                 175

Ile Asp Val His Val Leu Ala Asp Ala Phe Lys Arg Tyr Leu Leu Asp
                 180                 185                 190

Leu Pro Asn Pro Val Ile Pro Ala Ala Val Tyr Ser Glu Met Ile Ser
             195                 200                 205

Leu Ala Pro Glu Val Gln Ser Ser Glu Glu Tyr Ile Gln Leu Leu Lys
 210                 215                 220

Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                 245                 250                 255

Asn Leu Leu Asn Ala Arg Val Leu Ser Glu Ile Phe Ser Pro Met Leu
             260                 265                 270

Phe Arg Phe Ser Ala Ala Ser Ser Asp Asn Thr Glu Asn Leu Ile Lys
                 275                 280                 285

Val Ile Glu Ile Leu Ile Ser Thr Glu Trp Asn Glu Arg Gln Pro Ala
 290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                 325                 330                 335

Asp Ile Ser Arg Glu Glu Val Asn Glu Lys Leu Arg Asp Thr Ala Asp
                 340                 345                 350

Gly Thr Phe Leu Val Arg Asp Ala Ser Thr Lys Met His Gly Asp Tyr
             355                 360                 365

Thr Leu Thr Leu Arg Lys Gly Gly Asn Asn Lys Leu Ile Lys Ile Phe
 370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                 405                 410                 415

Asn Pro Lys Leu Asp Val Lys Leu Leu Tyr Pro Val Ser Lys Tyr Gln
                 420                 425                 430

Gln Asp Gln Val Val Lys Glu Asp Asn Ile Glu Ala Val Gly Lys Lys

```
            435                 440                 445
Leu His Glu Tyr Asn Thr Gln Phe Gln Glu Lys Ser Arg Glu Tyr Asp
450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Glu Asp Leu Pro His His Asp Glu Lys Thr Trp
610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
            660                 665                 670

Asn Lys Thr Ala Thr Gly Tyr Gly Phe Ala Glu Pro Tyr Asn Leu Tyr
        675                 680                 685

Ser Ser Leu Lys Glu Leu Val Leu His Tyr Gln His Thr Ser Leu Val
        690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 118
<211> LENGTH: 781
<212> TYPE: PRT
<213> ORGANISM: Homo sapiens

<400> SEQUENCE: 118

Met Ala Thr Gln Ala Asp Leu Met Glu Leu Asp Met Ala Met Glu Pro
1               5                   10                  15

Asp Arg Lys Ala Ala Val Ser His Trp Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
```

```
                    85                  90                  95
Ala Met Phe Pro Glu Thr Leu Asp Glu Gly Met Gln Ile Pro Ser Thr
                100                 105                 110

Gln Phe Asp Ala Ala His Pro Thr Asn Val Gln Arg Leu Ala Glu Pro
                115                 120                 125

Ser Gln Met Leu Lys His Ala Val Val Asn Leu Ile Asn Tyr Gln Asp
            130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
                195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
        450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510
```

```
Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
            770                 775                 780

<210> SEQ ID NO 119
<211> LENGTH: 1037
<212> TYPE: PRT
<213> ORGANISM: Homo sapiens

<400> SEQUENCE: 119

Met Gly Val Arg Asn Cys Leu Tyr Gly Asn Asn Met Ser Gly Gln Arg
1               5                   10                  15

Asp Ile Pro Pro Glu Ile Gly Glu Gln Pro Glu Gln Pro Pro Leu Glu
                20                  25                  30

Ala Pro Gly Ala Ala Pro Gly Ala Gly Pro Ser Pro Ala Glu Glu
            35                  40                  45

Met Glu Thr Glu Pro Pro His Asn Glu Pro Ile Pro Val Glu Asn Asp
50                  55                  60

Gly Glu Ala Cys Gly Pro Glu Val Ser Arg Pro Asn Phe Gln Val
65                  70                  75                  80

Leu Asn Pro Ala Phe Arg Glu Ala Gly Ala His Gly Ser Tyr Ser Pro
                85                  90                  95

Pro Pro Glu Glu Ala Met Pro Phe Glu Ala Glu Gln Pro Ser Leu Gly
```

```
                100             105             110
Gly Phe Trp Pro Thr Leu Glu Gln Pro Gly Phe Pro Ser Gly Val His
            115             120             125
Ala Gly Leu Glu Ala Phe Gly Pro Ala Leu Met Glu Pro Gly Ala Phe
        130             135             140
Ser Gly Ala Arg Pro Gly Leu Gly Gly Tyr Ser Pro Pro Pro Glu Glu
145             150             155             160
Ala Met Pro Phe Glu Phe Asp Gln Pro Ala Gln Arg Gly Cys Ser Gln
                165             170             175
Leu Leu Leu Gln Val Pro Asp Leu Ala Pro Gly Gly Pro Gly Ala Ala
            180             185             190
Gly Val Pro Gly Ala Pro Pro Glu Glu Pro Gln Ala Leu Arg Pro Ala
        195             200             205
Lys Ala Gly Ser Arg Gly Gly Tyr Ser Pro Pro Glu Glu Thr Met
210             215             220
Pro Phe Glu Leu Asp Gly Glu Gly Phe Gly Asp Asp Ser Pro Pro Pro
225             230             235             240
Gly Leu Ser Arg Val Ile Ala Gln Val Asp Gly Ser Ser Gln Phe Ala
                245             250             255
Ala Val Ala Ala Ser Ser Ala Val Arg Leu Thr Pro Ala Ala Asn Ala
            260             265             270
Pro Pro Leu Trp Val Pro Gly Ala Ile Gly Ser Pro Ser Gln Glu Ala
        275             280             285
Val Arg Pro Pro Ser Asn Phe Thr Gly Ser Ser Pro Trp Met Glu Ile
        290             295             300
Ser Gly Pro Pro Phe Glu Ile Gly Ser Ala Pro Ala Gly Val Asp Asp
305             310             315             320
Thr Pro Val Asn Met Asp Ser Pro Pro Ile Ala Leu Asp Gly Pro Pro
                325             330             335
Ile Lys Val Ser Gly Ala Pro Asp Lys Arg Glu Arg Ala Glu Arg Pro
            340             345             350
Pro Val Glu Glu Glu Ala Ala Glu Met Glu Gly Ala Ala Asp Ala Ala
        355             360             365
Glu Gly Gly Lys Val Pro Ser Pro Gly Tyr Gly Ser Pro Ala Ala Gly
        370             375             380
Ala Ala Ser Ala Asp Thr Ala Arg Ala Ala Pro Ala Ala Pro Ala
385             390             395             400
Asp Pro Asp Ser Gly Ala Thr Pro Glu Asp Pro Asp Ser Gly Thr Ala
                405             410             415
Pro Ala Asp Pro Asp Ser Gly Ala Phe Ala Ala Asp Pro Asp Ser Gly
            420             425             430
Ala Ala Pro Ala Ala Pro Ala Asp Pro Asp Ser Gly Ala Ala Pro Asp
        435             440             445
Ala Pro Ala Asp Pro Asp Ser Gly Ala Ala Pro Asp Ala Pro Ala Asp
        450             455             460
Pro Asp Ala Gly Ala Ala Pro Glu Ala Pro Ala Ala Pro Ala Ala
465             470             475             480
Glu Thr Arg Ala Ala His Val Ala Pro Ala Ala Pro Asp Ala Gly Ala
                485             490             495
Pro Thr Ala Pro Ala Ala Ser Ala Thr Arg Ala Ala Gln Val Arg Arg
            500             505             510
Ala Ala Ser Ala Ala Pro Ala Ser Gly Ala Arg Arg Lys Ile His Leu
        515             520             525
```

```
Arg Pro Pro Ser Pro Glu Ile Gln Ala Ala Asp Pro Pro Thr Pro Arg
    530                 535                 540

Pro Thr Arg Ala Ser Ala Trp Arg Gly Lys Ser Glu Ser Ser Arg Gly
545                 550                 555                 560

Arg Arg Val Tyr Tyr Asp Glu Gly Val Ala Ser Ser Asp Asp Asp Ser
                565                 570                 575

Ser Gly Asp Glu Ser Asp Asp Gly Thr Ser Gly Cys Leu Arg Trp Phe
            580                 585                 590

Gln His Arg Arg Asn Arg Arg Arg Lys Pro Gln Arg Asn Leu Leu
        595                 600                 605

Arg Asn Phe Leu Val Gln Ala Phe Gly Gly Cys Phe Gly Arg Ser Glu
    610                 615                 620

Ser Pro Gln Pro Lys Ala Ser Arg Ser Leu Lys Val Lys Lys Val Pro
625                 630                 635                 640

Leu Ala Glu Lys Arg Arg Gln Met Arg Lys Glu Ala Leu Glu Lys Arg
                645                 650                 655

Ala Gln Lys Arg Ala Glu Lys Lys Arg Ser Lys Leu Ile Asp Lys Gln
            660                 665                 670

Leu Gln Asp Glu Lys Met Gly Tyr Met Cys Thr His Arg Leu Leu Leu
        675                 680                 685

Leu Gly Ala Gly Glu Ser Gly Lys Ser Thr Ile Val Lys Gln Met Arg
690                 695                 700

Ile Leu His Val Asn Gly Phe Asn Gly Glu Gly Gly Glu Glu Asp Pro
705                 710                 715                 720

Gln Ala Ala Arg Ser Asn Ser Asp Gly Glu Lys Ala Thr Lys Val Gln
                725                 730                 735

Asp Ile Lys Asn Asn Leu Lys Glu Ala Ile Glu Thr Ile Val Ala Ala
            740                 745                 750

Met Ser Asn Leu Val Pro Pro Val Glu Leu Ala Asn Pro Glu Asn Gln
        755                 760                 765

Phe Arg Val Asp Tyr Ile Leu Ser Val Met Asn Val Pro Asp Phe Asp
    770                 775                 780

Phe Pro Pro Glu Phe Tyr Glu His Ala Lys Ala Leu Trp Glu Asp Glu
785                 790                 795                 800

Gly Val Arg Ala Cys Tyr Glu Arg Ser Asn Glu Tyr Gln Leu Ile Asp
                805                 810                 815

Cys Ala Gln Tyr Phe Leu Asp Lys Ile Asp Val Ile Lys Gln Ala Asp
            820                 825                 830

Tyr Val Pro Ser Asp Gln Asp Leu Leu Arg Cys Arg Val Leu Thr Ser
        835                 840                 845

Gly Ile Phe Glu Thr Lys Phe Gln Val Asp Lys Val Asn Phe His Met
    850                 855                 860

Phe Asp Val Gly Gly Gln Arg Asp Glu Arg Arg Lys Trp Ile Gln Cys
865                 870                 875                 880

Phe Asn Asp Val Thr Ala Ile Ile Phe Val Val Ala Ser Ser Ser Tyr
                885                 890                 895

Asn Met Val Ile Arg Glu Asp Asn Gln Thr Asn Arg Leu Gln Glu Ala
            900                 905                 910

Leu Asn Leu Phe Lys Ser Ile Trp Asn Asn Arg Trp Leu Arg Thr Ile
        915                 920                 925

Ser Val Ile Leu Phe Leu Asn Lys Gln Asp Leu Leu Ala Glu Lys Val
    930                 935                 940
```

```
Leu Ala Gly Lys Ser Lys Ile Glu Asp Tyr Phe Pro Glu Phe Ala Arg
945                 950                 955                 960

Tyr Thr Thr Pro Glu Asp Ala Thr Pro Glu Pro Gly Asp Pro Arg
            965                 970                 975

Val Thr Arg Ala Lys Tyr Phe Ile Arg Asp Glu Phe Leu Arg Ile Ser
            980                 985                 990

Thr Ala Ser Gly Asp Gly Arg His Tyr Cys Tyr Pro His Phe Thr Cys
            995                 1000                1005

Ala Val Asp Thr Glu Asn Ile Arg Arg Val Phe Asn Asp Cys Arg
        1010                1015                1020

Asp Ile Ile Gln Arg Met His Leu Arg Gln Tyr Glu Leu Leu
        1025                1030                1035

<210> SEQ ID NO 120
<211> LENGTH: 90
<212> TYPE: PRT
<213> ORGANISM: Homo sapiens

<400> SEQUENCE: 120

Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu
                85                  90

<210> SEQ ID NO 121
<211> LENGTH: 746
<212> TYPE: PRT
<213> ORGANISM: Homo sapiens

<400> SEQUENCE: 121

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
        50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140
```

```
Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp
            180                 185                 190

Pro Glu Glu Arg Glu Glu Lys Gln Lys Asp Leu Glu Asp His Arg Asp
                195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
                260                 265                 270

Gln Arg Glu Gln Ser Leu His Ser Phe His Thr Leu Phe Cys Arg Arg
            275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
    355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
    515                 520                 525

Pro Cys Asp Ser Ser Cys Pro Cys Val Ile Ala Gln Asn Phe Cys Glu
    530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
```

```
            565                 570                 575
Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 122
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 122
caaatgttgc ttgtctggtg                                               20

<210> SEQ ID NO 123
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 123
gtcagtcgag tgcacagttt                                               20

<210> SEQ ID NO 124
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 124
ggaagcaagt acttcacaag gg                                            22

<210> SEQ ID NO 125
<211> LENGTH: 21
<212> TYPE: DNA
<213> ORGANISM: Artificial sequence
<220> FEATURE:
<223> OTHER INFORMATION: Synthetic sequence: Primer
```

```
<400> SEQUENCE: 125
ggaaagtcac taggagcagg g                                     21

<210> SEQ ID NO 126
<211> LENGTH: 4
<212> TYPE: PRT
<213> ORGANISM: Artificial sequence
<220> FEATURE:
<223> OTHER INFORMATION: Synthetic sequence: Linker

<400> SEQUENCE: 126

Gly Gly Ser Gly
1
```

POLYPEPTIDE VACCINE

FIELD OF THE INVENTION

The present invention relates to the fields of cell biology, molecular biology and biochemistry. This invention also relates to the field of medicine. In particular, it relates to prevention and treatment of diseases, in particular cancer, as well as compositions for such use.

SEQUENCE LISTING

In accordance with 37 CFR 1.52(e)(5), the present specification makes reference to a Sequence Listing submitted electronically in the form of an ASCII text file (entitled "Sequence_Listing_ST25.txt", created on Sep. 21, 2018, and 320 KB in size). The entire contents of the Sequence Listing are herein incorporated by reference, with the intention that, upon publication (including issuance), this incorporated sequence listing will be inserted into the published document immediately before the claims.

BACKGROUND TO THE INVENTION

Cancer has been the subject of intense investigation in the past two decades. However, the underlying causes responsible for cancer metastasis are poorly understood and most types of cancer preventions are still limited. Effective ways to prevent cancer metastasis are urgently needed.

Antibody based therapy has proven to be effective for cancer treatment; however, this approach has been traditionally limited to extracellular or secreted proteins expressed by cancer cells[1,2]. Thus, a number of potential cancer or tumour markers and cancer antigens have been identified in the literature and antibody therapies have been developed against some of them.

For example, the well-known cancer therapy Herceptin (Trastuzumab) is a monoclonal antibody that can kill HER2-positive cancer cells. Herceptin binds to the HER2 (human epidermal growth factor receptor 2) antigen on the cancer cell. Likewise, Bevacizumab (Avastin™) is a monoclonal antibody targeted against vascular endothelial growth factor (VEGF), one of the growth factors implicated in the formation of new blood vessels. By inhibiting angiogenesis, Bevacizumab prevents tumour cells from receiving a constant supply of blood to receive the oxygen and nutrients the tumour needs to survive.

However, the applicability of antibody therapeutics for different cancers is not universal. One of the limitations that has prevented the general use of antibody therapeutics is the large size of antibody molecules and their consequent inability to cross the plasma or cell membrane. In the absence of modification, antibodies (including monoclonal antibodies) are only generally suitable for targeting cancer antigens located at the surface or exterior of host cells[14,15]. In the examples above, HER2 receptor is located on the cell surface and is hence accessible for antibody binding by Herceptin. Likewise, VEGF is secreted into the bloodstream and is able to be bound by Bevacizumab.

Most oncogenic proteins are intracellular proteins (such as intracellular phosphatases, intracellular kinases, transcription factors, etc), and have remained under-explored by the approach of antibody therapies. The long held view that antibodies are too large to penetrate cell membrane has hampered the technology of antibody therapy used in targeting intracellular proteins.

There is therefore an urgent need for effective ways of treating and preventing cancer metastasis. Antibodies have not hitherto been used for targeting intracellular antigens or cancer markers because of the inability of the antibodies to cross the cell membrane and the consequent inaccessibility of the antigen.

Antibody-based therapies have better specificity and thus improved efficacy over standard chemotherapy regimens. Because antibodies are viewed as too large to access intracellular (inside the cell) locations, antibody therapy has traditionally targeted extracellular (outside the cell or cell surface) proteins expressed by cancer cells. However, a large pool of oncogenic proteins is found within the cell (such as intracellular phosphatases/kinases and transcription factors) and has therefore not been pursued for antibody therapies.

We previously showed three different antibodies could respectively target three intracellular proteins: PRL-3 (phosphatase of regenerating liver 3), a cancer-associated phosphatase; EGFP (enhanced green fluorescent protein), a general reporter; and mT (polyomavirus middle T), the polyomavirus middle T oncoprotein (WO2011/065923). Yet, only PRL-3 intracellular phosphatase (an enzyme) has been linked to human cancer metastasis (see Saha et al., Science 294; 1343 (2001) and Wang et al., Cancer cell 18; 52-63 (2010)), the other two intracellular proteins (EGFP and middle T) are used to elucidate the general phenomena that antibody can target intracellular proteins. However, the use of oncoproteins as cancer vaccines is controversial, and a need exists to develop improved oncoprotein cancer vaccines that are more specific, and exhibit less cross-reaction with homologous proteins to reduce side effects, whilst achieving similar, or improved, therapeutic results.

Oncogenic mutations are very common in contributing to multiple human cancers. However, these oncogenic mutations are often detected in intracellular proteins or intracellular domains of cell surface proteins. Our recent works suggest an unconventional concept that intracellular oncoproteins can be targeted by therapeutic antibodies or peptide vaccination. In this new consideration generating antibodies against those specific mutations or vaccination using mutant peptides could specifically ablate cancer cells expressing respective mutated targets, but sparing normal tissues unharmed. However, making antibodies one by one in vitro specifically against countless point mutations discovered so far is very difficult and not practical. Therefore, vaccination using mutant peptides could be a choice.

SUMMARY OF THE INVENTION

As described herein, intracellular oncoproteins can be targeted with vaccination to prevent cancer and cancer metastasis.

As described herein, wild-type C57BL6 mice intravenously (i.v.) injected either with B16F0 or B16F10 melanoma cells, followed by i.v. injection with PRL-3 monoclonal antibody (mAb) showed that PRL-3 mAb can reduce tumors formed by B16F0 melanoma cells that express endogenous PRL-3 intracellular phosphatase,[1] but not those by B16F10 melanoma cells that do not express PRL-3.

C57BL6 mice i.v. injected with either EGFP-B 16F0 or EGFP-B16F10 cells in which both cell lines were engineered to overexpress EGFP, followed by i.v. injection with EGFP monoclonal antibody showed that regardless of PRL-3 expression status, EGFP mAb could eradicate tumors formed by both EGFP-B 16F0 and EGFP-B 16F 10 melanoma cell lines.

Further, polyomavirus middle T (Py-mT)-transgenic young females i.v. injected with mT antibody showed that the mT antibody could effectively reduce the formation of mT-expressing breast tumors.

Moreover, C57BL6 mice vaccinated with PRL-3 or EGFP antigens showed significant reduction in the formation of metastatic tumors expressing either PRL-3 or EGFP protein respectively, as compared with un-immunized mice. Furthermore, Py-mT mice vaccinated with mT antigen significantly prevented tumor formation in mammary glands. The results obtained from 194 wild type mice demonstrate that cancer metastasis caused by intracellular oncoproteins can be successfully blocked with antibody therapy and vaccination.

As shown herein, young PymT transgenic mice injected with fragments of the middle T protein exhibited reduced incidence of breast tumor than mice immunized with GST (negative control). Moreover, immunization of mice with Her2/neu fragments containing only a fragment of the intracellular domain inhibited the formation of Her2/neu expressing tumors formed by B16F0 melanoma cancer cells.

Further, MMTV-PymT mice vaccinated with Estrogen Receptor peptides or with Estrogen Receptor antibody have reduced burden of mammary tumors compared to mice immunized with GST (negative control).

We therefore provide for methods of treating cancers and preventing cancer metastasis with fragments of intracellular oncoprotein. The term "intracellular oncoprotein" as used herein may include oncoproteins that have an intracellular region. For example, membrane anchored proteins may have extracellular, transmembrane, and intracellular domains or regions.

The fragment may be a fragment of a region of the oncoprotein that comprises a mutation as compared to the wild-type, or non-oncogenic protein. The mutation may be associated with, or causative of, cancer (i.e. an oncogenic mutation).

There is provided, according to an aspect of the present invention, use of a vaccine therapy comprising an intracellular oncoprotein fragment for vaccination to stimulate a host to produce its own antibodies to prevent tumor formation.

Also provided is polypeptide for use in a method of stimulating the production of anti-intracellular oncoprotein antibodies in a subject in need thereof, the polypeptide being a fragment of the intracellular oncoprotein having between 10 and 150 amino acids, preferably between 10 and 100 amino acids. A method of stimulating the production of anti-intracellular oncoprotein antibodies in a subject in need thereof, comprising administering a polypeptide which is a fragment of the intracellular oncoprotein, having between 10 and 150 amino acids is also provided.

The polypeptide may be a fragment of an oncoprotein that is intracellular, or a fragment of an intracellular region of an oncoprotein. The fragment may comprise an oncogenic mutation.

The polypeptide may comprise a plurality of fragments. Thus, more than one fragment of an oncoprotein may be provided in one polypeptide. More than one polypeptide may be administered to a patient. Some or all of those polypeptides may comprise more than one oncoprotein fragment. The one or more oncoprotein fragments may be fragments of the same oncoprotein, or may be fragments from different oncoproteins. In some cases, the polypeptide comprises more than one copy of the same fragment.

We provide, according to another aspect of the present invention, a method of treatment of cancer, preferably metastatic cancer, in an individual suffering or suspected to be suffering from cancer. The method may comprise administering a therapeutically effective amount of a fragment of an intracellular oncoprotein to the individual. The intracellular oncoprotein may have been determined as being expressed in the cancer that the individual is suffering from.

The fragment may correspond to a region of the oncoprotein that comprises a mutation. That is, the fragment may comprise an oncogenic mutation. An advantage of targeting an oncogenic mutation, for example using a peptide that comprises a fragment of an oncoprotein that includes an oncogenic mutation, is that an immune response specific to a cancer may be generated, leaving normal cells unharmed.

The patient may be administered a plurality of oncoprotein fragments. The plurality of oncoprotein fragments may be combined into one or more peptides that each comprises a plurality of different peptides, each optionally linked by a peptide linker. The fragments may be from the same oncoprotein, or different oncoproteins. The method may involve inducing the patient to produce anti-cancer antibodies, for example antibodies against the oncoprotein or oncogenic mutation of the oncoprotein fragment. The method may involve administering the fragment or peptide with an adjuvant.

The intracellular oncoprotein fragment may be such that it does not comprise an extracellular domain or a transmembrane domain. The intracellular oncoprotein fragment may comprise a cytoplasmic or nuclear oncoprotein fragment.

The intracellular oncoprotein fragment may comprise a portion of an Estrogen Receptor protein, for example ER (estrogen receptor), or a Hepatitis B virus protein such as HBV X-protein, PRL-3 protein, VHZ, Her2/neu or polyomavirus middle T (Py-mT) protein, Kras, EGFR, B-raf, PI3KCA, beta-catenin, GNAS, Ret, EZH2 or GNAQ.

The cancer may be associated with or caused by overexpression of the intracellular oncoprotein of which an oncoprotein fragment is used for immunization. The cancer may be selected from the group consisting of: breast cancer, hepatocellular cancer such as hepatocellular carcinoma, ovarian cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma.

The cancer may comprise a metastatic cancer.

The method may be such that the number of metastatic tumours in a treated individual is reduced by at least 50%, at least 60%, at least 70%, at least 80% or at least 90%, compared to an untreated individual. In some cases, metastasis of the cancer is entirely prevented.

As a further aspect of the present invention, there is provided an intracellular oncoprotein fragment, or a variant, homologue, or derivative thereof, for use in a method of prevention of cancer, such as metastatic cancer, the method comprising administering a prophylactically effective amount of an intracellular oncoprotein fragment, variant, homologue, or derivative thereof, to an individual suffering or suspected to be suffering from cancer.

We provide, according to another aspect of the present invention, a pharmaceutical composition comprising (a) an intracellular oncoprotein fragment, or a variant, homologue or derivative thereof, together with a pharmaceutically acceptable excipient, diluent or carrier.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

Embodiments and experiments illustrating the principles of the invention will now be discussed with reference to the accompanying figures in which:

FIG. 3 is a diagram showing that mT Ab effectively inhibits the formation of breast tumors expressing mT oncoprotein. A, Genotyping was used to identify transgenic MMTV-PymT females. Mice #2, #6, #7, and #10 are heterozygote transgenic females (+/−). B, #2 and #6 transgenic mice remained untreated as controls to monitor the progression of mammary gland tumor progression. #7 and #10 transgenic mice received mT antibody i.v. injection. At the end of the experiment (3-month), all mice were sacrificed. The sizes and weights of the breast tissues (tumors) were measured. The 5 pairs of mammary glands were indicated and showed as 4 groups in respective lower panel. Bar: 1 0.5 cm. C, The morphology of the whole mount breast tissues was examined in breasts from untreated (a), treated (b), and wild type (c). E. Kaplan-Meier survival curves were used to compare 'treated' and 'untreated' group of MMTV-PymT heterozygous transgenic females. F. Fraction indicated at the Y-axis represents percentage of tumor-bearing mice verse total mice (n) in each group. Column represents type of mice indicated at the X-axis.

FIG. 4 is a diagram showing that immunization of MMTV-PyMT mice with mT antigen could prevent the formation of breast tumors that express mT intracellular protein. A, a therapeutic plan of vaccination with mT antigen. B-D. MMTV-PymT heterozygous transgenic mice (TG) were used for the experiment. TG females (#43, #44, #45) were immunized with GST protein. By ELISA analysis, these mice had no mT antibody in their sera and showed dramatic progression of mammary gland tumors. In contrast, TG females (#37, #40, #41) were immunized with GST-mT fusion protein; these mice had high levels of mT antibodies in their sera and showed significantly repression of mammary gland tumors. The 10 mammary glands were shown as 4 groups at the bottom of each panel. Top two groups of breasts consist of the top three pairs of mammary glands, while bottom two groups represent the bottom two pairs of mammary glands. Weights of total 10 mammary glands were measured. Wild type mice (n=3) were used as controls. Bar: 1.5 cm. E, Kaplan-Meier survival curves were compared between 'immunized' and 'unimmunized' MMTV-PymT mice, with median survival time (p=0.0004) clearly longer in mT-immunized group (19.5-week) versus unimmunized group (14.5-weeks). F. Summary of results between immunized and unimmunized mice. N stands for number of mice in each group; fraction in each column represents proportion of tumor-bearing MMTV-PymT mice verse total TG females used.

FIG. 6 is a diagram showing that mice immunized with PRL-3, EGFP, or mT intracellular antigens could prevent PRL-3, EGFP and mT expressing tumors. A, a therapeutic plan of vaccination with respective antigen. B, Un-immunized, PRL-3-immunized or GFP-immunized mice were then challenged with either 1 million EGFP-FO or EGFP-F10 cancer cells via tail veins. All the organs were examined 3 weeks post-cancer cell injection and photographed with fluorescent microscopy to show morphologies of metastatic tumors. Black tumors represent non-EGFP expressing melanoma cells, whereas green tumors represent those expressing EGFP. C, An overview of MMTV-PymT heterozygous transgenic females: a. Unimmunized MMTV-PymT mice b. mT-immunized mice showed reduction breast tumors. D, Summary of results between unimmunized and immunized mice with intracellular antigens. 84 mice were used in vaccination experiment. N stands for number of mice in each group; fraction in each column represents proportion of mice bearing heavy tumors.

FIG. 7 is a diagram showing that generation of PRL-3 chimeric mAb specifically reacts with PRL-3 antigen. A. A schematic diagram outlining the major steps of chimeric mAb construction. B. PRL-3 chimeric mAb recognizes EGFP-PRL-3 overexpressed in DLD-I human colorectal cancer cells by indirect immunofluorescence: a, distribution of EGFP-PRL-3 in fixed DLD-I cells (green); b, PRL-3 chimeric antibody and anti-human Texas-Red to reveal the binding to PRL-3 protein; c, merged image. Bar: 20 µfi. C. Cell lysate derived from DLD-I cells overexpressing EGFP-PRL-3, and lysates derived from CHO stable cell lines overexpressing myc-PRL-3, myc-PRL-1, and myc-PRL-2 were analyzed by western blot. PRL-3 chimeric antibody specifically recognized EGFP-PRL-3 (48 kDa) and myc-PRL-3 (20 kDa), but does not react with myc-PRL-1 and myc-PRL-2.

FIG. 9 is a diagram showing that PRL-3 chimeric mAb inhibits the formation of metastatic tumors formed by A2780 cells and HCT-1 16 cells that express endogenous PRL-3. A. Total cell lysates were prepared from HCT 1 16-luc2, HCT-1 16, A2780, and NCI-H460 cancer cell lines. Endogenous PRL-3 protein was detected in HCT1\6-luc2, HCT-1 16, and A2780 cells, but not in H460. B: On day 1, nude mice (n=6) were injected with $1 \times 10^6$ HCT-1\6-luc2 cancer cells and subsequently administered with PRL-3 chimeric mAb (n=3, treated) or PBS (n=3, untreated) on day 3, followed by two intravenous administrations of the PRL-3 chimeric mAb for 7-week. Both cancer cells and antibodies were injected via tail vein. I VIS® Imaging System was used to track and monitor tumor development in vivo at week 7. C. On day 1, nude mice were injected with $1 \times 10^6$ cancer cells and treated as described in B. Paired experiments (untreated/treated) were terminated when mice appeared very sick. Experiment durations are indicated on the top of each panel. D. Summary of therapeutic results from mouse PRL-3 (R3-mAb) or chimeric PRL-3 (R3-hAb) antibody therapies in nude mice injected with three human cancer cell lines. Percentages of tumor-bearing mice were averaged from each group (n=numbers of mice) and indicated at the Y-axis. 101 mice in total were used in this experiment.

FIG. 14 is a diagram showing that the outcome of the treatment is highly associated with tissue expression patterns of the targets. A, B. The protein expression patterns of PRL-3 and PRL-2 in normal mouse tissues by western blot, GAPDH was used as a loading control. C. HCT-1 16 (PRL-2 positive cell line) recipients fail to respond to PRL-2 antibody (the antibody also cross-reacts with PRL-1) therapy, most likely due to the fact that PRL-2 is ubiquitously expressed in most of mouse tissues that we have examined.

FIG. 16 shows sequences of fragments of Her2/neu oncoprotein and mT oncoprotein used in Examples 40 and 41 (SEQ ID NOs: 1-8). The Her2a intracellular peptide is unique for Her2, and does not cross react with EGFR (Her1).

FIG. 18: Mice immunized with Her2a short peptide or fragment could inhibit the formation of Her2-expressing tumors formed by B16F0 melanoma cancer cells. (A) A vaccination plan with Her2a short peptide, Her2 extra fragment. (B) At week 16, Her2 short peptide immunized, Her2 extra-immunized, and unimmunized mice, were then challenged with 1 million B16F0 cancer cells via tail veins. All the organs were examined at ~17 days after cancer cell injection and photographed to show morphologies of metastatic tumors. Black tumors represent B16F0 melanoma cells. (C, upper) ELISA analysis was confirmed to show that Her2 short peptide immunized, Her2 extra fragment immunized (but not unimmunized) mice had high levels of Her2 antibodies in their sera. (C, lower). A total numbers of lung tumors from each mouse were shown. N=3 in each group. Her2jp' is equivalent to Her2-extra.

FIG. 20: shows sequences for Estrogen Receptor (ER) and HBV-X protein (SEQ ID NOs: 9-17). Estrogen Receptor peptides are used in the experiments of which the results are detailed in FIG. 21.

ER-red and ER-purple represent two regions (or fragments) indicated with red and purple sequences.

Figure 21:
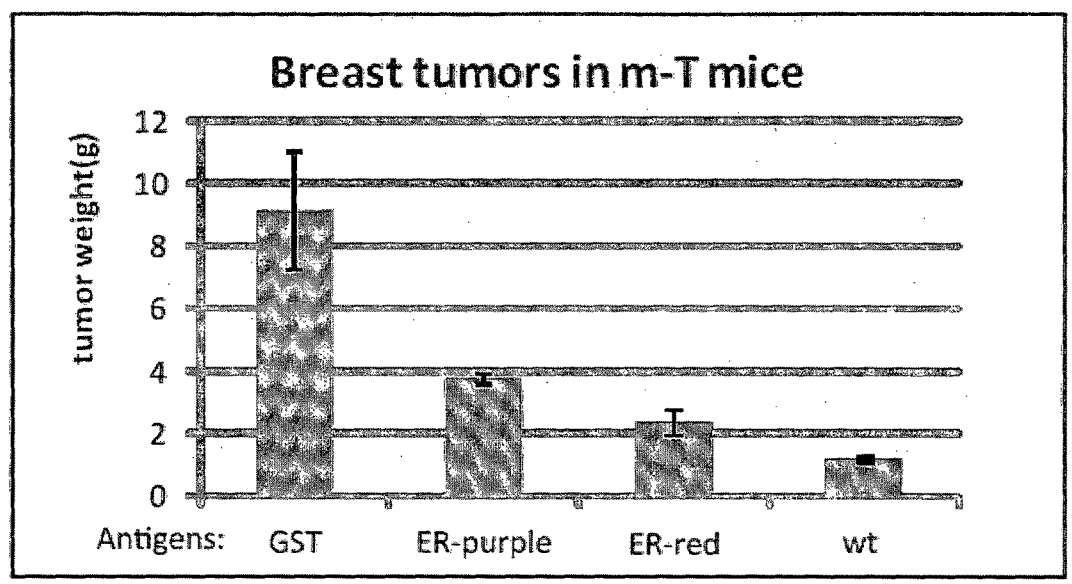

FIG. 21: MMTV-PymT TG young females vaccinated with Estrogen Receptor peptides (ER-purple and ER-red) to reduce the burden of mammary tumors. (A) A therapeutic plan of vaccination with Estrogen Receptor peptides (ER-purple or ER-red). (B) To confirm that targeting tumors are expressing Estrogen Receptor for suitable treatment, a western blot was performed to show that Estrogen Receptor protein is expressing in tumor (T. breast and T. lung) (lane 4-5) tissues from MMTV-PymT TG adult females. (C) For a negative control, immunized mice with GST antigen, which is not expressing in the target tumors, immunized with ER-purple peptide and ER-red peptide, these two group of peptides showed marked repression of tumors compared to GST immunized control mice.

The 10 mammary glands were shown as four tissue groups at the bottom of each panel. Scale bars, 1.0 cm. (D) An average weight of mammary glands from each group of mice was shown together with wildtype (wt) mice as a control for normal breast sizes (mean±SD).

Figure 22:
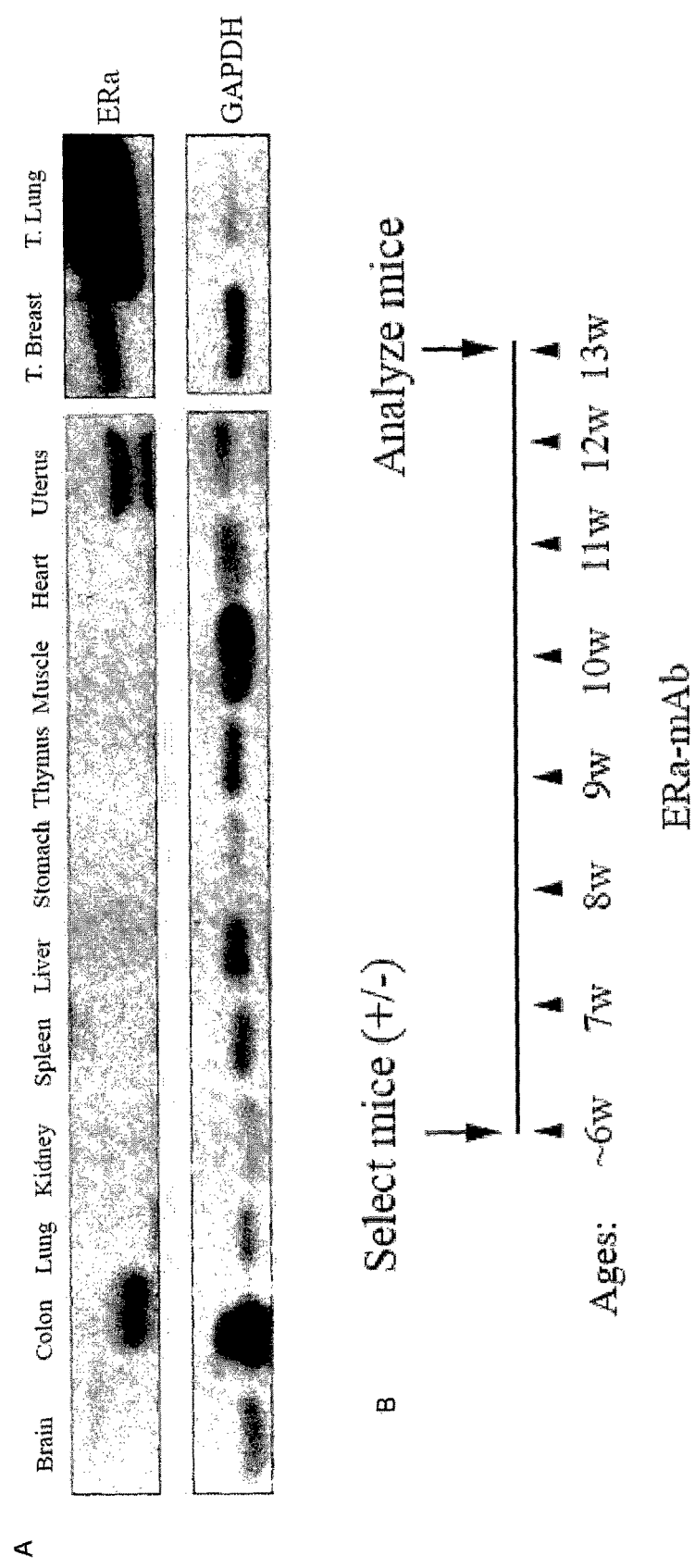

FIG. 22: The outcome of the antibody treatment is highly associated with tissue expression patterns of the targets. A. The protein expression patterns of Estrogen Receptor (ERa) in normal mouse tissues together with tumor (T. breast and T. lung) tissues were examined by western blot using ERa antibody, GAPDH was used as a loading control. B. A therapeutic schedule of estrogen receptor 1 (ERa) antibody-treatment C. Student's t test analysis revealed a significant difference in average breast tumor weight between untreated and ERa-treated groups (P=0.0163) (mean±SD) P<0.05 was regarded statistically significant. D. At the end (13-week old), all mice were killed and examined. The sizes and weights of the breast tissues (tumors) were measured. The five pairs of mammary glands were indicated and shown as four groups in respective lower panels.

Figure 23:
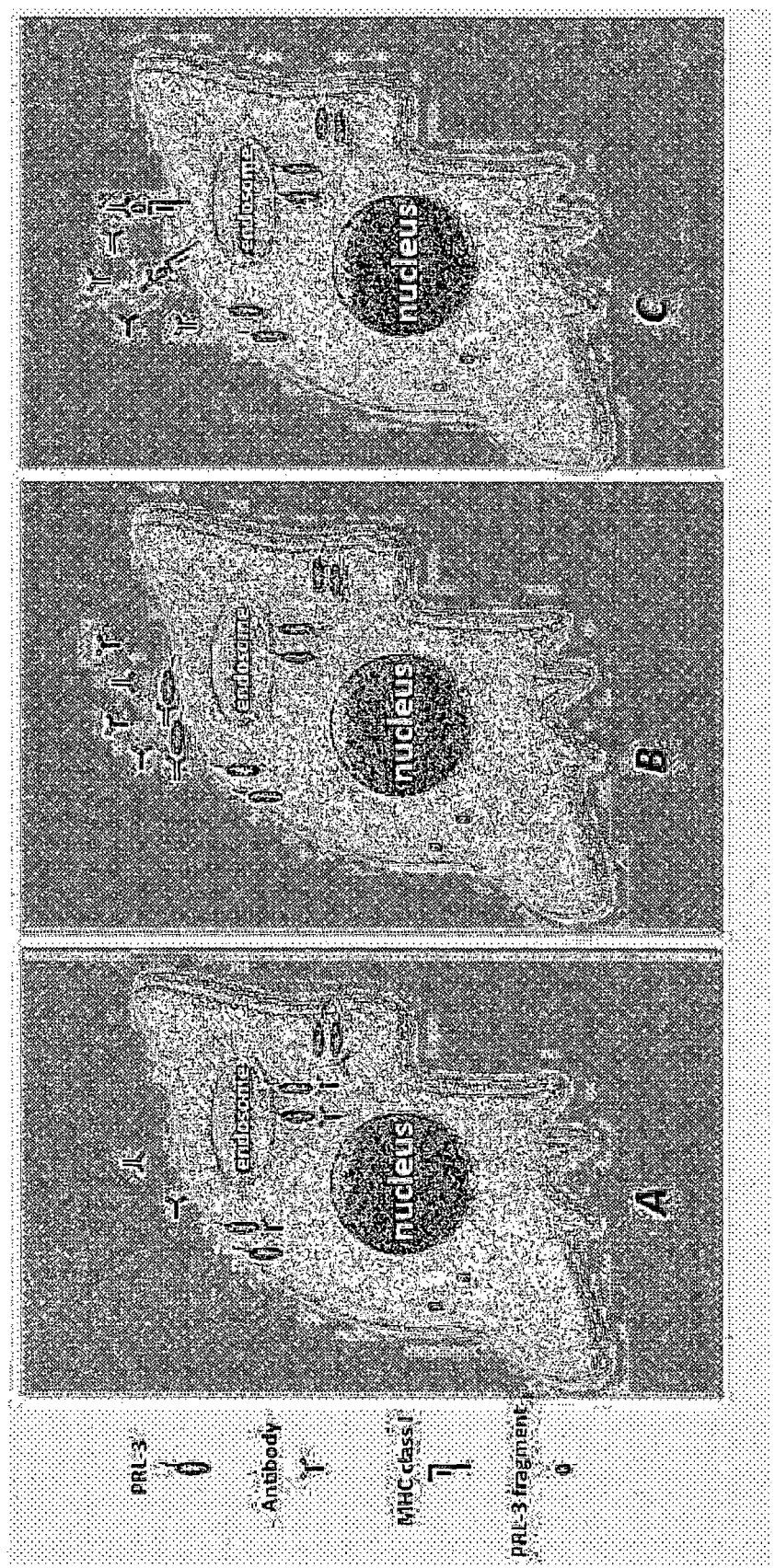

FIG. 23: Three possible mechanisms for antibody targeting intracellular antigens A. Antibodies may potentially enter PRL-3 expressing cells to target intracellular PRL-3 and neutralize its function. B. Some of the intracellular PRL-3 may be externalized and displayed on the surface of cancer cells by unconventional secretion. C. Proteolytic fragments of intracellular PRL-3 may be presented by MHC class I molecules to attract Cytotoxic T cells.

Figure 24:
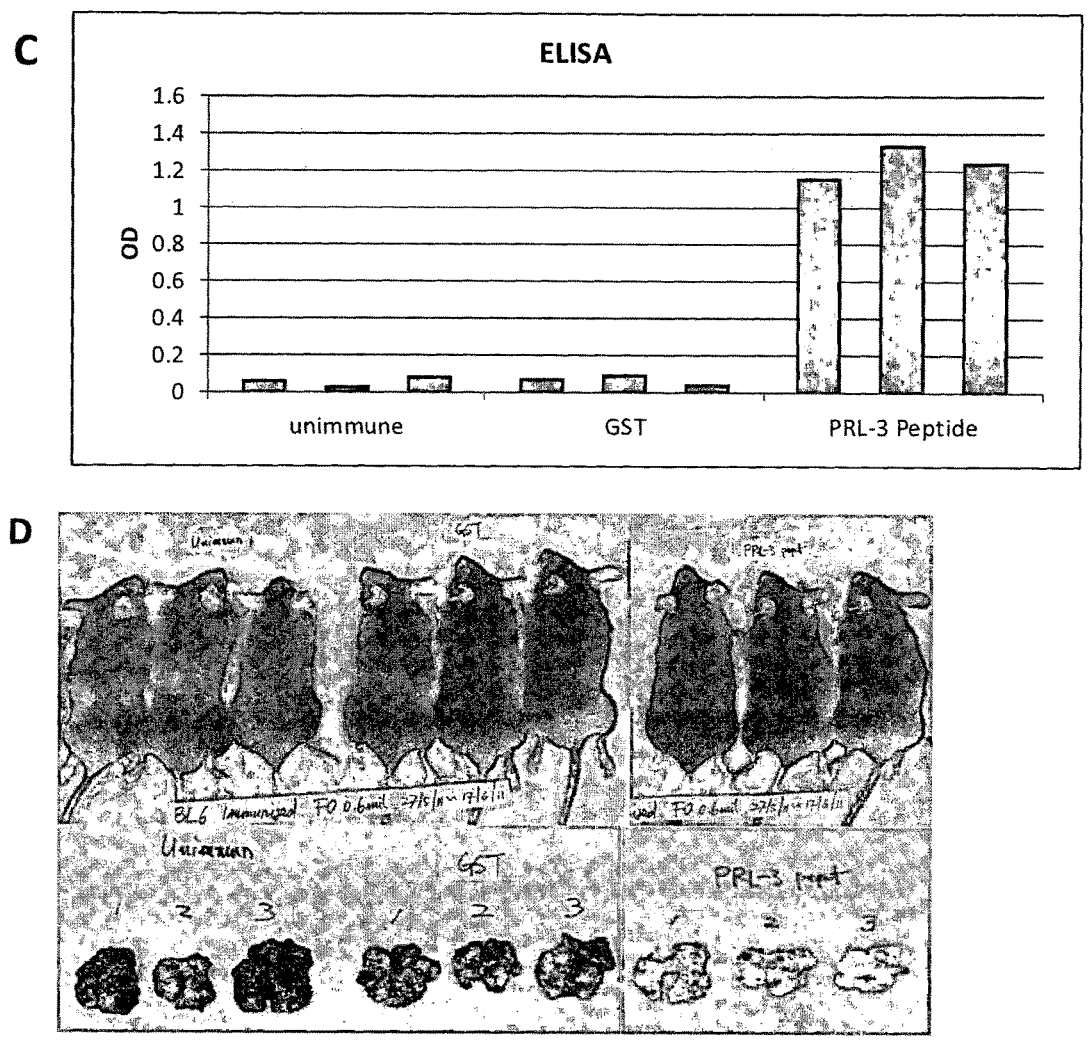

FIG. 24: Vaccination of PRL-3 peptide (EVTYDKTPLE-KDGITVGGSGDPHTHKTRC (SEQ ID NO: 18)-KLH) could block tumors formed by PRL-3 expressing cancer cell line (B16F0) in C57BL6 mice.

Figure 25:
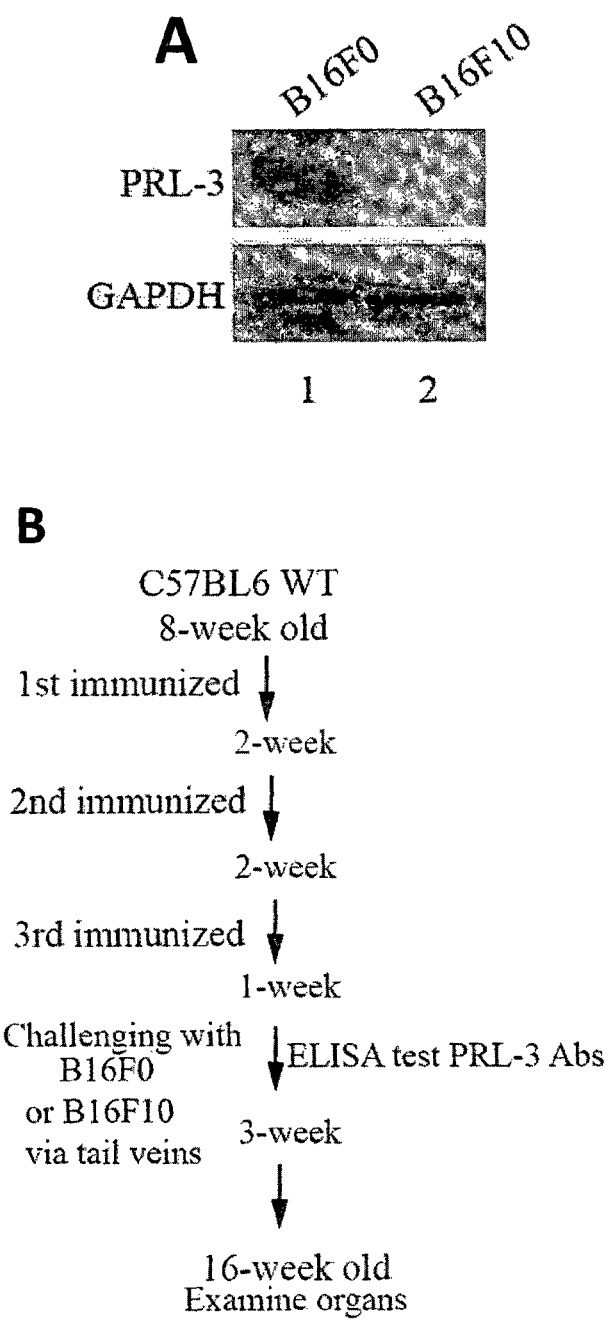

FIG. 25: vaccination of PRL-3 peptide could reduced tumours formed by PRL-3 expressing cells (B16F0) but not by PRL-3 non-expressing (B16F10) in C57BL6 mice.

Figure 26:
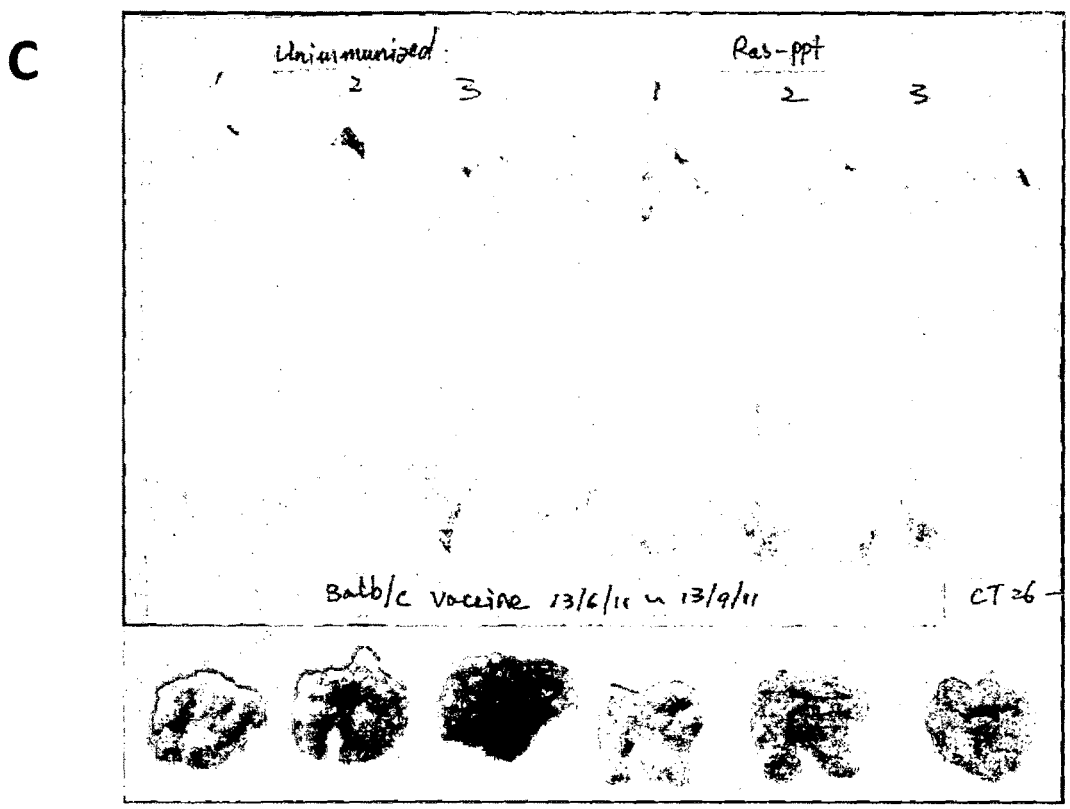

FIG. 26: Balb/c mice immunized with Ras mutated peptide (CMTEYKLVWGADGVGKSALT) (SEQ ID NO: 19) could block tumours formed by CT-26 cancer cells expressing Ras (G12D) mutation.

FIG. 27: A. peptides containing oncogenic mutations (mutation indicated in bold) (SEQ ID NOs: 20-41). B. other oncogenic mutations FIG. 28. Oncogenic mutations identified from share. gene.com/mutation_classification/cancer.variants.txt

DETAILED DESCRIPTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

To explore the possibility of targeting intracellular proteins, in this study, we have chosen to focus on three representative intracellular targets for anticancer therapies in animal models.

We select a cancer associated-PRL-3 intracellular phosphatase as a target for the PRL-3 antibody therapy. PRL-3 is one of the three members (PRL-1, -2, and -3) in the PRL (phosphatase of regenerating liver) family which was identified in 1994 and 1998[5,6]. The three PRLs form a subgroup of the protein tyrosine phosphatase (PTP) family[7].

PRL-3 was first linked to colorectal cancer metastasis in 2001. Subsequently, upregulation of individual PRLs-PTPs was reported to be correlated with numerous types of advanced human metastatic cancers when compared with their normal counterparts[9].

The PRL phosphatases represent an intriguing group of proteins being validated as biomarkers and therapeutic targets in human cancers[10]. PRLs are intracellular C-terminally prenylated phosphatases, while mutant forms of PRLs that lack the prenylation signal are often localized in nuclei[11,12].

The localization of PRL-1 and PRL-3 to the inner leaflet of the plasma membrane and early endosomes has been revealed by EM immunogold labeling[13]. Targeting PRLs by exogenous reagents to ablate PRLs-cancer cells requires their penetration into cells and is a challenging task.

We chose the cytosolic enhanced green fluorescent protein (EGFP), a popular reporter protein originally isolated from the jellyfish *Aequorea victoria* that fluoresces green when exposed to blue light. EGFP is an intracellular protein that sometimes enters the nucleus. As a neutral exogenous protein, EGFP serves as an artificial 'cancer cell specific intracellular protein' in EGFP-B 16F0 and EGFP-B16F 10 melanoma cells.

These EGFP-overexpressing melanoma cells will then be targeted by EGFP mAb. We expect that EGFP antibody should have less undesired side effect in the animal model as EGFP is not expressed in the host tissues.

We selected a well known oncoprotein, the polyomavirus middle T (mT) intracellular kinase, as the third target[14]. We used the mammary cancer model of Py-mT transgenic heterozygous females (+/−) carrying the mT oncogene under the transcriptional control of the mouse mammary tumor virus promoter/enhancer. The transgenic mice have been widely used as excellent mouse tumor models for decades in the cancer research community to assess the relative contribution of the metastatic mammary tumor phenotype[15,16].

We selected the well known oncoprotein Her2 (also known as ErbB-2). We injected C57BL6 mice with B16F0 melanoma cells as a model of cancer metastasis, and investigated whether Her2 fragments could inhibit the formation of Her2-expressing tumors.

Fragment and peptide vaccination is using shorter sequences designed and selected from whole oncoprotein sequences as antigens to stimulate host immune system to produce antibody against that specific fragment or peptide derived from the whole oncoproteins, which is expressing in the tumor cells. The 'fragment and peptide' vaccination is expected to be more specific and less cross reacting with their homology members in the same family. Compared to whole oncoprotein vaccine, fragment or peptide vaccine therefore has less side effect and is more specific. Sequences located in the whole oncoproteins, which cross react with other family members can be deleted and avoided. The resulting unique peptide is very specific to that target and does not react with its related target sequences.

To obtain a better understanding and extend our previous promising pre-clinical data[17] to future clinical applications in human, herein, we performed the entire antibody therapy study in wild type animal models to reveal a hitherto unrecognized concept that antibody therapy can be used for targeting intracellular-oncoproteins.

Oncogenic mutations are common in contributing to human cancers. Since modern technology can easily identify patients whose tumors are associated or caused by a specific oncogenic mutation, we could then design peptides corresponding to these oncogenic mutations. Vaccine with this specific mutant peptide could potentially trigger patient's immune system against the mutant proteins, the patients will produce suitable antibody "drugs" and cytotoxic T lymphocytes (CTLs) for their own anticancer therapeutics. Since vaccine could elicit long-lived immunity, when the correct antigens (peptide or gene fragment) were used to trigger patients' immune system to make their own antibody and CTLs against the correct mutated targets in ablating their tumors, they could achieve outcomes similar to antibody therapeutics.

Since dendritic cells (DCs) are antigen-presenting cells (APCs) which play a critical role in the regulation of the adaptive immune response, large numbers of DCs could be isolated and generated from CD34+ bone marrow precursors or from CD14+ monocytes in vitro. In vitro vaccination will educated the APCs to be able to present the peptide antigens at their cell surface. Reintroducing the educated APCs back to the same host to trigger B and T cell responses to these peptide antigens and produce antibody and CTLs to ablate cancer cells that express the specific antigens.

Alternatively, peptides synthesised to contain target antigens, optionally including oncogenic mutations, may be administered to the patient, to educate their immune system in vivo.

The Examples demonstrate that each of the above intracellular proteins can be targeted by antibodies against the cognate antigens.

If an antibody can recognize its intracellular antigen, it may be that an intracellular antigen could potentially be used for vaccination to stimulate host immune system and produce antibodies against it. This prompted us to explore vaccination with intracellular oncoproteins against tumors which express specific intracellular antigens.

Vaccination is inexpensive yet effective in stimulating host immunity. Compared with extracellular antigens, intracellular proteins used in vaccination receive much less attention because of their intracellular location. The main objective of this vaccination is to artificially activate the immune system against a particular intracellular protein to prime the antibody in some individuals against certain malignant cells expressing that intracellular protein thus preventing tumor formation in the future.

Next, we used the same three intracellular antigens (PRL-3, EGFP, and mT) to perform vaccination in C57BL6 wild type mice. We obtained interesting results, as shown in the Examples, that mice immunized with an intracellular tumor antigen are able to eradicate these cancer cells expressed that specific tumor antigen to reduce the formations of tumors. More importantly, the data suggest the possibility of vaccination to prevent disease progression for individuals who are genetically at high risk in developing certain cancers caused by known intracellular oncoproteins. Such specific active immunotherapy of cancer, if successful and effective have clear advantages over passive immunotherapy.

In this study, we used 194 mice (FIG. 6) for both antibody therapies and vaccinations with intracellular proteins for anticancer. Cancer research is rapidly moving towards individualized cancer therapy, as oncologists begin to use tailoring treatment strategies to individual patients. Antibody therapy and Vaccination may fulfill the promise of personalized treatment and could be the future of individualized medicine because we all have the ability to make antibodies for our own recovery.

Currently, vaccines are mainly used to prevent bacterial and viral infections and to target a few extracellular proteins (receptors) on cancer cells. Our data indicate that strategies targeting intracellular oncoproteins hold enormous promise for cancer prevention in the future.

Oncoproteins as described herein are proteins involved in the regulation or synthesis of proteins linked to tumorigenic cell growth. Oncoproteins may be oncogenic polypeptides, involved in the transformation of normal cells into cancer cells. Oncoproteins may have higher expression in tumor cells than in normal cells. The oncoproteins are intracellular, meaning that they are located inside the cell, for example in the nucleus or cytoplasm, or attached to the intracellular surface of the cell membrane. Preferably, the oncoproteins are self-antigens, meaning that they are proteins normally found in the animal, and form part of the protein population expressed from the genome of the animal, and are not heterologous to that animal, such as viral proteins.

Alternatively, the intracellular oncoprotein may be an oncoprotein that has an intracellular region. For example it may be a membrane anchored protein that has a region which extends into the cytoplasm.

Oncoprotein can be a non-self-antigen, such as viral protein expressed by infected cells.

In some cases the intracellular oncoprotein is not derived from a microorganism. For example, is not a viral oncoprotein, or is not a bacterial oncoprotein, or is not a fungal oncoprotein. In some cases the oncoprotein is not an HPV oncoprotein. Preferably, the oncoprotein is a self-antigen. One potential advantage of using intracellular self-antigens is that they may have a better chance of provoking an immune response than extracellular self-antigens because immune cells targeting extracellular self-antigens are generally eliminated during development.

Prevention of Cancer by Vaccination with Intracellular Oncoproteins

Previously therapeutic antibodies were thought to have access only to molecules that appear on the outer surface of cells. According to the expectation in the literature, targeting intracellular PRLs and such other intracellular oncoproteins with antibodies to ablate cancer cells and cancer metastasis has never been previously thought to be possible because of their intracellular location.

Accordingly, vaccination with intracellular oncoproteins to prevent cancer cell formation, cancer cell growth and cancer metastasis has never been previously thought to be possible. We have shown that this is not the case. Moreover, we have shown that vaccination with fragments of intracellular oncoproteins is also possible, and may have improved efficacy as compared with fragments of extracellular oncoproteins.

Vaccination with intracellular oncoproteins or fragments thereof, as disclosed herein, may result in stimulation of antibody production by the host. B cells may be stimulated to produce antibodies specific to the intracellular oncoprotein or fragment thereof. Thus, vaccination may result in stimulation of a B cell response specific to the intracellular oncoprotein or fragment thereof.

We therefore provide generally for fragments of cancer causing oncoproteins, which oncoproteins are intracellular in nature, as cancer vaccines, particularly vaccines against cancer metastasis, or to curb the spread or growth of a cancer.

We provide for use of an oncoprotein fragment, which oncoprotein is intracellular in nature, in a method of prevention of cancer including cancer metastases associated with cancer causing oncoproteins.

Vaccination may involve a single fragment from a particular oncoprotein (i.e. a homogenous population of identical peptides). Alternatively, peptides with more than one sequence may be used. For example, a mixture of peptides of sequence X and sequence Y. The peptides may be overlapping, or from different regions of an oncoprotein. In some cases the peptides do not span all, or substantially all, of the oncoprotein. That is to say that the mixture of peptides encompasses only part of the oncoprotein. In some cases, a mixture of different peptides from more than one oncoprotein may be used. Where a mixture of different peptides is used (either different peptides from the same oncoprotein, or peptides from different oncoproteins), these may be administered simultaneously or sequentially. Preferably, each of the peptides will be capable of inducing a host to produce antibodies against the intracellular oncoprotein.

According to the invention, only a single peptide may be used. Alternatively a mixture of 2, 3, 4, 5, 6, 7, 8, 9, 10, 11, 12, 13, 14, 15, 16, 17, 18, 19, 20, 21, 22, 23, 24, 25 or more peptides may be used.

We provide for methods of preventing cancer including cancer metastases associated with cancer causing oncoproteins, which oncoproteins are intracellular in nature, by administration of a prophylactically effective amount of a fragment of the intracellular oncoprotein to a patient in need thereof.

We provide a pharmaceutical composition comprising an intracellular oncoprotein fragment, together with a pharmaceutically acceptable excipient, diluent or carrier. We provide for the use of such a pharmaceutical composition for the prevention of cancer including cancer metastasis.

Since dendritic cells (DCs) are antigen-presenting cells (APCs) which play a critical role in the regulation of the adaptive immune response, we could isolate and generate large numbers of DCs from CD34+ bone marrow precursors or from CD14+ monocytes in vitro. In vitro vaccination will educate the APCs to be able to present the peptide antigens at their cell surface. The educated APCs may be reintroduced back to the same host to trigger B and T cell responses to these peptide antigens and produce antibody and CTL responses to ablate cancer cells that express the specific tumor antigens.

Alternatively, or additionally a patient's immune system may be directly educated using vaccination with an oncoprotein or fragment. Oncoproteins, antigens and/or mutations specific to a patient's cancer may be identified. This may include intracellular or extracellular oncoproteins, antigens and/or mutations. Peptides containing the relevant fragments of these oncoproteins, antigens and/or mutations may then be synthesised and used as a vaccine. Vaccination may involve the administration of the peptides in the presence or absence of one or more adjuvants. For example, Freund's complete adjuvant. Immunisation may involve administering the peptides at multiple times or locations. For example, at monthly intervals. To test the efficacy of immunisation, ELISA may be used to determine whether peptide specific antibodies have been produced by the patient.

Thus, one or more different peptides may be administered to a patient. Peptides containing fragments of particular oncoproteins, epitopes or oncogenic mutations which are known to be associated with, or a cause of, a patients cancer may be selected for administration to that peptide. Thus, the mixture of peptides chosen may be particular for (i.e. personalised to) an individual patient. A mixture of 1, 2, 3, 4, 5, 6, 7, 8, 9, 10, 11, 12, 13, 14, 15, 16, 17, 18, 19, 20, 25, 30, 35, 40, 45, 50 or more peptides may be selected.

Thus, methods of treatment may involve the step of determining the presence of particular oncogenic mutations or oncoproteins in a sample obtained from a patient. The sample may be a tumor biopsy, or a blood or urine sample. Antigen specific to the tumor may be determined by any suitable method, for example Western blot, ELISA or PCT methods. Peptides may designed or chosen to correspond to oncoproteins or oncogenic mutations that are known to be present in the patient.

Intracellular Oncoproteins

Intracellular oncoproteins and intracellular antigens are known in the art and may include, amongst others, any one or more of the following, or their variants, derivatives, homologues or fragments.

Suitable intracellular oncoproteins will be appreciable by the skilled person. Genes specifically up-regulated during tumor formation but poorly or not expressed in host tissues are particularly promising as tumor-specific targets. For cancers that show a genetic link, immunization of immune-competent young susceptible family members with an antigen (epitope-based peptide vaccine) that is associated with the familial cancer could prime the immune system against that oncoprotein. These endogenously stimulated antibodies could then potentially combat cancer cells expressing that particular oncoprotein. The results described herein suggest that antibody-based therapy and vaccination against cancer may be extended to a wider variety of intracellular oncoproteins as therapeutic targets. The whole class of intracellular oncoproteins previously thought to be un-targetable by therapeutic antibodies or vaccinations can now expand the scope for tailor-made cancer therapies as well as usher in a new era of cancer vaccines. We expect that one potential advantage of using intracellular self-antigens is that they may have a better chance of provoking an immune response than extracellular self-antigens because immune cells targeting extracellular self-antigens are generally eliminated during development. We found that compared to exogenously delivered antibodies, antigen-induced antibody therapy could achieve similar antitumor therapeutic efficacy. Because existing conventional clinical antibody therapy is costly, vaccination may be more useful and economical as a means of inducing high titers of antigen-induced antibodies. This concept of "cancer vaccination" is promising and challenging.

Estrogen Receptor

An oncoprotein useful in the present invention is Estrogen Receptor (ER). The oncoprotein may be human ER. It may comprise or consist of the protein sequence set out at P03372 (GI: 544257) (SEQ ID NO: 42).

Estrogen Receptor and fragments thereof will be useful for treatment of breast cancer caused by, or associated with, overexpression of estrogen receptor (ER). Antibodies against ER or vaccination using ER oncoprotein or a fragment thereof could be used to prevent spreading. This is particularly useful to target ER positive breast cancer patients regardless of the expression of Her2 or other proteins.

Estrogen Receptor (ER) is a ligand-activated transcription factor composed of several domains important for hormone binding, DNA binding, and activation of transcription. Alternative splicing results in several ER mRNA transcripts, which differ primarily in their 5-prime untranslated regions. The translated receptors show less variability (see OMIM reference 133430).

Estrogen Receptor is a well-known intracellular receptor (see Ross-Innes C S, Stark R, Holmes K A, et al. Cooperative interaction between retinoic acid receptor alpha and estrogen receptor in breast cancer. Genes Dev. 2010; 24:171-182).

Hepatitis B Virus (HBV) Proteins

Hepatitis B proteins may be suitable for use in the invention. HBV exists as 8 genotypes.

One suitable HBV protein is the HBV X-protein. HBV X-protein is localized in the nucleus of infected cells. Most hepatocellular carcinoma (HCC) are associated with HBV infection. Accordingly, HBV proteins may be useful for treating HCC, antibody targeting viral protein to specifically destroy virally infected cells whilst leaving normal cells unharmed.

Protein sequences for HBV-X protein have been deposited at GenBank and are suitable for use in the present invention. For example, the term "HBV-X protein" may be used to refer to a protein comprising or consisting of the sequence set out at GenBank CBX46805.1 (GI: 310923520)

(SEQ ID NO: 43), or EMBL accession FR714506.1 (SEQ ID NO: 44), or a protein encoded by a gene having a sequence as set out at Accession AB670311.1 (GI: 371919030) (SEQ ID NO: 44).

PRL-3

The following text is adapted from OMIM entry 606449.

PRL-3 is also known as Protein-Tyrosine Phosphatase, Type 4A, 3; PTP4A3. The chromosomal location of PRL-3 is at gene map locus 8q24.3.

In the heart, protein kinases regulate contractility, ion transport, metabolism, and gene expression. Phosphatases, in addition to their role in dephosphorylation, are involved in cardiac hypertrophy and dysfunction.

By database searching and screening of a heart cDNA library, Matter et al. 2001, Biochem. Biophys. Res. Commun. 283: 1061-1068 identified a cDNA encoding PTP4A3, which they termed PRL3. The deduced PRL3 protein is 76% identical to PRLI (PTP4A1; 601585) and 96% identical to mouse Prl3. Northern blot analysis revealed expression of an approximately 2.3-kb PRL3 transcript predominantly in heart and skeletal muscle, with lower expression in pancreas. This expression pattern is distinct from the wider expression of PRL1 and PRL2 (PTP4A2; 601584). In situ hybridization analysis localized PRL3 expression to cardiomyocytes. Tris glycine gel analysis showed that PRL3 is expressed as a 22-kD protein. Functional and mutation analyses indicated that phosphate cleavage is dependent on cysl 04 of PRL3. Overexpression of PRL3 resulted in increased cell growth. Western blot analysis showed dephosphorylation of pl30cas (BCAR1; 602941) in response to angiotensin II (106150), suggesting a role for PRL3 in the modulation of intracellular calcium transients induced by angiotensin II.

To gain insights into the molecular basis for metastasis, Saha et al. 2001, Science 294: 1343-1346 compared the global gene expression profile of metastatic colorectal cancer with that of primary cancers, benign colorectal tumors, and normal colorectal epithelium. PRL3 was expressed at high levels in each of 18 cancer metastases studied but at lower levels in nonmetastatic tumors and normal colorectal epithelium. In 3 of 12 metastases examined, multiple copies of the PRL3 gene were found within a small amplicon located at chromosome 8q24.3. Saha et al. (2001) concluded that the PRL3 gene is important for colorectal cancer metastasis.

Using the Stanford G3 radiation hybrid panel and database sequence analysis, Saha et al. (2001) mapped the PRL3 gene to surrounding marker 145.20. The PRL3 gene is also tightly linked to marker SHGC-22154, which is located at 8q24.3, approximately 3 Mb from the 8q telomere.

Mouse and human PRL-3 proteins were described in detail in Li et al (2005), Clin Cancer Res; I 1:2195-204.

PRL-3 Sequences

The methods and compositions described here make use of PRL-3 polypeptides, which are described in detail below. As used here, the term "PRL-3" is intended to refer to a sequence selected from the following.

| Unigene | Description |
|---|---|
| AF041434.1 | *Homo sapiens* potentially prenylated protein tyrosine phosphatase hPRL-3 mRNA, complete cds (SEQ ID NO: 45) |
| BT007303.1 | *Homo sapiens* protein tyrosine phosphatase type IVA, member 3 mRNA, complete cds (SEQ ID NO: 46) |
| AK 128380.1 | *Homo sapiens* cDNA FLJ46523 fis, clone THYMU3034099 (SEQ ID NO: 47) |
| NM_007079.2 | *Homo sapiens* protein tyrosine phosphatase type IVA, member 3 (PTP4A3), transcript variant 2, mRNA (SEQ ID NO: 48) |
| AY819648.1 | *Homo sapiens* HCV p7-transregulated protein 2 mRNA, complete cds (SEQ ID NO: 49) |
| BC003105.1 | *Homo sapiens* protein tyrosine phosphatase type IVA, member 3, mRNA (cDNA clone MGC: 1950 IMAGE: 3357244), complete cds (SEQ ID NO: 50) |
| NM_03261 1.1 | *Homo sapiens* protein tyrosine phosphatase type IVA, member 3 (PTP4A3), transcript variant 1, mRNA (SEQ ID NO: 51) |
| AK31 1257.1 | *Homo sapiens* cDN A, FLJ 18299 (SEQ ID NO: 52) |
| U87168.1 | Human protein tyrosine phosphatase homolog hPRL-R mRNA, partial cds (SEQ ID NO: 53) |
| AJ276554.1 | *Homo sapiens* mRNA for protein tyrosine phosphatase hPRL-3, short form (SEQ ID NO: 54) |
| BC066043.1 | *Mus musculus* protein tyrosine phosphatase 4a3, mRNA (cDNA clone MGC: 90066 IMAGE: 6415021), complete cds (SEQ ID NO: 55) |
| AK190358.1 | *Mus musculus* cDNA, clone: YI G0102103, strand: plus, reference: ENSEMBL: Mouse-Transcript-ENST: ENSMUST00000053232, based on BLAT search (SEQ ID NO: 56) |
| CT010215.1 | *Mus musculus* full open reading frame cDNA clone RZPDo836H0950D for gene Ptp4a3, Protein tyrosine phosphatase 4a3; complete cds, incl. stopcodon (SEQ ID NO: 57) |
| AK 147489.1 | *Mus musculus* adult male brain UNDEFINED CELL LINE cDNA, RIKEN full-length enriched library, clone: M5C1053F14 product: protein tyrosine phosphatase 4a3, full insert sequence (SEQ ID NO: 58) |
| AK172192.1 | *Mus musculus* activated spleen cDNA, RIKEN full-length enriched library, clone: F830102P03 product: protein tyrosine phosphatase 4a3, full insert sequence (SEQ ID NO: 59) |
| AK 143702.1 | *Mus musculus* 6 days neonate spleen cDNA, RIKEN full-length enriched library, clone: F43001 1 C20 product: protein tyrosine phosphatase 4a3, full insert sequence (SEQ ID NO: 60) |
| AF035645.1 | *Mus musculus* potentially prenylated protein tyrosine phosphatase mPRL-3 (Prl3) mRNA, complete cds (SEQ ID NO: 61) |

| Unigene | Description |
| --- | --- |
| NM 008975.2 | *Mus musculus* protein tyrosine phosphatase 4a3 (Ptp4a3), mRNA (SEQ ID NO: 62) |
| AKO 14601.1 | *Mus musculus* 0 day neonate skin cDNA, RIKEN full-length enriched library, clone: 4632430E19 product: protein tyrosine phosphatase 4a3, full insert sequence (SEQ ID NO: 63) |
| AK004562. | *Mus musculus* adult male lung cDNA, RIKEN full-length enriched library, clone: 1200003F10 product: protein tyrosine phosphatase 4a3, full insert sequence (SEQ ID NO: 64) |
| AK003954.1 | *Mus musculus* 18-day embryo whole body cDNA, RIKEN full-length enriched library, clone: 1110029E17 product: protein tyrosine phosphatase 4a3, full insert sequence (SEQ ID NO: 65) |
| BC027445.1 | *Mus musculus* protein tyrosine phosphatase 4a3, mRNA (cDNA clone MGC: 36146 I AGE: 4482106), complete cds (SEQ ID NO: 66) |

A "PRL-3 polypeptide" may comprise or consist of a human PRL-3 polypeptide, such as the sequence having Unigene accession number AF041434.1 (SEQ ID NO: 45).

Homologues variants and derivatives thereof of any, some or all of these polypeptides are also included. For example, PRL-3 may include Unigene Accession Number BC066043.1 (SEQ ID NO: 55).

VHZ

The methods and compositions described here make use of VHZ, which is described in detail below.

VHZ is also known as DUSP23, MOSP, LDP-3, DUSP25, FLJ20442 and RP11-190A12.1

As used here, the term "VHZ" may refer to a polypeptide sequence having GenBank Accession number NP_060293.2 (SEQ ID NO: 67), NP_081001.1 (SEQ ID NO: 68), XP_341 157.1 (SEQ ID NO: 69), XP_001 170819.1 (SEQ ID NO: 70), XP_001 170835.1 (SEQ ID NO: 70), XP_545747.2 (SEQ ID NO: 71), NP_001076078.1 (SEQ ID NO: 72), NP_00101 1371.1 (SEQ ID NO: 73), NP_783859.1 (SEQ ID NO: 74), NP_001034709.1 (SEQ ID NO: 75), XP_001480730.1 (SEQ ID NO: 68), XP_001 1 17253.1 (SEQ ID NO: 76) or XP_001 1 17256.1 (SEQ ID NO: 76).

A "VHZ polypeptide" may comprise or consist of a human VHZ polypeptide, such as the sequence having accession number NP 060293 (SEQ ID NO: 67).

With regard to nucleic acid sequences, the terms "VHZ polynucleotide", "VHZ nucleotide" and "VHZ nucleic acid" may be used interchangeably, and should be understood to specifically include both cDNA and genomic VHZ sequences. These terms are also intended to include a nucleic acid sequence capable of encoding a VHZ polypeptide and/or a fragment, derivative, homologue or variant of this.

Where reference is made to a VHZ nucleic acid, this should be taken as a reference to any member of the VHZ family of nucleic acids. Of particular interest are VHZ nucleic acids selected from the group consisting of: NM_017823.3 (SEQ ID NO: 77), NM_026725.2 (SEQ ID NO: 78), XM_341 156.3 (SEQ ID NO: 79), XM_001 170819.1 (SEQ ID NO: 80), XM_170835.1 (SEQ ID NO: 81), XM_545747.2 (SEQ ID NO: 82), NM_001082609.1 (SEQ ID NO: 83), NM_00101 1371.1 (SEQ ID NO: 84), N_175732.1 (SEQ ID NO: 85), NM_001039620.1 (SEQ ID NO: 86), XM_001480680.1 (SEQ ID NO: 87), XM_001 1 17253.1 (SEQ ID NO: 88) or XM 001 1 17256.1 (SEQ ID NO: 89).

Also included are any one or more of the nucleic acid sequences set out as "Other VHZ nucleic acid sequences" below.

For example, the VHZ nucleic acid may comprise a human VHZ sequence having GenBank Accession Number NM 017823.3 (SEQ ID NO: 77).

Her2

Her2/neu (also known as ErbB-2) stands for "human epidermal growth factor receptor 2" and is a protein giving higher aggressiveness in breast cancers. It is a member of the ErbB protein family, more commonly known as the epidermal growth factor receptor family. HER2/neu has also been designated as CD340 (cluster of differentiation 340) and p185. HER2 is a cell membrane surface-bound receptor tyrosine kinase and is normally involved in the signal transduction pathways leading to cell growth and differentiation.

As described herein, HER2 may refer to a polypeptide sequence selected from GenBank accession numbers NP_004439.2 (SEQ ID NO: 90), NP_001005862.1 (SEQ ID NO: 91), NP_001003817.1 (SEQ ID NO: 92), AAI67147.1 (SEQ ID NO: 93)

A "Her2 polypeptide" as referred to herein may comprise or consist of a human HER2 polypeptide sequence, such as that of accession number P04626.1 (SEQ ID NO: 93)

Her2 polypeptides are described in U.S. Pat. No. 6,333, 169 and EP1418235.

Other oncoproteins useful in the invention include EGFR (GenBank accession numbers CAA25240 (SEQ ID NO: 94) (GI:119533; SEQ ID NO: 93), ADZ75461.1 (GI326467049)) (SEQ ID NO: 95), SHP1 (GenBank accession numbers NP002822.2 (GI: 18104989) (SEQ ID NO: 96), NP536858.1 (GI: 18104991) (SEQ ID NO: 97), NP536859.1 (SEQ ID NO: 98) (GI: 18104991; SEQ ID NO: 97)), Tiam (GenBank accession numbers NP003244.2 (GI: 115583670) (SEQ ID NO: 99), AAA98443.1 (GI: 897557) (SEQ ID NO: 100), Q13009.2 (GI: 152031709)) (SEQ ID NO: 99), Myc (GenBank accession numbers AAA59886.1 (GI: 188975) (SEQ ID NO: 101), AAA59887.1 (GI: 188977) (SEQ ID NO: 102), CAA25015.2 (GI: 29839758) (SEQ ID NO: 103), NP002458.2 (GI: 71774083)) (SEQ ID NO: 104), Ras (GenBank accession number AAA34557.1 (GI: 171374)) (SEQ ID NO: 105) and Runx-1 (GenBank accession number NP001079966.1 (GI: 148232064)) (SEQ ID NO: 106).

Preferred intracellular oncoprotein targets include Androgen Receptor (AAA51772; GI: 178882) (SEQ ID NO: 107), Her2 (P04626.1; GI:119533 (SEQ ID NO: 93), targeting the intracellular domain of the receptor), Mutant Ras (GenBank accession number AAA34557.1; GI: 171374) (SEQ ID NO: 105), Jak (AAA19626.1; GI:508731) (SEQ ID NO: 108), FLT3 (ITD3; CAA81393.1; GI:406323) (SEQ ID NO: 109), Runx1 (AA136381.1; GI:223459612) (SEQ ID NO: 110), Tiam, Gfi (NP_005254.2 GI:71037377) (SEQ ID NO: 111), Cot (MAP3K8; CAG47079.1; GI:49457560) (SEQ ID NO: 112), Myc, SHP1, FGF (CAA28027.1; GI:31362) (SEQ ID NO: 113).

Other preferred oncoproteins include KRas (V-Ki-ras2 Kirsten rat sarcoma viral oncogene homologue; GenBank P01116.1 GI:131875) (SEQ ID NO: 114); EGFR (Epidermal growth factor receptor; P00533.2 GI:2811086) (SEQ ID NO: 115); BRaf (P15056.4 GI:50403720) (SEQ ID NO: 116); PI3KCA (Phosphatidylinositol 3-kinase regulatory subunit alpha; P27986.2 GI:118572681) (SEQ ID NO: 117); Beta-catenin (CAA61107.1 GI:860988) (SEQ ID NO: 118); GNAS (guanine nucleotide binding protein; Q5JWF2.2 GI:116248089) (SEQ ID NO: 119); Ret (CAA73131.1 GI:1946207) (SEQ ID NO: 120) and EZH2 (histone-lysine N-methyltransferase; enhancer of zeste homolog 2; Q15910.2 GI:3334180) (SEQ ID NO: 121).

Oncogenic mutations include those listed in enclosed FIGS. 27 and 28, and obtainable from share.gene.com/mutation_classification/cancer.variants.txt Oncogenic Mutations An oncogenic mutation is a mutation in a gene that is associated with, or causative of, cancer. The mutation may be a substitution, deletion or addition of a single amino acid residue. Alternatively, it may affect more than one amino acid residue. A number of oncogenic mutations are known in the art. Certain oncogenic mutations are listed at share.gene.com/mutation_classification/cancer.variants.txt. Oncogenic mutations may be identified by comparing the sequence of a protein obtained from, or associated with, a cancer, with a homologous protein obtained from an individual who is not suffering from cancer. Methods for comparing protein sequences are well known in the art.

Protein Fragments and Peptides

Protein fragments or peptides (used interchangeably herein) according to the invention are small polypeptides, peptides or peptide mimetics based on or comprising a contiguous sequence of amino acid residues from an intracellular oncogenic protein or an intracellular portion of an oncogenic protein. The protein fragments and peptides do not comprise the entire oncogenic protein. Peptides may comprise or consist of a fragment of an oncoprotein which is normally located within the cell, or a fragment of an oncoprotein corresponding to a region of that oncoprotein which is normally located within the cell.

A protein fragment or peptide according to the present invention may have a maximum length of 150, 140, 130, 120, 110 or 100 amino acids and less than the full length of the corresponding oncoprotein. More preferably the maximum peptide length is 90 amino acids, still more preferably 80 amino acids, still more preferably 70 amino acids, still more preferably 60 amino acids, still more preferably 50 amino acids, still more preferably 40 amino acids, still more preferably the maximum length is chosen from one of 30, 29, 28, 27, 26, 25, 24, 23, 22, 21, 20, 19, 18, 17, 16, 15, 14, 13, 12, 11, 10 or 9 amino acids. For example, a peptide may have a maximum length of 150, 140, 130, 120, 110, 100, 90, 80, 70, 60, 50, 40, 30, 25, 20 or 15 amino acids.

A protein fragment or peptide according to the present invention may have a minimum length of 7 amino acids. More preferably the minimum length is chosen from one of 7, 8, 9, 10, 11, 12, 13, 14, 15, 16, 17, 18, 19, 20, 21, 22, 23, 24, or 25 amino acids.

A peptide according to the present invention may have any length between said minimum and maximum. Thus, for example, a peptide may have a length of from 5 to 100, from 7 to 100, 7 to 80, 7 to 60, 7 to 50, 7 to 40, 8 to 30, 10 to 25, 12 to 20, 9 to 15 amino acids, 8 to 11 amino acids, 9 to 11 amino acids, 9 to 13 amino acids or 9 to 14 amino acids. In particular, the peptide may have an amino acid length chosen from one of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 72, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In some embodiments the protein fragment may be one of between 10 and 50, between 10 and 40, between 10 and 30, between 10 and 20, between 15 and 50, between 15 and 40, between 15 and 30, between 15 and 20, between 20 and 50, between 20 and 40, between 20 and 30, between 20 and 25, between 25 and 50, between 25 and 40, between 25 and 30, between 30 and 50, between 30 and 40, or between 40 and 50 amino acids in length.

The protein fragment or peptide may have a length anywhere between the said minimum and maximum length.

The protein fragment or peptide preferably comprises at least one epitope (optionally two or more epitopes) of the oncoprotein which is recognised by the immune system of the patient, and is preferably capable of stimulating the production of anti-oncoprotein antibodies in the patient.

In some embodiments the amino acid sequence of the fragment comprises or consists of a contiguous sequence of amino acids present in the corresponding full length oncoprotein.

A protein fragment or peptide may be designed to encompass an oncogenic mutation. That is to say, that the peptide is fragment of the region of the oncoprotein that includes a mutation. The mutation may be present in the oncoprotein as compared to the wild-type or non-oncogenic form of the protein. Thus, the peptide may have a sequence specific to an oncogenic form of a protein. The peptide may have 1, 2, 3, 4, 5, 6, 7, 8, 9, 10, 11, 12, 13, 14, 15, 16, 17, 18, 19, 20 or more amino acids on one or both sides of the mutation. The peptide may have the same number of amino acids on each side of the mutation, or may have different numbers of amino acids on each side of the mutation.

Since modern technology can easily identify patients whose tumors are associated with, or caused by, a specific oncogenic mutation, we could then design peptides corresponding to these oncogenic mutations.

In other embodiments the fragment has at least 60% amino acid sequence identity to a contiguous sequence of amino acids present in the corresponding full length protein. More preferably, the degree of sequence identity is one of 65%, 70%, 75%, 80%, 85%, 87%, 90%, 91%, 92%, 93%, 94%, 95%, 96%, 97%, 98%, 99% or 100% identity.

The present invention incorporates derivatives and mimetics of a contiguous sequence of amino acids from an oncoprotein that forms a protein fragment.

Peptides may be synthesised to include a single epitope or single region of the oncoprotein, and may include an oncogenic mutation. Alternatively, peptides may include a combination of more than one region of an oncoprotein or more than one epitope. For example, 2, 3, 4, 5, 6, 7, 8, 9, 10 or more regions or epitopes of the same or different oncoproteins may be combined in the same peptide. This may involve the use of short linker peptides to connect the more than one region or epitope. The linker may consist of 1, 2, 3, 4, 5, 6, 7, 8, 9, 10, 11, 12, 13, 14, 15 or more amino acids. Peptide derivatives include variants of a given sequence of amino acids and may include naturally occurring allelic variants and synthetic variants which have substantial amino acid sequence identity to the peptide sequence as identified in the wild type full length protein allergen.

Peptide derivatives may include those peptides having at least 60% amino acid sequence identity and which are capable of stimulating generation of anti-oncoprotein antibodies.

Peptide derivatives preferably differ from the corresponding amino acid sequence in the oncoprotein by less than 5 amino acids. More preferably, the number of different amino acids is 4 amino acids or less, 3 amino acids or less, 2 amino acids or less or only 1 amino acid.

Peptide derivatives may arise through natural variations or polymorphisms which may exist between the members of a protein family from which the peptide is derived. All such derivatives are included within the scope of the invention.

Peptide derivatives may result from natural or non-natural (e.g. synthetic) interventions leading to addition, replacement, deletion or modification of the amino acid sequence.

Conservative replacements and modifications which may be found in such polymorphisms may be between amino acids within the following groups:
(i) alanine, serine, threonine;
(ii) glutamic acid and aspartic acid;
(iii) arginine and leucine;
(iv) asparagine and glutamine;
(v) isoleucine, leucine and valine;
(vi) phenylalanine, tyrosine and tryptophan;
(vii) methionine and leucine;
(viii) cysteine and valine.

Peptide derivatives may also be provided by modifying an amino acid sequence from the oncoprotein, e.g. in order to resist degradation of the peptide.

Peptide Mimetics

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. some peptides may be unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

With regard to the present invention, a peptide mimetic is one form of peptide derivative. A method of identifying a peptide derivative capable of stimulating an immune response may comprise the step of modifying the peptide structure to produce a peptide mimetic. This peptide mimetic may optionally be subject to testing in an antibody production assat. This process of modification of the peptide or peptide mimetic and testing may be repeated a number of times, as desired, until a peptide having the desired effect, or level of effect, on anti-oncoprotein antibody proliferation is identified.

The modification steps employed may comprise truncating the peptide or peptide mimetic length (this may involve synthesising a peptide or peptide mimetic of shorter length), substitution of one or more amino acid residues or chemical groups, and/or chemically modifying the peptide or peptide mimetic to increase stability, resistance to degradation, transport across cell membranes and/or resistance to clearance from the body.

Intracellular Oncoprotein Epitopes

The anti-intracellular oncoprotein antibodies may specifically bind to an epitope on the intracellular oncoprotein.

Methods are known in the art to determine an epitope that is bound by a particular antibody. Such epitope mapping methods are described for example in Hanson et al., (2006). Respiratory Research, 7: 126. Furthermore, a skilled person will be able to generate antibodies and screen them for particular properties.

Polypeptides

A "polypeptide" refers to any peptide or protein comprising two or more amino acids joined to each other by peptide bonds or modified peptide bonds, i.e., peptide isosteres.

"Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for protein modifications and nonprotein cofactors", Meth Enzymol (1990) 182:626-646 and Rattan et al, "Protein Synthesis: Posttranslational Modifications and Aging", Ann NY Acad-Sci (1992) 663:48-62.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralising antibodies in vivo.

As applied to intracellular oncoproteins, the resultant amino acid sequence may have one or more activities, such as biological activities in common with a intracellular oncoprotein polypeptide, for example a human intracellular oncoprotein. For example, a intracellular oncoprotein homologue may have a increased expression level in cancer cells compared to normal breast cells. In particular, the term "homologue" covers identity with respect to structure and/or function providing the resultant amino acid sequence has intracellular oncoprotein activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the intracellular oncoprotein nucleic acid sequence.

Where reference is made to the "activity" or "biological activity" of a polypeptide such as an intracellular oncoprotein, these terms are intended to refer to the metabolic or physiological function of the intracellular oncoprotein, including similar activities or improved activities or these activities with decreased undesirable side effects. Also included are antigenic and immunogenic activities of the intracellular oncoprotein. Examples of such activities, and methods of assaying and quantifying these activities, are known in the art, and are described in detail elsewhere in this document.

Prophylactic and Therapeutic Methods

We disclose methods of treating an abnormal condition, such as cancer, related to excessive amounts of intracellular oncoprotein expression or activity. Methods of preventing cancer (i.e., prophylaxis) also suitably employ the same or similar approaches.

In general terms, our methods involve manipulation of cancer cells, by modulating (such as down-regulating) the expression, amount or activity of intracellular oncoprotein in the cell. The methods may involve destroying or eradicating cancer cells. The cancer cells may comprise intracellular oncoprotein expressing cancer cells. The cancer cells may be ones which over-express intracellular oncoprotein, compared to non-cancerous cells. Our methods may comprise exposing a patient to an intracellular oncoprotein fragment.

The cancer cells may be from intracellular oncoprotein positive cancer patients. Thus, our methods may comprise eradicating intracellular oncoprotein-overexpressing cancer cells from intracellular oncoprotein positive cancer patients.

A step of detecting modulated intracellular oncoprotein expression, amount or activity in a cell may be conducted before or after the manipulation step. The detection step may detect up-regulated or down-regulated intracellular oncoprotein expression, amount or activity. Any of the methods of modulating or down-regulating intracellular oncoprotein, as described in detail elsewhere in this document, or known in the art, may be used.

In particular, the method may comprise exposing the cell to an anti-intracellular oncoprotein antibody capable of specifically binding to intracellular oncoprotein. In the context of an individual suffering or suspected to be suffering from cancer, the method may comprise administering a therapeutically effective amount of intracellular oncoprotein fragment to the individual. Intracellular oncoprotein fragments and methods of administering them are described in detail elsewhere in this document.

According to our methods, a cancer cell becomes non-cancerous or the invasive or metastatic cancer cell becomes non-invasive or non-metastatic as a result of the manipulation. The cancer may in particular comprise a cancer such as an invasive or metastatic cancer selected from the group consisting of: colorectal cancer, ovarian cancer, breast cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma.

As intracellular oncoprotein is associated with aggressiveness and invasiveness of cancer, the level of intracellular oncoprotein may be detected in a cell of an individual with cancer, in a cancer or non-cancer cell, and the aggressiveness of the cancer assessed. A high level of intracellular oncoprotein amount, expression or activity compared with a normal cell indicates an aggressive or invasive cancer, and a stronger or harsher therapy may therefore be required and chosen. Similarly, a lower level may indicate a less aggressive or invasive therapy.

The approaches described here may be used for therapy of any intracellular oncoprotein related disease in general. Intracellular oncoprotein related diseases include proliferative diseases and in particular include cancer. For example, a intracellular oncoprotein related disease may include metastatic cancer, invasive cancer or aggressive cancer.

The methods of the invention are useful for treating or preventing the formation of cancer in individuals who have not yet developed a cancer, or who exhibit no symptoms or early stage symptoms of cancer. The individual may have been identified as susceptible, or likely to suffer from, a cancer through the assessment of the prevalence of that cancer in family members. For example, the presence of a cancer associated with a particular intracellular oncoprotein in one or more family members, such as siblings, maternal or paternal relatives, is indicative that the person is also likely to develop that cancer. For example, an infant or young adult whose parent(s) have developed a cancer associated with an intracellular oncoprotein may be determined to be likely to suffer from, or at risk from developing, a cancer associated with that (intracellular) oncoprotein.

The person who has been identified as likely to develop a cancer associated with an intracellular oncoprotein may be administered one or more doses of intracellular oncoprotein fragment based vaccine prior to developing the cancer, or prior to developing symptoms associated with the cancer. Alternatively or additionally, one or more of the doses may be administered after the person has developed the cancer, or has developed symptoms associated with the cancer.

The intracellular oncoprotein fragment based vaccine may be administered in a prime-boost administration regime, wherein the person is administered with a first dose of intracellular oncoprotein fragment vaccine, followed by one or more further doses of intracellular oncoprotein fragment vaccine. Suitable prime-boost administration regimes will be well known to those skilled in the art. For example, a first dose of the intracellular oncogene fragment based vaccine may be administered at time point zero, with further doses being oncoprotein one week, one month, three months, one year, or other suitable time period later. In some cases, subsequent doses are administered one week, one month, three months, one year or other time period following administration of the previous dose.

The method may further comprise the step of analysing whether the patient produces antibodies that are specific to the intracellular oncoprotein, following administration of the intracellular oncoprotein fragment vaccine.

The methods and compositions described here suitably enable an improvement in a measurable criterion in an individual to whom the treatment is applied compared to one who has not received the treatment.

For this purpose, a number of criteria may be designated, which reflect the progress of cancer or the well-being of the patient. Useful criteria may include tumour size, tumour dimension, largest dimension of tumour, tumour number, presence of tumour markers (such as alpha-feto protein), degree or number of metastates, etc.

Thus, as an example, a treated individual may show a decrease in tumour size or number as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in tumour size of a particular tumour, or decrease in tumour number, or both, compared to an individual who has not been treated.

For example, a intracellular oncoprotein related disease may be defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, tumour formation, tumour metastasis, tumour spread, etc. By the term "treatment" we mean to also include prophylaxis or alleviation of cancer.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostrate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leiomyosarcoma, rhabdomyosarcoma, colon carcinoma, ovarian cancer, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neuroblastoma and retinoblastoma.

The cancers treatable or preventable by the present invention are associated with expression of particular oncoproteins. Cancer cells may express, or aberrantly express (e.g. overexpress), a particular oncoprotein, or incorrectly process the oncoprotein such that it is found at higher levels in the cancer cells than in normal cells.

For example, a sample (e.g. biopsy) is obtained from a subject having a cancer, or suspected of having a cancer, or being at risk of developing a cancer. The sample is tested to determine if a selected oncoprotein, preferably an intracellular oncoprotein is aberrantly expressed, or if the patient is a carrier for a particular isoform or mutant of the oncoprotein that is correlated with a higher risk of cancer development. Accordingly, the subject can be graded for treatment based on the oncoprotein expression profile and treatment (which may be preventative) can be commenced using a protein fragment(s) or peptide(s) according to the present invention.

Over-expression of an oncoprotein comprises expression at a level that is greater than would normally be expected for a cell or tissue of a given type. As such, over-expression may be determined by comparing the level of expression of a protein between cells. For example, a comparison may be made between a cancerous cell and a non-cancerous (healthy) cell of the same type and preferably from the same tissue type (although optionally from a different subject). In another example, a comparison may be made between a cell type present in cancer tissue and a corresponding cell type present in non-cancerous tissue (optionally in the same subject).

Levels of expression may be quantitated for absolute comparison, or relative comparisons may be made.

In some embodiments over-expression of a protein may be considered to be present when the level of expression in the test sample is at least 1.1 times that in the control sample. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that in the control sample.

The approach to therapy described herein involving use of intracellular oncoprotein fragments may be combined with other approaches for therapy of such disorders including expression of anti-sense constructs directed against intracellular oncoprotein polynucleotides as described here, and administering them to tumour cells, to inhibit gene function and prevent the tumour cell from growing or progressing.

Anti-sense constructs may be used to inhibit gene function to prevent growth or progression in a proliferative cell.

Antisense constructs, i.e., nucleic acid, such as RNA, constructs complementary to the sense nucleic acid or mRNA, are described in detail in U.S. Pat. No. 6,100,090 (Monia et al.), and Neckers et al, 1992, Crit Rev Oncog 3(1-2): 175-231, the teachings of which document are specifically incorporated by reference.

In a particular example, cancer may be treated or prevented by reducing the amount, expression or activity of intracellular oncoprotein in whole or in part, for example by siRNAs capable of binding to and destroying intracellular oncoprotein mRNA.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al, Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the intracellular oncoprotein nucleic acid sequence.

Alternatively, double-stranded (ds) RNA is a powerful way of interfering with gene expression in a range of organisms that has recently been shown to be successful in mammals (Wianny and Zernicka-Goetz, 2000, Nat Cell Biol 2:70-75). Double stranded RNA corresponding to the sequence of a intracellular oncoprotein polynucleotide can be introduced into or expressed in oocytes and cells of a candidate organism to interfere with intracellular oncoprotein activity.

Other methods of modulating intracellular oncoprotein gene expression are known to those skilled in the art and include dominant negative approaches. Again, these may be combined with antibody therapy using anti-intracellular oncoprotein antibodies. Thus, another approach is to use non-functional variants of intracellular oncoprotein polypeptide in this document that compete with the endogenous gene product resulting in inhibition of function.

Intracellular oncoprotein gene expression may also be modulated by as introducing peptides or small molecules which inhibit gene expression or functional activity. Such peptides or small molecules may be administered in combination with anti-intracellular oncoprotein antibodies for the treatment of cancer such as metastatic cancer.

Thus, compounds identified by assays as binding to or modulating, such as down-regulating, the amount, activity or expression of intracellular oncoprotein polypeptide may be administered to tumour or proliferative cells to prevent the function of intracellular oncoprotein polypeptide. Such a compound may be administered along with a pharmaceutically acceptable carrier in an amount effective to down-regulate expression or activity intracellular oncoprotein, or by activating or down-regulating a second signal which controls intracellular oncoprotein expression, activity or amount, and thereby alleviating the abnormal condition.

Alternatively, gene therapy may be employed to control the endogenous production of intracellular oncoprotein by the relevant cells such as cancer cells in the subject. For example, a polynucleotide encoding a intracellular oncoprotein siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-intracellular oncoprotein siRNA such that the packaging cell now produces infectious viral particles containing the sequence of interest. These producer cells may be administered to a subject for engineering cells in vivo and regulating expression of the intracellular oncoprotein polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of intracellular oncoprotein is decreased in a cancer cell. Furthermore, in such embodiments, treatment may be targeted to, or specific to, such cancer cells. The expression of intracellular oncoprotein may be specifically decreased only in diseased cells (i.e., those cells which are cancerous), and not substantially in other non-diseased cells. In these methods, expression of intracellular oncoprotein may be not substantially reduced in other cells, i.e., cells which are not cancer cells. Thus, in such embodiments, the level of intracellular oncoprotein remains substantially the same or similar in non-cancer cells in the course of or following treatment.

Patients

The subject to be treated may be any animal or human. The subject is preferably mammalian, more preferably human. The subject may be a non-human mammal, but is more preferably human. The subject may be male or female. The subject may be a patient. Therapeutic uses may be in human or animals (veterinary use).

Polypeptide Sequences

It will be understood that polypeptide sequences disclosed here are not limited to the particular sequences set forth in this document, but also include homologous sequences obtained from any source, for example related cellular homologues, homologues from other species and variants or derivatives thereof, provided that they have at least one of the biological activities of an anti-intracellular oncoprotein antibody, as the case may be.

This disclosure therefore encompasses variants, homologues or derivatives of the amino acid sequences set forth in this document, as well as variants, homologues or derivatives of the amino acid sequences encoded by the nucleotide sequences disclosed here. Such sequences are generally referred to as a "intracellular oncoprotein" sequence.

Biological Activities

In some embodiments, the sequences comprise at least one biological activity of an intracellular oncoprotein fragment, as the case may be.

The biological activity may comprise an immunological activity. The intracellular oncoprotein fragment may comprise an identical or similar immunological activity as compared to intracellular oncoprotein antibody or its humanised versions. By "immunological activity" we mean the capability of the anti-intracellular oncoprotein antibody, to induce a specific immune response in appropriate animals or cells on binding with a intracellular oncoprotein antigen.

The activity may include inhibition of cancer activity as for example measured by reduction of tumour size or tumour number, or inhibition of metastatic activity, such as for example measured by the assays described in the Examples. The reduction or inhibition may be conveniently assayed by causing carcinogenesis in a test animal, administering the intracellular oncoprotein fragment to the animal and determining an effect of the intracellular oncoprotein fragment as compared to a similar control animal that has not been so treated. The Examples describe such an assay in detail.

The intracellular oncoprotein fragment may have tumour inhibition or metastasis inhibition activity that is the same as, reduced from, or elevated from, the cognate fragment. For example, the intracellular oncoprotein fragment may be at least 10%, such as 20%, such as 30%, 40% 50%, 60%, 70%, 80%, 90% or more, effective compared to the cognate antibody. By this we mean that, say, if the cognate fragment is capable of reducing tumour number by 90% (see the Examples), the intracellular oncoprotein fragment may be capable of reducing tumour number by 90%, 85%, 80%, 75%, 70%, 65%, 60%, 55%, 50%, 45%, 40%, 35%, 30%, etc, as compared to an untreated animal.

Other assays that detect antibody events can also be used, instead of, or in addition to, the assays described.

Homologues

The intracellular oncoprotein fragment polypeptides disclosed include homologous sequences obtained from any source, for example related viral/bacterial proteins, cellular homologues and synthetic peptides, as well as variants or derivatives thereof. Thus polypeptides also include those encoding homologues of intracellular oncoprotein fragment from other species including animals such as mammals (e.g. mice, rats or rabbits), in particular humans.

In the context of the present document, a homologous sequence or homologue is taken to include an amino acid sequence which is at least 60, 70, 80 or 90% identical, such as at least 95 or 98% identical at the amino acid level over at least 30, such as 50, 70, 90 or 100 amino acids with a relevant polypeptide sequence, for example as shown in the sequence listing herein. In the context of this document, a homologous sequence is taken to include an amino acid sequence which is at least 15, 20, 25, 30, 40, 50, 60, 70, 80 or 90% identical, such as at least 95 or 98% identical at the amino acid level, such as over at least 15, 25, 35, 50 or 100, such as 200, 300, 400 or 500 amino acids with the sequence of a relevant polypeptide. Although homology can also be considered in terms of similarity (i.e. amino acid residues having similar chemical properties/functions), in the context of the present document homology may be expressed in terms of sequence identity. The sequence identity may be determined relative to the entirety of the length the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified.

However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al, 1984, Nucleic Acids Research 12:387). Examples of other software than can perform sequence comparisons include, but are not limited to, the BLAST package (see Ausubel et al, 1999 ibid—Chapter 18), FASTA (Atschul et al, 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package, or in the case of other software, the default matrix, such as BLOSUM62, may be used.

Once the software has produced an optimal alignment, it is possible to calculate % homology, such as % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. The resultant amino acid sequence may retain substantially the same activity as the unmodified sequence, such as having at least the same activity as the anti-intracellular oncoprotein antibody polypeptides shown in this document, for example in the sequence listings. Thus, the key feature of the sequences—namely ability to bind to intracellular oncoprotein polypeptides or tumour reduction activity, as described elsewhere—may be retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of intracellular oncoprotein fragments are likely to comprise conservative amino acid substitutions. Conservative substitutions may be defined, for example according to the Table below. Amino acids in the same block in the second column such as those in the same line in the third column may be substituted for each other:

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

Intracellular oncoprotein fragments, homologues, variants and derivatives may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be such that it will not hinder the function of the protein of interest sequence. Proteins may also be obtained by purification of cell extracts from animal cells. In the present case, a fusion protein may comprise two or more fragments of one or more oncoproteins, optionally further including a linker peptide. The fragments may be from the same oncoprotein or different oncoproteins. The fusion protein may comprise two or more copies of the same fragment, or overlapping fragments of the same epitope or oncogenic mutation.

The intracellular oncoprotein polypeptides, variants, homologues and derivatives disclosed here may be in a substantially isolated form. It will be understood that such polypeptides may be mixed with carriers or diluents which will not interfere with the intended purpose of the protein and still be regarded as substantially isolated. A intracellular oncoprotein fragment variant, homologue or derivative may also be in a substantially purified form, in which case it will generally comprise the protein in a preparation in which more than 90%, e.g. 95%, 98% or 99% of the protein in the preparation is a protein.

The anti-intracellular oncoprotein fragment polypeptides, variants, homologues and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

The intracellular oncoprotein fragment polypeptides, variants, homologues, and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The intracellular oncoprotein fragment polypeptides, variants, homologues, and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell.

The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the intracellular oncoprotein polypeptides, variants, homologues, and derivatives disclosed here are expressed may be used in assay systems to identify candidate substances which interfere with or enhance the functions of the polypeptides in the cell.

Polynucleotide Sequences

The variable regions, monoclonal antibody sequences and humanised antibody sequences may comprise polynucleotides. These may comprise DNA or RNA.

They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or poly lysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Variants, Derivatives and Homologues

The terms "variant", "homologue" or "derivative" in relation to a nucleotide sequence described in this document include any substitution of, variation of, modification of, replacement of, deletion of or addition of one (or more) nucleotides from or to the sequence. The resulting sequence may be capable of encoding a polypeptide which has intracellular oncoprotein binding activity as described elsewhere in this document.

As indicated above, with respect to sequence identity, a "homologue" has such as at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to a relevant sequence.

There may be at least 95% identity, such as at least 96% identity, such as at least 97% identity, such as at least 98% identity, such as at least 99% identity. Nucleotide homology comparisons may be conducted as described above. A sequence comparison program such as the GCG Wisconsin Bestfit program described above may be used for this purpose. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, such as 269, 223 and 318 variable region, antibody and humanised antibody or any variant, fragment or derivative thereof, or to the complement of any of the above. Nucleotide sequences may be at least 1 nucleotides in length, such as at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, such as at least 80 or 90% and such as at least 95% or 98% homologous to the corresponding nucleotide sequences presented herein over a region of at least 20, such as at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

We disclose nucleotide sequences that can hybridise to a nucleic acid, or a fragment, homologue, variant or derivative thereof, under stringent conditions (e.g. 65° C. and O.I×SSC {I×SSC=0.15 M NaCl, 0.015 M $Na_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the disclosed sequences under conditions of medium to high stringency.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, such as at least 20, for example at least 25, 30 or 40 nucleotides in length, and are also encompassed by the term polynucleotides as used herein. Fragments may be less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PGR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Intracellular Oncoprotein Polypeptides and Nucleic Acids

Intracellular oncoprotein polypeptide homologues, variants, derivatives and fragments may be defined similarly, as set out in the previous paragraphs.

Where the context permits, a reference to intracellular oncoprotein polypeptide should be taken to include reference to an intracellular oncoprotein polypeptide homologue, variant, derivative or fragment. Similarly, a reference to intracellular oncoprotein polypeptide should be taken to include reference to a intracellular oncoprotein polypeptide homologue, variant, derivative or fragment.

Similarly, where the context permits, a reference to intracellular oncoprotein nucleic acid should be taken to include reference to a intracellular oncoprotein nucleic acid homologue, variant, derivative or fragment. Similarly, a reference to intracellular oncoprotein polypeptide should be taken to include reference to a intracellular oncoprotein nucleic acid homologue, variant, derivative or fragment.

Anti-Intracellular Oncoprotein Fragment Production

The intracellular oncoprotein fragment can be produced by recombinant DNA methods or synthetic peptide chemical methods that are well known to those of ordinary skill in the art.

By way of example, the intracellular oncoprotein fragments may be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for activity in vitro and in vivo.

The intracellular oncoprotein can be synthesized in a standard microchemical facility and purity checked with HPLC and mass spectrophotometry. Methods of peptide synthesis, HPLC purification and mass spectrophotometry are commonly known to those skilled in these arts.

The intracellular oncoprotein fragments may also be expressed under in vitro and in vivo conditions in a transformed host cell into which has been incorporated the DNA sequences described here (such as variable sequences) or allelic variations thereof and which can be used in the prevention and/or treatment of cancer related diseases.

The term "vector" includes expression vectors and transformation vectors. The term "expression vector" means a construct capable of in vivo or in vitro expression. The term "transformation vector" means a construct capable of being transferred from one species to another.

Vectors which may be used for expression include recombinant viral vectors, in particular recombinant retroviral vectors (RRV) such as lentiviral vectors, adenoviral vectors including a combination of retroviral vectors.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag pol and/or env gene and/or other genes essential for replication. Vectors which may be used include recombinant pox viral vectors such as fowl pox virus (FPV), entomopox virus, vaccinia virus such as NYVAC, canarypox virus, MVA or other non-replicating viral vector systems such as those described for example in WO9530018.

Pox viruses may be engineered for recombinant gene expression and for the use as recombinant live vaccines in a dual immunotherapeutic approach. The principal rationale for using live attenuated viruses, such as viruses, as delivery vehicles and/or vector based vaccine candidates, stems from their ability to elicit cell mediated immune responses. The viral vectors, as outlined above, are capable of being employed as delivery vehicles and as vector based vaccine candidates because of the immunogenicity of their constitutive proteins, which act as adjuvants to enhance the immune response, thus rendering a nucleotide sequence of interest (NOI) such as a nucleotide sequence encoding an intracellular oncoprotein more immunogenic.

The pox virus vaccination strategies have used recombinant techniques to introduce NOIs into the genome of the pox virus. If the NOI is integrated at a site in the viral DNA which is non-essential for the life cycle of the virus, it is possible for the newly produced recombinant pox virus to be infectious, that is to say to infect foreign cells and thus to express the integrated NOI. The recombinant pox virus prepared in this way can be used as live vaccines for the prophylaxis and/or treatment of pathologic and infectious disease and/or cancer.

Other requirements for pox viral vector delivery systems include good immunogenicity and safety. MVA is a replication-impaired vaccinia strain with a good safety record. In most cell types and normal human tissue, MVA does not replicate. Limited replication of MVA is observed in a few transformed cell types such as BHK21 cells. Carroll et al (1997 Vaccine) 5: 387-394) have shown that the recombinant MVA is equally as good as conventional recombinant vaccinia vectors at generating a protective CD8+ T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use as a delivery vehicle.

The nucleotide sequence of interest, and of which expression is desired, may operably linked to a transcription unit. The term "transcription unit" as described herein are regions of nucleic acid containing coding sequences and the signals for achieving expression of those coding sequences independently of any other coding sequences. Thus, each transcription unit generally comprises at least a promoter, an optional enhancer and a polyadenylation signal. The term "promoter" is used in the normal sense of the art, e. g. an R A polymerase binding site. The promoter may contain an enhancer element. The term "enhancer" includes a DNA sequence which binds to other protein components of the transcription initiation complex and thus facilitates the initiation of transcription directed by its associated promoter. The term "cell" includes any suitable organism. The cell may comprise a mammalian cell, such as a human cell.

The term "transformed cell" means a cell having a modified genetic structure. For example, as described here, a cell has a modified genetic structure when a vector such as an expression vector has been introduced into the cell. The term "organism" includes any suitable organism. The organism may comprise a mammal such as a human.

Here the term "transgenic organism" means an organism comprising a modified genetic structure. For example, the organism may have a modified genetic structure if a vector such as an expression vector has been introduced into the organism.

Intracellular Oncoprotein Fragment Expression

We further describe a method comprising transforming a host cell with a or the nucleotide sequences described in this document.

We also provide a method comprising culturing a transformed host cell-which cell has been transformed with a or the such nucleotide sequences under conditions suitable for the expression of the intracellular oncoprotein fragment encoded by said nucleotide sequences.

We further provide a method comprising culturing a transformed host cell-which cell has been transformed with a or the such nucleotide sequences under conditions suitable for the expression of the intracellular oncoprotein fragment encoded by said nucleotide sequences; and then recovering said intracellular oncoprotein fragment from the transformed host cell culture.

Thus, intracellular oncoprotein fragment encoding nucleotide sequences, fusion proteins or functional equivalents thereof, may be used to generate recombinant DNA molecules that direct the expression thereof in appropriate host cells.

By way of example, intracellular oncoprotein fragment may be produced in recombinant E. coli, yeast or mammalian expression systems, and purified with column chromatography.

The nucleotide sequences encoding the intracellular oncoprotein fragment may be operably linked to a promoter sequence capable of directing expression of the intracellular oncoprotein fragment encoding nucleotide sequences in a suitable host cell. When inserted into the host cell, the transformed host cell may be cultured under suitable conditions until sufficient levels of the intracellular oncoprotein fragment are achieved after which the cells may be lysed and the intracellular oncoprotein fragment is isolated.

Host cells transformed with the intracellular oncoprotein fragment encoding nucleotide sequences may be cultured under conditions suitable for the expression and recovery of the intracellular oncoprotein fragment from cell culture. The protein produced by a recombinant cell may be secreted or may be contained intracellularly depending on the sequence and/or the vector used. As will be understood by those of skill in the art, expression vectors containing the intracellular oncoprotein fragment encoding nucleotide sequences can be designed with signal sequences which direct secretion of the intracellular oncoprotein fragment encoding nucleotide sequences through a particular prokaryotic or eukaryotic cell membrane. Other recombinant constructions may join the intracellular oncoprotein fragment encoding nucleotide sequence to a nucleotide sequence encoding a polypeptide domain which will facilitate purification of soluble proteins (Kroll D J et al (1993) DNA Cell Biol 12:441-5 3', see also the discussion below on vectors containing fusion proteins).

The intracellular oncoprotein fragment may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif 3-26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen, San Diego, Calif.) between the purification domain and the intracellular oncoprotein fragment is useful to facilitate purification.

The nucleotide sequences described here may be engineered in order to alter a the intracellular oncoprotein fragment encoding sequences for a variety of reasons, including but not limited to alterations which modify the cloning, processing and/or expression of the gene product.

For example, mutations may be introduced using techniques which are well known in the art, e.g., site-directed mutagenesis to insert new restriction sites, to alter glycosylation patterns or to change codon preference.

In another embodiment, a or the natural, modified or recombinant intracellular oncoprotein fragment encoding nucleotide sequences may be ligated to a heterologous sequence to encode a fusion protein. By way of example, fusion proteins comprising the intracellular oncoprotein fragment or an enzymatically active fragment or derivative thereof linked to an affinity tag such as glutathione-S-transferase (GST), biotin, His6, ac-myc tag (see Emrich et al 1993 Biochem Biophys Res Commun 197(1): 21220), hemagglutinin (HA) (as described in Wilson et al (1984 Cell 37 767) or a FLAG epitope (Ford et al 1991 Protein Expr Purif April; 2 (2):95-107). May be produced The fused recombinant protein may comprise an antigenic coprotein such as GST, beta-galactosidase or the lipoprotein D from *Haemophilus influenzae* which are relatively large co-proteins, which solubilise and facilitate production and purification thereof. Alternatively, the fused protein may comprise a carrier protein such as bovine serum albumin (BSA) or keyhole limpet haemocyanin (KLH). In certain embodiments, the marker sequence may comprise a hexa-histidine peptide, as provided in the pQE vector (Qiagen Inc) and described in Gentz et al (1989 PNAS 86: 821-824). Such fusion proteins are readily expressable in yeast culture (as described in Mitchell et al 1993 Yeast 5:715-723) and are easily purified by affinity chromatography. A fusion protein may also be engineered to contain a cleavage site located between the nucleotide sequence encoding the intracellular oncoprotein fragment and the heterologous protein sequence, so that the intracellular oncoprotein fragment may be cleaved and purified away from the heterologous moiety. In another embodiment, an assay for the target protein may be conducted using the entire, bound fusion protein. Alternatively, the co-protein may act as an adjuvant in the sense of providing a generalised stimulation of the immune system. The co-protein may be attached to either the amino or carboxy terminus of the first protein.

Although the presence/absence of marker gene expression suggests that the nucleotide sequence for intracellular oncoprotein fragment is also present, its presence and expression should be confirmed. For example, if the intracellular oncoprotein fragment encoding nucleotide sequence is inserted within a marker gene sequence, recombinant cells containing the intracellular oncoprotein fragment coding regions may be identified by the absence of the marker gene function. Alternatively, a marker gene may be placed in tandem with an intracellular oncoprotein fragment encoding nucleotide sequence under the control of a single promoter.

Expression of the marker gene in response to induction or selection usually indicates expression of the intracellular oncoprotein fragment as well.

Additional methods to quantitate the expression of a particular molecule include radiolabeling (Melby P C et al 1993 J Immunol Methods 159:235-44) or biotinylating (Duplaa C et al 1993 Anal Biochem 229-36) nucleotides, co amplification of a control nucleic acid, and standard curves onto which the experimental results are interpolated.

Quantitation of multiple samples may be speeded up by running the assay in an ELISA format where the intracellular oncoprotein fragment of interest is presented in various dilutions and a spectrophotometric or calorimetric response gives rapid quantitation.

Altered intracellular oncoprotein fragment nucleotide sequences which may be made or used include deletions, insertions or substitutions of different nucleotide residues resulting in a nucleotide sequence that encodes the same or a functionally equivalent intracellular oncoprotein fragment. By way of example, the expressed intracellular oncoprotein fragment may also have deletions, insertions or substitutions of amino acid residues which produce a silent change and result in a functionally equivalent intracellular oncoprotein fragment. Deliberate amino acid substitutions may be made on the basis of similarity in polarity, charge, solubility, hydrophobicity, hydrophilicity. and/or the amphipathic nature of the residues as long as the binding affinity of the anti-intracellular oncoprotein fragment is retained. For example, negatively charged amino acids include aspartic acid and glutamic acid: positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Gene therapy whereby the anti-intracellular oncoprotein fragment encoding nucleotide sequences as described here is regulated in vivo may also be employed. For example, expression regulation may be accomplished by administering compounds that bind to the anti-intracellular oncoprotein antibody encoding nucleotide sequences, or control regions associated with the intracellular oncoprotein fragment encoding nucleotide sequence or its corresponding RNA transcript to modify the rate of transcription or translation.

By way of example, the intracellular oncoprotein fragment encoding nucleotide sequences described here may be under the expression control of an expression regulatory element, usually a promoter or a promoter and enhancer. The enhancer and/or promoter may be preferentially active in a hypoxic or ischaemic or low glucose environment, such that the intracellular oncoprotein fragment encoding nucleotide sequences is preferentially expressed in the particular tissues of interest, such as in the environment of a tumour cell or mass. Thus, any significant biological effect or deleterious effect of the intracellular oncoprotein fragment encoding nucleotide sequences on the individual being treated may be reduced or eliminated. The enhancer element or other elements conferring regulated expression may be present in multiple copies.

The promoter and/or enhancer may be constitutively efficient, or may be tissue or temporally restricted in their activity. Examples of suitable tissue restricted promoters/enhancers are those which are highly active in tumour cells such as a promoter/enhancer from a MUC1 gene, a CEA gene or a STV antigen gene. Examples of temporally restricted promoters/enhancers are those which are responsive to ischaemia and/or hypoxia, such as hypoxia response elements or the promoter/enhancer of agrp78 or agrp94 gene. The alpha fetoprotein (AFP) promoter is also a tumour-specific promoter. Another promoter-enhancer combination is a human cytomegalovirus (hCMV) major immediate early (MIE) promoter/enhancer combination.

The promoters may be tissue specific. That is, they may be capable of driving transcription of a intracellular oncoprotein fragment encoding nucleotide sequences in one tissue while remaining largely "silent" in other tissue types.

The term "tissue specific" means a promoter which is not restricted in activity to a single tissue type but which nevertheless shows selectivity in that they may be active in one group of tissues and less active or silent in another group. A desirable characteristic of such promoters is that they possess a relatively low activity in the absence of activated hypoxia-regulated enhancer elements, even in the target tissue. One means of achieving this is to use "silencer" elements which suppress the activity of a selected promoter in the absence of hypoxia.

The term "hypoxia" means a condition under which a particular organ or tissue receives an inadequate supply of oxygen.

The level of expression of a or the intracellular oncoprotein fragment encoding nucleotide sequences under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be used. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Combination Therapy

The methods and compositions described here, including intracellular oncoprotein fragment vaccines, may be used in combination with other compositions and procedures for the treatment of diseases.

By way of example, the intracellular oncoprotein fragment vaccines may also be used in combination with conventional treatments of diseases such as cancer. For example, a tumor may be treated conventionally with surgery, radiation or chemotherapy combined with intracellular oncoprotein fragment vaccine may be subsequently administered to the patient to extend the dormancy of micrometastases and to stabilize any residual primary tumor.

The intracellular oncoprotein fragment vaccine can be delivered with a therapeutically effective agent at the same moment in time and at the same site. Alternatively, the intracellular oncoprotein fragment vaccine and the therapeutically effective agent may be delivered at a different time and to a different site. The intracellular oncoprotein fragment vaccine and the therapeutically effective agent may even be delivered in the same delivery vehicle for the prevention and/or treatment of cancer.

Intracellular oncoprotein fragment vaccine may be used in combination with cytotoxic agents for the prevention and/or treatment of angiogenesis and/or cancer. Cytotoxic agents such as ricin, linked to intracellular oncoprotein fragment provides a tool for the destruction of cells that express intracellular oncoprotein or intracellular oncoprotein. These cells may be found in many locations, including but not limited to, micrometastases and primary tumours.

Intracellular oncoprotein fragment vaccine may be used in combination with a pro-drug activating enzyme in gene therapy. Instead of or as well as being selectively expressed in target tissues, the intracellular oncoprotein antibody and/or intracellular oncoprotein vaccine may be used in combination with another molecule, such as a pro-drug activation enzyme or enzymes which have no significant effect or no deleterious effect until the individual is treated with one or more pro-drugs upon which the enzyme or enzymes act. In the presence of the pro-drug activation enzyme, active treatment of an individual with the appropriate pro-drug leads to enhanced reduction in tumour growth or survival.

A pro-drug activating enzyme may be delivered to a tumour site for the treatment of a cancer. In each case, a suitable pro-drug is used in the treatment of the patient in combination with the appropriate pro-drug activating enzyme. An appropriate pro-drug is administered in conjunction with the vector. Examples of pro-drugs include: etoposide phosphate (with alkaline phosphatase, Senter et al 1988 Proc Natl Acad Sci 85: 48424846); 5-fluorocytosine (with cytosine deaminase, Mullen et al 1994 Cancer Res 54: 1503-1506); Doxorubicin-N-p-hydroxyphenoxyacetamide (with Penicillin-V-Amidase, Kerr et al 1990 Cancer Immunol Immunother 31: 202-206); Para-N-bis(2-chloroethyl) aminobenzoyl glutamate (with carboxypeptidase G2); Cephalosporin nitrogen mustard carbamates (with beta-lactamase); SR4233 (with P450 Reductase); Ganciclovir (with HSV thymidine kinase, Borrelli et al 1988 Proc Natl Acad Sci 85: 7572-7576); mustard pro-drugs with nitro reductase (Friedlos el al 1997 J Med Chem 40: 1270-1275) and Cyclophosphamide (with P450 Chen et al 1996 Cancer Res 56: 1331-1340).

Examples of pro-drug activation enzymes include a thymidine phosphorylase which activates the 5-fluoro-uracil pro-drugs capcetabine and furtulon; thymidine kinase from Herpes Simplex Virus which activates ganciclovir; a cytochrome P450 which activates a pro-drug such as cyclophosphamide to a DNA damaging agent; and cytosine deaminase which activates 5-fluorocytosine. An enzyme of human origin may be used.

Other suitable molecules include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives thereof (such as with an associated reporter group). When included, such coding sequences may be typically operatively linked to a suitable promoter, which may be a promoter driving expression of a ribozyme(s), or a different promoter or promoters, such as in one or more specific cell types.

The molecules may be proteins which are secreted from the cell. Alternatively the molecules are not secreted and are active within the cell. In either event, the molecules may demonstrate a bystander effector or a distant bystander effect; that is the production of the expression product in one cell leading to the killing of additional, related cells, either neighbouring or distant (e.g. metastatic), which possess a common phenotype.

Suitable molecules for use in the treatment or prophylaxis of cancer include proteins (or nucleic acids encoding proteins) which: destroy the target cell (for example a ribosomal toxin), act as: tumour suppressors (such as wild-type p53); activators of anti-tumour immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumour cells (for example with secreted antitumour antibody-ribosomal toxin fusion protein), indirectly stimulate destruction of bystander tumour cells (for example cytokines to stimulate the immune system or procoagulant proteins causing local vascular occlusion) or convert a precursor substance to a toxic substance which destroys bystander tumour cells (eg an enzyme which activates a prodrug to a diffusible drug).

Antisense transcripts or ribozymes which interfere with expression of cellular genes for tumour persistence (for example against aberrant myc transcripts in Burkitts lymphoma or against bcr-abl transcripts in chronic myeloid leukemia) may be delivered to enhance cancer cell killing function or metastasis preventing function of the anti-intracellular oncoprotein antibody and/or intracellular oncoprotein vaccine. The use of combinations of such molecules is also envisaged.

Examples of hypoxia regulatable therapeutic molecules can be found in PCT/GB95/00322 (WO-A-9521927).

Pharmaceutical Compositions

The intracellular oncoprotein fragment vaccines may be effective in treating cancer related diseases.

We disclose a method of preventing a cancer related disease with vaccination with an intracellular oncoprotein fragment as a vaccine.

The intracellular oncoprotein fragments for use as vaccines may be provided as isolated and substantially purified proteins and protein fragments in pharmaceutically acceptable compositions using formulation methods known to those of ordinary skill in the art.

The intracellular oncoprotein fragment vaccine may be administered in the form of a pharmaceutical composition. Such a pharmaceutical composition may include a therapeutically effective amount of anti-intracellular oncoprotein antibody and/or intracellular oncoprotein vaccine, together with a suitable excipient, diluent or carrier.

The intracellular oncoprotein fragment vaccine may in particular be introduced into the circulation of a patient, for example by being injected into a patient via, e.g., a vein.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

These compositions can be administered by standard routes. These include but are not limited to: oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, subcutaneous or intramuscular) routes.

The intracellular oncoprotein fragment vaccine formulations may conveniently be presented in unit dosage form and may be prepared by conventional pharmaceutical techniques. Such techniques include the step of bringing into association the active ingredient and the pharmaceutical carriers or excipient(s). In general, the formulations are prepared by uniformly and intimately bringing into association the active ingredient with liquid carriers or finely divided solid carriers or both, and then, if necessary, shaping the product.

In addition, the intracellular oncoprotein fragment vaccine may be incorporated into biodegradable polymers allowing for sustained release of the compound, the polymers being implanted in the vicinity of where drug delivery is desired, for example, at the site of a tumor or implanted so that the anti-intracellular oncoprotein antibody and/or intracellular oncoprotein vaccine is slowly released systemically. The biodegradable polymers and their use are described, for example, in detail in Brem et of (1. Neurosurg 1991 74:441-446). Osmotic minipumps may also be used to provide controlled delivery of high concentrations of anti-intracellular oncoprotein antibody and/or intracellular oncoprotein vaccine through cannulae to the site of interest, such as directly into a metastatic growth or into the vascular supply to that tumor.

The intracellular oncoprotein fragment vaccine may be linked to cytotoxic agents which are infused in a manner designed to maximize delivery to the desired location. For example, ricin-linked high affinity anti-intracellular oncoprotein antibody and/or intracellular oncoprotein vaccine are delivered through a cannula into vessels supplying the target site or directly into the target. Such agents are also delivered in a controlled manner through osmotic pumps coupled to infusion cannulae.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations described here may include other agents conventional in the art having regard to the type of formulation in question.

The intracellular oncoprotein fragment vaccine conjugates may be administered in any suitable way, usually parenterally, for example intravenously or intraperitoneally, in standard sterile, non-pyrogenic formulations of diluents and carriers, for example isotonic saline (when administered intravenously). Once the intracellular oncoprotein fragment vaccine conjugate has bound to the target cells and been cleared from the bloodstream (if necessary), which typically takes a day or so, the pro-drug is administered, usually as a single infused dose, or the tumour is imaged. If needed, because the intracellular oncoprotein fragment vaccine conjugate may be immunogenic, cyclosporin or some other immunosuppressant can be administered to provide a longer period for treatment but usually this will not be necessary.

The dosage of the intracellular oncoprotein fragment vaccine described here will depend on the disease state or condition being treated and other clinical factors such as weight and condition of the human or animal and the route of administration of the compound.

Depending upon the half-life of the intracellular oncoprotein fragment vaccine in the particular animal or human, the intracellular oncoprotein fragment vaccine can be administered between several times per day to once a week. It is to be understood that the methods and compositions described here have application for both human and veterinary use. The methods described here contemplate single as well as multiple administrations, given either simultaneously or over an extended period of time.

The timing between administrations of the intracellular oncoprotein fragment vaccine conjugate and pro-drug may be optimised in a routine way since tumour/normal tissue ratios of conjugate (at least following intravenous delivery) are highest after about 4-6 days, whereas at this time the absolute amount of conjugate bound to the tumour, in terms of percent of injected dose per gram, is lower than at earlier times.

Therefore, the optimum interval between administration of the intracellular oncoprotein fragment vaccine conjugate and the pro-drug will be a compromise between peak tumour concentration of enzyme and the best distribution ratio between tumour and normal tissues. The dosage of intracellular oncoprotein fragment vaccine conjugate will be chosen by the physician according to the usual criteria. At least in the case of methods employing a targeted enzyme such as β-glucosidase and intravenous amygdalin as the toxic pro-drug, 1 to 50 daily doses of 0.1 to 10.0 grams per square meter of body surface area, preferably 1.0-5.0 g/m$^2$ are likely to be appropriate. For oral therapy, three doses per day of 0.05 to 10.0 g, preferably 1.0-5.0 g, for one to fifty days may be appropriate. The dosage of the intracellular oncoprotein fragment vaccine conjugate will similarly be chosen according to normal criteria, particularly with reference to the type, stage and location of the tumour and the weight of the patient. The duration of treatment will depend in part upon the rapidity and extent of any immune reaction to the intracellular oncoprotein vaccine conjugate.

The invention further provides methods of treatment in which a patient is induced to generate antibodies against an intracellular oncoprotein. Such methods involve administration of a fragment of that intracellular oncoprotein to a patient in need of such treatment. The peptide may be a fragment of an oncoprotein that comprises an oncogenic mutation. The method may comprise the step of identifying the presence of one or more oncoproteins or oncogenic mutations in a sample obtained from the patient, prior to administering the peptide comprising a fragment of the oncoprotein, or comprising the oncogenic mutation identified as present in the patient. The sample may be a tumor sample such as a biopsy, or may be another sample such as a tissue, urine, blood, mucus, or other sample. The presence of a particular oncoprotein or oncogenic mutation may be determined by western blot, or by an ELISA or PCT based method. Suitable methods are known in the art.

Diseases

Intracellular oncoprotein fragment vaccine described here, for example in the form of pharmaceutical compositions, may be used in the prevention and/or treatment of cancer.

For the purposes of this document, the term "cancer" can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

Intracellular oncoprotein vaccine described here, for example in the form of pharmaceutical compositions, can also be used in the treatment of cancer related disorders.

Such disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osier-Webber Syndrome; myocardial angiogenesis; plaque neovascularization; telangiectasia; hemophiliac joints; angiofibroma; wound granulation; coronary collaterals; cerebral collateralsl arteriovenous malformations; ischemic limb angiogenesis; neovascular glaucoma; retrolental fibroplasia; diabetic neovascularisation; helicobacter related diseases, fractures, vasculogenesis, hematopoiesis, ovulation, menstruation and placentation.

EXAMPLES

Our results demonstrated that upon tumor-specific antigen challenge, host immunity could be stimulated to produce endogenous antibodies against the specific antigen leading to tumor inhibition. This concept of 'cancer vaccination' has long been a promising but challenging prospect[21]. Importantly, we found that antigen-induced-antibody therapy could achieve similar anti-tumor therapeutic efficacy compared to exogenously delivered antibodies. In addition to being more economical, we believe that the former approach may be more useful than the latter as we naturally have huge potential flexibility to generate high titers of antigen-induced anti-tumor antibodies within ourselves. Although using Oncoprotein' for vaccination does not seem a practical thought, we do believe this approach is worth for future investigation. An oncoprotein should sit properly at its native subcellular localization with its neighborhood partners for correct communication in order to preserve an oncogenic function in cancer cell signaling network. When an 'oncoprotein' was isolated from its native dynamic complexity of sub-cellular localization, it may lose its connections and unable to perform its normal biological roles in such an 'isolated' situation.

Our in vivo data reveal a hitherto unrecognized phenomenon that immune-therapies can target not only extracellular—but also intracellular-oncoproteins for anticancer activity.

Examples Section E1 (Examples 1 to 18).
Proof-of-Concept for Targeting Intracellular Oncoproteins with Antibody Therapy or Vaccination Section E1 comprises Examples 1 to 18. Example 1 is an Introduction to Section E1, Examples 2 to 10 are Materials and Methods for Section E1, Examples 11 to 16 are Results for Section E1, Example 17 is a Discussion of Section E1, Example 18 is References for Section E1.

Example 1. Introduction (Section E1)

Monoclonal antibodies (mAbs) have proven to be potent and highly specific biological agents against some of humanity's most deadly diseases[1]. To exploit the ability of antibodies to specifically bind to biological targets, significant research and development have focused on developing monoclonal antibodies against extracellular/cell surface oncogenic targets. The first wave of success from such molecular targeted cancer therapeutics was the FDA approval of the anti-vascular endothelial growth factor antibody bevacizumab (Avastin) and the anti-HER2/neu antibody trastuzumab (Herceptin) for use in treatment of colorectal and breast cancers respectively[2]. These are examples of antibodies which work conventionally against extracellular proteins. Unfortunately, the majority of cellular proteins is intracellular and has thus remained underexplored by the approach of antibody therapies[3] due to the general view that intracellular locations are inaccessible to antibodies. However, numerous experimental findings and clinical observations since 1978 have suggested otherwise, immunologists have showed that penetration of auto-antibodies into living cells may be a common cellular phenomenon[4,5].

To prove the concept of possible immunotherapies against intracellular targets, we selected three intracellular targets for cancer treatments in this study, namely phosphatase of regenerating liver 3 (PRL-3), Enhanced Green Fluorescent Protein (EGFP), and polyomavirus middle T (mT) oncoprotein. PRL-3 is one of the three PRL-phosphatases identified between 1994 and 1998[6,7], and the PRL-1, PRL-2, and PRL-3 form a subgroup of the protein tyrosine phosphatase (PTP) family[8]. PRLs are intracellular C-terminally prenylated phosphatases[9,10], and the localization of PRL-1 and PRL-3 to the inner leaflet of the plasma membrane and early endosomes have been revealed by EM immunogold labeling[11]. The PRL phosphatases represent an intriguing group of proteins being validated as biomarkers and therapeutic targets in human cancers. Upregulation of PRL-3 mRNA level was first found to tightly correlate with colorectal cancer metastasis in 2001 by the global gene expression profiles of metastatic colorectal cancer with that of primary cancers, benign colorectal tumors, and normal colorectal epithelium using serial analysis of gene expression (SAGE) technology[12]. PRL-3 protein levels also have been reported to be elevated in an average of 22.3% of cancer samples (n=1008)[13]. Additionally, upregulation of individual PRLs have been reported to be correlated with numerous types of advanced human metastatic cancers when compared with their normal counterparts[14]. Thus, oncogenic PRL-3 was chosen as an ideal intracellular target for the study.

Secondly, to explore whether the antibody therapy could have a general application against other intracellular proteins, we chose a popular reporter protein, the cytosolic enhanced green fluorescent protein (EGFP) originally isolated from the jellyfish *Aeguorea victoria*. EGFP expresses itself as an intracellular protein with a nucleo-cytoplasmic localization pattern. Since EGFP is not expressed in the host tissues, when artificially overexpressed in cancer cells, EGFP serves as a cancer cell specific intracellular protein. This allowed us to check whether EGFP-directed antibody therapy would specifically eradicate EGFP-expressing tumors and show any non-specific undesired side effects to the host.

Finally, to test the principle of antibody therapy in another animal tumor model, we use a well known mammary cancer model of MMTV-PymT transgenic mice[15] carrying the middle T (mT) oncogene under the transcriptional control of the mouse mammary tumor virus promoter/enhancer. Such transgenic mice have been widely used as excellent spontaneous tumor models for decades in the cancer research community to assess the relative contribution of the metastatic mammary tumor phenotype[16,17].

Vaccines are inexpensive and yet effective in treating existing cancer or prevent cancer development[18]. Such specific active immunotherapy of cancer, if successful, has clear advantages over passive immunotherapy. If an antibody could recognize its intracellular antigen we can expect that an intracellular antigen could be used to trigger natural antibody production by the host immune system to achieve a similar effect of the antibody therapy against cancer. Here, we extend our study to evaluate the reliability of vaccinations with purified PRL-3, EGFP and mT proteins for antigen-induced antibody therapies.

Example 2. Materials and Methods (Section E1):
Cell Lines and Cell Culture

BI 6F0 (CRL-6322) and B I 6F10 (CRL-6475) murine melanoma cell lines (derived from the C57BL/6J strain) were purchased from the American Type Culture Collection (ATCC, Manassas, Va.). Cells were grown in RPMI medium supplemented with 10% fetal bovine serum and antibiotics and maintained in 37° C. incubator supplied with 5% $CO_2$.

Example 3. Materials and Methods (Section E1):
Western Blot Analysis

Detailed steps were described in our previous study[22].

Example 4. Materials and Methods (Section E1):
Antibodies

Mouse monoclonal antibodies (clone #318, IgGI) were generated in-house, as described previously[22]. EGFP mouse monoclonal antibody (sc-9996, IgG2a) and Polyoma virus-middle T antigen (PymT) rat monoclonal antibodies (sc-53481, IgG2b) were from Santa Cruz biotechnology, Inc.

Example 5. Materials and Methods (Section E1):
Construction of GST-PRL-3, GST-Middle T Plasmids, and Preparation of the GST-Fusion Proteins The detailed steps for generating GST-PRL-3 fusion proteins were described previously. To make GST-middle T: forward primer and reverse primer were used for PCR using pXJ40 vector (i.e. pXJ40-PyMT) as a template. The PCR fragments were digested with BamH1 and EcoR1 and ligated into respective sites of the pGEX-KG vector. The preparations of GST-fusion protein were described in detail previously[22].

Example 6. Materials and Methods (Section E1):
Experimental Metastasis Assay[23]

All animal studies were approved by the Institutional Animal Care and Use Committee (1ACUC) and were carried out in accordance with the policies of Institute of Molecular and Cell Biology's Review Board (1 RB), Singapore[18]. C57BL6 and Scid mice were from BRC (Biological Resources Centre. Agency for Science, technology and Research, Singapore), muMT mice were from The Jackson Laboratory, USA, Rag $2^{-/-}$ mice were from Taconic, USA, Rag $T^{1'}$ mice were from Taconic, USA. 8-week old mice were injected with one million cancer cells via their tail vein (day 1). The treated mice were administrated with mAbs via tail vein on day 3 and subsequent administration twice a week. 4-week old transgenic mice (PymT) were divided into two groups receiving anti-mT antibody or PBS, twice per week. Mice were sacrificed and all organs were inspected for the presence of macroscopic metastases. Metastatic tumors or organs were removed and fixed in 4% paraformaldehyde for histological analysis. Lung metastatic nodules were counted under a dissecting microscope. The numbers of mice used in antibody therapies in each experiment are summarized in FIG. 5G.

Example 7. Materials and Methods (Section E1):
Genotyping of MMTV-PymT Mice

The MMTV-PymT mouse strain was purchased from Mouse Models of Human Cancers Consortium (MMHCC). Females fail to lactate so this strain is maintained by breeding heterozygous (Tg/+) males with FVB/N (+/+) wild type females. Tail tip DNAs were extracted with DNA digestion buffer (12 ml: 10.08 ml, 1.2 ml of 1 Ox GB* buffer, 0.6 ml 10% Triton X-100, 0.12 ml of 2-mercaptoethanol). *Gitschier's Buffer (10 ml: 3.35 ml of 2M Tris pH 8.8, 1.66 ml of 1M $(NH_4)_2SO_4$J 0.34 ml of 0.5M $MgCl_2$, 1.65 ml MQ $H_2O$). Forward primer P001: 5'-cAA ATG TTG cTT GTc TGG TG-3' (SEQ ID NO: 122) and reverse primer P002: 5'-GTc AGT cGA GTG cAc AGT TT-3' (SEQ ID NO: 123) were used to PCR wild type 200 bp fragment. Forward primer P001: 5'-GGA AGc AAG TAc TTc AcA AGG G-3' (SEQ ID NO: 124) and reverse primer P004: 5'-GGA AAG TcA cTA GGA GcA GGG-3 (SEQ ID NO: 125) were used to PCR 566 bp transgene fragment. The genotyping procedure has been described previously (inouse.ncicrf.gov/pitocols).

Example 8. Materials and Methods (Section E1):
Whole Mount Preparation and Carmine Alum Stain All procedures below were carried out at room temperature. Abdominal mammary glands were excised during necropsy for whole mount preparations, spread on glass slides, and fixed in Carnoy's fixative (6 parts 100% ethanol, 3 parts chloroform, and 1 part glacial acetic acid) for 4 h. Subsequently, the tissue was washed in 70% ethanol for 15 min, and the ethanol was changed gradually to distilled water then was finally rinsed in distilled water for 5 min. Staining was carried out overnight in carmine alum stain.

The tissue was then dehydrated in graded alcohol solutions (70, 95, and 100%; 15 min each) and was cleared in two changes of xylene, mounted, and coverslipped using Permount. Whole mounts were observed under a Leica dissecting microscope (Leica Microsystems GmbH, Wetzlar, Germany), and digital images were recorded using a SPOT FLEX® color digital camera (Diagnostic Instruments, Inc. Sterling Heights, Mich.) using a SPOT software package (Version 4.5, Diagnostic Instruments, Inc. Sterling Heights, Mich.).

Example 9. Materials and Methods (Section E1): Immunization of C57BL6 Mice and MMTV-PymT Transgenic Mice Freund's Complete Adjuvant is the form that contains killed cells of *Mycobacterium butyricum* to enhance the immune response. The Complete Adjuvant is used in initial injections. The form that does not contain this bacterium is known as Freund's Incomplete Adjuvant that is used to boost in subsequence injections. 8-week old C57BL6 mice were immunized by intraperitoneal injection with a total volume of 200 µl Freund's Adjuvant: PRL-3 (20 µg) or EGFP (20 µg) in 100 µl saline mixed with 100 µl of complete adjuvant (Cat#77140, Pierce). 4-week old MMTV-PymT TG mice were immunized by intraperitoneal injection with a total volume of 200 µl Freund's Adjuvant: mT (10 µg) antigen in 100 µl saline mixed with 100 µl of complete adjuvant (Cat#77140, Pierce). The next two immunizations were injected with a total volume of 200 µl incomplete adjuvant (Cat#77145, Pierce). The second and third injections were done two-week intervals. Subsequently, 100-200 µl of tail bleed was collected in a heparin-coated capillary tube, plasma was prepared from the blood sample, and the antibody titer was measured by ELISA. The detailed steps of ELISA were described previously[22]. Mice with high titers of PRL-3, EGFP, or mT antibodies in their sera were selected for experiment and further analysis, The numbers of mice used for vaccinations are summarized in FIG. 6D.

Example 10. Materials and Methods (Section E1): ELISA Assay

PRL-3 and mT antigen stocks were made in carbonate-bicarbonate buffer with pH 7.4. 100 µl solution containing 50 ng of appropriate antigen was added to each 96-well plate and incubated at 4° C. overnight to coat the antigen onto the plate. The plate was then blocked with 3% BSA in PBS containing 0.05% Tween 20 for 1 hour at 37° C. and then washed three times with PBS. Blood serum (1.0 µl) from each mouse was diluted in 100 µl of blocking solution and added to each well, and then incubated for 2 hours at 37° C. 100 µl of appropriate secondary antibody conjugated with HRP (Pierce, USA) diluted at 1:5000 in PBS was added to each well and incubated at 37° C. for 1 hour. The plate was rinsed with PBS containing 0.05% Tween-20 three times followed by 3 washes with sterile water. The substrate, 100 µl of Turbo-TMB™ (Pierce, USA)), was added to each well and incubated for 10 min at room temperature. The reaction was stopped by adding 100 µl of concentrated H2SO4. Absorbance was measured at 450 nm using a Dynatech MR7000 plate reader (Dynatech, USA).

Example 11. Materials and Methods (Section E1): Statistical Analysis

Use Kaplan-Meier method to estimate cumulative survival rates for 'treated' verse 'untreated' mice. A p value of <0.05 was considered statistically significant.

Figure 1:
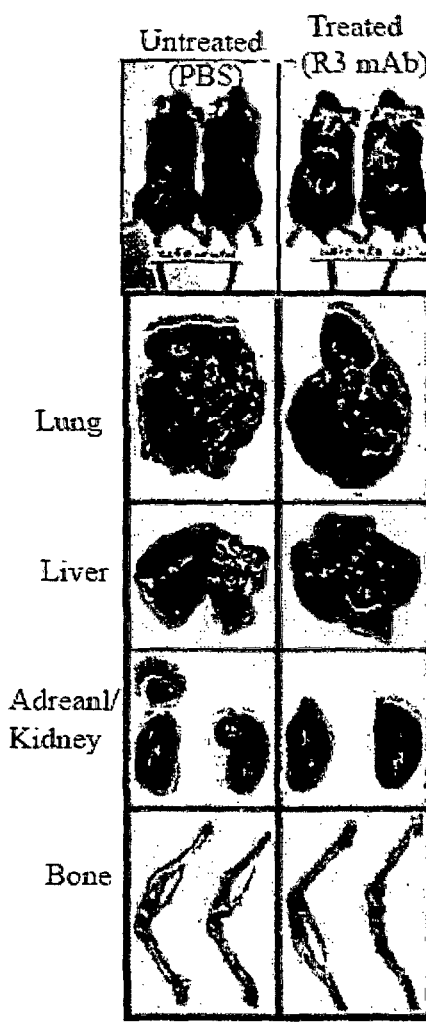
FIG. 1 is a diagram showing that PRL-3 mAb effectively inhibits the formation of metastatic tumors formed by PRL-3 expressing cancer cells. A, Total cell lysates were prepared from B16F0 and B16F10 melanoma cancer cells and endogenous PRL-3 protein expression was determined using immunoblot. GAPDH was used as a loading control. B, C57BL6 mice were injected with $1 \times 10^6$ B16F0 cells (on day 1) followed by PRL-3 mouse antibody (mAb, clone #318) treatment with therapeutic plan. C. On day 17-20, tumors were frequently found in the lung, liver, adrenal gland, kidney, and bone in untreated mice (n=5), while the PRL-3 mAb eliminates the formation of tumors in most tissues of treated mice (n=5). D, The body weight of PRL-3 mAb 'treated' B 16F0 recipient mice constantly increased. throughout the duration of the experiment. E, Parallel experiments were performed with non-PRL-3 expressing BI 6F10 melanoma cancer cell line and no therapeutic outcome was obtained with PRL-3 mAb therapy. F, The body weights of both treated and untreated B16F10 receipt mice constantly decreased over the duration of the experiment.
Figure 1:
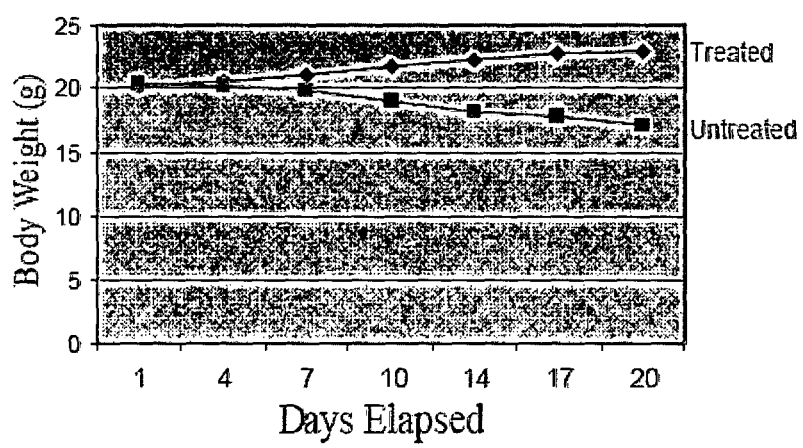
Figure 1:
Figure 1:
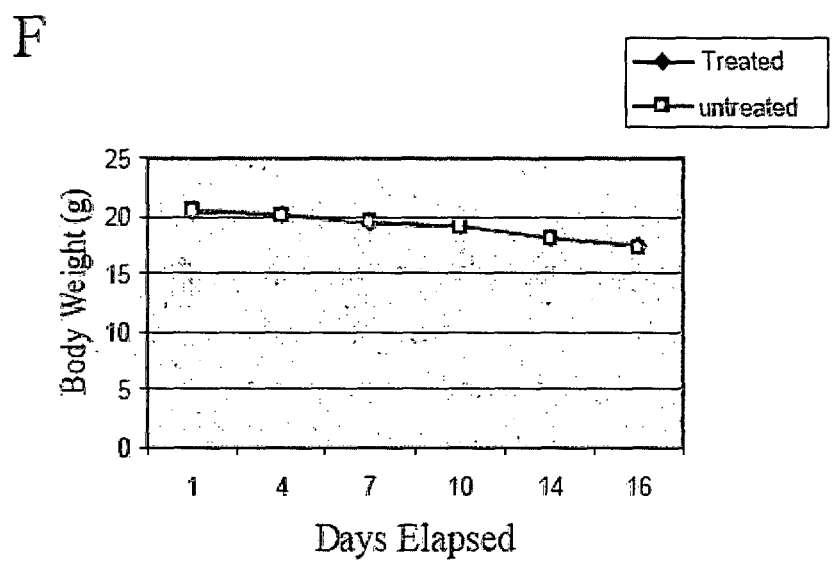

Example 12. Results (Section E1): In C57BL6 Wild Type Mice, PRL-3 mAb (IgGI) Effectively Retards Metastatic Tumors that Express Endogenous PRL-3 Protein We have previously demonstrated the efficacy of antibody therapy against intracellular PRL proteins in an immunocompromised nude mice metastatic tumor model[19]. To examine this therapeutic approach in a more relevant model for future clinical applications, we extended this study to examine if the antibody treatment could function in immunocompetent C57BL6 wild type mice. On day 1, mice (8-week old) were intravenously (i.v.) injected via lateral tail vein with C57BL6-derived B 16F0 (F0) melanoma cancer cells, which express endogenous PRL-3 (FIG. 1 A, lane 1). On day 3, mice were divided into 'untreated' and 'treated' groups which then received two administrations of PBS or PRL-3 mAb respectively per week during the whole duration of the experiment (FIG. 1B). At the end of the experiment (day 17), 'untreated' mice displayed severe weight loss, multiple metastatic tumors in various organs including the lung, liver, adrenal gland, kidney and bone. In contrast, 'treated' mice appeared more active and healthier in appearance. The 'treated' mice group, but not the 'untreated' group, constantly gained body weight throughout the duration of the experiment, in line with a reduction in tumor metastases (FIG. 1 C-D). To confirm the specificity of the PRL-3 mAb, an identical experiment was conducted in parallel, in which mice were intravenously injected with C57BL6-derived B16F10 (F10) cells, another melanoma cell line, which expresses very low levels of PRL-3 (FIG. 1 A, lane 2). By the end of the experiment (on day 17), all F10 recipients had developed metastases in the ovary, adrenal gland, kidney, and bone, regardless of whether they had received PRL-3 mAb. Both groups of mice experienced significant loss in body weight and appeared weak/inactive (FIG. 1 E-F), indicating that non-PRL-3 expressing F10 recipients had a poor response to PRL-3 antibody treatment. Note that F10 recipients develop more aggressive metastatic tumors in lungs (FIG. 1E) compared to lungs from F0 recipients (FIG. 1C). These data suggest that the efficiency of the PRL-3 antibody treatment was tightly correlated with PRL-3 expression status of the cancer cells but not with the degree of metastatic activities. The current data derived from immunocompetent wild-type C57BL6 mice thus substantiate our previous findings from immunocompromised nude mice[19].

Figure 2:
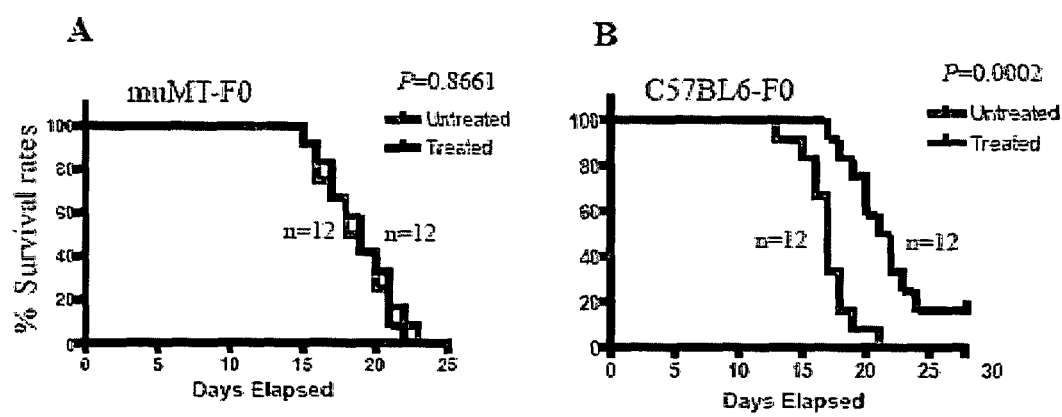
FIG. 2 is a diagram showing that B-cells are important in mediating the antibody therapeutic event. A. Kaplan-Meier survival curves were used to compare the 'treated' and 'untreated' groups of B-cell deficient muMT mice injected with B16F0 cells. No difference in median survival rate for untreated (18.5 days) and treated (19 days) groups was evident. B. Kaplan-Meier analysis of wild-type C57BL6 mice injected with B16F0 had a statistically significant difference (.P=0.0002) in median, survival between untreated (17 days) and treated (21.5 days) groups. C. Kaplan-Meier analysis of wild-type C57BL6 mice C57BL6 mice injected with B16F10 had no statistically significant difference between untreated (16.5 days) and treated (17.5 days). D. The results between treated and untreated mice were summarized. The numbers of ineffective (or tumor-bearing) mice were placed at the numerator and the total numbers of mice were placed at the denominator. Fraction indicated at the Y-axis represents percentage of tumor-bearing mice verse total mice (n) in each group. Column represents type of mice indicated at the X-axis.
Figure 2:
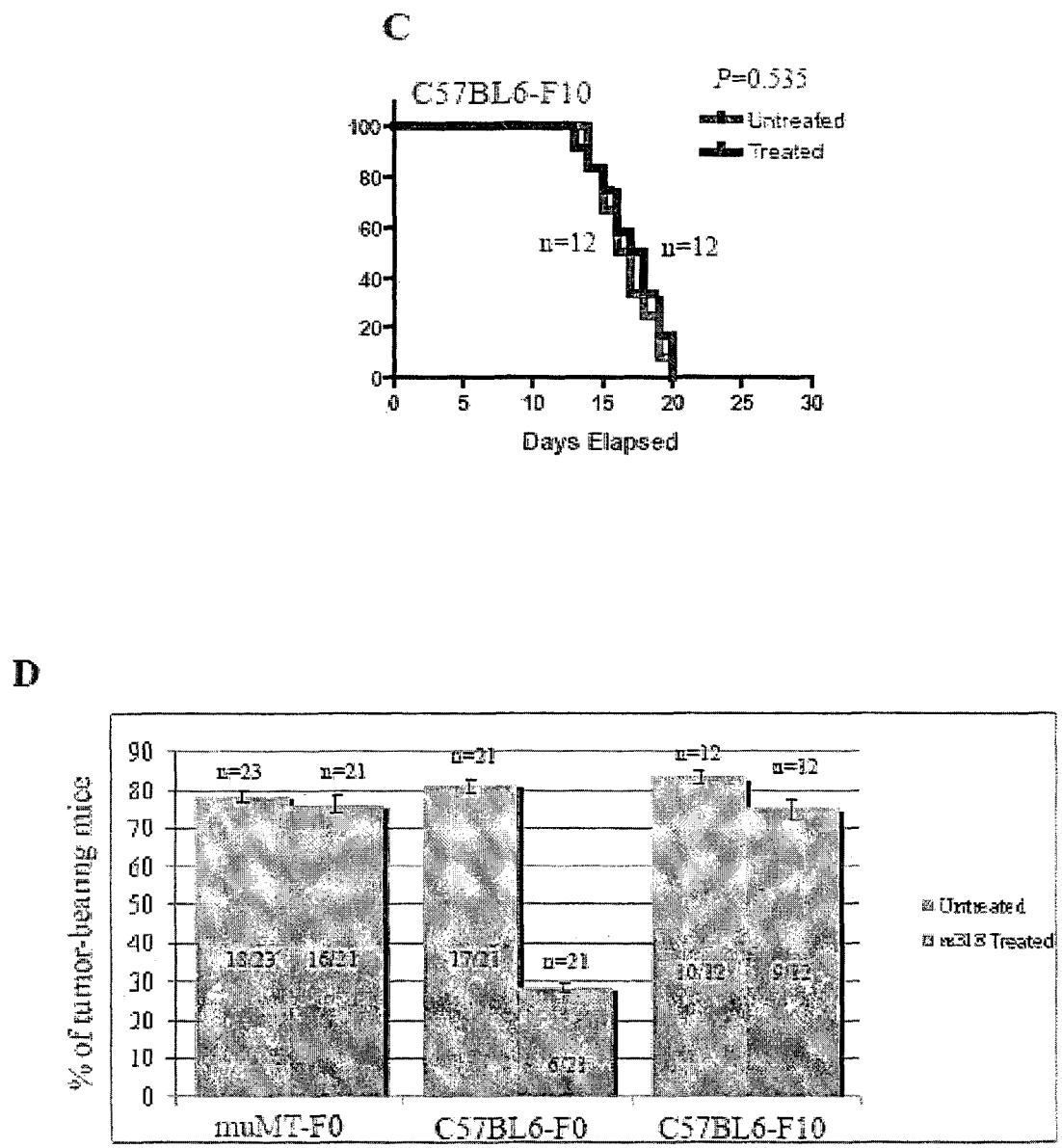

Example 13. Results (Section E1): In B-Cell-Deficient Mice, PRL-3 mAb (IgGI) Fails to Retard Metastatic Tumors that Express Endogenous PRL-3 Protein To investigate if lymphocytes are involved in the effect of antibody therapy observed, we employed two engineered strains of immunodeficient mice: muMT mice, which are C57BL6 mice homozygous for an inactivating mutation of the membrane exon of the mu chain gene. They cannot form a preBCR and are consequently devoid of mature B lymphocytes. We also employed Rag-2 mice that carry a germline mutation in which a large portion of the RAG-2 coding region is deleted, thus giving rise to homozygous mutants (Rag2$^{-/-}$) which are viable but fail to produce mature B or T lymphocytes[21]. Kaplan-Meier survival curves were used to compare 'treated' and 'untreated' mice among muMT-FO, C57BL6-F0, and C57BL6-F10 mice. Surprisingly, we did not observe any PRL-3 mAb therapeutic efficacy in repressing tumors in muMT-FO mice, with PRL-3 mAb therapy having no impact in extending the life-span for muMT-FO mice with a median survival of 19 days for 'treated' and 18.5 days for 'untreated' mice (FIG. 2A, /? value=0.8661). Similarly, no difference in tumor metastases was observed between 'treated' and 'untreated' groups in B- and T-cell deficient Rag2-F0 mice (data not shown). In contrast, PRL-3 mAb therapy prolonged the survival rates for C57BL6-F0 mice with a median survival of 21.5 days for 'treated' but 17 days for 'untreated' mice (FIG. 2B, p=0002). In agreement with the previous finding, PRL-3 mAb therapy did not prolong the overall survival of C57BL6-F10 mice with non-PRL-3 expressing tumors with a median survival of 17.5 days for 'treated' and 16.5 day for untreated mice (FIG. 2C, >=0.535). To summarize the effectiveness of antibody therapy among the different mice backgrounds, we scored the ability for PRL-3 mAb to reduce the degree of metastatic tumor formation relative to untreated mice in each group. When the reduction of metastatic tumor formation by at least 70% (±10%) was scored as an effective outcome, a clear beneficial effect was seen only in the C57BL6-F0 group but not in the muMT-FO (FIG. 2D). Thus, PRL-3 antibody therapy likely requires mature B-cell function for anti-tumor activity.

Figure 5:
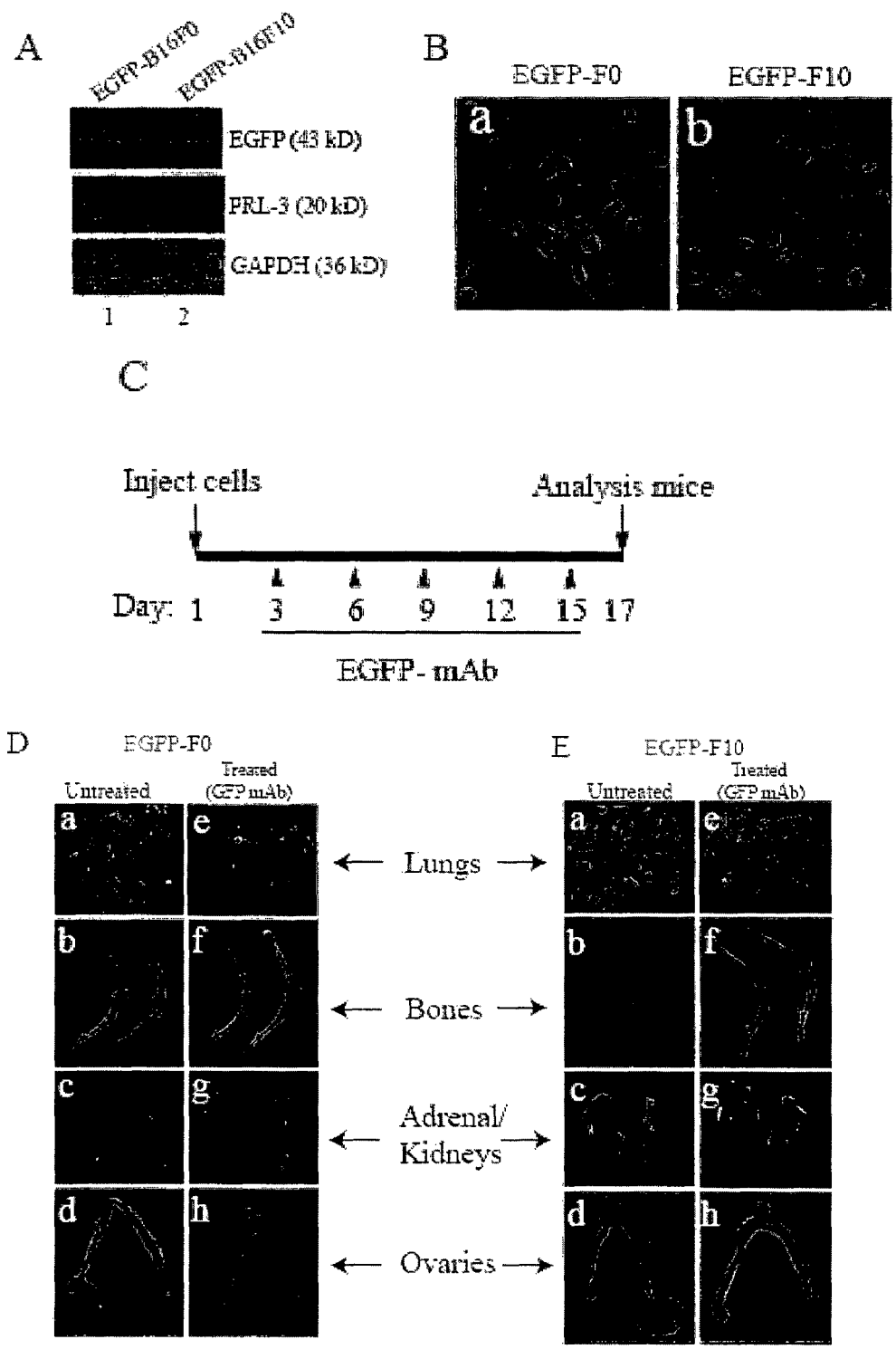
FIG. 5 is a diagram showing that PRL-3-, EGFP- or mT-Abs effectively inhibit the formation of PRL-3, EGFP, and mT expressing tumors. A, Total cell lysates were prepared from EGFP-FO and EGFP-FI O cancer cells. Exogenous EGFP protein was detected in both cell lines. PRL-3 was only expressed in EGFP-FO (but low in EGFP-FIO). GAPDH was used as the loading control. B, EGFP-FO and EGFP-FI O stable populations of pooled cells were showed to be heterogeneous expressing of EGFP. C. a therapeutic plan showed C57BL6 mice which were injected with $10^6$ cancer cells via tail veins (on day 1). Treated mice were i.v. injected with EGFP mAb. Untreated mice were i.v. injected with PBS. D-E, Organs were harvested, examined and imaged on 17-20 day. Tumors were found in lung, bone, adrenal, and ovary in the untreated group, but greatly reduced in treated mice. Note EGFP-Ab specifically inhibits EGFP-tumors, but not non-EGFP-tumors in lungs (panels, e). F. a. Untreated FVB/N-MMTV-PymT, b. mT mAb effectively inhibits the formation of breast tumors in transgenic MMTV-PymT mice c. non-transgenic mice show normal sizes of breast tissues as controls. G. Summary of results between untreated and treated mice with antibodies against intracellular targets. The numbers of ineffective (or tumor-bearing) mice were placed at the numerator and the total numbers of mice were placed at the denominator. 146 mice were tested by three different antibody therapies against their respective intracellular targets. N stands for number of mice in each group; fraction in each column represents proportion of mice bearing heavy tumors.

Example 14. Results (Section E1): In C57BL6 Mice, EGFP mAb (IgG2a) Effectively Blocks Metastatic Tumors that Express EGFP Protein The intriguing ability of PRL-3 mAb to inhibit tumor metastasis motivated us to investigate whether the therapeutic strategy could be applied to other intracellular proteins as well. Since EGFP is a non-cancer related protein, we chose to use EGFP as an intracellular protein marker specifically expressed in cancer cells. As EGFP is not expressed in the host tissues, we predicted that EGFP antibody should have few undesired side effects in the animal model. Utilizing pooled F0 and F10 melanoma cancer cell lines heterogeneously overexpressing exogenous EGFP protein (FIG. 5A, FIG. 5B), the EGFP-F0 and EGFP-F10 expressing cells were injected and treated with EGFP mAb following the same therapeutic schedule (FIG. 5C). As predicted, both EGFP-FO and EGFP-F10 cells responded equally well to EGFP antibody treatment in terms of tumor regressions regardless of PRL-3 expression. Notably, discrete clusters of green fluorescent or black metastatic tumors were found in the lungs (FIG. 5D-E, panels a, e). The non-EGFP expressing metastases in black thus served as internal negative controls to the green metastatic tumors in this model. Remarkably, EGFP mAb could specifically reduce numbers of EGFP-metastases but not that of non-EGFP-metastases (FIG. 5D-E, panels e), indicating that only EGFP-expressing tumors respond to EGFP mAb therapy. Upon scoring the results based on metastasis tumor load reduction, we found that the efficacy of the EGFP mAb effect was tightly correlated with EGFP expression status in cancer cells (FIG. 5G). Thus, antibody therapy depends on specific antibody-antigen interactions on (or within) cells for therapeutic efficacy.

Example 15. Results (Section E1): In MMTV-PymT Transgenic Mice, mT (Rat IgG2b) mAb Prevents the Formation of mT-Expressing Mammary Tumor Progression Having addressed that antibody therapy could work against both endogenous (such as PRL-3) and exogenous (such as EGFP) intracellular proteins, we asked if this approach could inhibit tumor formation in spontaneous tumor animal models. To this end, we chose popular MMTV-PymT transgenic mouse model of a spontaneous mammary tumorigenesis. MMTV-PymT transgenic mice express the polyomavirus middle T (mT) oncogenic protein, a DNA viral protein containing 421 amino acids which acts as a potent oncogene in the mammary epithelium. mT is represented linearly, tethered (21 aa) to the membrane at its carboxy-terminal end with a short KRSRHF motif likely exposed at the cell surface (too short to be an external epitope, in general). Therefore, most of this protein is facing the cytosolic compartment and has thus considered an intracellular protein[15]. Cells expressing the mT possess an enhanced metastatic potential[16]. All female carriers (genotype+/−) develop palpable mammary tumors (adenocarcinomas) at the age of 2-3 months (mouse.ncifcrf.gov/information/order livem ice.asp). Middle T expression is detected at high levels in male and female mammary glands, and the expression of mT oncogene is sufficient for mammary epithelial cell transformation. We used 44 heterozygous (+/−) young transgenic females-using RT-PCR to confirm their genotypes (FIG. 3A) and then divided them into 'treated' (n=18) and 'untreated' (n=26) groups. To determine if mT antibody could reduce mT-expressing mammary tumor development, 'treated' mice were i.v. injected with mT antibody at 4-week of age, followed by two administrations of antibody weekly for the whole duration of the experiment for about 3-months (FIG. 3B). In FIG. 3C, 'untreated' mice (#2, #6) and 'treated' mice (#7, #10) were selected as representative examples; an FVB/N non-transgenic female (#3) was used as a control for normal sizes of mammary glands (5 pairs). Histopathological examination of the mammary glands of 'untreated' mice exhibited irregular formation of side branches, enlarged terminal buds, and some large multi-lobular tumor masses (FIG. 3D, a). In contrast, breast tissue from treated mice, displayed more normal growth and development compared with a normal breast from wild-type mouse (FIG. 3D, b-c). Using the Kaplan-Meier method to estimate cumulative survival rates for 'treated' verse 'untreated' MMTV-PymT transgenic mice, we found that the mT Ab therapy could prolong the life-span of treated mice, leading an increased in the median survival for 'treated' MMTV-PymT mice to 19.5-week compared to 15 weeks for untreated mice (FIG. 3E, /?=0.0018). In all, we found that 100% (26/26) of 'untreated' mice carried dramatic breast tumors, while only 16.6% (3/18) of mT antibody treated mice developed tumor-bearing breasts, with the rest showing significant reduction in the formation of metastatic breast tumors that express mT oncogene (FIG. 3F, and FIG. 5F). These results suggested that the extensive repression of spontaneous tumor formation could be achieved by treating MMTV-PymT mice with mT antibody alone.

Example 16. Results (Section E1): C57BL6 Mice Vaccinated with PRL-3 Protein or EGFP Resisted the Formation of PRL-3- or EGFP-Expressing Tumors Having successfully demonstrated how three distinct intracellular proteins (PRL-3, EGFP, and mT) could be targeted with their respective antibodies, we next asked if intracellular proteins could be targeted by natural antibodies generated by the immune response upon antigen challenge (vaccination). We proceeded to immunize 8-week old C57BL6 mice with three doses (20 g each) of PRL-3 antigen (n=16) or EGFP protein (n=14) at 2-week intervals (FIG. 6A). At the end of the immunization, sera from 14-week old immunized C57B16 mice were tested for their antibody titers against PRL-3 antigen or EGFP protein by ELISA (data not shown). Successfully immunized mice were subsequently divided into two groups, i.v. injected with either EGFP-FO (PRL-3 positive) or EGFP-F10 (PRL-3 negative) melanoma cells. Compared to un-immunized mice (n=18) (FIG. 6B, a-d), PRL-3-immunized mice displayed reduced metastatic tumors formed by EGFP-FO cancer cells in adrenal, ovary and lung (FIG. 6B, e-g). This was expected as EGFP-FO melanoma cells express both EGFP and PRL-3 proteins, which should respond to both EGFP and PRL-3 antibody therapies. Remarkably, compared to metastatic lung from unimmunized-mice (FIG. 6B, d), the PRL-3-immunized mice were not able to reduce the degree of aggressiveness of metastatic lung tumors formed by EGFP-F 10 melanoma cells (FIG. 6B, h), which do not express PRL-3 protein (FIG. 5A). Again, this suggested that antigen-induced, naturally produced PRL-3 antibodies have no impact on inhibiting non-PRL-3 expressing EGFP-F 10 tumors. Elegantly, we showed that GFP-immunization could reduce metastatic tumors formed by both EGFP-FO and EGFPFI O cancer cells in the adrenal gland, ovary and lung (FIG. 6B, i-1) regardless of PRL-3 expressing levels. Taken together, these, results suggested that the induction of anti-PRL-3 or anti-EGFP antibodies in the host immune system upon vaccination could specifically inhibit the formation of PRL-3- or EGFP-expressing tumors respectively.

Example 17. Results (Section E1): MMTV-PymT Transgenic Young Females Vaccinated with mT Antigen Prevented the Formation of Mammary Gland mT Tumors To further confirm the possibility of cancer vaccination with intracellular proteins; we again employed the MMTV-PymT transgenic mammary tumor model. 38 FVB/N heterozygous females (4-week old) were divided into GST-immunized (n=3), GST-mT-immunized (n=17), and unimmunized (n=18) control groups. Mice were subjected to immunize with three doses (10 µg each) of GST or GST-mT antigen respectively, at 2-week intervals (FIG. 4A). Such mice were examined by ELISA for the titers of mT antibody to confirm the existence of mT antibody in their blood circulation (see FIG. 4B for representative example). Comparing to GST-immunized mice (#43, #44, #45), remarkably, mT-immunized mice (#37, #40, #41) exhibited a dramatic reduction in size and weight of mammary gland tumors (FIG. 4C-D), with the average weights of breast tissues/mouse from GST-immunized, GST-mT-immunized, and wild-type control mice found to be 5.6 g, 1.3 g, and 0.6 g, respectively (FIG. 4D). The results of the vaccination experiment are summarized in FIG. 6C-D. Kaplan-Meier survival curves demonstrated that the mT antigen could prolong the mean survival rates (p=0.0004) for immunized mice (19.5-week) compared to the unimmunized group (14.5-week) (FIG. 4E), indicating a positive benefit of cancer vaccination in extending survival time dramatically. Collectively, the data suggest that antigen-induced host mT antibody could again effectively prevent spontaneous breast tumor formations by cancer cells expressing mT.

Example 18. Discussion (Section E1)

Despite advancements in extracellular protein targeting, intracellular protein targeting has received little attention in terms of antibody therapy. Our findings presented here document a unique proof-of-concept in which anti-cancer antibody therapy against intracellular proteins could dramatically reduce tumor progression in vivo.

Here, we demonstrated the efficacy of antibody therapy against two intracellular proteins (PRL-3 and EGFP) against murine melanoma metastases in wild type C57BL6 mice. Similar success was obtained against intracellular mT antigen in the MMTV-PymT transgenic mice spontaneous tumor model as well. The therapeutic response observed appears to be isotype-independent, as IgG 1 (PRL-3 mAb), IgG2a (EGFP mAb), IgG2b (PymT rat mAb), and self-generated antibodies could effectively inhibit tumor progression. Proper antibody-antigen interactions seem to be the predominating factor; targeting tumors with non-related antibodies produced no beneficial response at all. Intriguingly, we also found that mature B-cells constitute an important component of the antibody therapy response. These results mirror a recent report in which B-cells were found to be essential to the anti-DR5 antibody therapy against colon adenocarcinoma[23].

Our results also demonstrated that upon tumor-specific antigen challenge, host immunity could be stimulated to produce endogenous antibodies against the specific antigen leading to tumor inhibition. This concept of 'cancer vaccination' has long been a promising but challenging prospect'[9]. Importantly, we found that compared to exogenously delivered antibodies, antigen-induced-antibody therapies can achieve similar anti-tumor therapeutic efficacy. We believe that it may be more useful and economical as we naturally have huge potential flexibility to generate high titers of antigen-induced antibodies ourselves. Although using Oncoproteins' for vaccination does not seem a practical thought, we do believe this approach is worth for future investigation. In order to preserve an oncogenic function in cancer cell signaling network, an Oncoprotein' should precisely locate at its native subcellular context coordinated with its neighborhood partners for correct communication. When an Oncoprotein' is isolated from its native dynamic complexity of sub-cellular localization, it may lose its connections and be unable to perform its normal biological roles.

The work presented here outlines a potential methodology for future clinical cancer treatments. First, primary tumors are removed and examined to identify of tumor-specific antigens. This is followed by the introduction of specific chimeric or humanized antibodies against the tumor antigen to eliminate disseminated cells, thus inhibiting micro-metastases formation[24]. This step may well prevent further spreading or relapse in cancer patients.

Alternatively, for cancers that are tightly genetically predisposed, immunization of immunocompetent young susceptible family members with an antigen that is associated with the familial cancer could 'prime' the immune system against that oncoprotein. These endogenously stimulated antibodies would be long-lasting, and would neutralize cancer cells expressing that particular oncoprotein. We base this approach on our observation that a very small amount of mT antigen (10 µg) introduced into a young MMTV-PymT transgenic mice could activate host immune system and produce mT antibody to inhibit mT-expressing tumor formation, allowing asymptomatic survival for up to 4-months. Extending weeks of life-span in mice may be comparable to prolonging decades in humans.

Ultimately, the pre-clinical data presented here suggests a general application for cancer treatments by using exogenous and endogenous antibody therapy targeting both extra- and intra-cellular tumor specific-antigens. Since existing conventional clinical antibody therapy is costly, we urge researchers to look at further developing the robust antigen-induced-antibody therapy response investigated here. For greater therapeutic response, we feel that this approach could be combined together with other immune-stimulatory agents for best effect. With cancer research rapidly moving towards individualized cancer therapy, our strategy for specific targeting of intracellular (or extracellular) oncoproteins hold enormous promise for tailored cancer therapy in the future.

Example 19. References (Section E1)

1. K. Imai and A. Takaoka, Comparing Antibody and Small-Molecule Therapies for Cancer. Nat Rev Cancer. 6(9), 714-727 (2006).
2. J. Cohen and A. Wilson, New Challenges to Medicare Beneficiary Access to mAbs. mAbs. 1(1), 56-66 (2009).
3. M. Baker, Upping the Ante on Antibodies. Nat Biotechnol. 23(9), 1065-1072 (2005).
4. A. Ruiz-Arguelles and D. Alarcon-Segovia, Penetration of Autoantibodies into Living Cells. Isr Med Assoc J. 3(2), 121-126 (2001).
5. D. Alarcon-Segovia, A. Ruiz-Arguelles and E. Fishbein, Antibody to Nuclear Ribonucleoprotein Penetrates Live Human Mononuclear Cells through Fc Receptors. Nature. 271(5640), 67-69 (1978).
6. R. H. Diamond, D. E. Cressman, T. M. Laz, C. S. Abrams and R. Taub, Prl-1, a Unique Nuclear Protein Tyrosine Phosphatase, Affects Cell Growth. Mol Cell Biol. 14(6), 3752-3762 (1994).
7. Q. Zeng, W. Hong and Y. H. Tan, Mouse Prl-2 and Prl-3, Two Potentially Prenylated Protein Tyrosine Phosphatases Homologous to Prl-1. Biochem Biophys Res Comm. 244(2), 421-427 (1998).
8. A. Alonso, J. Sasin, N. Bottini, I. Friedberg, I. Friedberg, A. Osterman, A. Godzik, T. Hunter, J. Dixon and T. Mustelin, Protein Tyrosine Phosphatases in the Human Genome. Cell. 117(6), 699-711 (2004).
9. X. Si, Q. Zeng, C. H. Ng, W. Hong and C. J. Pallen, Interaction of Farnesylated Prl-2, a Protein-Tyrosine Phosphatase, with the Beta-Subunit of Geranylgeranyl-transferase II. J Bio Chem. 276(35), 32875-32882 (2001).
10. J. Wang, C. E. Kirby and R. Herbst, The Tyrosine Phosphatase Prl-1 Localizes to the Endoplasmic Reticulum and the Mitotic Spindle and Is Required for Normal Mitosis. J Biol Chem. 277(48), 46659-46668 (2002).
11. Q. Zeng, X. Si, H. Horstmann, Y. Xu, W. Hong and C. J. Pallen, Prenylation-Dependent Association of Protein-Tyrosine Phosphatases Prl-1, -2, and -3 with the Plasma Membrane and the Early Endosome. J Biol Chem. 275 (28), 21444-21452 (2000).
12. S. Saha, A. Bardelli, P. Buckhaults, V. E. Velculescu, C. Rago, B. St Croix, K. E. Romans, M. A. Choti, C. Lengauer, K. W. Kinzler and B. Vogelstein, A Phosphatase Associated with Metastasis of Colorectal Cancer. Science. 294(5545), 1343-1346 (2001).
13. H. Wang, L. A. Vardy, C P. Tan, J. M. Loo, K. Guo, J. Li, S. G. Lim, J. Zhou, W. J. Chng, S. B. Ng, H. X. Li and Q. Zeng, Pcbp1 Suppresses the Translation of Metastasis-Associated Prl-3 Phosphatase. Cancer Cell. 18(1), 52-62 (2010).
14. J. A. Sager, S. Benvenuti and A. Bardelli, Prl-3: A Phosphatase for Metastasis? Cancer Biol Ther. 3(10), 952-953 (2004).
15. S. M. Dilworth, Polyoma Virus Middle T Antigen and Its Role in Identifying Cancer-Related Molecules. Nat Rev Cancer. 2(12), 951-956 (2002).
16. C. T. Guy, R. D. Cardiff and W. J. Muller, Induction of Mammary Tumors by Expression of Polyomavirus Middle T Oncogene: A Transgenic Mouse Model for Metastatic Disease. Mol Cell Biol. 12(3), 954-961 (1992).
17. Y. Husemann, J. B. Geigl, F. Schubert, P. Musiani, M. Meyer, E. Burghart, G. Forni, R. Eils, T. Fehm, G. Riethmuller and C. A. Klein, Systemic Spread Is an Early Step in Breast Cancer. Cancer Cell. 13(1), 58-68 (2008).
18. E. Gilboa, The Promise of Cancer Vaccines. Nat Rev Cancer. 4(5), 401-411 (2004).
19. K. Guo, J. P. Tang, C. P. B. Tan, H. Wang and Q. Zeng, Monoclonal Antibodies Target Intracellular Prl Phosphatases to Inhibit Cancer Metastases in Mice. Cancer Biol Ther. 7(5), 750-757 (2008).
20. T. von der Weid, N. Honarvar and J. Langhorne, Gene-Targeted Mice Lacking B Cells Are Unable to Eliminate a Blood Stage Malaria Infection. J Immunol. 156(7), 2510-2516 (1996).
21. Y. Shinkai, G. Rathbun, K. P. Lam, E. M. Oltz, V. Stewart, M. Mendelsohn, J. Charron, M. Datta, F. Young and A. M. Stall, Rag-2-Deficient Mice Lack Mature Lymphocytes Owing to Inability to Initiate V(D)J Rearrangement. Cell. 68(5), 855-867 (1992).
22. J. Li, K. Guo, V. W. C. Koh, J. P. Tang, B. Q. Gan, H. Shi, H. X. Li and Q. Zeng, Generation of Prl-3- and Prl-1-Specific Monoclonal Antibodies as Potential Diagnostic Markers for Cancer Metastases. Clin Cancer Res. 11(6), 2195-2204 (2005).
23. Haynes N M, Hawkins E D, Li M, McLaughlin N M, Hammerling G J, Schwendener R, Winoto A, Wensky A, Yagita H, Takeda K, Kershaw M H, Darcy P K, Smyth M J. CD 11c+ dendritic cells and B cells contribute to the tumoricidal activity of anti-DR5 antibody therapy in established tumors. J Immunol. 185(1):532-41 (2010).
24. B. Weigelt, J. L. Peterse and L. J. van't Veer, Breast Cancer Metastasis: Markers and Models. Nat Rev Cancer. 5(8), 591-602 (2005).

Examples Section E2 (Examples 20 to 38). Host Immunity is Crucial for the Anticancer Efficacy of a Chimeric Antibody Targeting Intracellular PRL-3 in Animal Models Section E2 comprises Examples 20 to 38. Example 20 is an Introduction to Section E2, Examples 21 to 29 are Materials and Methods for Section E2, Examples 30 to 36 are Results for Section E2, Example 37 is a Discussion of Section E2, Example 38 is References for Section E2.

Example 20. Introduction (Section E2)

A century ago, the German chemist Paul Ehrlich proposed the concept of antibodies as "magic bullets". Indeed, monoclonal antibodies (mAbs) have proven to be nature's biological warheads against some of humanity's most deadly diseases[1,2]. In general, antibody targeted therapy has much less toxicity than chemotherapy with small molecule inhibitors. Antibodies constitute the most rapidly growing class of human therapeutics and are ideal agents for recognizing and destroying malignant cells via the immune system. However, this therapeutic approach has been limited to surface or secreted proteins expressed by cancer cells[3,4], in part due to the assumption that antibodies are too large (150 kDa) to penetrate the cell membrane. As a consequence, a wide spectrum of intracellular oncoproteins remains unexplored in terms of an antibody therapy approach. However, the concept that intact antibodies are unable to penetrate into viable cells has been challenged by a plethora of experimental findings and clinical observations[5,6,7]. Over the past 30 years, immunologists have found that autoantibodies found in the serum of patients with different autoimmune diseases can somehow bind their respective intracellular antigens[6,7,8]. Although it is not certain that the antibodies to intracellular proteins that are found in autoimmune patients actually cause the disease, or even cell destruction, we nevertheless emphasize our main contribution of this work is that antibodies to intracellular protein can exert therapeutic effects.

PRL-1 (phosphatase of regenerating liver-1), PRL-2, and PRL-3 represent an intriguing subgroup of the intracellular protein tyrosine phosphatases (PTP). Individual PRLs are overexpressed in a variety of cancer cell lines and cancer tissues when compared with their normal counterparts[9]. A recent important review well describes these PRL-PTPs in cancer progression[10]. PRLs are intracellular C-terminally prenylated phosphatases. The localization of PRL-1 and PRL-3 to the inner leaflet of the plasma membrane and early endosomes was revealed by EM immunogold labeling"[12]. In contrast, the mutant forms of PRLs that lack the prenylation signal are localized in the nuclei[13]. PRL-3 was first discovered as a metastasis-associate phosphatase linked to colorectal cancer (CRC) metastasis with the finding that it was the only gene overexpressed in 100% of liver metastasis of CRC[14]. Overexpression of PRLs has subsequently shown to have a causative role in promoting cancer metastases and they become potential unique targets for diverse cancer treatment[15]. However, as these phosphatases are intracellularly localized, the conventional approach using therapeutic antibodies would seem a daunting task. In our earlier study, we reported an unexpected observation that mouse monoclonal antibodies (mAbs) against PRL-1 and PRL-3 were able to block experimental metastasis of cancer cells over-expressing intracellular EGFP-tagged PRL-1 and PRL-3[16].

In this study, we further evaluate the reliability of such targeting strategy using a newly-generated chimeric PRL-3 antibody. Here we extend our earlier findings for potential future clinical therapeutics against intracellular oncoproteins in five important aspects. Firstly, we generated and utilized clinically-relevant chimeric antibodies instead of mouse antibodies.

Secondly, we treated mice harboring naturally-occurring human cancer cells that express endogenous PRL-3 instead of exogenous PRL-3 in Chinese hamster cells (CHO). Thirdly, we showed that depletion of nature killer (K) cells enhances tumor engraftment. Fourthly, using paired nude and scid mouse models, we discovered the crucial role of B-cells in determining the outcome of our antibody therapy. Finally, using fluorescent labeled antibodies to track antibody-tumor binding activities by IVIS live imaging system; we proposed two working models for the antibody therapy in treated and untreated mice. An evidence-based hitherto concept is proposed for a possible approach in targeting intracellular oncoproteins with antibody therapies. The results suggest that an evaluation of a wide spectrum of intracellular oncoproteins (such as phosphatases, kinases. transcription factors) as possible targets for anticancer therapy may be warranted.

Example 21. Materials and Methods (Section E2): Generation of Specific PRL-3 Human/Mouse Chimeric mAb (Clone #318)

For PRL-3 chimeric mAb generation, total RNA was extracted from 6×10[6] hybridoma cells (clone#318)[19] using the RNeasy Mini Kit (QIAGEN, cat#74104). The RNAs were then reverse-transcribed into cDNA using Superscript II RNase H (Invitrogen, Cat 18064-014). The resulting total cDNAs were used as templates to generate the 'universal variable region' using Ig-Prime Kits (Novagen, cat#69831-3) for PCR (95° C.-4° C.-72° C., 30 cycles). The PCR fragment was cloned into the PCRII-TOPO-Vector with a TA cloning kit (Invitrogen, part#45-0640). The PCR fragment was cut with Mfe I and XhoI, and then inserted into the respective sites of a human IgG I constant region expression vector-pCMV-human IgGI[17] to join the mouse variable region of heavy chain (clone #318)[18] with the human IgG 1 constant region. Similar PCR procedures were performed for the mouse variable region of the light chain (clone #318) with ends containing restriction sites for ApaLI and Pst 1. The PCR fragment was cut with ApaLI and Pst I and then inserted into the respective sites of a human IgGI constant region expression vector containing the variable region of the heavy chain of clone #318. The complete construct was transiently transfected into 293T cells cultured in ultra-low IgG FBS (Gibco, 16250-078). The chimeric mAb was subsequently harvested from the culture supernatant and concentrated up to 40 times with centrifugal filter devices (Millipore, cat#UFC900596). The chimeric mAb was tested for its specificity by indirect immunofluorescence (IF) and Western blot analysis.

Example 22. Materials and Methods (Section E2): Cell Lines and Cell Culture

HCT1 16 (CCL-247) human colorectal carcinoma cell line, H460 (NCI-H460) human non-small lung cancer cell line, A431 (CRL-1555) human epidermoid carcinoma cell line, B16F0 (CRL-6322), and B16F10 (CRL-6475) mouse melanoma cell lines were purchased from the American Type Culture Collection (ATCC, Manassas, Va.). A27.80 (Cat#931 12519) human ovarian cancer cell line was purchased from ECACC, UK. Cells were grown in appropriate media recommended by the suppliers.

Example 23. Materials and Methods (Section E2): Western Blot Analysis

Generation of mouse PRL-3 monoclonal antibody and Western blot procedures have been described previously[18]. GAPDH antibody was from Cell Signaling Technology (Beverly, Mass.).

Example 24. Materials and Methods (Section E2): Experimental Metastatic Assay in Mice[20]

1×10[6] cancer cells were injected into the circulation of eight-week old nude mice (Jackson Labs, USA) via the tail vein on day 1. Either chimeric PRL-3 mAb or mouse PRL-3 or PRL-1 mAbs was used to treat mice; the first antibody treatment was carried on day 3 post-cancer cell injection, followed by two administrations per week. For control untreated group, PBS was administrated via tail vein. All animal studies were approved by the Institutional Review Board of the IMCB, in strict compliance with rules and policies of the Animal Facility Center of The Agency for Science, Technology and Research (A* STAR), Singapore.

Example 25. Materials and Methods (Section E2): Depletion of NK Cells

Anti-asialo GM 1 anti-serum (rabbit) was purchased from Wako Pure Chemical Industries, Ltd (Osaka 540-8605, Japan). The GM1 anti-serum (50 µĩ) was injected into the circulation of eight-week old nude mice (Jackson Labs, USA) via the tail vein 24 h before the experimental metastasis assay.

Example 26. Materials and Methods (Section E2): Statistical Analysis

The Kaplan-Meier method was used to estimate cumulative survival rates, and differences in survival rates, p-values less than 0.01 were considered to be significant.

Example 27. Materials and Methods (Section E2): Antibody Labeling and IVIS Live Imaging Purified PRL-3 antibody was labeled with CF™ 750 Dye Antibody Labeling Kits (www.biotium.coin/product/product info/Newproduct/Mix-n-Stain Kits.asp). Labeled antibodies were injected via tail vein 1 hr before live imaging. Bioware Ultra Cell Line HCT 116-luc2 (www.caliper-LS.com) is a luciferase expressing cell line which was stably transfected with firefly luciferase gene (luc2) under the human ubiquitin C promoter. HCT1 16-Luc2 cell line was established by using HCT1 16 human adenocarcinoma (ATCC, CCL-247™) and transducing lentivirus containing luciferase 2 gene under the control of human ubiquitin C promoter (pGL4 luc2). $1 \times 10^6$ HCT 116-luc2 cancer cells were injected into tail veins of 8-week old nude mice (Jackson Labs, USA). Antibody was injected into treated mice via tail veins on day 3, follow by two antibody injections per week. After 7-week treatment, mice are injected by an intraperitoneal route with a luciferin solution (15 mg/ml or 30 mg/kg, in PBS, dose of 150 mg/kg) that is allowed to distribute in awaked animals for about 5-15 minutes. The mice are placed into a clear plexiglass anesthesia box (2.5-3.5% isofluorane) that allows unimpeded visual monitoring of the animals using IVIS® Spectrum Imaging System 3D Series to track and monitor tumor development in vivo. The results between treated verse untreated mice were determined.

Example 28. Materials and Methods (Section E2): FACS Analysis

The human epidermoid carcinoma cell line A431 was grown in DMEM with high glucose (4.5 g/L), supplemented with 10% FBS and 5% antibiotic. B 16F0 and B 16F10 cells were grown in RPM I, supplemented with 10% FBS and 5% antibiotics. Cells ($5 \times 10^6$) were dislodged from the dishes with non-enzymatic pre-warmed cell dissociation solution (Sigma, Cat# c-5914) and transferred to 5 ml polystyrene tubes and washed once with complete medium. The cells were then incubated with 1 µĩ EGFR (Genentech, USA) or 5 µĩ PRL-3 primary mouse antibodies[18] in 100 µĩ of complete medium for 1 hr at room temperature (RT). Cells were agitated every 15 mins to prevent clumping. Cells were then washed 2× with complete medium and incubated for I hr at RT with goat anti-mouse AlexaFluor 546 antibody (Invitrogen, USA), washed, and re-suspended in 1 ml complete medium prior to analysis using BD FACS Caliber. Raw data was processed using WinMDI ver2.8 software.

Example 29. Materials and Methods (Section E2): Histopathologic Analyses Using Immunohistochemistry (IHC)

Human lung tissue arrays 009-01-004; and CCOO-01-006; CC04-01-CCO4 were purchased from Cybrdi, Inc. (Rockville, Md. 20850 USA: cybrdi.com/index.php). Human AML bone marrow samples were obtained from the National University Hospital-National University of Singapore (NUH-N US) Tissue Repository with approval of the Institutional Review Board (IRB) of NUH-NUS for research uses. The use of all human tissue samples including commercial samples were approved by Institutional Review Board (IRB) of the Institute of Molecular and Cell Biology. We used Dako En Vision™ Systems K 1395 (Dako, Carpinteria, Calif.) to perform IHC analysis[18,19].

Example 30. Results (Section E2): Generation of PRL-3 Mouse/Human Chimeric Antibodies (Clone #318)

Figure 12:
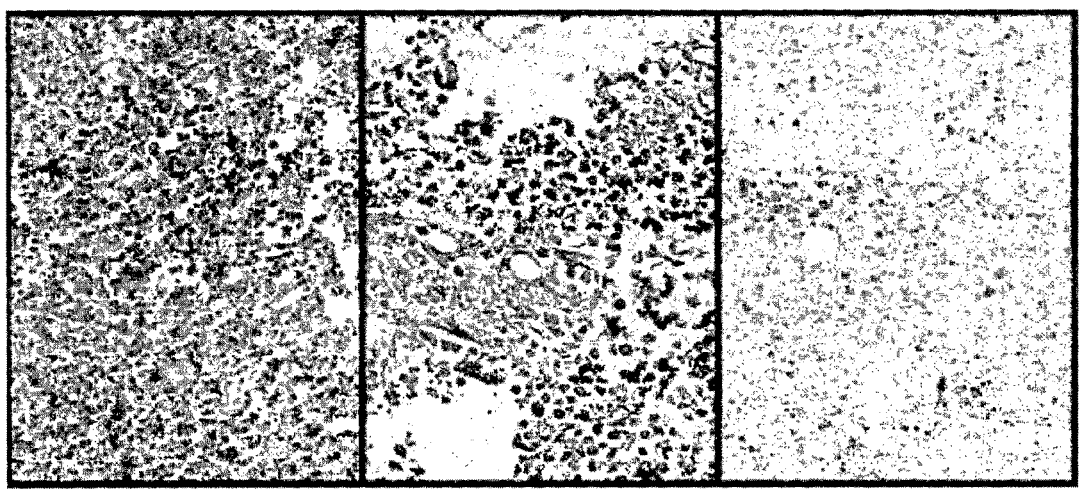
FIG. 12 is a diagram showing that PRL-3 protein is upregulated in lung cancers and AML. A. Representative IHC staining of PRL-3 expression in lung squamous cell carcinoma. B. lung adenocarcinoma. Scale bar: 100 μlη. C. The percentages of PRL-3-positive lung cancers as detected with immunohistochemistry (IHC) are summarized, grouped according to cancer subtypes. D. AML bone marrow samples were examined by IHC, 24 out of 69 (35%) showed PRL-3 expression. Three selected images were shown.

We previously reported that PRL-3 or PRL-1 mouse mAbs could specifically target their respective intracellular PRL-3 or PRL-1 phosphatase to inhibit cancer metastases in nude mice[16]. In an attempt to translate our laboratory findings to clinical setting, we have engineered a mouse/human chimeric mAb against PRL-3 to minimize the potential antigenicity of the mouse mAb in human. Using recombinant DNA technology, we separately fused the constant domains of heavy or light chains of the human IgGI molecule[17] with the mouse variable regions of PRL-3 mAb (clone#318)[18] by transgenic fusion of the immunoglobulin genes (FIG. 7A). The expression construct was transfected into Human Embryonic Kidney 293T cells to produce recombinant PRL-3 chimeric mAb that was then harvested from the culture medium and further concentrated. The antigen-binding specificity of the PRL-3 chimeric mAb was well conserved as confirmed by performing indirect immunofluorescence on DLD-1 cells that overexpress exogenous EGFP-PRL-3 (FIG. 7B) and western blot analyses (FIG. 7C). The PRL-3 chimeric mAb specifically recognized EGFP-PRL-3 (~48 kDa) and myc-PRL-3 (~21 kDa) (FIG. 7C, lane 1-2) but react with neither myc-PRL-1 nor myc-PRL-2 proteins (FIG. 7C, lane 3-4). A 50% cell Inhibitory Cytotoxic concentration (IC50) was carried out in a mouse melanoma B 16F0 cells for the chimeric antibody and we observed no cellular toxicity in viability even at high concentrations (40 g/ml) when cells were cultured in 10% FBS medium under normal culture conditions (data not shown). Since PRL-1, -2, and -3 are overexpressed in a broad range of human cancers[19], we anticipate that the PRL-antibodies are likely to have broad applications to block different types of PRLs-positive cancer spreading, especially in some lethal malignancies such as lung cancers and acute myeloid leukemiaJAML) that often relapse within short timeframes. Amongst lung cancers, we found PRL-3 is overexpressed in 31% of squamous cell carcinoma and 26% of adenocarcinoma (FIG. 1 A-C), two main subtypes of highly recurrent non-small cell lung carcinoma comprising 80% of human lung cancer (en.wikipedia.org/wiki/Lung_cancer#Non-small_cell_lung_carcinoma_0.28NSCLC.29). We also found that PRL-3 is overexpressed in 35% (24 out of 69 cases) of AML (FIG. 12D). A few injections of PRL-3 chimeric antibody therapies will clean up the leftover of micro-metastasis and circulating cancer cells after the surgery of PRL-3-positive cancers to prevent the recurrence.

Example 31. Results (Section E2): PRL-3 Chimeric Antibody Effectively Inhibits the Metastatic Tumors Formed by B16F0 Cancer Cells that Express Endogenous PRL-3 but not by B16F10 Cancer Cells that do not Express Endogenous PRL-3

Figure 8:
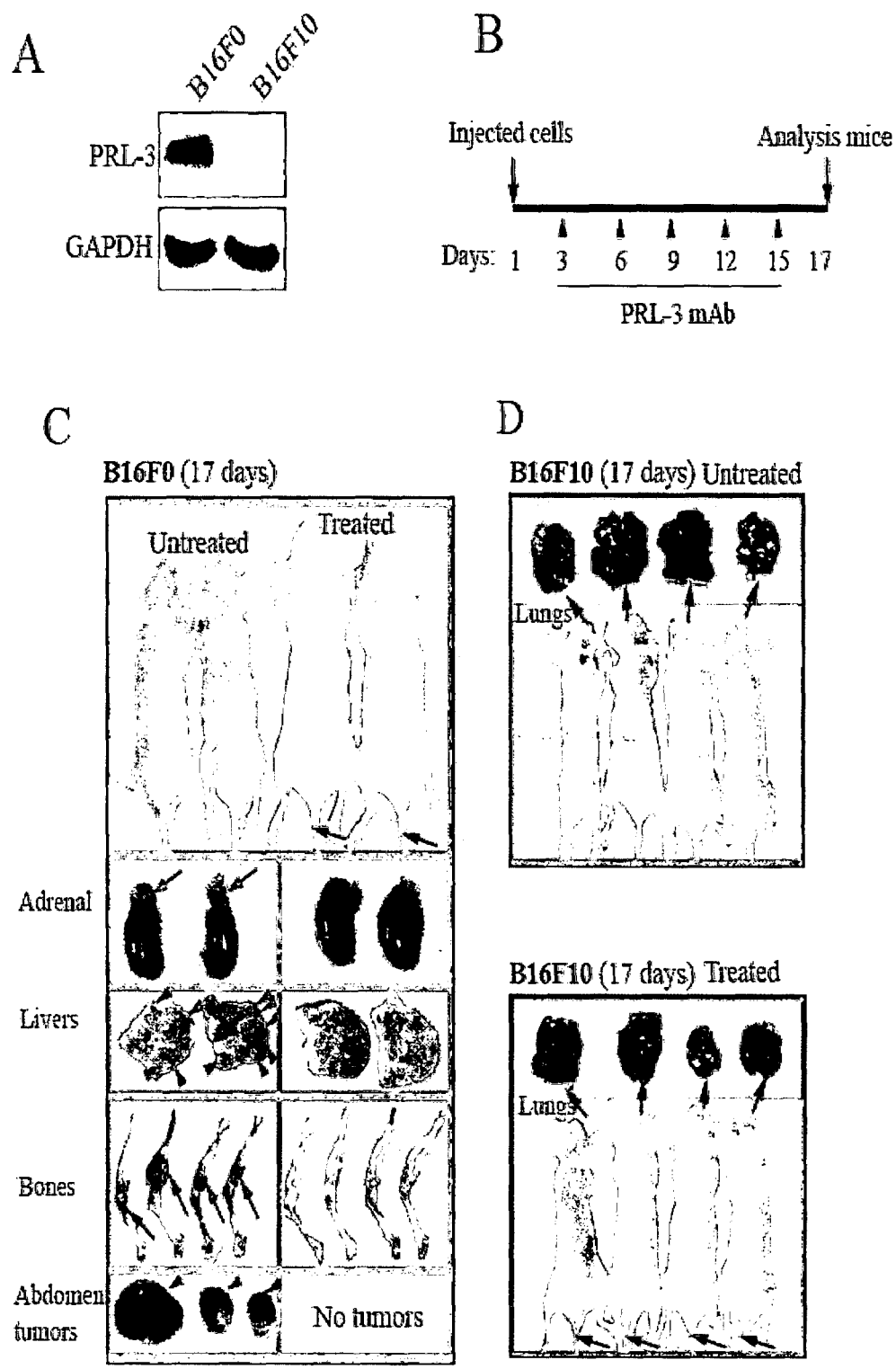
FIG. 8 is a diagram showing that PRL-3 chimeric antibody effectively inhibits the formation of metastatic tumors formed by BI 6F0 cells that express endogenous PRL-3 A. Total cell lysates were prepared from F0 and F10 melanoma cells and analyzed by immunoblot. Abundant endogenous PRL-3 protein was detected in F0 but was almost undetectable in FI 0 cells. B. On day 1, nude mice (n=27) were injected with $1 \times 10^6$ F0 cells via tail vein, followed by two intravenous administrations of the PRL-3 chimeric mAb per week (day 3, 6, 9, 12, 15). C. At the end of the experiment (day 17), mice were photographed and tissues were dissected. Metastatic tumors were found in the adrenal gland, liver, bone, and abdomen in untreated mice (left), but not in treated mice (right). D. nude mice (n=22) were injected with $1 \times 10^6$ F10 cells for the experiment. At the end of the experiment (day 17), dozens of lung metastatic tumors were found both in untreated (top panel) and treated mice (bottom panel). E. Kaplan-Meier survival curves for 'treated' and 'untreated F10 recipients were shown.
Figure 8:
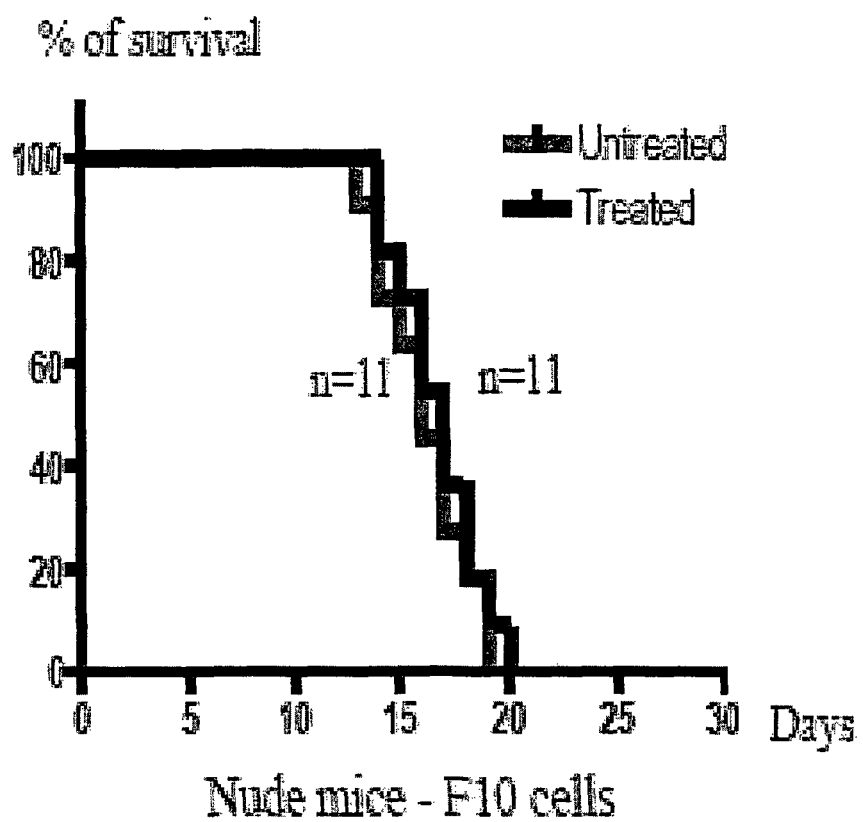

To find a clinically relevant animal model for PRL-3-associated cancers, we screened dozens of cancer cell lines for the expression of endogenous PRL-3 protein levels by Western blot analysis. Ideal cell line pairs for our animal models should present contrasting levels of endogenous PRL-3 and should have the ability to induce metastatic tumors in mice within short timeframes. We found two mouse melanoma cell lines B16F0 and B16F10 (F0 and F10) that could fulfill the criteria for the desired experiment. Although F10 cells are naturally more metastatic than F0 cells, we found that parental F0 cells express higher levels of endogenous PRL-3 protein than F10 cells (FIG. 8A), suggesting that F10 cell metastatic activity might be no longer PRL-3 dependent. When we employed an experimental metastatic assay[20] in which cultured cancer cells were introduced into the circulation of nude mice by lateral tail vein injection, both F0 and F10 cell lines can rapidly form multiple metastatic tumors in mice within 17 days. Such aggressive in vivo metastasis models allow us to see the differences in efficacy shortly after antibody therapy between treated and untreated groups. On day 3 (the latest time we can delay in treatment) post cancer cell injections, chimeric-PRL-3 antibodies were administrated similarly via tail veins into the 'treated mice', followed by two subsequent administrations of the antibody per week (FIG. 8B). At the end of the experiment, we found that the PRL-3 chimeric antibody could eradicate tumors formed by PRL-3 expressing F0 cancer cells; the metastatic tumors in multiple tissues were dramatically reduced in 'treated mice' at the end of the experiments (FIG. 8C). The Kaplan-Meier survival analysis for F0 recipients will discuss later (FIG. 1 OA, c). In a parallel experiment, the PRL-3 antibody had no effect in blocking metastatic tumors formed by F10 cancer cells that do not express PRL-3 protein. Hundreds of metastatic tumors were found in the lungs of both treated and untreated F10 cell recipients, and no obvious difference was seen between 'untreated mice' (FIG. 8D, upper panel) and 'treated mice' (FIG. 8D, lower panel). Furthermore, Kaplan-Meier survival analysis demonstrated that the PRL-3 antibody could not extend the survival time for 'treated' FI 0 recipients (FIG. 8E).

Example 32. Results (Section E2): PRL-3 Chimeric Antibodies Effectively Inhibit the Formation of Metastatic Tumors Formed by Human Cancer Cells that Express Endogenous PRL-3, but not by Cancer Cells that do not Express Endogenous PRL-3

In addition to mouse F0 melanoma cells, we further found that HCT1 16-luc2, HCT-1 16 human colorectal cancer cell line, and A2780 human ovarian cancer cell line express endogenous PRL-3 protein (FIG. 9A lanes: 1-3). A2780 has also been reported as a PRL-3 positive cell line previously[21]. As a control, we found a human non-small lung cancer cell line (NCI-H460) which does not express endogenous levels of PRL-3 (FIG. 9A lane 4). Regardless PRL-3 positive or negative, the four human cancer cell lines can rapidly form metastatic tumors in nude mice within 1-2 months respectively. HCT-1 16-luc2 is a luciferase expressing cell line which was stably transfected with firefly luciferase gene (luc2) in HCT-1 16 cells. The cell line was established by transducing lentivirus containing luciferase 2 gene under the control of human ubiquitin C promoter. This cell line can be used in vivo by Xenogen's IVIS® Spectrum Series imaging to monitor tumor formation. Using this system, we demonstrated that the PRL-3 antibody could (. inhibit metastasis of HCT1 16-luc2 cancer cells as a clear reduction of metastatic lung tumors in live imaging at 7 week of antibody therapy was observed (FIG. 9B). Furthermore, significant differences were found between PRL-3 antibody treated and untreated mice at 2-month post-inoculation with HCT-1 16 cells (FIG. 9C, a) and at 1-month post-inoculation with A2780 cells (FIG. 9C, b). The PRL-3 mAb-treated animals appeared vibrant and healthy (up to 4-month), whereas the untreated mice had all lost weight and were moribund. In paralleled, NCI-H460 (PRL-3 negative cells) recipients did not respond to PRL-3 antibody treatment (FIG. 9C, c). Taken together, these results further support the conclusion that the efficiency of the PRL-3 antibody treatment is tightly correlated with PRL-3 expression status of the cancer cells. We showed that the efficiency of both mouse- and chimeric-PRL-3 antibody therapies is comparable (FIG. 9D).

Example 33. Results (Section E2): NK Cells are Important in Anticancer Therapy

Figure 13:
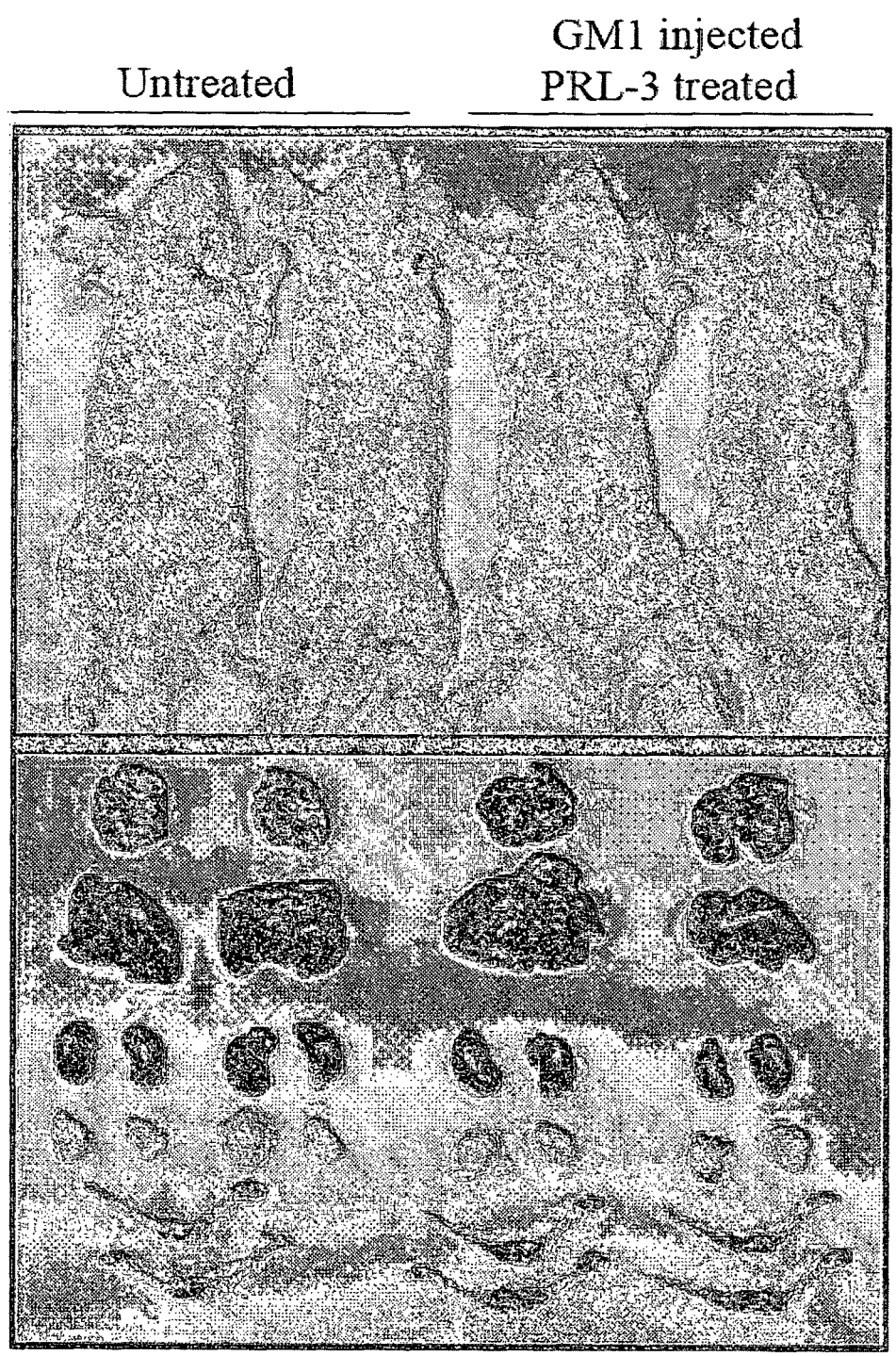
FIG. 13 is a diagram showing that NK cells in Innate Immune system are involved in the therapy. Nude mice were injected (n=2) and un-injected (n=2) with GM1 antibody 24 hrs before the experiment. On day 1, all mice were injected with I×I 0$^6$ F0 cells via tail vein, followed by two intravenous administrations of the PRL-3 chimeric mAb per week (day 3, 6, 9, 12, 15) in GM1 injected mice. On day 18, the therapeutic efficacy was examined. GMI injected nude mice showed more severe tumors (in black)-bearing burden in lung, liver, adrenal, testis, and bone than GM 1 un-injected mice, regardless PRL-3 mAb treated or untreated.

We then investigated if nature killer (NK) cells play a role in the PRL-3 antibody therapy since NK cells are a type of cytotoxic lymphocyte that constitute a major component of the innate immune system. To deplete the nude mice's NK cells, we pre-injected nude mice with anti-asialo GM-1 antibody[22]. Our above-mentioned procedures of the antibody therapy were performed in these GM 1-injected nude mice. We found that the efficacy of therapies was essentially lost in GM-1 injected mice (FIG. 13). Even worse, such GM 1 injected nude mice showed more severe tumors (in black)-bearing burden in lung, liver, adrenal, testis, and bone than un-injected ones, indicating that innate immune system is important in our antibody therapy. NK cells have been demonstrated to have a role in human hematopoietic stem cell graft rejection[22], removal of NK cells may result in abolishment of graft rejection of NK cell activities, leading tumor engraftment more successfully, therefore, GM1 injected 'PRL-3-treated' mice were worse than GMI-un-injected 'PRL-3-untreated' mice in terms of tumor growth.

Figure 10B:
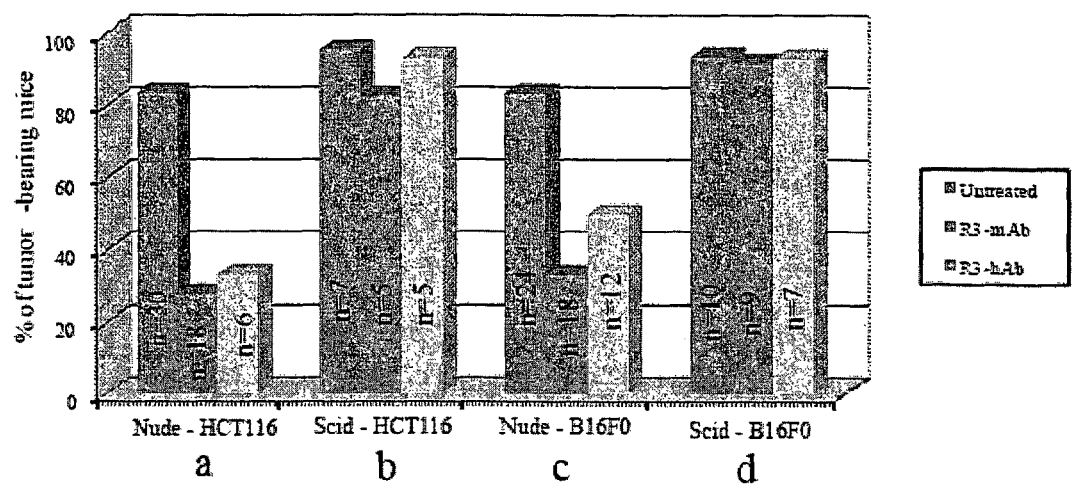
FIG. 10 is a diagram showing that B-cells are important in mediating therapeutic efficacy of PRL-3 chimeric antibody. A. Kaplan-Meier survival curves of 'treated' and 'untreated' HCT-1 16-injected nude and scid mice (a, b). Kaplan-Meier survival curves of 'treated' and 'untreated' BI 6F0-injected nude and scid mice (c, d). B. Summary of results for therapeutic experiments in nude and scid mice (a-d). Percentages of tumor-bearing mice were averaged from each group (n=numbers of mice) and indicated at the Y-axis. 151 mice in total were used in this experiment.

Example 34. Results (Section E2): B-Cells May be Important in Mediating the Therapeutic Effects of PRL-3 Antibodies Thus far, we performed the PRL-3 antibody therapies in T-cell deficient nude mice. To address if B lymphocytes are critical in our antibody therapy model, we next performed antibody therapies in Severe Combined Immunodeficiency (scid) mice, which lack functional lymphocytes because they carry a deficiency that impairs rearrangement of separate gene elements of the immunoglobulin and T-cell antigen receptor genes, thus, disrupting the differentiation and maturation of both B- and T-lymphocyte progenitor cells. They thus show a severe combined immunodeficiency affecting both B and T lymphocytes, although they have normal NK cells, macrophages, and granulocytes. For HCT-1 16-induced metastatic tumors, Kaplan-Meier analysis of survival curves of PRL-3 antibody treated versus untreated mice showed a statistically significant (P<0.001) increase in life span of nude mice but not scid mice (FIG. 10A, a-b). Intriguingly, we found a 45% increase in the median survival time for the treated HCT-116-injected nude mice (16 weeks) compared to untreated mice (11 weeks). In contrast, in untreated or treated groups of HCT-116-injected scid mice, we observed no difference in the effect of PRL-3 antibody therapy, which showed similar median survival duration (11 weeks). Furthermore, we employed F0 PRL-3 positive cancer cell line to confirm this finding using similar strategies. In FO-injected nude mice (FIG. 10A, c-d), PRL-3 antibody treatment increased median survival duration by 47% (24 days for treated, versus 17 days for untreated). Consistently, the antibody had no effect in untreated or treated FO-injected scid mice, with both groups showing similar median lifespan (~17 days). The mechanism is independent of antibody species, as similar results were obtained using mouse or chimeric PRL-3 antibodies (FIG. 10B, a-d). Collectively, the Results from these genetic mouse models suggest that PRL-3 antibody efficacy against metastatic tumor formation is dependent on host B-cell but not T cells. We suggest that other than antibody production, B-cell may have additional function to secrete unknown factor(s) that could facilitate the actions of antibodies. Indeed, our preliminary data shows that B-cells may secrete factors that could facilitate antibody uptake by the cancer cells. We observed a substantial increase in the internalization of antibody in PRL-3 positive F0 cells when the assay was performed in presence of culture supernatant from human B cells. Parallel, PRL-3 null F10 cells were unable to harbor any antibody either in presence of the B cell conditioned media or in presence of live B cells (data not shown).

Figure 11A:
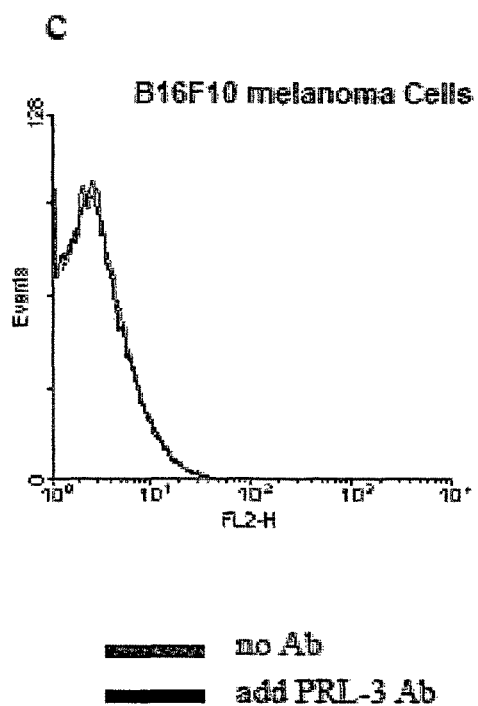
FIG. 11 is a diagram showing that A. PRL-3 is not detectable at the cell surface, a. Peak-shift was observed between A431 cells incubated with EGF-receptor antibody (black line) compared to A431 cells without incubation of EGF-receptor antibody (red line), b. Peak-shift was not observed between FO cells incubated with PRL-3 mAb (black line) and without Ab (red line). c. Peak-shift was not observed between F10 cells incubated with PRL-3 mAb (black line) and without Ab (red line). B Labeled antibodies were intravenously injected 1 hr before I VIS live imaging based working models: a. Treated mice. Early delivery of the antibody will persistently attack cancer cells to prevent them from further progression, resulting in micro-metastases in open stages, as such, fluorescent labeled PRL-3 antibody can access and bind to metastatic lung tumors in 'treated mice'. We observed strong fluorescent labeled lung in treated mice, b, Untreated mice. The uncontrolled cancer cells rapidly multiplied. They freely developed into macro-metastases and established defense territory, some kind of tumor microenvironment, which makes less accessible to antibody and immune system, as consequences, fluorescent labeled PRL-3 antibodies were not able to label metastatic lung tumors in 'untreated mice'. We therefore are unable to observe fluorescent labeled metastatic lungs in untreated mice. In H&E stain section, black arrows showed a clear boundary ('fence') of the metastatic lung tumor from untreated B 16F0 recipients. Scale bar: 200 μlη. Red arrows indicated blood vessels.

Example 35. Results (Section E2): PRL-3 Antigen is Insignificant at the Cell Surface A possible mechanism of PRL-3 antibody action could be the binding of a cell surface antigen, triggering a B-cell dependent elimination of the PRL-3 expressing cell. However, to date, no reports describe a cell surface localization of PRL-3. To address the possibility of PRL-3 antibody binding its antigen on the cell surface, we used a FACS assay routinely used in cell surface labeling. As a positive control, anti-EGFR antibody binding of the EGFR-overexpressing human epidermoid carcinoma A431 cell line was used for this assay. We found that incubation of A431 cells with anti-EGFR antibodies caused a distinct peak-shift in the FACS assay (FIG. 11A, a). However, no peak shift was observed for either F0 (PRL-3 positive) or F10 (PRL-3 negative) cells incubated with or without anti-PRL-3 antibody (FIG. 11A, b-c). These results imply that cell surface PRL-3 antigen, if any, was unlikely to be the major cause of antibody binding and uptake. However, since immune system constantly battles invaders, such as bacteria and viruses, and cancer cells in vivo, the cancer cells can be destructed and somehow expose their intracellular protein to immune system. If this is so, the same possibility may apply to other intracellular oncoproteins as well.

Example 36. Results (Section E2): IVIS Live Imaging-Based Working Models

Figure 11B:
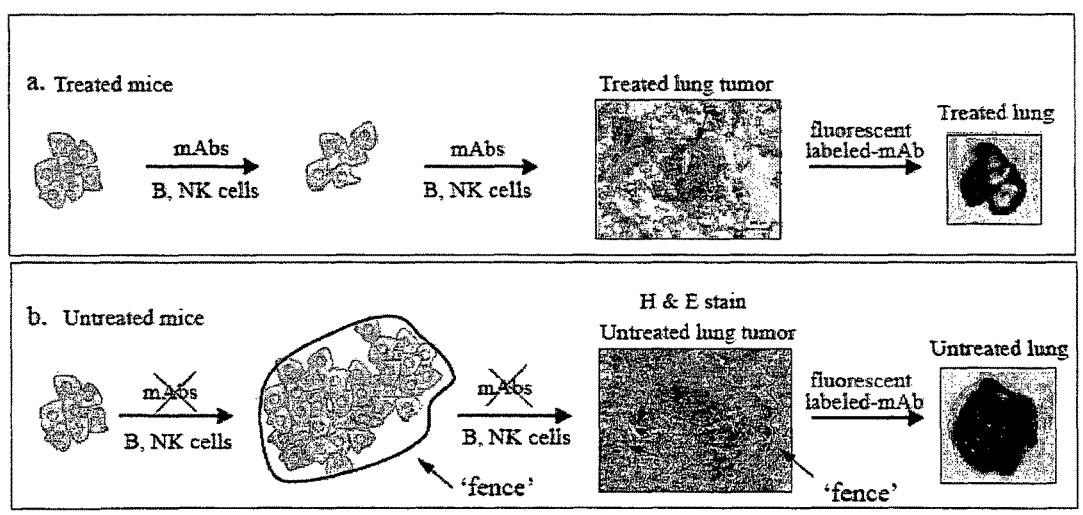

In our animal model systems, we found that antibody therapies were ineffective after 3-days post cancer cells injection, suggesting that the first 3-day may be sufficient for cancer cell engraftment in new tissues. Using IVIS system to track sites of metastatic tumors through labeled antibody-antigen binding, we herein proposed two working models (FIG. 11B), a. Treated mice. 1. at early stages, cancer cells were in clusters, timely introduction of the antibodies could somehow capture antigen-specific cancer cells in the circulatory, or in the lymphatic system together with the help of lymphocytes (such as B, and NK cells) via innate immune system to destroy and remove these cancer cells. 2. Escaped cancer cells will be able to arrive at new organs for implantations; therefore, the constant delivery of the antibody to the circulation is important to unplug these incipient tumors and prevent them from further development, destructing and clearing them from the host immune system. 3. The incipient tumors in 'treated mice' have no chance to develop tumors fully and therefore were in open-stages exposed to immune system. In addition, we found higher blood vessel density in small tumors (H&E lung sections) than in large tumors. As such, fluorescent labeled antibodies could easily access via blood circulation to metastatic lung tumors in 'treated mice'. We therefore observed the 'treated' metastatic lungs with strong florescent labeled, b. Untreated mice. The above-mentioned early steps had been missing; the unchecked cancer cells were rapidly multiplied in the host. The massive cancer cells were uncontrolled implanted and had sufficient time to develop micro- to macro-metastases, building up their territory with tumor boundaries 'fences' as defense system with close-stages away from the immune system. Furthermore, we found lower blood vessel density in large areas of tumor, insufficient blood supply results in necrosis (not shown). As consequences, fluorescent labeled antibodies were less accessible via blood supply to reach metastatic lung tumors in 'untreated mice'. We therefore found the 'untreated' metastatic lungs with weak florescent labeled.

Example 37. Discussion (Section E2)

PRL-3 is up-regulated in numerous types of human cancer. It is foreseeable that the PRL-3 chimeric antibody will be a promising therapeutic agent in blocking diverse PRL-3-associated cancer metastases. We hope to start with our effort on a few lethal malignancies (such as lung cancer and AML) that often relapse within short timeframes. Since these cancers are aggressive, therapeutic effects are easily observed and the outcomes between treated and untreated patients can be clearly defined. Especially, leukemic cells are easily accessible and are in direct contact with antibodies in the circulating system. The terminal patients suffering from these aggressive cancers are more likely to be recruited into clinical trials. Hopefully, success in these examples may make an impact on targeting other intracellular oncoproteins with antibody therapies, which is an important area of translational research and will provide a viable alternative treatment to cancer patients.

The molecular mechanism(s) behind these unconventional findings presented here remains elusive and is actively being investigated. Currently, understanding how antibody destroys tumors in vivo is still a 'dark box' to us. Similarly, it has been more than two decades to aim at understanding the mechanism(s) of the well-known anti-HER2/neu antibody therapy, although the anti-HER2/neu antibody has been in clinical uses for years in treating breast cancers[23]. Anticipating unraveling the 'dark box' using in vitro system may be unrealistic because a major consideration of traditional in vitro cell culture system is far simplified due to the limitation of single cell type grown in an incubator, typically using medium supplemented with 10% fetal bovine serum, lack of immune system involved, which was unlikely to be able to actually mimic in vivo complexities of multiple types of cells and organs, in 100% native blood circulation and lymphatic system. Whatever mechanism is, the central part of this study is that antibodies to intracellular protein can exert therapeutic effects, and more importantly, the effect is reproducible. If we can see the same therapeutic effect in humans that could be of enormous value in cancer treatment to support for the under-recognized notion that antibody therapy can be used for targeting intracellular antigens.

Nevertheless, our hard attempts in understanding the possible events within the 'dark box' enable us to achieve several conclusions from this study:

1. The PRL-3 Antibody Treatment is Tightly Correlated with PRL-3 Expression Status of the Cancer Cells.

We demonstrate that the chimeric antibody could indeed successfully block the formation of metastatic tumors derived from several cancer cell lines (B 16F0, HCT-1 16, and A2780) that express endogenous intracellular PRL-3 phosphatase. The inhibition is specific as the antibody had no effect in blocking the formation of metastatic tumors derived from other cancer cell lines (B16F10, H460) that do not express PRL-3. Previously, we had demonstrated that mouse PRL-3 antibody had no effect in inhibiting metastatic lung tumors formed by CT26 mouse colon cells, another PRL-3 negative cancer cell line[16]. Taken together, the data support the notion that the efficiency of either mouse or chimeric PRL-3 antibody treatment is tightly correlated with PRL-3 expression status of the cancer cells. If the metastatic property of cancer cells was not due to PRL-3 overexpression (such as B16F10, H460, CT26 cells), the administration of PRL-3 mAb has no effect in blocking tumors formed by these PRL-3 negative cells. Furthermore, we previously[6] had shown that PRL-1 mAb specifically blocks PRL-1 (but not PRL-3) metastatic tumors; while PRL-3 mAb specifically blocks PRL-3 (but not PRL-1) metastatic tumors though PRL-1 and PRL-3 share very high homology in protein sequence. These results imply that PRL antibody therapy is highly specific to its antigen and does not involve cross-reactivity with other non-specific cell surface proteins.

2. NK Cells in 'Innate Immune System' are Involved in the Therapy.

To understand if innate immune system is involved in the antibody therapy, we intravenously injected GM1 antibody via tail vein into nude mice to deplete NK cells, which are a type of cytotoxic lymphocytes that constitute a major component of the innate immune system. In the absence of NK cells, we found, anti-PRL-3 antibody did not exhibit therapeutic effects. Furthermore, tumor-engraftment was dramatically enhanced (FIG. 13), indicating that NK cells normally play a critical role in graft-rejection for implantation of foreign cells. Previously, mounting evidence suggests that NK cells play an important part in the destruction of incipient tumours[24].

3. ADCC May Also be Involved in the Therapy.

The best characterized mechanism of antibody therapy is antibody-dependent cellular cytotoxicity (ADCC). In ADCC, antibodies bind to specific cell surface antigens and trigger an Fc-mediated immune response involving cytotoxic CD8 T cells, complement activation, and/or NK cell activity. Although we did not observe any peak-shift in our FACS analysis of PRL-3 cell surface antigens in both PRL-3 positive F0 cells and PRL-3 negative FI 0 cells, we could not rule out a possibility that these cancer cells were under abnormal inflammatory pressure, which may cause the destruction of cancer cells to release and expose their intracellular proteins to be attacked by the antibody and somehow trigger specific immune response, leading lymphocyte to remove these cancer cells. Alternatively, in vivo, cancer cells are under hypoxic stress and serum deprivation, conditions that arrest cells at G] and Go phases[25]. It is possible that these conditions may cause release of intracellular antigens for the antibody to recognize. If so, other intracellular oncoproteins may also encounter the similar situations, they therefore can be similarly targeted with antibody therapies.

4. 'Adaptive Immune System' (IgM and/or B Cells) are Important in the mAb Therapeutic Effect.

We employed athymic nude mice and immunodeficient scid mice for the tumour reduction experiments and achieved the therapeutic effect only in nude mice but not in scid mice. The major differences between nude and scid mice are that nudes are T-cell deficient, but have functional IgM antibodies and B cells, while scids have no functional adaptive immune system including B-, T-cells, and IgM and other antibodies. Both nudes and scids have intact innate immune system including NK cell and complement activity, but with positive responses seen only in the nude (but not in scid) mice, indicate that mature B cells (but not T cell), and possibly IgM/serum antibodies, are important. As the antibodies were exogenously introduced into mice, the requirement of B-cells for anti-metastatic PRL-3 antibody activity is hypothesized that an alternative role for B-cell in the antibody response, possibly via secretion of unidentified factor(s) that modulates any given antibodies for the host response. Collectively, we emphasize that intricate interplay of innate and acquired immune system is crucial for the anticancer efficacy of a chimeric antibody targeting intracellular PRL-3 oncoprotein.

5. Not all Intracellular Oncoproteins can be Targeted with Antibody Therapy

Desirable anti-cancer therapeutic agents should specifically target cancer cells while leaving normal tissues unharmed. It should be emphasized that the PRL-3 chimeric antibody therapy has little detectable side effect in nude mice since PRL-3 expression in normal tissues is not ubiquitous. We showed that PRL-3 protein was detected in only a few organs such as the spleen, brain, and pancreas (FIG. 14A). In contrast, PRL-2 is ubiquitously expressed in most of mouse tissues (FIG. 14B). As expected, PRL-2 antibody therapy to PRL-2 expressing cancers was unsuccessful (FIG. 14C). The PRL-2 antibody-treated mice died 1-week earlier or showed worse outcomes than untreated mice, which might be due to PRL-2's ubiquitous expression in most of mouse tissues, implicating a possibility of PRL-2 antibody may attack normal tissues to cause this undesired side-effect. The results suggest that a good therapeutic target should be more specifically to tumor antigen without harming host normal tissues.

6. Antibody Therapy Against Intracellular Oncoprotein is Clinically Relevant.

To generate a very aggressive cancer model for treatment, we directly injected 1 million cancer cells into the circulation of a nude mouse; the total blood volume in nude mouse is 8% of its body weight (8% of ~19 g=1.5 ml). The total blood volume in a man (50 kg) is around 4.7 liters. If 1 million cancer cells were injected into ~1.5 ml blood circulation in nude mouse; which is comparable to 3133 (4.7 liter/1.5 ml) millions cancer cells in ~4.7 liter blood in a man. The remarkable therapeutic effect by starting antibody (intravenously injected into tail vein) treatment even 3 days post-cancer cell injection indicates the treatment is intriguingly effective. If we can achieve similar life span extension in treated patients to that of mouse system, it will be comparable in years in humans in term of the total life span and the extended life expectancy. From these preclinical studies to reality, we anticipate that a few injections of chimeric antibody is very critical to reduce recurrence rate, as the PRL-3 antibodies will clean up circulating cancer cells[26] or unplugging invisible incipient tumors after surgical removal of visible PRL-3-associated solid tumors.

At this end, the lack of any observable side effect in nude mice upon PRL-3 antibody therapy further alludes to its potential clinical benefits. Our data prompts a reevaluation of a wide spectrum of tumor-specific intracellular oncoproteins as possible targets for anti-cancer mAb therapy, thus realizing the full potential of these 'magic bullets'.

Example 38. References (Section E2)

1. D. Hanahan and R. A. Weinberg, The Hallmarks of Cancer. Cell. 100(1), 57-70 (2000).
2. J. M. Reichert, C. J. Rosensweig, L. B. Faden and M. C. Dewitz, Monoclonal Antibody Successes in the Clinic. Nat Biotechnol. 23(9), 1073-1078 (2005).
3. K. Imai and A. Takaoka, Comparing Antibody and Small-Molecule Therapies for Cancer. Nat Rev Cancer. 6(9), 714-727 (2006).
4. M. Baker, Upping the Ante on Antibodies. Nat Biotechnol. 23(9), 1065-1072 (2005).
5. Ruiz-Arguelles and D. Alarcon-Segovia, Penetration of Autoantibodies into Living Cells. Isr Med Assoc J. 3(2), 121-126 (2001).
6. D. AlarcoA n-Segovia, L. Llorente, A. Ruiz-Arguelles, Y. Richaud-Patin and B. Perez-Romano, Penetration of Anti-DNA Antibodies into Mononuclear Cells Causes Apoptosis. Arthritis Rheum. 38, SI 79-182 (1995).
7. D. Portales-PeArez, D. AlarcoA n-Segovia, L. Llorente, R.-A. e. A, C. Abud-Mendoza, L. Baranda, H. De-la-Fuente, T. Ternyck, R. Gonzalez-Amaro and J., Penetrating Anti-DNA Monoclonal Antibodies Induce Activation of Human Peripheral Blood Mononuclear Cells. J Autoimmun. 11(5), 563-571 (1998).
8. T. D. Golan, A. E. Gharavi and K. B. Elkon, Penetration of Autoantibodies into Living Epithelial Cells. J Invest Dermatol. 100(3), 316-322 (1993).
9. B. J. Stephens, H. Han, V. Gokhale and D. D. Von Hoff, Prl Phosphatases as Potential Molecular Targets in Cancer. Mol Cancer Ther. 4(11), 1653-1661 (2005).
10. D. C. Bessette, D. Qiu and C. J. Pallen, Prl Ptps: Mediators and Markers of Cancer Progression. Cancer Metastasis Rev. 27(2), 231-252 (2008).
11. J. Wang, C. E. Kirby and R. Herbst, The Tyrosine Phosphatase Prl-1 Localizes to the Endoplasmic Reticulum and the Mitotic Spindle and Is Required for Normal Mitosis. J Biol Chem. 277(48), 46659-46668 (2002).
12. Q. Zeng, X. Si, H. Horstmann, Y. Xu, W. Hong and C. J. Pallen, Prenylation-Dependent Association of Protein-Tyrosine Phosphatases Prl-1, -2, and -3 with the Plasma Membrane and the Early Endosome. J Biol Chem. 275 (28), 21444-21452 (2000).
13. X. Si, Q. Zeng, C. H. Ng, W. Hong and C. J. Pallen, Interaction of Farnesylated Prl-2, a Protein-Tyrosine Phosphatase, with the Beta-Subunit of Geranylgeranyl-transferase Ii. J Biol Chem. 276(35), 32875-32882 (2001).
14. S. Saha, A. Bardelli, P. Buckhaults, V. E. Velculescu, C. Rago, B. St Croix, K. E. Romans, M. A. Choti, C. Lengauer, K. W. Kinzler and B. Vogelstein, A Phosphatase Associated with Metastasis of Colorectal Cancer. Science. 294, 1343-1346 (2001).
15. Q. Zeng, J.-M. Dong, K. Guo, J. Li, H.-X. Tan, V. Koh, C. J. Pallen, E. Manser and W. Hong, Prl-3 and Prl-1 Promote Cell Migration, Invasion, and Metastasis. Cancer Res. 63(11), 2716-2722 (2003).
16. K. Guo, J. P. Tang, C. P. B. Tan, H. Wang and Q. Zeng, Monoclonal Antibodies Target Intracellular Prl Phosphatases to Inhibit Cancer Metastases in Mice. Cancer Biol Ther. 7(5), 750-757 (2008).
17. J. H. Brendon, C. M. Adrianus and P. C. Angeline, Passive Immunoprophylaxis and Therapy with Humanized Monoclonal Antibody Specific for Influenza a H5 Hemagglutinin in Mice. Respir Res. 7, 126-136 (2006).
18. J. Li, K. Guo, V. W. Koh, J. P. Tang, B. Q. Gan, H. Shi, H. X. Li and Q. Zeng, Generation of Prl-3- and PH-1-Specific Monoclonal Antibodies as Potential Diagnostic Markers for Cancer Metastases. Clin Cancer Res 11(6), 2195-2204 (2005).
19. H. Wang, L. A. Vardy, C. P. Tan, J. M. Loo, K. Guo, J. Li, S. G. Lim, J. Zhou, W. J. Chng, S. B. Ng, H. X. Li and Q. Zeng, Pcbp1 Suppresses the Translation of Metastasis-Associated Prl-3 Phosphatase. Cancer cell. 18(1), 52-62 (2010).
20. B. Weigelt, L. P. Johannes and L. J. v. t. Veer, Breast Cancer Metastasis Markers and Models. Nat Rev Cancer. 5(8), 591-602 (2005).
21. F. Polato, A. Codegoni, R. Fruscio, P. Perego, C. Mangioni, S. Saha, A. Bardelli and M. Broggini, Prl-3 Phosphatase Is Implicated in Ovarian Cancer Growth. Clin Cancer Res. 11(19 Pt 1), 6835-6839 (2005).
22. H. Yoshino, T. Ueda, M. Kawahata, K. Kobayashi, Y. Ebihara, A. Manabe, R. Tanaka, M. Ito, S. Asano, T. Nakahata and K. Tsuji, Natural Killer Cell Depletion by Anti-Asialo Gml Antiserum Treatment Enhances Human Hematopoietic Stem Cell Engraftment in Nod/Shi-Scid Mice. Bone Marrow Transplant. 26(11), 1211-1216 (2000).
23. M. Kasai, T. Yoneda, S. Habu, Y. Maruyama, K. Okumura and T. Tokunaga, In Vivo Effect of Anti-Asialo Gml Antibody on Natural Killer Activity. Nature. 291(5813), 334-335 (1981).
24. S. Park, Z. Jiang, E. D. Mortenson, L. Deng, O. Radkevich-Brown, X. Yang, H. Sattar, Y. Wang, N. K. Brown, M. Greene, Y. Liu, J. Tang, S. Wang and Y. X. Fu, The Therapeutic Effect of Anti-Her2 Neu Antibody Depends on Both Innate and Adaptive Immunity. Cancer Cell. 18(2), 160-170 (2010).
25. S. Cooper, Reappraisal of Serum Starvation, the Restriction Point, GO and GI Phase Arrest Points. FASEB J. 17(3), 333-340 (2003).
26. Y. Hiisemann, J. B. Geigl, F. Schubert, P. Musiani, M. Meyer, E. Burghart, G. Forni, R. Eils, T. Fehm, G. Riethmuller and C. A. Klein, Systemic Spread Is an Early Step in Breast Cancer. Cancer cell. 13(1), 58-68 (2008).

Examples Section E3 (Example 39). Immunization of C57BL6 Mice with VHZ and Monitoring Tumor Development Example 39: Section E3: Immunization of C57BL6 Mice with VHZ and Monitoring Tumor Development 8-week-old C57BL6 mice were immunized by intraperitoneal injection with a total volume of 200 ml Freund's Adjuvant: 20 mg of VHZ antigen in 100 ml saline mixed with 100 ml of complete adjuvant (Cat#77140, Pierce).

The next two immunizations were injected with a total volume of 200 ml adjuvant: 20 mg of VHZ antigen in 100 ml saline mixed with 100 ml of incomplete adjuvant (Cat#77145, Pierce).

The second and third injections were administrated every 2 weeks, 100-200 ml of tail bleed was collected in a heparin-coated capillary tube.

Plasma was prepared from blood sample and antibody titer was measured by ELISA.

The detailed steps of ELISA were described previously.

Mice with high titers of VHZ antibodies in their sera were selected and lateral tail vein injected with 1×106 VHZ-expressing cancer cells.

Figure 15:
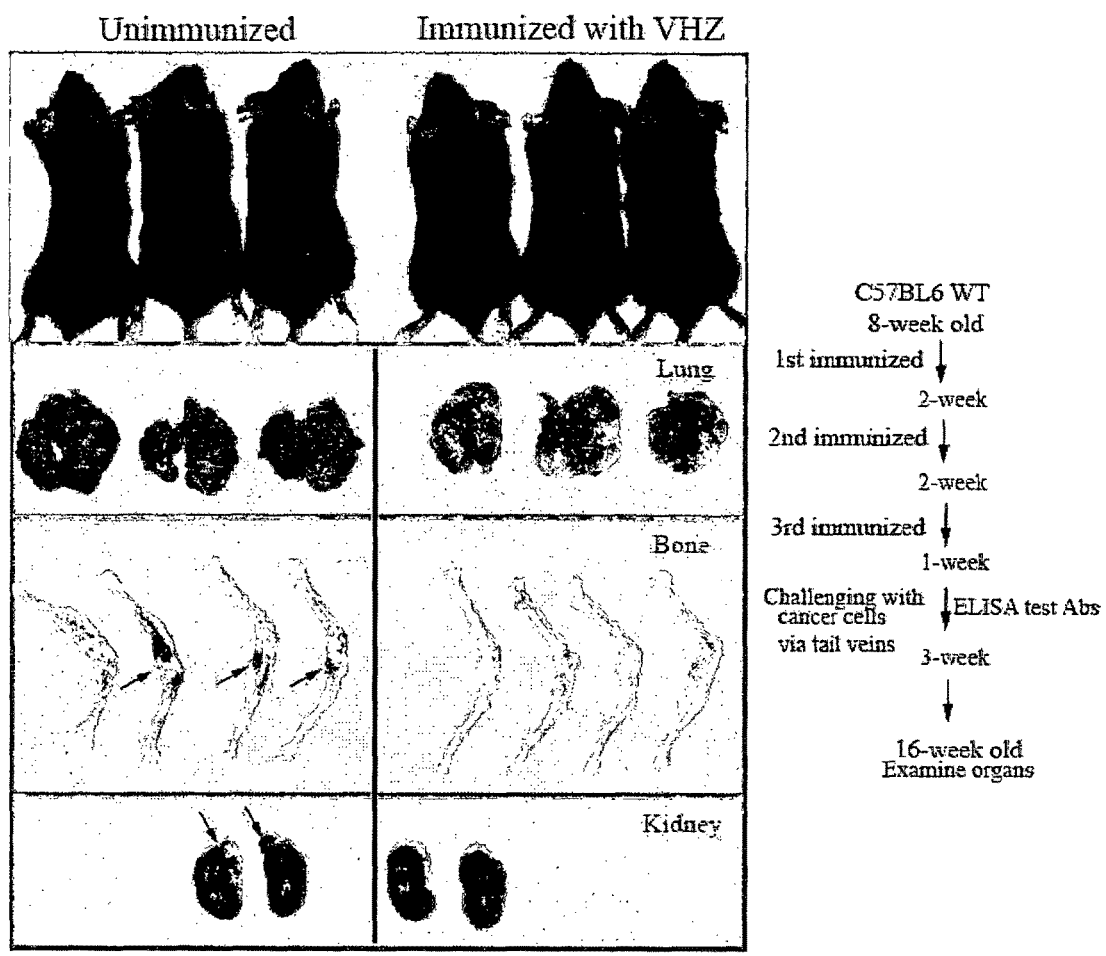
FIG. 15 shows the results of immunization of C57BL6 mice with VHZ and monitoring tumor development. 8-week old C57BL6 mice were immunized by intraperitoneal injection with a total volume of 200 ml Freund's Adjuvant: 20 mg of VHZ antigen in 100 ml saline mixed with 100 ml of complete adjuvant (Cat#77140, Pierce). The next two immunizations were injected with a total volume of 200 ml adjuvant: 20 mg of VHZ antigen in 100 ml saline mixed with 100 ml of incomplete adjuvant (Cat#77145, Pierce). The second and third injections were administrated every 2 weeks, 100-200 ml of tail bleed was collected in a heparin-coated capillary tube. Plasma was prepared from blood sample and antibody titer was measured by EL1SA. The detailed steps of ELISA were described previously. Mice with high titers of VHZ antibodies in their sera were selected and lateral tail vein injected with 1×106 VHZ-expressing cancer cells. Unvaccinated mice serve as a negative control in this study.

The results are shown in FIG. 15. FIG. 15 shows that mice vaccinated with VHZ antigen can prevent VHZ-expressing tumors. Unvaccinated mice serve as a negative control in this study.

Examples Section E4 (Examples 40, 41, 42)

Example 40: Section E4: Immunization with Her2/Neu Peptide Fragments

Generally, vaccine has been associated with infectious diseases but our immune system is also able to combat with cancerous cells. As such, inducing host immunity against oncoproteins will be a paradigm shift to maximize our immune system to fight against cancer cells for the therapeutic outcome. Multiple proteins/factors can cause a normal cell to become cancerous. However, if we are able to identify at least one of them (not necessary all of them), we are able to target at that protein with its specific antibody to kill the cancerous cells expressing that specific protein. Although one may feel uncomfortable to accept an idea of using 'oncoproteins' for vaccination, it is worth noting that the purified oncoproteins used as antigens in this study are unlikely to be oncogenic on their own because they are not sitting at their native subcellular location. Therefore, they are not able to interact with their native neighbourhood partners to elicit pathway-specific responses to drive tumorigenesis. These purified forms of "oncoproteins" have lost their specific intracellular spatiotemporal localization and therefore they are only proteins. Nonetheless, a more conservative approach would be the use of specific peptide antigens (partial oncoproteins) to achieve similar therapeutic results. Epitope-based peptide (or fragment) vaccination will be more specific and less cross-reacting with homologous proteins to reduce side effects.

In this study we used 4 Her2 fragments (see FIG. 16):
1. Her2 extracellular fragment (Her2 extra-)
2. Her2 intracellular fragment (Her2 intra-)
3. Her2 C-terminal fragment (Her2 C-terminal)
4. Her2a short peptide (Her2 peptide)

Figure 17:
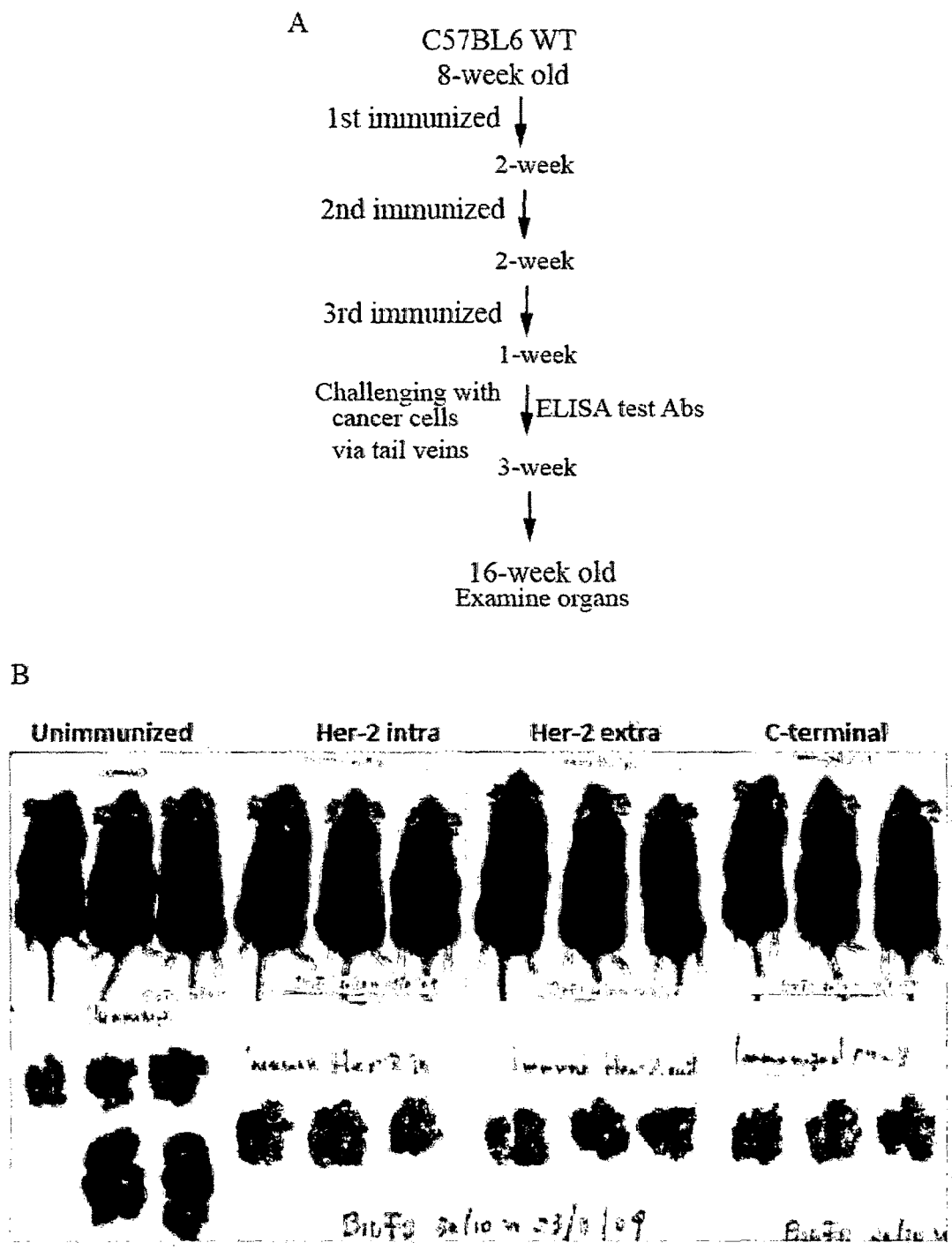
FIG. 17: Mice immunized with Her2 fragments could inhibit the formation of Her2-expressing tumors formed by B16F0 melanoma cancer cells. (A) A vaccination plan with Her2 intra-, extra-, and C-terminal fragments. (B) At week 16, unimmunized, Her2 intra-immunized, or Her2 extra-immunized mice, and Her2 C-terminal immunized mice were then challenged with 1 million B16F0 cancer cells via tail veins. All the organs were examined at ~17 days after cancer cell injection and photographed to show morphologies of metastatic tumors. Black tumors represent B16F0 melanoma cells. (C, upper) ELISA analysis was confirmed to show that Her2 fragments immunized (but not unimmunized) mice had high levels of Her2 antibodies in their sera. (C, lower). A total numbers of lung tumors from each mouse were counted and shown. N=3 in each group.

As shown in FIG. 17, mice immunized with Her2 fragments could inhibit the formation of Her2-expressing tumors formed by B16F0 melanoma cancer cells. At week 16, unimmunized, Her2 intra-immunized, or Her2 extra-immunized mice, and Her2 C-terminal immunized mice were then challenged with 1 million B16F0 cancer cells via tail veins. All the organs were examined at ~17 days after cancer cell injection and photographed to show morphologies of metastatic tumors. As shown in FIG. 17 (c, upper) ELISA analysis confirmed that Her2 fragment immunized mice had high levels of Her2 antibodies in their sera. As shown in FIG. 17 (c, lower), the total numbers of lung tumors (black tumors in panel B represent B16F0 melanoma cells) from each mouse was counted.

As shown in FIG. 18, mice immunized with Her2a short peptide could inhibit the formation of Her2-expressing tumors formed by B16F0 melanoma cancer cells. At week 16, Her2 short peptide immunized, Her2 extra-immunized (immunized with Her2-extracellular fragment), and unimmunized mice, were then challenged with 1 million B16F0 cancer cells via tail veins. All the organs were examined at ~17 days after cancer cell injection and photographed to show morphologies of metastatic tumors. ELISA analysis was confirmed to show that Her2 short peptide immunized, Her2 extra fragment immunized (but not unimmunized) mice had high levels of Her2 antibodies in their sera (see panel C, upper). A total numbers of lung tumors from each mouse were shown in panel C, lower.

Example 41: Section E4: Immunization of MMTV-PymT Transgenic Mice with a Fragment of mT Oncoprotein To apply a general concept of using target peptide vaccination, again, we examined a second tumor model, MMTV-PymT transgenic (TG) mice spontaneous tumor model, which carry the mT intracellular DNA viral protein under the transcriptional control of the mouse mammary tumor virus promoter/enhancer as a model of oncogene-induced mammary tumorigenesis (9). All female carriers (genotype+/−) develop palpable mammary tumors (adenocarcinomas) at the age of 3 months. The mT expression is detected at high levels in mammary glands, and the expression of mT oncogene is sufficient for mammary epithelial cell transformation (10). These TG mice have been widely used as excellent spontaneous tumor models for decades by the cancer research community (10, 18).

Figure 19:
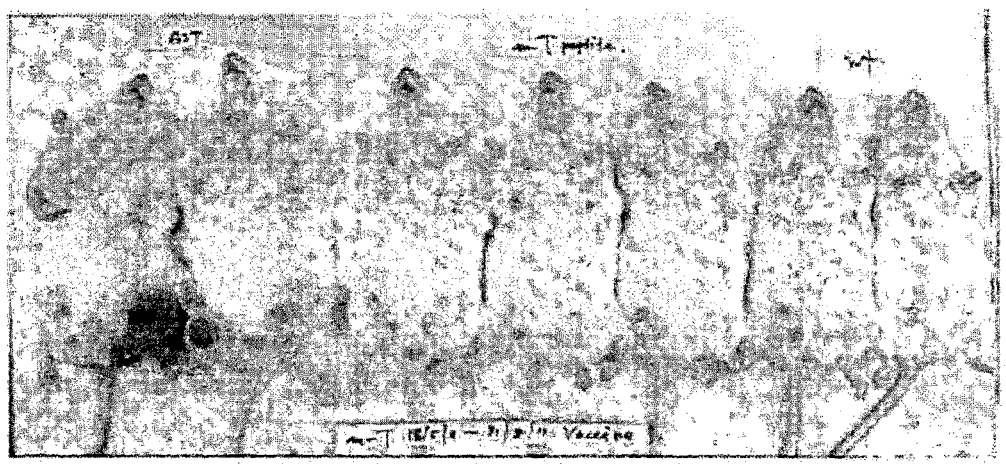
FIG. 19: MMTV-PymT TG young females vaccinated with mT peptide reduce the formation of mammary tumors. (A) A therapeutic plan of vaccination with mT peptide. (B) mT-peptide immunized mice showed marked repression of tumors compared to GST-immunized mice (unrelated immunized mice as negative control). (C, upper) the 10 mammary glands were shown as four groups at the bottom of each panel. (C, lower) An average weight of mammary glands from each mouse was shown, using WT mice as controls for normal sizes of mammary glands.
Figure 19:
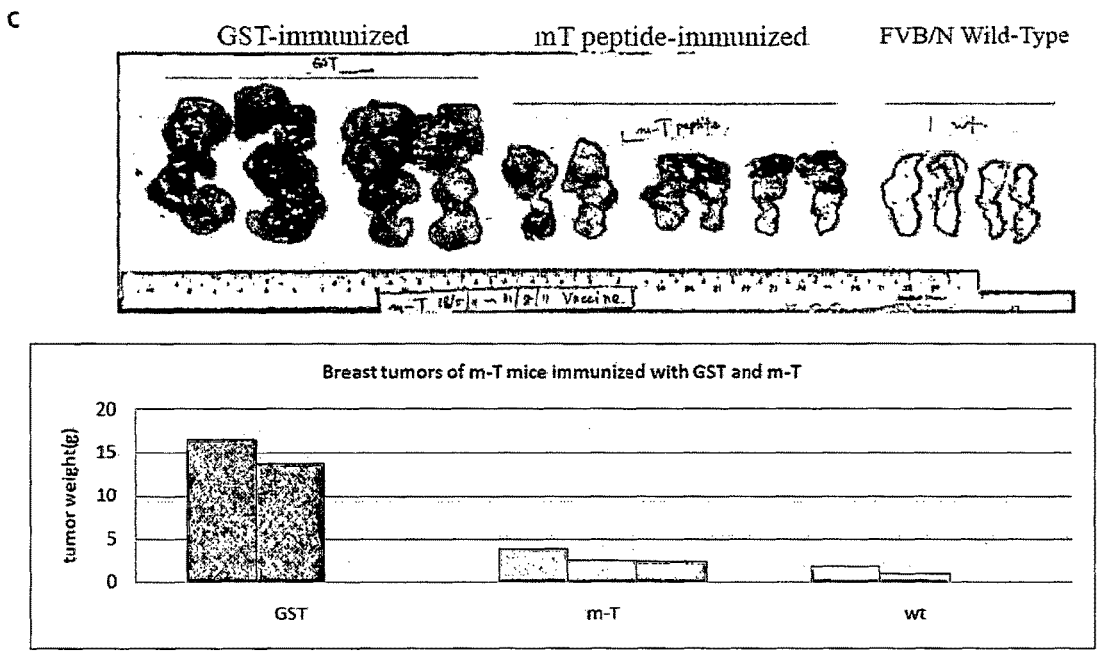

MMTV-PymT TG young females vaccinated with mT peptide (see FIG. 16) reduce the formation of mammary tumors. mT-peptide immunized mice showed marked repression of tumors compared to GST-immunized mice (unrelated immunized mice as negative control), as shown in FIG. 19 a small peptide of the mT oncoprotein achieved effective prevention from breast tumors progression in the model of MMTV-PymT transgenic mice.

Example 42: Section E4: Immunization of MMTV-PymT Transgenic Mice with a Fragment of Estrogen Receptor We further examined the MMTV-PymT transgenic (TG) mouse spontaneous tumor model described above. Estrogen Receptor was expressed at high levels in m-T mice, and particularly in breast tissue.

MMTV-PymT TG young females vaccinated with ER-Red and ER-purple peptide (See FIG. 20) which are fragments of Estrogen Receptor. Both ER-Red and ER-purple immunized mice showed marked regression of tumors compared to GST-immunized mice (unrelated immunized mice as negative control) as shown in FIG. 21. A small peptide of ER achieved effective prevention from breast tumor progression in the model of MMTV-PymT transgenic mice.

MMTV-PymT mice were injected with ERa-mAb weekly for 13 weeks. Treated mice showed a statistically significant reduction in breast tumor weight compared to untreated mice (see FIG. 22).

Example 43: Section E4: Immunization of Mice with HBV-X Protein Fragment

We are examining whether Hepatitis B X protein could be used to treat liver cancer. HBV X-protein is located in the nucleus of infected cells.

Panels of liver cancer cell lines that express X-protein are examined for their ability to form tumors in vivo. The lines with the highest tumor forming capability are used.

Mice are injected with anti-X-protein antibody to investigate the ability of the anti-X-protein antibody to block tumor formation from X-protein expressing liver cancer cells. Anti-X-protein antibody is administered to the mice according to the protocols outlined above.

Mice are injected with X-protein and X-protein fragments (see FIG. 20) to trigger the host immune system to produce antibodies against X-protein to prevent the formation of tumors that express X-protein. Vaccination protocols as described above are used.

The spontaneous hepatocellular carcinoma (HCC) mouse model, which mimics human liver cancer development may also be used to examine the effects of anti-X-protein antibody, X-protein and X-protein fragment vaccination on hepatocellular carcinoma. The signalling pathways involved in HCC development are discussed in Signalling pathways and treatment of hepatocellular carcinoma is discussed in Whittaker S, Marais R, Zhu A X. The role of signaling pathways in the development and treatment of hepatocellular carcinoma. Oncogene. 2010; 29:4989-5005.

Example 44: Section E4: Discussion

Genes specifically up-regulated during tumor formation but poorly or not expressed in host tissues are particularly promising as tumor-specific targets. For cancers that show a genetic link, immunization of immune-competent young susceptible family members with an antigen (epitope-based peptide vaccine) that is associated with the familial cancer could prime the immune system against that oncoprotein. These endogenously stimulated antibodies could then potentially combat cancer cells expressing that particular oncoprotein.

This study suggests that antibody-based therapy and vaccination against cancer may be extended to a wider variety of intracellular oncoproteins as therapeutic targets. The whole class of intracellular oncoproteins previously thought to be un-targetable by therapeutic antibodies or vaccinations can now expand the scope for tailor-made cancer therapies as well as usher in a new era of cancer vaccines. We expect that one potential advantage of using intracellular self-antigens is that they may have a better chance of provoking an immune response than extracellular self-antigens because immune cells targeting extracellular self-antigens are generally eliminated during development. We found that compared to exogenously delivered antibodies, antigen-induced antibody therapy could achieve similar antitumor therapeutic efficacy. Because existing conventional clinical antibody therapy is costly, vaccination may be more useful and economical as a means of inducing high titers of antigen-induced antibodies. This concept of "cancer vaccination" is promising and challenging.

This study indicates that antibodies against Hepatitis B virus (HBV) proteins (such as the HBV X-protein localized in the nucleus of infected cells) (Whittaker et al; Oncogene 29; 4989-5005 (2010)) could be used as therapeutic intracellular targets for hepatocellular carcinoma (HCC) as most HCC are associated with HBV infection, antibody targeting viral protein will specifically destroy virally infected cells but leave normal cell unharmed. Similarly, for breast cancer caused by overexpression of estrogen receptor (ER), antibodies against ER or vaccination using ER fragment could be used to prevent spreading. This is particular useful to target ER positive breast cancer patients regardless of the expression of Her2 or other proteins.

A potential scheme in future cancer treatment could be to remove/biopsy of primary tumor, identify at least one tumor-expressing antigen using immunohistochemistry, and administer either antibodies against that specific tumor marker or a therapeutic vaccine that stimulates antibodies against it. For patients with a strong family history of cancer, immunization of young susceptible family members with an antigen associated with the familial cancer could also prime the immune system against tumor cells expressing that antigen. If the myriad of previously unexplored candidate target proteins are investigated, a new era of tailor-made personalized cancer therapies will soon become reality.

Although the molecular mechanism(s) behind our untraditional findings remains elusive and needs to be deciphered, a number of possible mechanisms of antibody actions can be envisaged (FIG. 22). Firstly (model A), the antibody may potentially enter PRL-3 expressing cells to target intracellular PRL-3 and neutralize its function. We observed that about ~10% of PRL-3 expressing cancer cells could take up antibodies in culture and this uptake was enhanced by 6-folds upon serum starvation. (Guo et al., Cancer Therapy 2008) Serum-starvation is used to arrest cells at G1 and G0 phases. (Cooper et al., FASEB J. 2003; 17:333-340). It is possible that particular stages (perhaps G1-G0) of the cell cycle can contribute to the abilities of cells to take up the antibodies. In vivo, cancer cells are under hypoxic stress and serum deprivation, conditions that might enhance the abilities of cancer cells to take up antibodies. It was reported that antibody can be taken into live human mononuclear cells through surface Fc receptor (Alarcon-Segovia Nature 1978: 271; 67-69). We found that the phenomenon of antibody uptake was abolished if endocytosis was blocked by NH4Cl or when cells were incubated mice (unpublished data), suggesting that most likely, these antibodies bind to cell surface proteins followed by endocytosis or pinocytosis. Once in the endocytic compartments, the antibodies could be released into the cytosol.

Secondly (model B), some of the intracellular antigens may be externalized and displayed on the surface of cancer cells by unconventional secretion (24), enabling the antibodies to bind and trigger immune responses such as antibody-dependent cellular cytotoxicity (ADCC).

Thirdly (model C), proteolytic fragments of intracellular targets may be presented by major histocompatibility (MHC) class I molecules to attract Cytotoxic T cells (CTLs) to mediate cell mediated lysis of cancer cells. In addition, a small fraction of intracellular antigens is released due to necrosis or cancer cell lysis, resulting in antigen-antibody complex within the tumor and stimulating local inflammatory response to attract immune cells in targeting neighbouring viable cancer cells within tumor. The most probable mechanism could be a combination of several modes, possibly including complement-mediated events that are actually involved in achieving the final therapeutic consequence of antibodies against intracellular oncoproteins. Currently, the understanding of how antibody destroys tumors in vivo is still a "dark box". This is similar to anti-HER2/neu antibody therapeutic mechanism; it has been more than two decades and we still do not fully comprehend its mechanism(s) even though the antibody has been in clinical use for years to treat breast cancers (Husemann et al., Cancer Cell 2008; 13:58-68).

Using in vitro cell culture system to unravel or reassemble the in vivo "dark box" may be unrealistic because the traditional in vitro cell culture system is over simplified.

There exists the limitation of single cell type grown in an incubator which typically uses medium supplemented with 10% (hence lacking 90%) fetal bovine serum and non-involvement of immune system. The in vitro system is also unlikely to actually mimic in vivo complexities of multiple types of cells and organs, coordinating in 100% native blood circulation and lymphatic system. Whatever mechanism is used, the central finding of this study is that antibodies to intracellular protein can exert therapeutic effects. Since the therapeutic effects of antibodies to intracellular proteins are substantial and reproducible, the incomplete understanding of the underlying mechanisms should not hinder future research in this new class of therapies.

Example 45: Immunization with Oncopeptides Designed Around Oncogenic Mutations 57BL/6 mice immunized with PRL-3 synthetic peptide using the vaccination protocol shown in FIG. 24B. The synthetic peptide comprised two different peptides, both fragments of the complete PRL-3 protein, and linked with a GGSG (SEQ ID NO: 128) linker (indicated in bold text), and had the sequence EVTYDKTPLEKDGITVGGSGDPHTH-KTRC(SEQ ID NO: 18)-KLH. As shown in FIG. 24C immunization resulted in the production of mutant peptide specific antibodies.

Following immunization, mice were challenged with B16F0 cells which express PRL-3 target protein (see FIG. 24A). Immunized mice were able to block tumor formation as compared to control mice which had not been immunized, or control mice immunized with GST (see FIG. 24D).

In another experiment, C57BL6 mice were challenged with B16F10 cells. Unlike B16F0 cells, B16F10 cells do not express PRL-3. Mice challenged with B16F10 cells were unable to block tumor formation, demonstrating that immunization induces a specific immune response.

Example 46: Mutation Peptide Vaccination Against Oncoproteins

Although many human tumor cell lines carry mutated oncoproteins, it is not possible to introduce these into wild type mice, since mice cannot tolerate human cancer cells, and die due to the strong immune responses that are generated.

Conversely, only limited numbers of mouse cancer cell lines carry mutated oncoproteins available for use in the mouse vaccine models. We only identified one mouse colon cancer cell line, CT26, which carries Ras (G12D) mutation. This cell line is able to induce tumors in Balb/c mice.

The immunization and challenge protocol used in this experiment is shown in FIG. 26A.

Immunisation of Balb/c mice with a peptide corresponding to region of the Ras oncoprotein containing the G12D mutation (CMTEYKLVVVGADGVGKSALT) was able to trigger host production of antibodies against tumors that expressed that specific point mutation in a target protein (see FIG. 26B).

Immunized mice were then injected with CT26 mouse cell line in a tumorigenesis study. Immunization was able to prevent CT-26 tumor formation in Balbc mice FIG. 26C).

Antibody therapy is costly; vaccination may be more useful and economical as a means of inducing high titers of antigen-induced antibodies. This concept of "cancer vaccination" is promising and challenging.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

---

The invention claimed is:

1. A method for the treatment of cancer, the method comprising administering to a patient in need thereof a therapeutically effective amount of a polypeptide, wherein the polypeptide comprises:
   a) a first fragment of Phosphatase of Regenerating Liver 3 (PRL3) consisting of the amino acid sequence EVTYDKTPLEKDGITV (amino acids 1 to 16 of SEQ ID NO:18);
   b) a linker peptide; and
   c) a second fragment of PRL3 consisting of the amino acid sequence DPHTHKTRC (amino acids 21 to 29 of SEQ ID NO:18);
wherein the linker peptide is situated between the first and second fragment of PRL3; and
wherein the polypeptide stimulates the production of anti-PRL3 anti-cancer antibodies in the patient thereby inhibiting cancer metastasis.

2. The method according to claim 1 wherein the patient has a primary cancer that expresses PRL3.

3. The method according to claim 1 wherein the cancer is associated with or caused by over-expression of PRL3.

4. The method according to claim 1 wherein the cancer is selected from the group consisting of: breast cancer, hepatocellular cancer, acute lymphocytic leukemia (ALL), acute myeloid leukemia (AML), adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CIVIL), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, testicular cancer, thyroid cancer, urinary system cancer, uterine sarcoma, vaginal cancer, vascular system, Waldenstrom's macroglobulinemia and Wilms' tumor.

5. The method of claim 1, wherein the linker peptide is between 1 and 15 amino acids in length.

6. The method of claim 1, wherein the polypeptide comprises SEQ ID NO: 18.

7. The method of claim 1, wherein the polypeptide further comprises a carrier protein.

8. The method of claim 7, wherein the carrier protein is keyhole limpet haemocyanin (KLH).

9. A method for inhibiting metastasis in a patient with a Phosphatase of Regenerating Liver 3 (PRL3) expressing cancer, the method comprising:
   a) identifying PRL3 expression in a patient's cancer; and
   b) administering a polypeptide which comprises:
      i) a first fragment of Phosphatase of Regenerating Liver 3 (PRL3) consisting of the amino acid sequence EVTYDKTPLEKDGITV (amino acids 1 to 16 of SEQ ID NO:18);
      ii) a linker peptide; and
      iii) a second fragment of PRL3 consisting of the amino acid sequence DPHTHKTRC (amino acids 21 to 29 of SEQ ID NO:18);
wherein the linker peptide is situated between the first and second fragment of PRL3; and
   wherein the patient is induced to produce anti-PRL3 anti-cancer antibodies, thereby inhibiting cancer metastasis.

10. The method of claim 9, wherein the linker peptide is between 1 and 15 amino acids in length.

11. The method of claim 9, wherein the polypeptide comprises SEQ ID NO: 18.

12. The method of claim 9, wherein the polypeptide further comprises a carrier protein.

13. The method of claim 12, wherein the carrier protein is keyhole limpet haemocyanin (KLH).

14. A method for treating cancer in a person, the method comprising:
   a) determining whether a person is suffering from a cancer associated with Phosphatase of Regenerating Liver 3 (PRL3); and
   b) administering to that person a polypeptide which comprises:
      i) a first fragment of Phosphatase of Regenerating Liver 3 (PRL3) consisting of the amino acid sequence EVTYDKTPLEKDGITV (amino acids 1 to 16 of SEQ ID NO:18);

ii) a linker peptide; and
iii) a second fragment of PRL3 consisting of the amino acid sequence DPHTHKTRC (amino acids 21 to 29 of SEQ ID NO:18);

wherein the linker peptide is situated between the first and second fragment of PRL3; and wherein the patient is induced to produce anti-PRL3 anti-cancer antibodies, thereby inhibiting cancer metastasis.

15. The method of claim 14, wherein the linker peptide is between 1 and 15 amino acids in length.

16. The method of claim 14, wherein the polypeptide comprises SEQ ID NO: 18.

17. The method of claim 14, wherein the polypeptide further comprises a carrier protein.

18. The method of claim 17, wherein the carrier protein is keyhole limpet haemocyanin (KLH).

19. A method of cancer vaccination, the method comprising administering to a patient a polypeptide which comprises:

a) a first fragment of Phosphatase of Regenerating Liver 3 (PRL3) consisting of the amino acid sequence EVTYDKTPLEKDGITV (amino acids 1 to 16 of SEQ ID NO:18);
b) a linker peptide; and
c) a second fragment of PRL3 consisting of the amino acid sequence DPHTHKTRC (amino acids 21 to 29 of SEQ ID NO:18);

wherein the linker peptide is situated between the first and second fragment of PRL3; and wherein the polypeptide stimulates the production of anti-PRL3 anti-cancer antibodies in the patient.

20. The method of claim 19, wherein the linker peptide is between 1 and 15 amino acids in length.

21. The method of claim 19, wherein the polypeptide comprises SEQ ID NO: 18.

22. The method of claim 19, wherein the polypeptide further comprises a carrier protein.

23. The method of claim 22, wherein the carrier protein is keyhole limpet haemocyanin (KLH).

* * * * *